(12) United States Patent
Bae et al.

(10) Patent No.: US 12,225,813 B2
(45) Date of Patent: Feb. 11, 2025

(54) ORGANIC COMPOUND AND ORGANIC ELECTROLUMINESCENT DEVICE COMPRISING THE SAME

(71) Applicant: DOOSAN SOLUS CO., LTD., Iksan-si (KR)

(72) Inventors: Hyung Chan Bae, Yongin-si (KR); Young Bae Kim, Yongin-si (KR); Ho Jun Son, Yongin-si (KR)

(73) Assignee: DOOSAN SOLUS CO., LTD., Iksan-si (KR)

( * ) Notice: Subject to any disclaimer, the term of this patent is extended or adjusted under 35 U.S.C. 154(b) by 798 days.

(21) Appl. No.: 16/615,891

(22) PCT Filed: May 2, 2018

(86) PCT No.: PCT/KR2018/005076
§ 371 (c)(1),
(2) Date: Nov. 22, 2019

(87) PCT Pub. No.: WO2018/216921
PCT Pub. Date: Nov. 29, 2018

(65) Prior Publication Data
US 2020/0144511 A1 May 7, 2020

(30) Foreign Application Priority Data
May 23, 2017 (KR) .......................... 10-2017-0063365

(51) Int. Cl.
| | | |
|---|---|---|
| H10K 85/60 | (2023.01) | |
| C07D 263/57 | (2006.01) | |
| C07D 405/10 | (2006.01) | |
| C07D 405/14 | (2006.01) | |
| C07D 409/10 | (2006.01) | |
| C07D 413/10 | (2006.01) | |
| C07D 413/14 | (2006.01) | |
| H10K 50/11 | (2023.01) | |
| H10K 50/15 | (2023.01) | |
| H10K 50/17 | (2023.01) | |
| H10K 71/00 | (2023.01) | |
| H10K 71/16 | (2023.01) | |
| H10K 101/10 | (2023.01) | |
| H10K 102/00 | (2023.01) | |

(52) U.S. Cl.
CPC ......... *H10K 85/654* (2023.02); *C07D 263/57* (2013.01); *C07D 405/10* (2013.01); *C07D 405/14* (2013.01); *C07D 409/10* (2013.01); *C07D 413/10* (2013.01); *C07D 413/14* (2013.01); *H10K 85/636* (2023.02); *H10K 85/657* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/17* (2023.02); *H10K 71/00* (2023.02); *H10K 71/164* (2023.02); *H10K 2101/10* (2023.02); *H10K 2102/351* (2023.02)

(58) Field of Classification Search
CPC ............. H01L 51/0067; H01L 51/0061; H01L 51/0071; H01L 51/0072; H01L 51/0073; H01L 51/006; H01L 51/5016; H01L 51/5056; H01L 51/5088; H01L 51/56; H01L 51/558; C07D 405/10; C07D 413/10; H10K 85/654; H10K 85/636; H10K 85/6574; H10K 85/657; H10K 85/6576; H10K 85/6572; H10K 50/17; H10K 50/11; H10K 50/15; H10K 2101/10
See application file for complete search history.

(56) References Cited

U.S. PATENT DOCUMENTS

| | | | |
|---|---|---|---|
| 2012/0056171 A1* | 3/2012 | Kim ........................ | C09B 57/00 |
| | | | 257/E51.026 |
| 2013/0256645 A1 | 10/2013 | Min et al. | |
| 2016/0172593 A1 | 6/2016 | Takada et al. | |

FOREIGN PATENT DOCUMENTS

| | | | | |
|---|---|---|---|---|
| CN | 106478609 A | | 3/2017 | |
| CN | 107337680 A | * | 11/2017 | ............. C07C 13/62 |

(Continued)

OTHER PUBLICATIONS

Yang et al., machine translation of CN 106478609 A (2017) pp. 1-12. (Year: 2017).*

(Continued)

*Primary Examiner* — Dylan C Kershner
(74) *Attorney, Agent, or Firm* — Sughrue Mion, PLLC

(57) ABSTRACT

A novel compound of the Chemical Formula 1 and an organic electroluminescent device including the compound are disclosed. The novel compound, when included in an organic material layer, preferably a light emitting layer, of an organic electroluminescent device, can improve luminous efficiency, driving voltage, lifetime and other properties of the organic electroluminescent device:

[Chemical Formula 1]

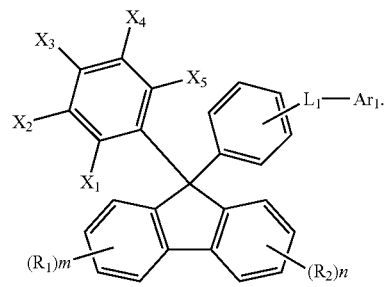

12 Claims, 1 Drawing Sheet

(56) References Cited

FOREIGN PATENT DOCUMENTS

| | | | |
|---|---|---|---|
| JP | 2003045662 A * | 2/2003 | |
| JP | 2012-526804 A | 11/2012 | |
| JP | 2016-113396 A | 6/2016 | |
| JP | 2016-534980 A | 11/2016 | |
| JP | 2017-508715 A | 3/2017 | |
| KP | 10-2011-0029831 A | 3/2011 | |
| KR | 10-2011-0043667 A | 4/2011 | |
| KR | 20140014956 A * | 2/2014 | |
| KR | 10-2015-0039673 A | 4/2015 | |
| KR | 10-2015-0074603 A | 7/2015 | |
| KR | 10-2015-0135123 A | 12/2015 | |
| KR | 10-2016-0049083 A | 5/2016 | |
| KR | 10-2018-0024891 A | 3/2018 | |
| WO | WO-2014185751 A1 * | 11/2014 | ........... C07D 239/26 |
| WO | WO-2015050391 A1 * | 4/2015 | ........... C07C 211/54 |
| WO | 2015/178732 A1 | 11/2015 | |
| WO | 2016/013867 A1 | 1/2016 | |
| WO | WO-2018043913 A1 * | 3/2018 | ........... C07D 263/57 |

OTHER PUBLICATIONS

Matsuura et al., machine translation of JP-2003045662-A (2003) pp. 1-27. (Year: 2003).*
Hyun et al., machine translation of KR-20140014956-A (2014) pp. 1-32. (Year: 2014).*
Tang et al., machine translation of CN-107337680-A (2017) pp. 1-25. (Year: 2017).*
Son et al., machine translation of WO-2018043913-A1 (2018) pp. 1-25. (Year: 2018).*
International Search Report for PCT/KR2018/005076 dated Aug. 17, 2018 (PCT/ISA/210).
Japanese Patent Office, Office Action issued Dec. 11, 2020 in Japanese Application No. 2019-564953.

* cited by examiner

[FIG. 1]
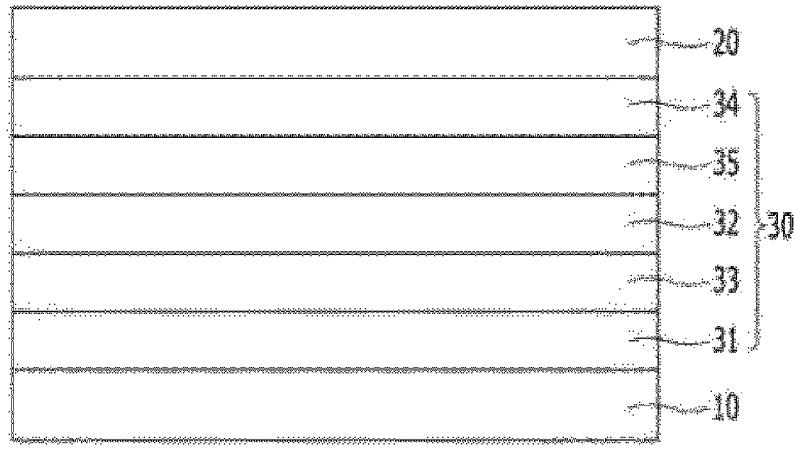
[FIG. 2]
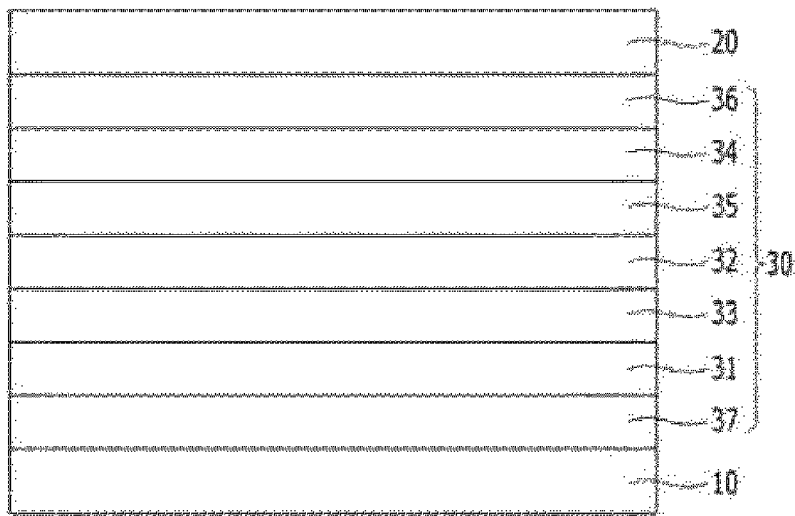

ORGANIC COMPOUND AND ORGANIC ELECTROLUMINESCENT DEVICE COMPRISING THE SAME

CROSS REFERENCE TO RELATED APPLICATIONS

This application is a National Stage of International Application No. PCT/KR2018/005076 filed May 2, 2018, claiming priority based on Korean Patent Application No. 10-2017-0063365 filed May 23, 2017.

TECHNICAL FIELD

The present invention relates to a novel organic compound capable of being used as a material for an organic electroluminescent device, and an organic electroluminescent device including the same.

BACKGROUND ART

With the observation of organic thin film light emission made by Bernanose in 1950s as a start, studies on organic electroluminescent (EL) devices have been continued leading to blue electroluminescence using a single anthracene crystal in 1965, and in 1987, an organic electroluminescent device having a laminated structure divided into functional layers of a hole layer and a light emitting layer has been proposed by Tang. After that, in order to manufacture organic electroluminescent devices with high efficiency and long lifetime, development has been made in the form of introducing each characteristic organic material layer into the device, which leads to the development of specialized materials used therein.

When a voltage is applied between the two electrodes in an organic electroluminescent device, holes and electrons are injected to an organic material layer from the anode and the cathode, respectively. When the injected holes and electrons meet, excitons are formed, and light emits when these excitons fall back to the ground state. Herein, materials used as the organic material layer may be divided into a light emitting material, a hole injection material, a hole transport material, an electron transport material, an electron injection material and the like depending on the function.

The light emitting material may be divided into, depending on the light emitting color, blue, green and red light emitting materials, and yellow and orange light emitting materials for obtaining better natural colors. In addition, in order to increase color purity and increase luminous efficiency through energy transfer, host/dopant series may be used as the light emitting material.

The dopant material may be divided into fluorescent dopants using organic materials and phosphorescent dopants using metal complex compounds including heavy atoms such as Ir or Pt. Herein, development of phosphorescent materials may enhance luminous efficiency up to 4 times compared to fluorescence theoretically, and therefore, studies on phosphorescent host materials have been widely progressed as well as on phosphorescent dopants.

So far, NPB, BCP, Alq$_3$ and the like have been widely known as materials of a hole injection layer, a hole transport layer, a hole blocking layer and an electron transport layer, and anthracene derivatives have been reported as a material of a light emitting layer. Particularly, among light emitting layer materials, metal complex compounds including Ir such as Firpic, Ir(ppy)$_3$ or (acac)Ir(btp)$_2$ having advantages in terms of efficiency enhancement have been used as blue, green and red phosphorescent dopant materials, and 4,4-dicarbazolylbiphenyl (CBP) has been used as a phosphorescent host material.

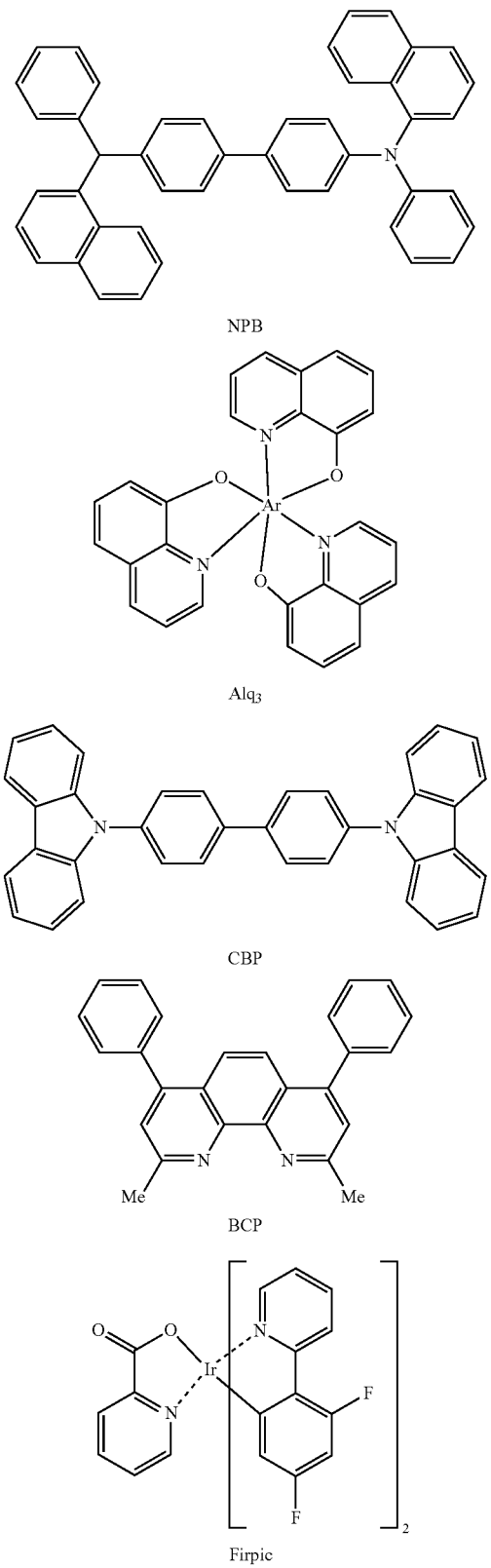

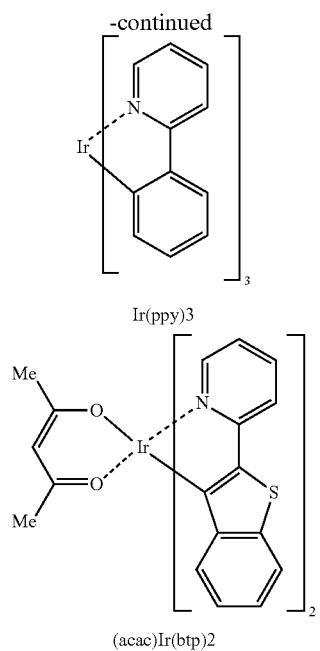

Ir(ppy)3

(acac)Ir(btp)2

However, although being advantageous in terms of a light emission property, existing organic material layer materials have a low glass transition temperature and thereby have very unfavorable thermal stability, which is not satisfactory in terms of an organic electroluminescent device lifetime. Accordingly, development of organic material layer materials having superior performance has been required.

DISCLOSURE

Technical Problem

The present invention is directed to providing a novel organic compound capable of being used in an organic electroluminescent device, and having excellent hole and electron injection and transport abilities, a light emitting ability and the like.

The present invention is also directed to providing an organic electroluminescent device including the novel organic compound, and thereby exhibiting a low driving voltage, high luminous efficiency, and an enhanced lifetime.

Technical Solution

In view of the above, one embodiment of the present invention provides a compound represented by the following Chemical Formula 1:

[Chemical Formula 1]

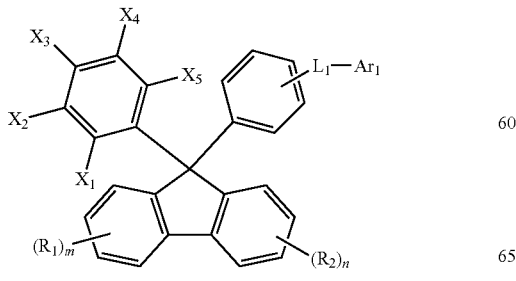

in Chemical Formula 1, $L_1$ is selected from the group consisting of a single bond, a $C_6 \sim C_{18}$ arylene group and a heteroarylene group having 5 to 18 nuclear atoms;

$Ar_1$ is selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group;

any one of $X_1$ and $X_2$, $X_2$ and $X_3$, $X_3$ and $X_4$, and $X_4$ and $X_5$ bonds to a ring represented by the following Chemical Formulae 2 to 4 to form a fused ring;

m and n are each independently an integer of 0 to 4;

$R_1$, $R_2$, and $X_1$ to $X_5$ not forming a fused ring with a ring represented by the following Chemical Formulae 2 to 4 are each independently selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$, $R_2$, and $X_1$ to $X_5$ not forming a fused ring with a ring represented by the following Chemical Formulae 2 to 4 are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylboron group, a $C_6 \sim C_{60}$ arylboron group, a $C_6 \sim C_6 \sim C_{60}$ arylphosphanyl group, a $C_6 \sim C_{60}$ mono or diarylphosphinyl group and a $C_6 \sim C_{60}$ arylsilyl group, and when substituted with a plurality of the substituents, these are the same as or different from each other;

[Chemical Formula 2]

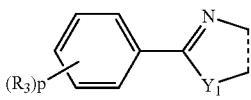

-continued

[Chemical Formula 3]

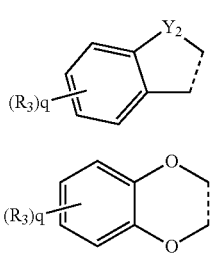

[Chemical Formula 4]

in Chemical Formulae 2 to 4,
a dotted line means a part that is fused to Chemical Formula 1;
p is an integer of 0 to 5;
q is an integer of 0 to 4;
$Y_1$ and $Y_2$ are each independently $N(R_4)$, O, S or $C(R_5)(R_6)$;
$R_3$ to $R_6$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and
the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$ to $R_6$, and an aromatic ring, a non-aromatic fused polycyclic ring, an aromatic heteroring and a non-aromatic fused heteropolycyclic ring formed by adjacent two $Ar_2$s bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

Another embodiment of the present invention provides an organic electroluminescent device including an anode, a cathode, and one or more organic material layers provided between the anode and the cathode, wherein at least one of the one or more organic material layers includes the compound of Chemical Formula 1.

The "halogen" in the present invention means fluorine, chlorine, bromine or iodine.

The "alkyl" in the present invention is a monovalent substituent derived from linear or branched saturated hydrocarbon having 1 to 40 carbon atoms. Examples thereof may include methyl, ethyl, propyl, isobutyl, sec-butyl, pentyl, iso-amyl, hexyl and the like, but are not limited thereto.

The "alkenyl" in the present invention is a monovalent substituent derived from linear or branched unsaturated hydrocarbon having one or more carbon-carbon double bonds and having 2 to 40 carbon atoms. Examples thereof may include vinyl, allyl, isopropenyl, 2-butenyl and the like, but are not limited thereto.

The "alkynyl" in the present invention is a monovalent substituent derived from linear or branched unsaturated hydrocarbon having one or more carbon-carbon triple bonds and having 2 to 40 carbon atoms. Examples thereof may include ethynyl, 2-propynyl and the like, but are not limited thereto.

The "aryl" in the present invention means a monovalent substituent derived from aromatic hydrocarbon having a single ring or two or more rings combined and having 6 to 60 carbon atoms. In addition, a monovalent substituent having two or more rings fused with each other, including only carbon (for example, the number of carbon atoms may be from 8 to 60) as a ring-forming atom, and with the whole molecule having non-aromaticity may also be included. Examples of such aryl may include phenyl, naphthyl, phenanthryl, anthryl, fluorenyl and the like, but are not limited thereto. The "heteroaryl" in the present invention means a monovalent substituent derived from monoheterocyclic or polyheterocyclic aromatic hydrocarbon having 5 to 60 nuclear atoms. Herein, one or more carbons, preferably 1 to 3 carbons, in the ring are substituted with a heteroatom selected from among N, O, P, S and Se. In addition, a monovalent group having two or more rings simply attached (pendant) or fused with each other, including a heteroatom selected from among N, O, P, S and Se as a ring-forming atom in addition to carbon, and with the whole molecule having non-aromaticity is interpreted to be included as well. Examples of such heteroaryl may include 6-membered monocyclic rings such as pyridyl, pyrazinyl, pyrimidinyl, pyridazinyl or triazinyl; polycyclic rings such as phenoxathienyl, indolizinyl, indolyl, purinyl, quinolyl, benzothiazole or carbazolyl; 2-furanyl, N-imidazolyl, 2-isoxazolyl, 2-pyridinyl, 2-pyrimidinyl and the like, but are not limited thereto.

The "aryloxy" in the present invention is a monovalent substituent represented by RO—, and R means aryl having 5 to 60 carbon atoms. Examples of such aryloxy may include phenyloxy, naphthyloxy, diphenyloxy and the like, but are not limited thereto.

The "alkyloxy" in the present invention is a monovalent substituent represented by R'O—, and R' means alkyl having 1 to 40 carbon atoms and is interpreted to include a linear, branched or cyclic structure. Examples of such alkyloxy may include methoxy, ethoxy, n-propoxy, 1-propoxy, t-butoxy, n-butoxy, pentoxy and the like, but are not limited thereto.

The "arylamine" in the present invention means amine substituted with aryl having 6 to 60 carbon atoms.

The "cycloalkyl" in the present invention means a monovalent substituent derived from monocyclic or polycyclic non-aromatic hydrocarbon having 3 to 40 carbon atoms.

Examples of such cycloalkyl may include cyclopropyl, cyclopentyl, cyclohexyl, norbomyl, adamantine and the like, but are not limited thereto.

The "heterocycloalkyl" in the present invention means a monovalent substituent derived from non-aromatic hydrocarbon having 3 to 40 nuclear atoms, and one or more carbons, preferably 1 to 3 carbons, in the ring are substituted with a heteroatom such as N, O, S or Se. Examples of such heterocycloalkyl may include morpholine, piperazine and the like, but are not limited thereto.

The "alkylsilyl" in the present invention means silyl substituted with alkyl having 1 to 40 carbon atoms, and the "arylsilyl" means silyl substituted with aryl having 5 to 60 carbon atoms.

The "fused ring" in the present invention means a fused aliphatic ring, a fused aromatic ring, a fused heteroaliphatic ring, a fused heteroaromatic ring, or a combined form thereof.

Advantageous Effects

A compound of the present invention has excellent thermal stability, carrier transport ability, light emitting ability and the like, and therefore, is useful as a material of an organic material layer of an organic electroluminescent device.

In addition, an organic electroluminescent device including a compound of the present invention in an organic material layer has greatly enhanced properties in terms of light emitting performance, driving voltage, lifetime, efficiency and the like, and can be effectively used in a full color display panel and the like.

DESCRIPTION OF DRAWINGS

FIG. 1 is a sectional diagram illustrating an organic electroluminescent device according to one embodiment of the present invention.

FIG. 2 is a sectional diagram illustrating an organic electroluminescent device according to one embodiment of the present invention.

MODE FOR DISCLOSURE

Hereinafter, the present invention will be described in detail.

1. Novel Organic Compound

A novel compound of the present invention may be represented by the following Chemical Formula 1:

[Chemical Formula 1]

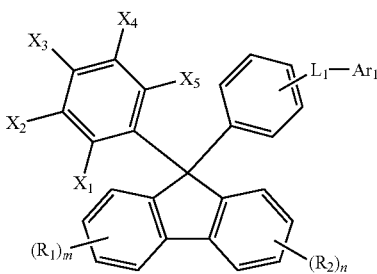

in Chemical Formula 1, $L_1$ is selected from the group consisting of a single bond, a $C_6 \sim C_{18}$ arylene group and a heteroarylene group having 5 to 18 nuclear atoms;

$Ar_1$ is selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group;

any one of $X_1$ and $X_2$, $X_2$ and $X_3$, $X_3$ and $X_4$, and $X_4$ and $X_5$ bonds to a ring represented by the following Chemical Formulae 2 to 4 to form a fused ring;

m and n are each independently an integer of 0 to 4;

$R_1$, $R_2$, and $X_1$ to $X_5$ not forming a fused ring with a ring represented by the following Chemical Formulae 2 to 4 are each independently selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylsulfonyl group, a $C_6 \sim C_{60}$ arylsulfonyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group, a $C_1 \sim C_{40}$ alkylcarbonyl group, a $C_6 \sim C_{60}$ arylcarbonyl group and a $C_6 \sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$, $R_2$, and $X_1$ to $X_5$ not forming a fused ring with a ring represented by the following Chemical Formulae 2 to 4 are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group and a $C_6 \sim C_{60}$ arylsilyl group, and when substituted with a plurality of the substituents, these are the same as or different from each other;

[Chemical Formula 2]

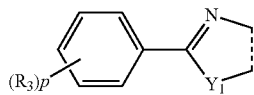

[Chemical Formula 3]

[Chemical Formula 4]

in Chemical Formulae 2 to 4,
a dotted line means a part that is fused to Chemical Formula 1;
p is an integer of 0 to 5;
q is an integer of 0 to 4;
$Y_1$ and $Y_2$ are each independently $N(R_4)$, O, S or $C(R_5)(R_6)$;
$R_3$ to $R_6$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and
the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$ to $R_6$, and an aromatic ring, a non-aromatic fused polycyclic ring, an aromatic heteroring and a non-aromatic fused heteropolycyclic ring formed by adjacent two $Ar_2$s bonding to each other are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

The present invention provides a novel fluorene-based compound having excellent thermal stability, carrier transport ability, light emitting ability and the like.

Specifically, the novel organic compound according to the present invention has a structure in which a specific moiety is fixed at a number 9 position of phenyl fluorene and an EWG having an excellent electron transport ability bonds to the other side to form a basic skeleton, and various substituents bond to such a basic skeleton.

Among organic material layers generally included in an organic electroluminescent device, a phosphorescent light emitting layer includes a host and a dopant in order to increase color purity and increase luminous efficiency. Herein, the host needs to have a higher triplet energy gap than the dopant. In other words, in order to effectively provide phosphorescent light emission from the dopant, energy of the host in the lowest excited state needs to be higher than energy of the dopant in the lowest emitted state.

However, the compound represented by Chemical Formula 1 provided in the present invention has a wide singlet energy level and a high triplet energy level. Furthermore, by introducing a specific substituent to such a structure, a higher energy level than a dopant may be obtained when used as a host of a light emitting layer.

In addition, the compound has high triplet energy as described above, and therefore, may prevent excitons produced in the light emitting layer from diffusing (migrating) to an adjacent electron transport layer or hole transport layer. Accordingly, the compound according to the present invention may be used as a material of an organic material layer of an organic electroluminescent device, and preferably, may be used as a material of a light emitting layer (blue, green and/or red phosphorescent host material).

In addition, in the compound of Chemical Formula 1, the compound molecular weight significantly increases by introducing various substituents, particularly an aryl group and/or a heteroaryl group, to the basic skeleton, which enhances a glass transition temperature leading to high thermal stability compared to existing light emitting materials (for example, CBP). In addition, the compound is effective in suppressing crystallization of an organic material layer.

As described above, when using the compound represented by Chemical Formula 1 as a material of an organic material layer, preferably a light emitting layer material (blue, green and/or red phosphorescent host material), an electron transport layer/injection layer material, a hole transport layer/injection layer material, a light emitting auxiliary layer material, a lifetime improving layer material, of an organic electroluminescent device in the present invention, performance and lifetime properties of the organic electroluminescent device may be greatly enhanced. Such an organic electroluminescent device may resultantly maximize performance of a full color organic light emitting panel.

The compound according to the present invention may be represented by the compounds illustrated below, but is not limited thereto.

According to preferred one embodiment of the present invention, the compound may be a compound represented by any one of the following Chemical Formulae 5 to 10:

[Chemical Formula 5]

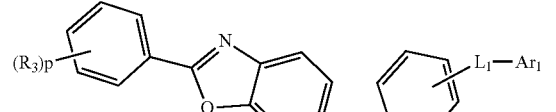

[Chemical Formula 6]

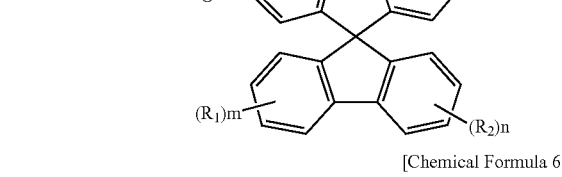

[Chemical Formula 7]

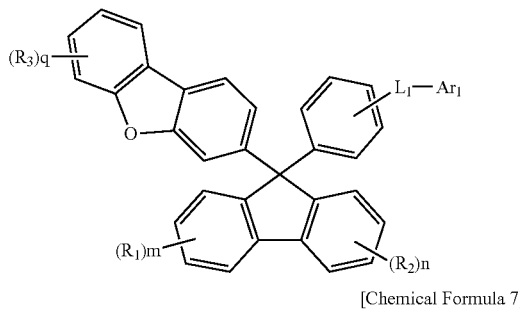

[Chemical Formula 8]

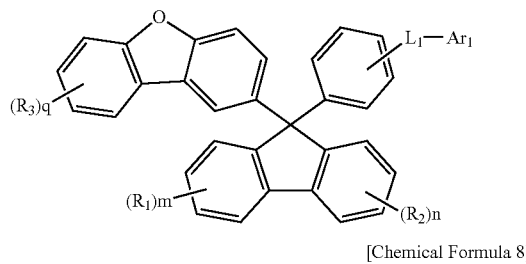

[Chemical Formula 9]

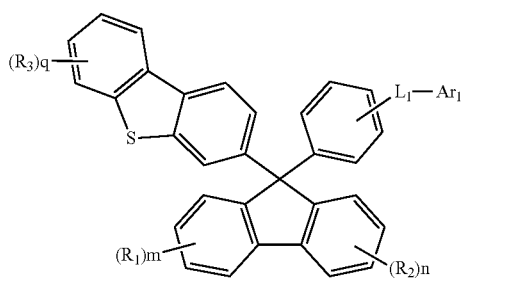

[Chemical Formula 10]

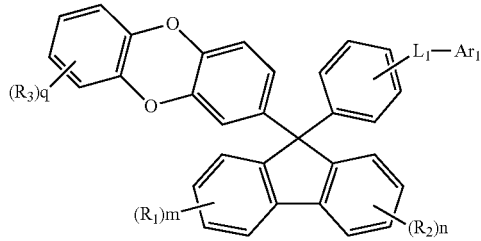

in Chemical Formulae 5 to 10, p, q, m, n, $R_1$ to $R_3$, $L_1$ and $Ar_1$ have the same definitions as in Chemical Formula 1.

According to preferred one embodiment of the present invention, $L_1$ may be a direct bond, or a linker selected from the group consisting of the following Chemical Formulae A-1 to A-6, and more preferably, may be a direct bond, or a linker represented by A-1, A-2, A-5 and A-6:

A-1

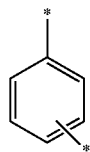

A-2

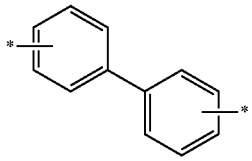

A-3

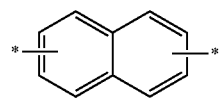

A-4

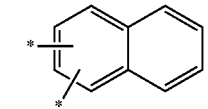

A-5

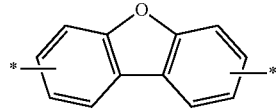

A-6

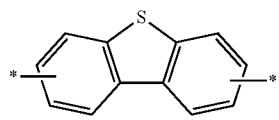

in Chemical Formulae A-1 to A-6,

* means a part where a bond is formed.

According to preferred one embodiment of the present invention, $Ar_1$ is selected from the group consisting of a $C_1$~$C_{40}$ alkyl group, a $C_6$~$C_{60}$ aryl group and a heteroaryl group having 5 to 60 nuclear atoms, and the alkyl group, the aryl group and the heteroaryl group of $Ar_1$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $Ar_1$ is selected from the group consisting of a methyl group, an ethyl group, a propyl group, a butyl group, a pentyl group, a phenyl group, a biphenyl group, a pyridinyl group, a pyrimidinyl group, a triazinyl group, a naphthalenyl group, a triazolopyridinyl group, a quinolinyl group, an isoquinolinyl group, a cinnolinyl group, a quinoxalinyl group and a quinazolinyl group, and the methyl group, the ethyl group, the propyl group, the butyl group, the pentyl group, the phenyl group, the biphenyl group, the pyridinyl group, the pyrimidinyl group, the triazinyl group, the naphthalenyl group, the triazolopyridinyl group, the quinolinyl group, the isoquinolinyl group, the cinnolinyl group, the quinoxalinyl group and the quinazolinyl group of $Ar_1$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $Ar_1$ is selected from the group consisting of a methyl group, an ethyl group, a propyl group, a butyl group, a pentyl group, a phenyl group, a biphenyl group, a pyridinyl group, a pyrimidinyl group, a triazinyl group, a naphthalenyl group, a triazolopyridinyl group, a quinolinyl group, an isoquinolinyl group, a cinnolinyl group, a quinoxalinyl group and a quinazolinyl group, and the methyl group, the ethyl group, the propyl group, the butyl group, the pentyl group, the phenyl group, the biphenyl group, the pyridinyl group, the pyrimidinyl group, the triazinyl group, the naphthalenyl group, the triazolopyridinyl group, the quinolinyl group, the isoquinolinyl group, the cinnolinyl group, the quinoxalinyl group and the quinazolinyl group of $Ar_1$ are each independently unsubstituted or substituted with one or more types of substituents selected from the group consisting of a methyl group, an ethyl group, a propyl group, a butyl group, a pentyl group, a phenyl group, a biphenyl group, a pyridinyl group, a pyrimidinyl group, a triazinyl group, a naphthalenyl group, a triazolopyridinyl group, a quinolinyl group, an isoquinolinyl group, a cinnolinyl group, a quinoxalinyl group and a quinazolinyl group, and when substituted with a plurality of the substituents, these are the same as or different from each other.

According to preferred one embodiment of the present invention, $Ar_1$ may be a substituent represented by the following Chemical Formula 11 or 12:

[Chemical Formula 11]

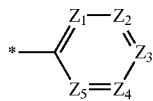

[Chemical Formula 12]

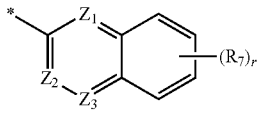

in Chemical Formulae 11 and 12,

* means a part where a bond is formed;

$Z_1$ to $Z_5$ are each independently N or $C(R_8)$;

r is an integer of 0 to 4;

$R_7$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bonds to adjacent groups to form a fused ring, and when $R_7$ is present in plural numbers, these are the same as or different from each other;

$R_8$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bonds to adjacent groups to form a fused ring, and when $R_8$ is present in plural numbers, these are the same as or different from each other; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_7$ and $R_8$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, the substituent represented by Chemical Formula 11 may be a substituent represented by the following Chemical Formula 13:

[Chemical Formula 13]

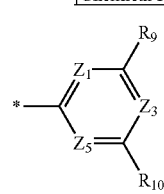

in Chemical Formula 13,

* means a part where a bond is formed;

$R_9$ and $R_{10}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_9$ and $R_{10}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other; and $Z_1$, $Z_3$ and $Z_5$ have the same definitions as in Chemical Formula 11.

According to preferred one embodiment of the present invention, the substituent represented by Chemical Formula 11 may be a substituent represented by any one of the following Chemical Formulae B-1 to B-5:

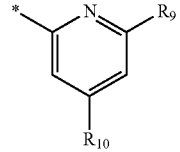

B-1

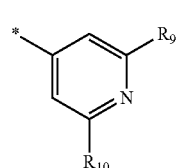

B-2

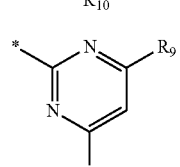

B-3

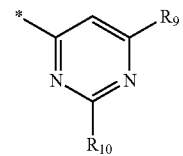

B-4

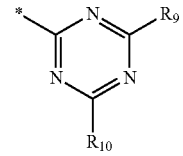

B-5 in Chemical Formulae B-1 to B-5,

* means a part where a bond is formed;

$R_9$ and $R_{10}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_9$ and $R_{10}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, $R_9$ and $R_{10}$ are each independently selected from the group consisting of a $C_1$~$C_{40}$ alkyl group, a $C_6$~$C_{60}$ aryl group and a heteroaryl group having 5 to 60 nuclear atoms; and the alkyl group, the aryl group and the heteroaryl group of $R_9$ and $R_{10}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_9$ and $R_{10}$ may be each independently selected from the group consisting of a phenyl group, a biphenyl group, a pyridinyl group, a pyrimidinyl group, a triazinyl group and a naphthalenyl group, and the phenyl group, the biphenyl group, the pyridinyl group, the pyrimidinyl group, the triazinyl group and the naphthalenyl group of $R_9$ and $R_{10}$ are each independently unsubstituted or substituted with one or more types of substituents selected from the group consisting of a $C_1 \sim C_{40}$ alkyl group, a $C_6 \sim C_{60}$ aryl group and a heteroaryl group having 5 to 60 nuclear atoms, and when substituted with a plurality of the substituents, these are the same as or different from each other.

According to preferred one embodiment of the present invention, $R_9$ and $R_{10}$ may be each independently selected from the group consisting of a phenyl group, a biphenyl group, a pyridinyl group, a pyrimidinyl group, a triazinyl group and a naphthalenyl group, and may be more preferably selected from the group consisting of a phenyl group, a biphenyl group and a pyridinyl group, and the phenyl group, the biphenyl group, the pyridinyl group, the pyrimidinyl group, the triazinyl group, and the naphthalenyl group of $R_9$ and $R_{10}$ are each independently unsubstituted or substituted with one or more types of substituents selected from the group consisting of a methyl group, an ethyl group, a butyl group, a propanyl group, a pentyl group, a phenyl group and a biphenyl group, and when substituted with a plurality of the substituents, these are the same as or different from each other.

According to preferred one embodiment of the present invention, $Ar_1$ may be a substituent represented by any one of the following Chemical Formulae C-1 to C-6:

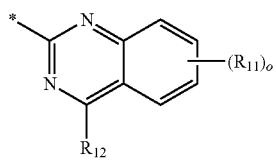

C-1

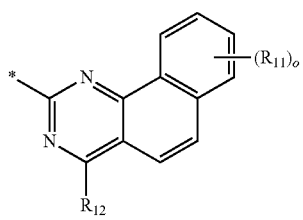

C-2

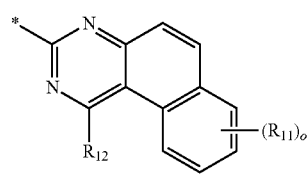

C-3

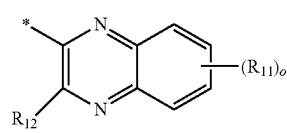

C-4

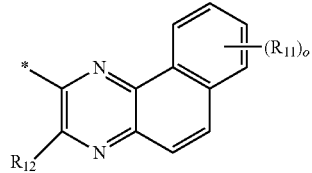

C-5

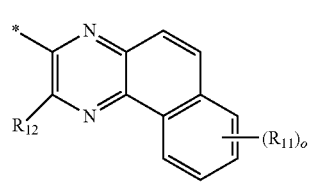

C-6 in Chemical Formulae C-1 to C-6,

* means a part where a bond is formed;

o is an integer of 0 to 4;

$R_{11}$ and $R_{12}$ are each independently selected from the group consisting of hydrogen, deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_3 \sim C_{40}$ cycloalkyl group, a heterocycloalkyl group having 3 to 40 nuclear atoms, a $C_6 \sim C_{60}$ aryl group, a heteroaryl group having 5 to 60 nuclear atoms, a $C_1 \sim C_{40}$ alkyloxy group, a $C_6 \sim C_{60}$ aryloxy group, a $C_3 \sim C_{40}$ alkylsilyl group, a $C_6 \sim C_{60}$ arylsilyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group and a $C_6 \sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{11}$ and $R_{12}$ are each independently unsubstituted or substituted with one or more types of substituents selected from the group consisting of deuterium, halogen, a cyano group, a nitro group, a $C_1 \sim C_{40}$ alkyl group, a $C_2 \sim C_{40}$ alkenyl group, a $C_2 \sim C_{40}$ alkynyl group, a $C_6 \sim C_{60}$ aryl group, a heteroaryl group having 5 to 60 nuclear atoms, a $C_6 \sim C_{60}$ aryloxy group, a $C_1 \sim C_{40}$ alkyloxy group, a $C_6 \sim C_{60}$ arylamine group, a $C_3 \sim C_{40}$ cycloalkyl group, a heterocycloalkyl group having 3 to 40 nuclear atoms, a $C_1 \sim C_{40}$ alkylsilyl group, a $C_1 \sim C_{40}$ alkylboron group, a $C_6 \sim C_{60}$ arylboron group, a $C_6 \sim C_{60}$ arylphosphanyl group, a $C_6 \sim C_{60}$ mono or diarylphosphinyl group and a $C_6 \sim C_{60}$ arylsilyl group, and when substituted with a plurality of the substituents, these are the same as or different from each other.

According to preferred one embodiment of the present invention, $R_{12}$ is selected from the group consisting of a $C_1$~$C_{40}$ alkyl group, a $C_6$~$C_{60}$ aryl group and a heteroaryl group having 5 to 60 nuclear atoms; and the alkyl group, the aryl group and the heteroaryl group of $R_{12}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{12}$ may be selected from the group consisting of a phenyl group, a biphenyl group, a pyridinyl group, a pyrimidinyl group, a triazinyl group and a naphthalenyl group, and the phenyl group, the biphenyl group, the pyridinyl group, the pyrimidinyl group, the triazinyl group and the naphthalenyl group of $R_{12}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

According to preferred one embodiment of the present invention, $R_{12}$ may be selected from the group consisting of a phenyl group, a biphenyl group, a pyridinyl group, a pyrimidinyl group, a triazinyl group and a naphthalenyl group, and may be more preferably selected from the group consisting of a phenyl group, a biphenyl group and a pyridinyl group, and the phenyl group, the biphenyl group, the pyridinyl group, the pyrimidinyl group, the triazinyl group and the naphthalenyl group of $R_{12}$ are each independently unsubstituted or substituted with one or more types of substituents selected from the group consisting of a methyl group, an ethyl group, a butyl group, a propanyl group, a pentyl group, a phenyl group and a biphenyl group, and when substituted with a plurality of the substituents, these are the same as or different from each other.

According to preferred one embodiment of the present invention, $Ar_1$ may be a substituent represented by the following Chemical Formula 14:

[Chemical Formula 14]

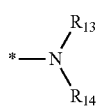

in Chemical Formula 14,
* means a part where a bond is formed;
$R_{13}$ and $R_{14}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bond to adjacent groups to form a fused ring; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{13}$ and $R_{14}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other.

According to preferred one embodiment of the present invention, $R_{13}$ and $R_{14}$ may be each independently selected from the group consisting of a $C_1$~$C_{30}$ alkyl group, a $C_6$~$C_{30}$ aryl group and a heteroaryl group having 5 to 30 nuclear atoms.

According to preferred one embodiment of the present invention, $R_{13}$ and $R_{14}$ may be each independently selected from the group consisting of hydrogen, a phenyl group, a biphenyl group, a terphenyl group, a naphthalenyl group and a fluorenyl group, but are not limited thereto.

The compound represented by Chemical Formula 1 of the present invention may be represented by the following compounds, but is not limited thereto:

Inv 1

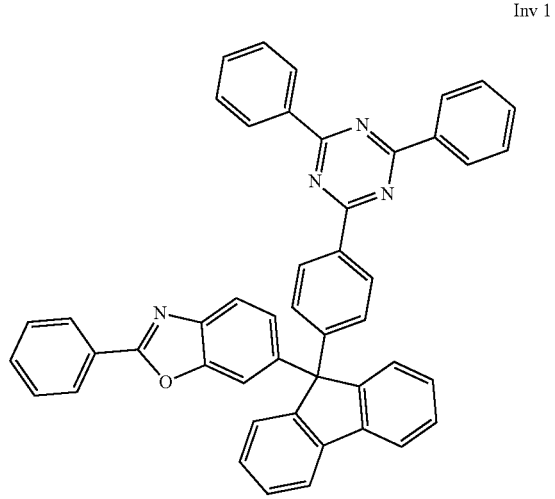

Inv 2
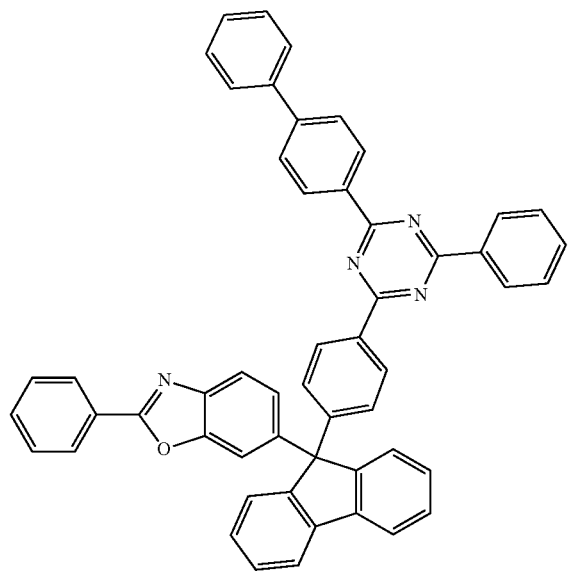
Inv 3
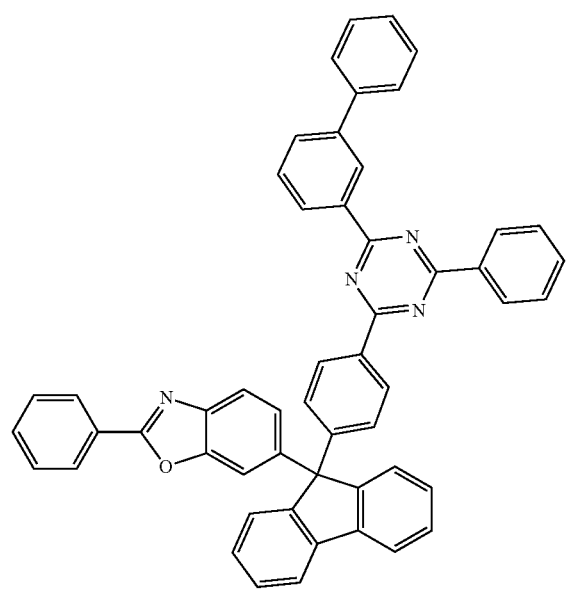
Inv 4
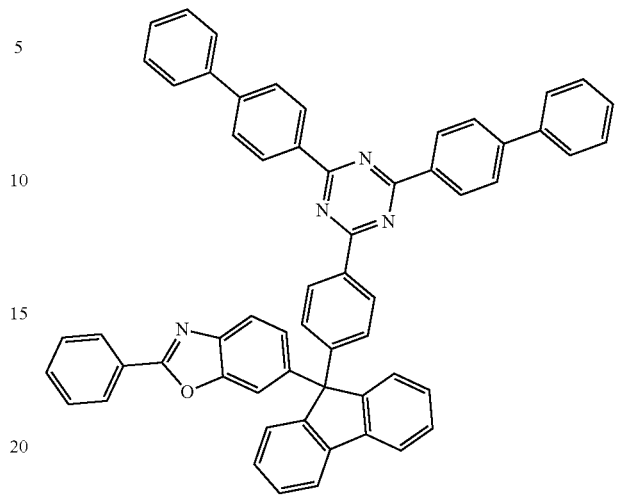
Inv 5
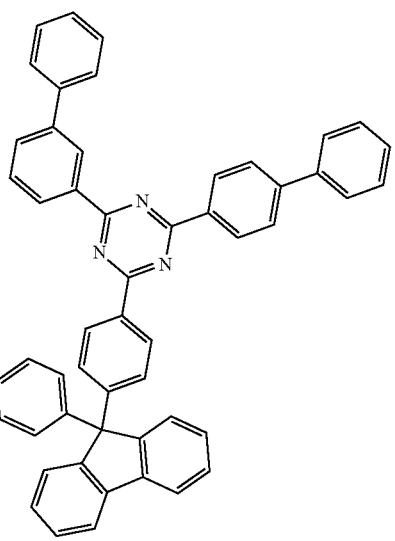

Inv 6
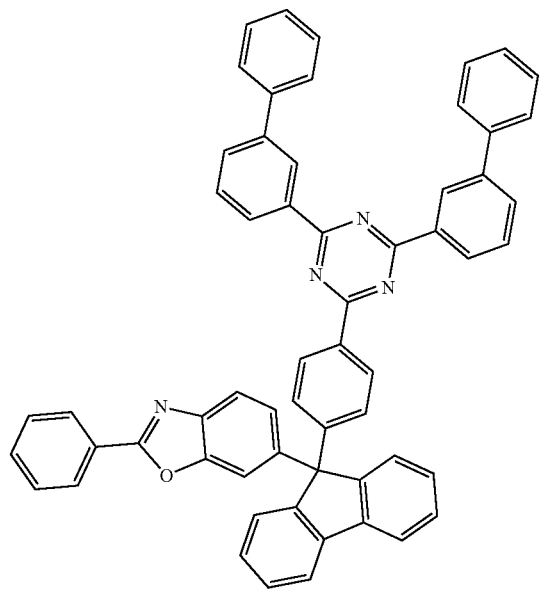
Inv 7
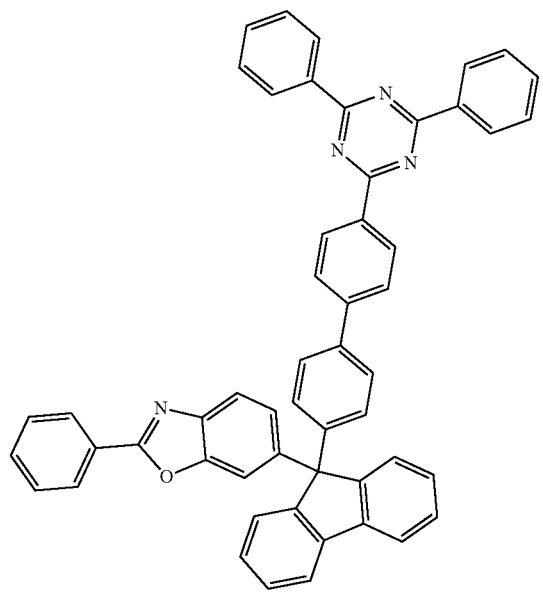
Inv 8
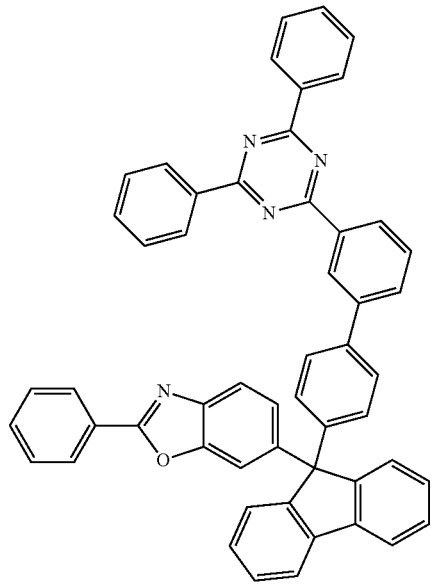
Inv 9
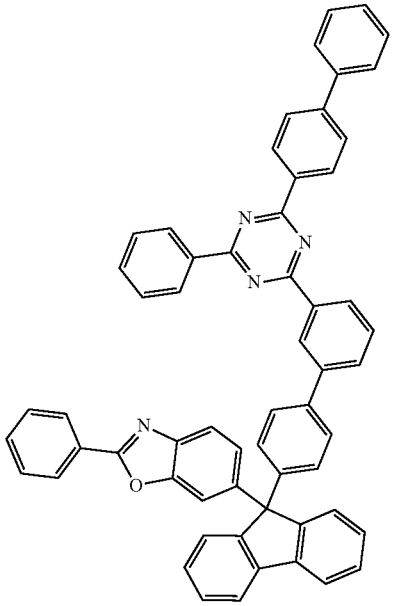

Inv 10
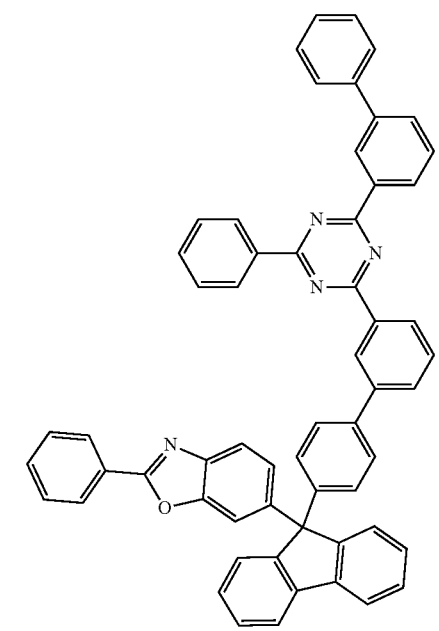
Inv 11
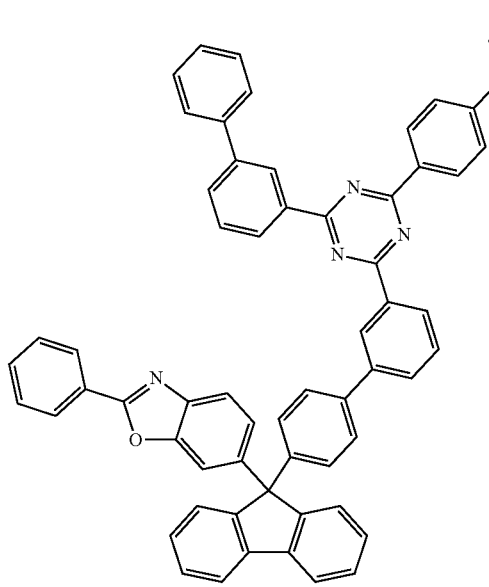
Inv 12
Inv 13
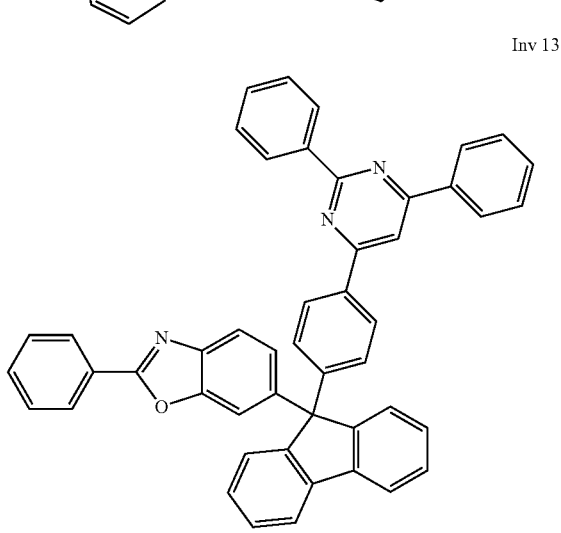
Inv 14
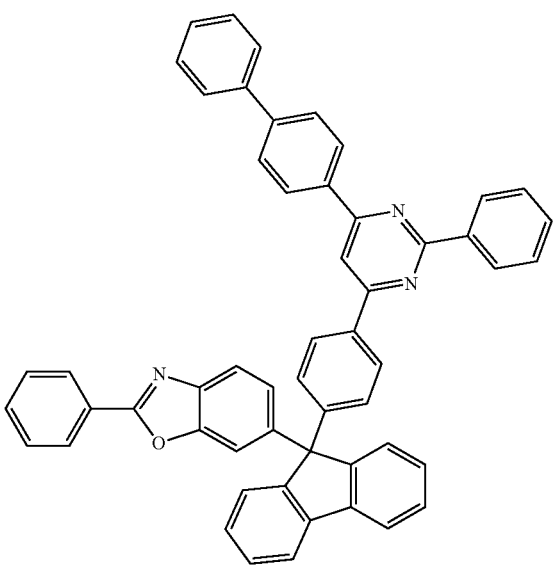

Inv 15
Inv 17
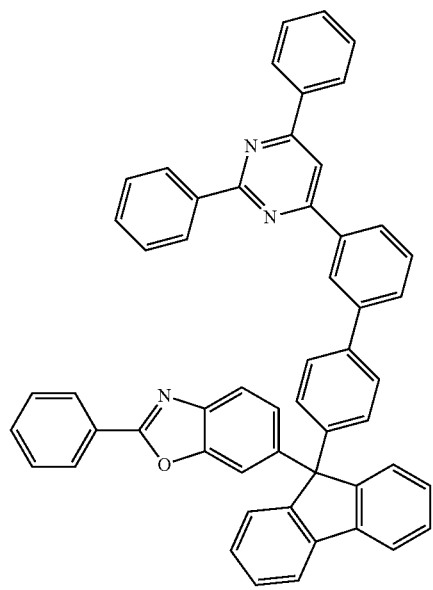
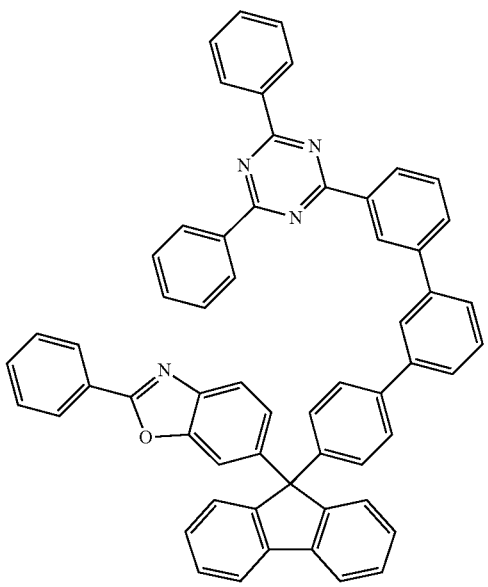
Inv 16
Inv 18
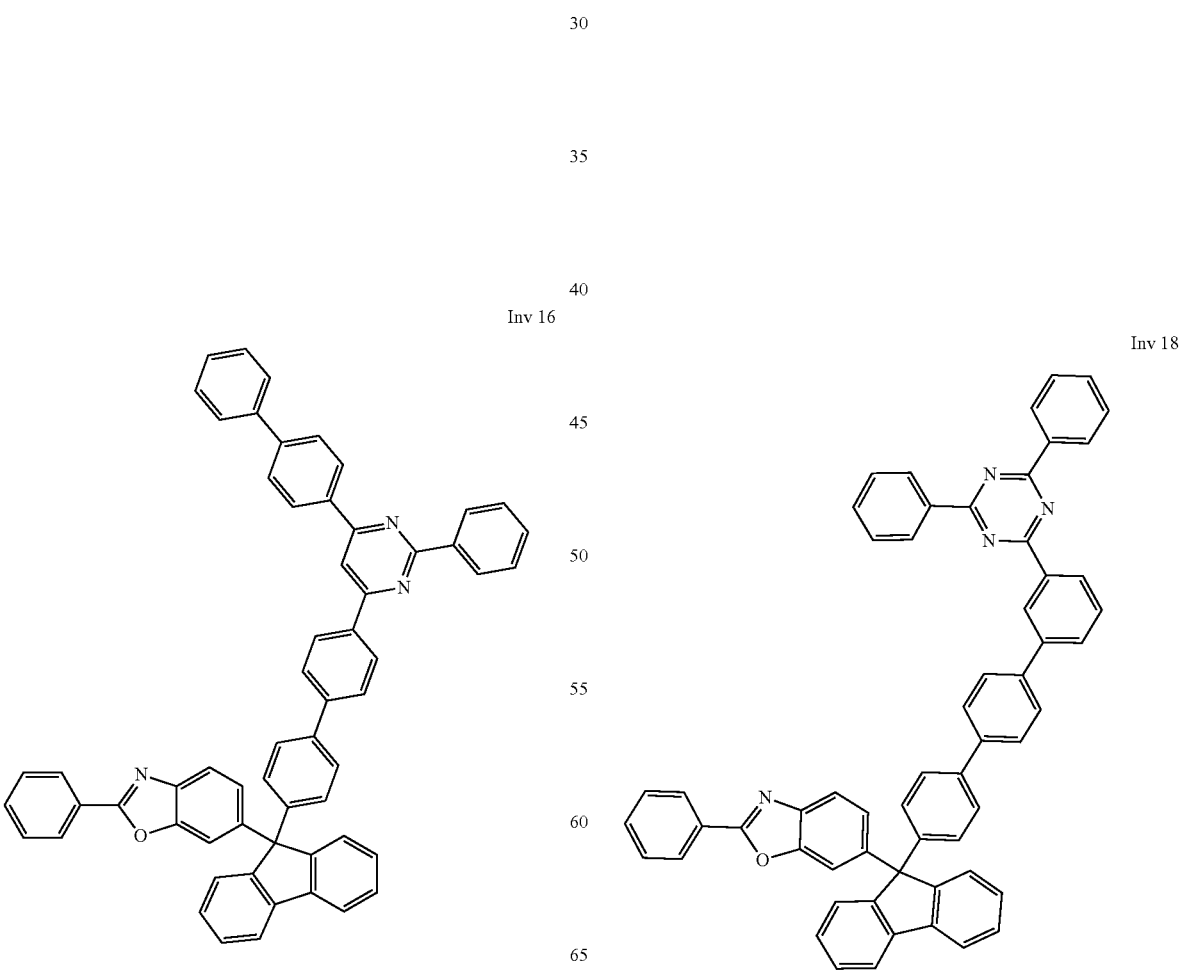

Inv 19
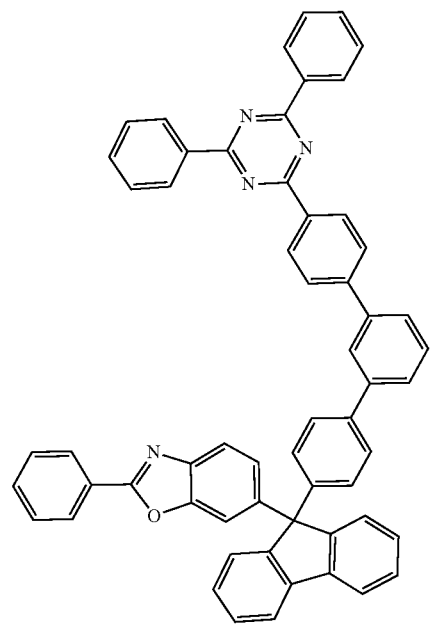
Inv 20
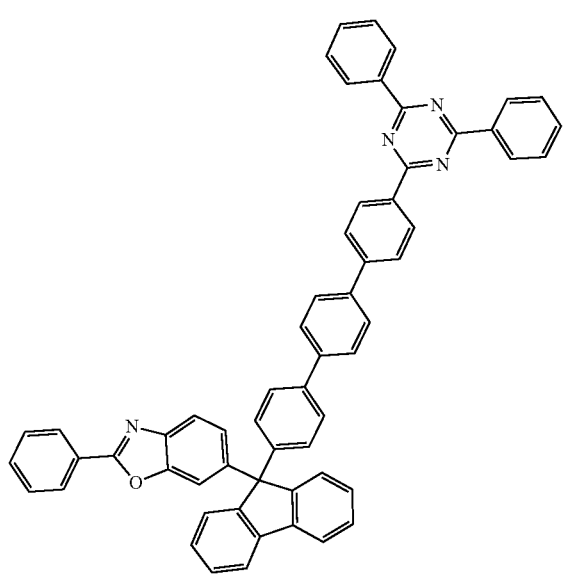
Inv 21
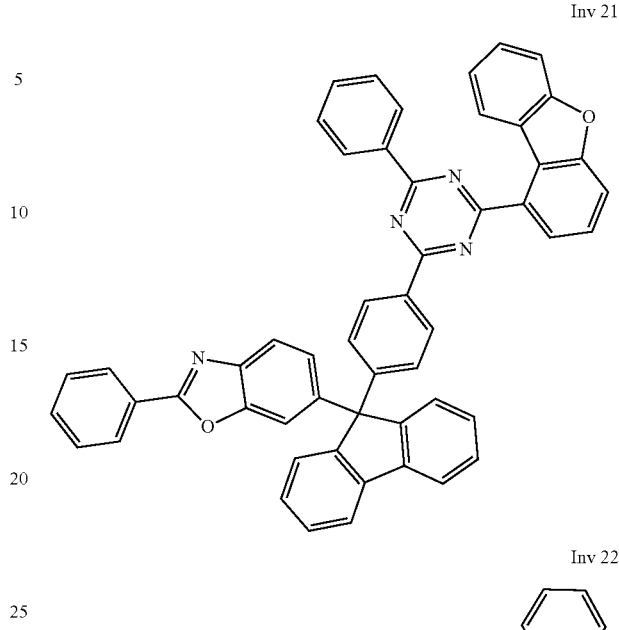
Inv 22
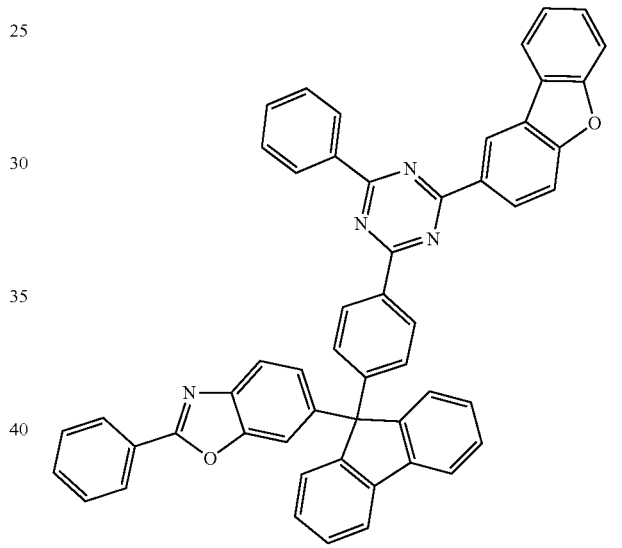
Inv 23
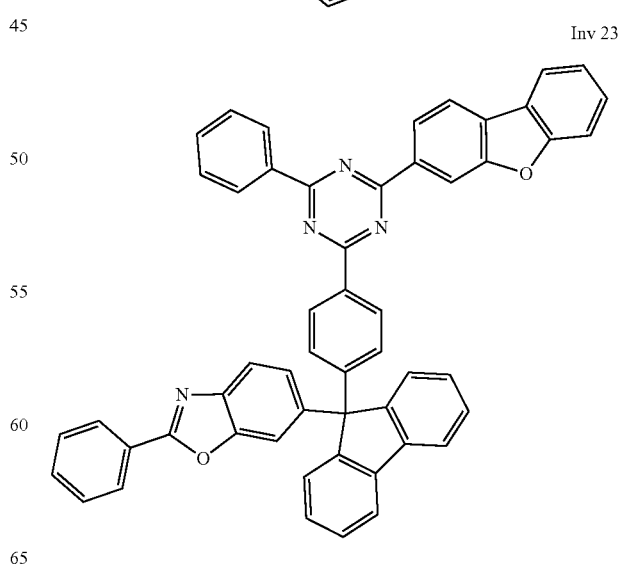

Inv 24
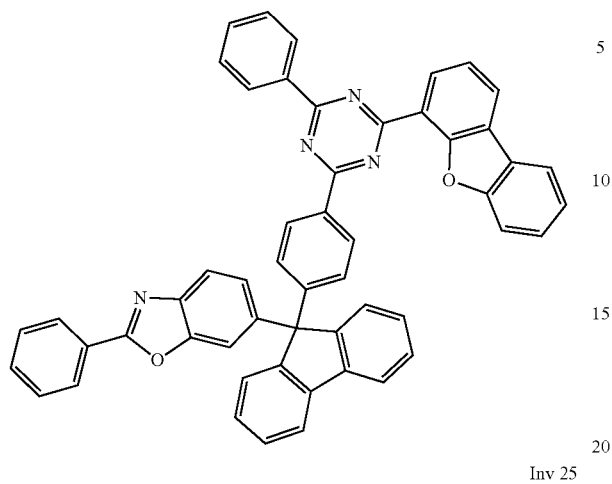
Inv 25
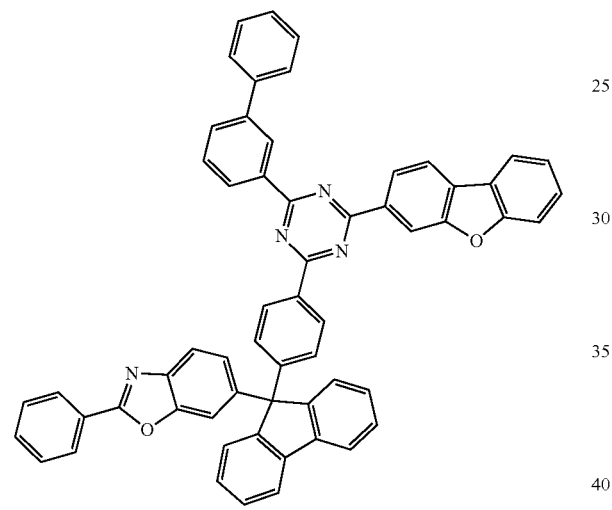
Inv 26
Inv 27
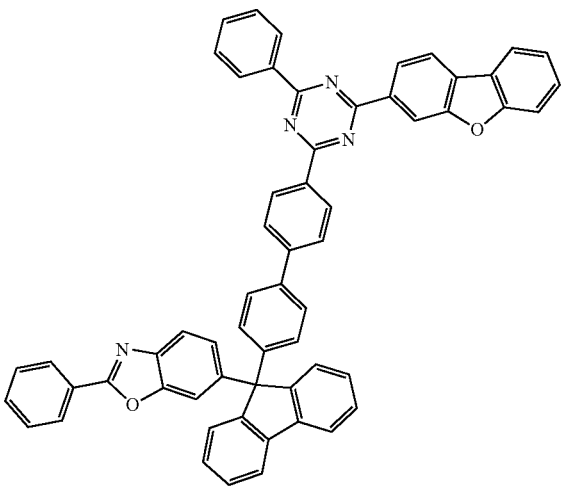
Inv 28
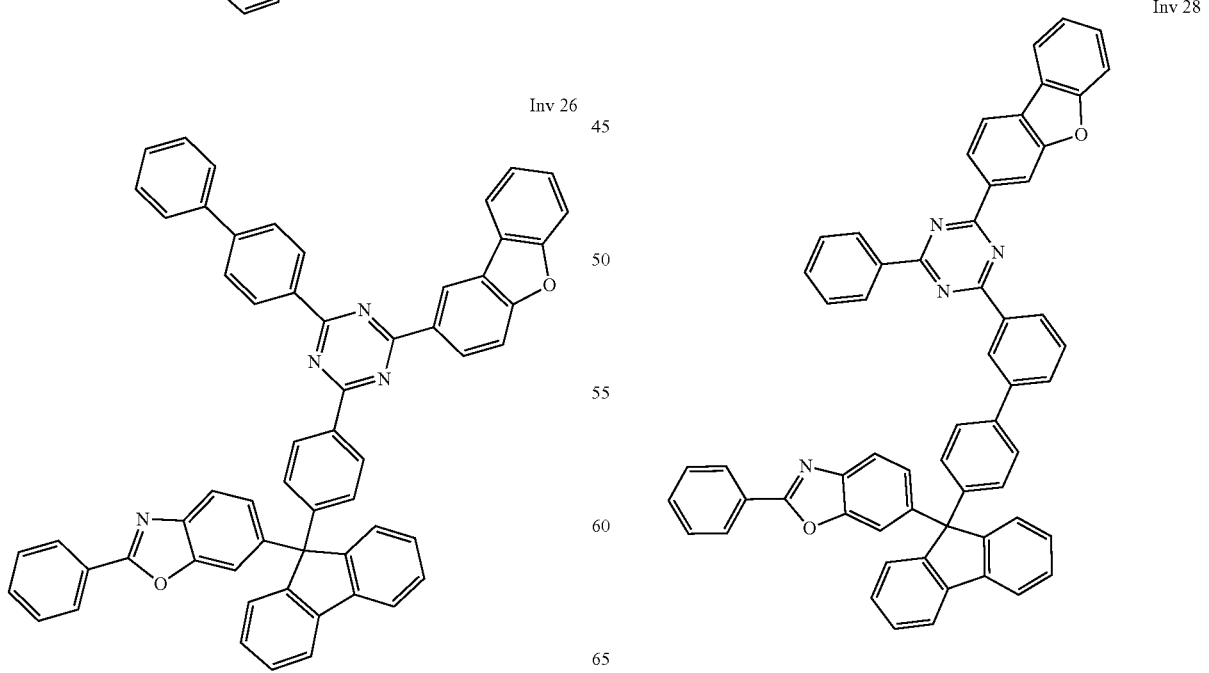

-continued
Inv 29
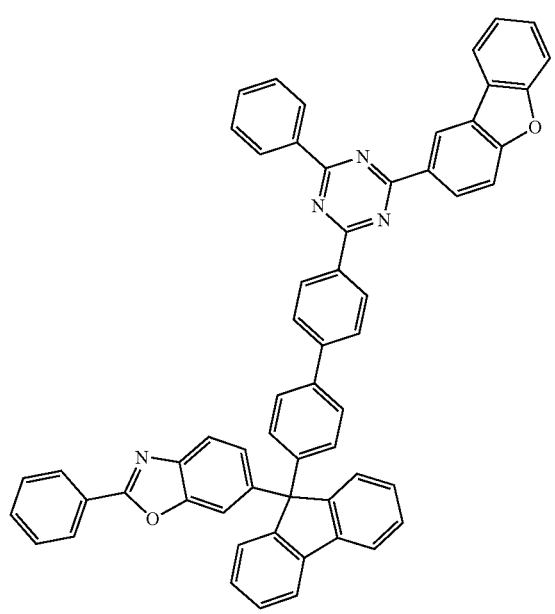
Inv 30
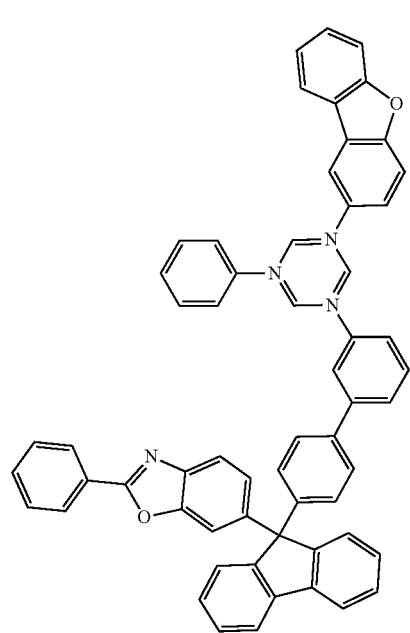
Inv 31
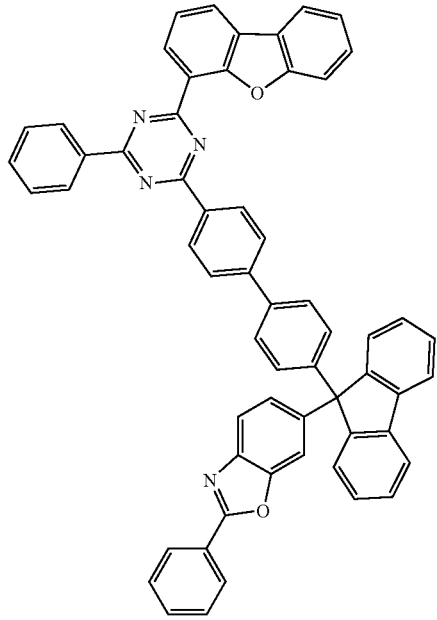
Inv 32
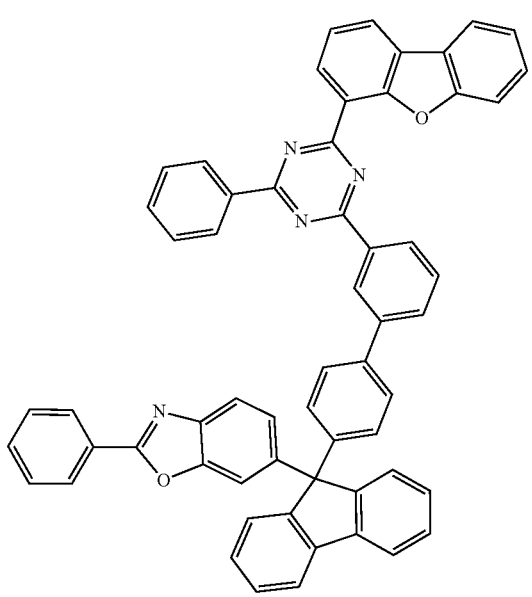

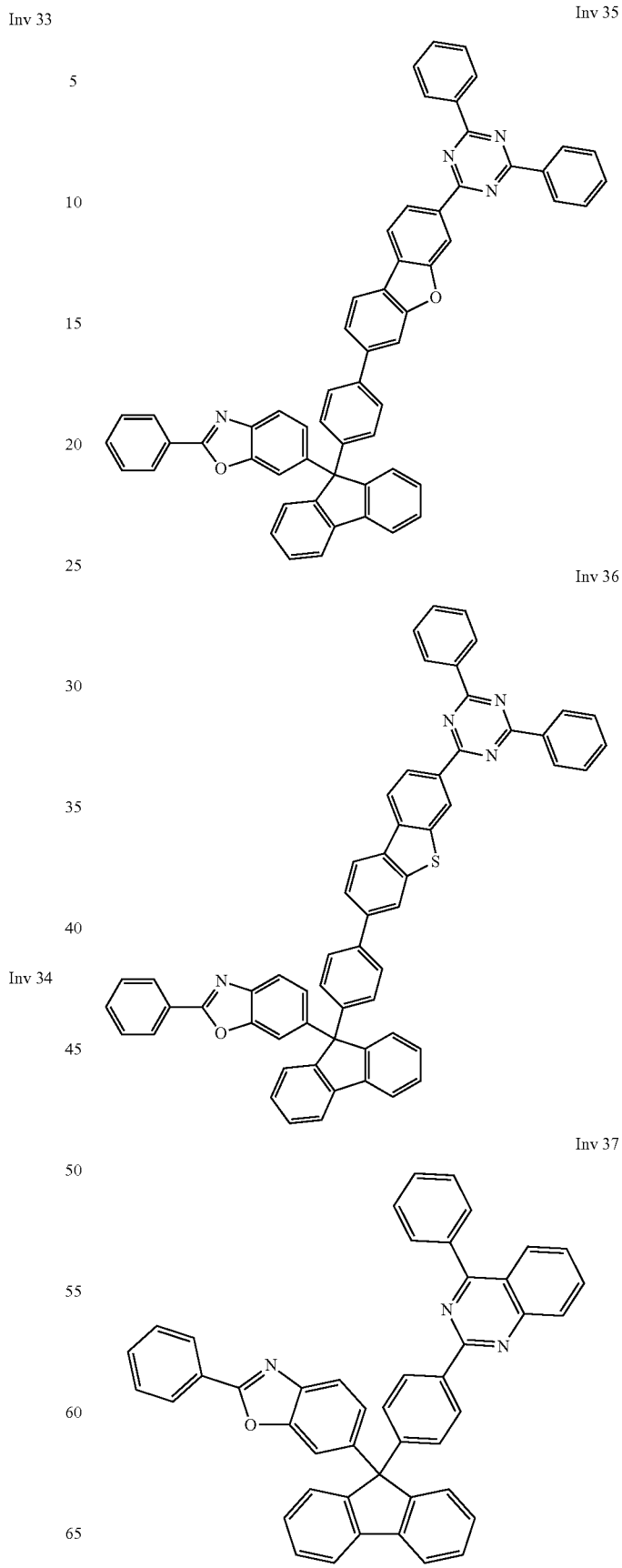

Inv 38
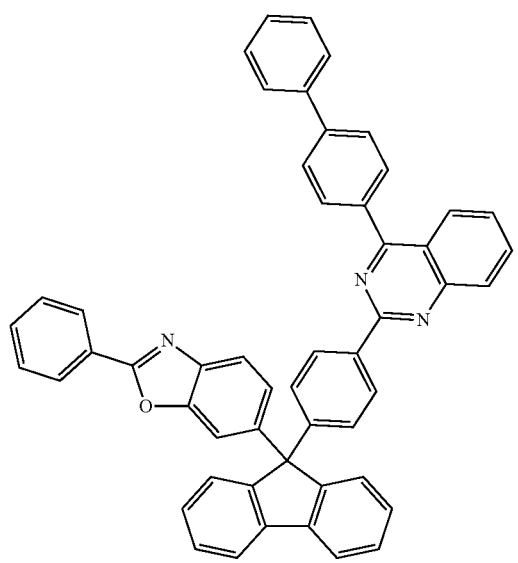
Inv 39
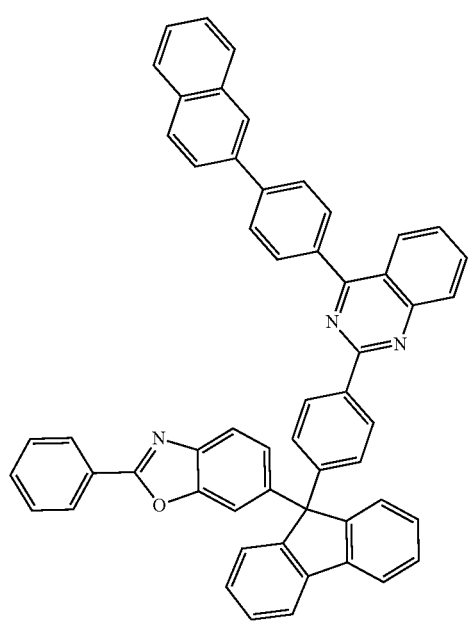
Inv 40
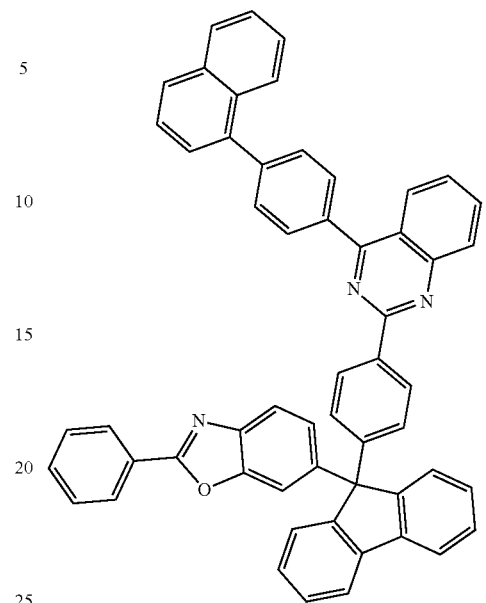
Inv 41
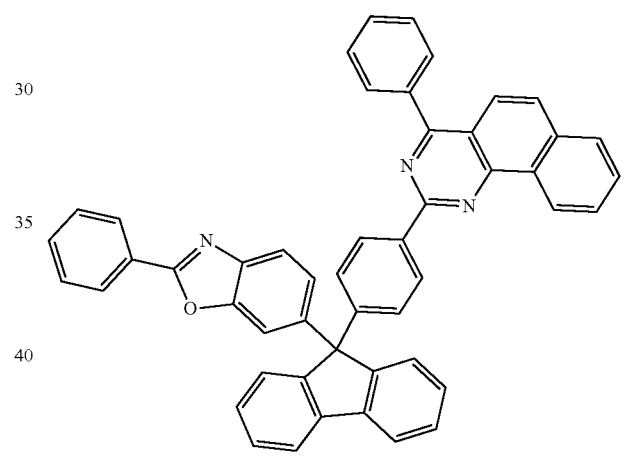
Inv 42
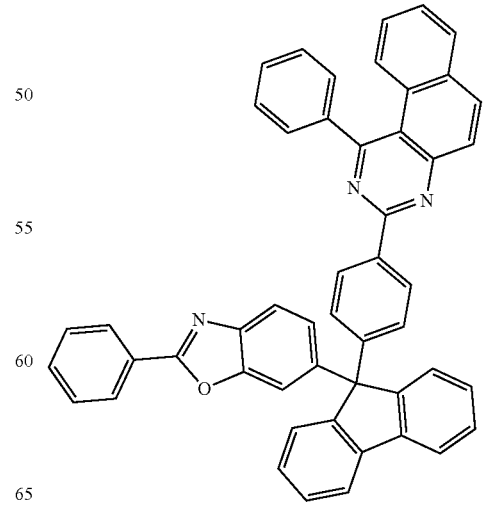

-continued
Inv 43
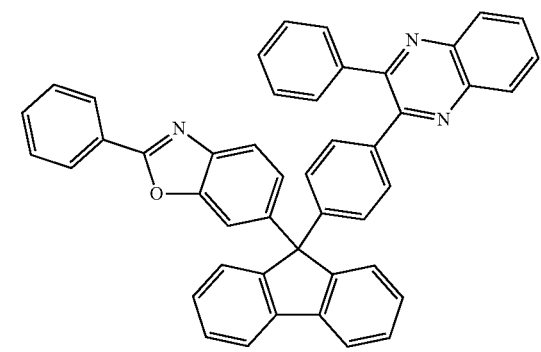
Inv 44
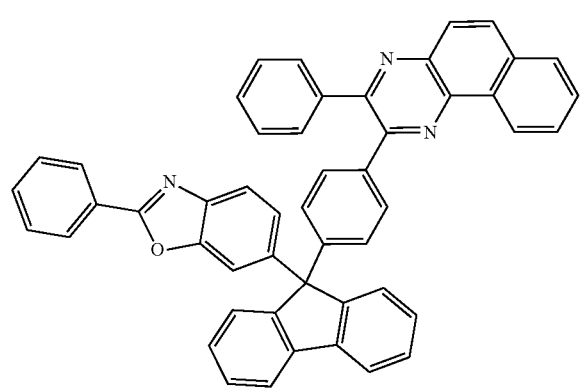
Inv 45
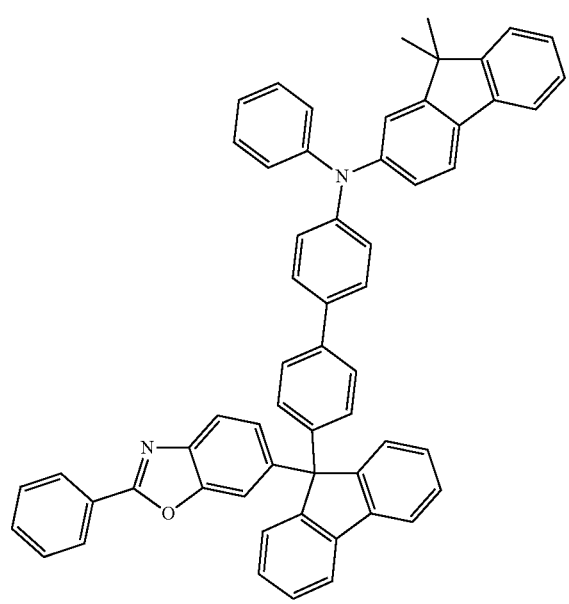
-continued
Inv 46
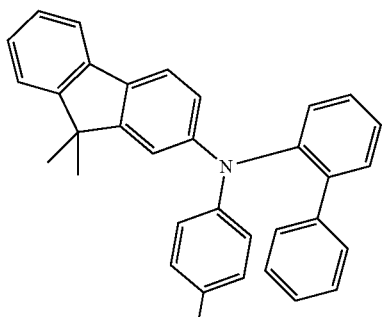
Inv 47
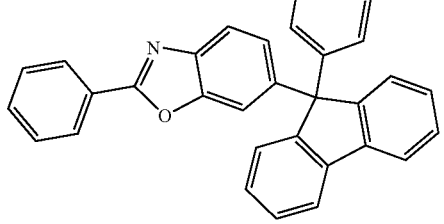
Inv 48
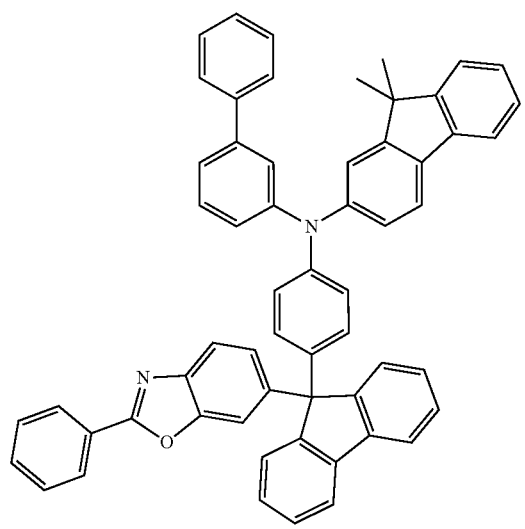

Inv 49
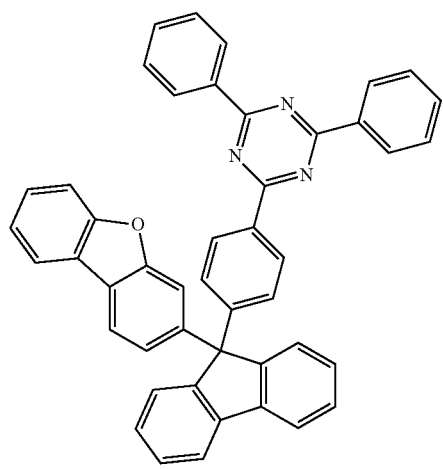
Inv 50
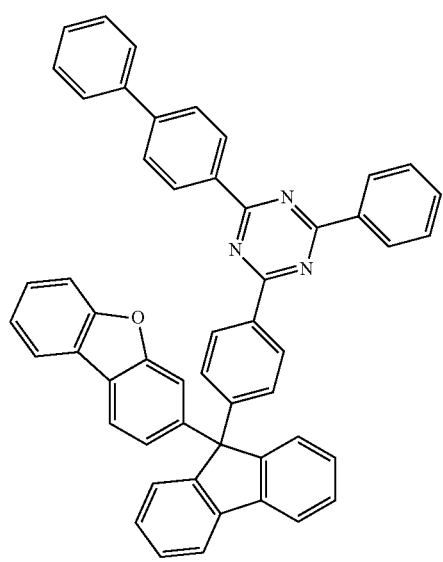
Inv 51
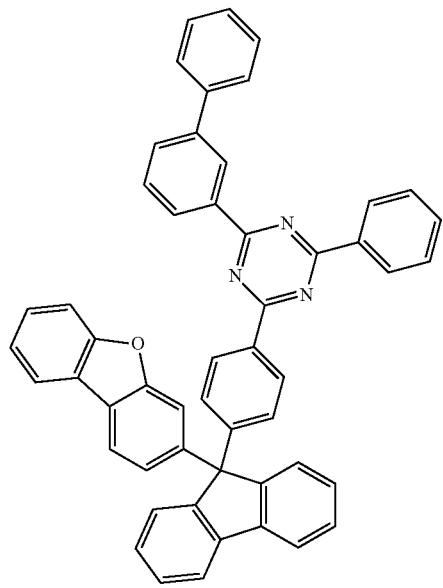
Inv 52
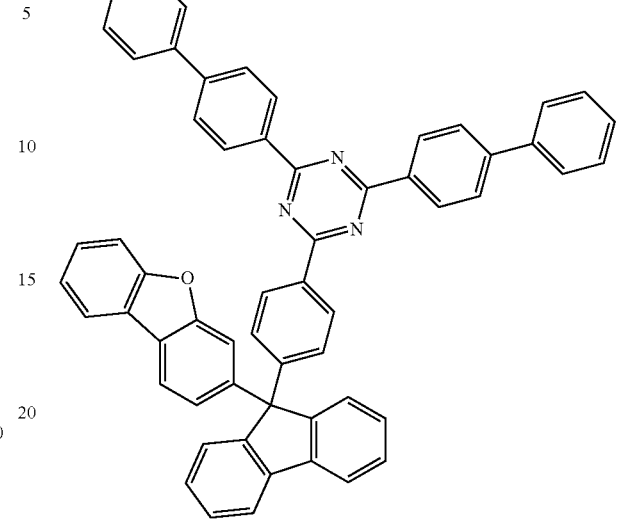
Inv 53
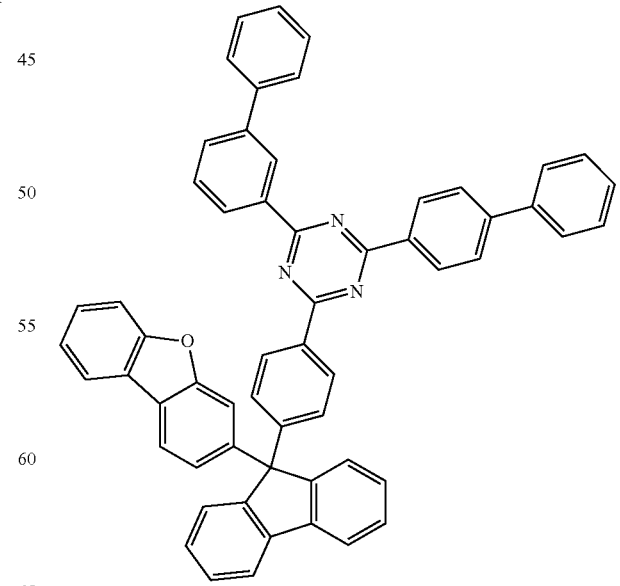

Inv 54
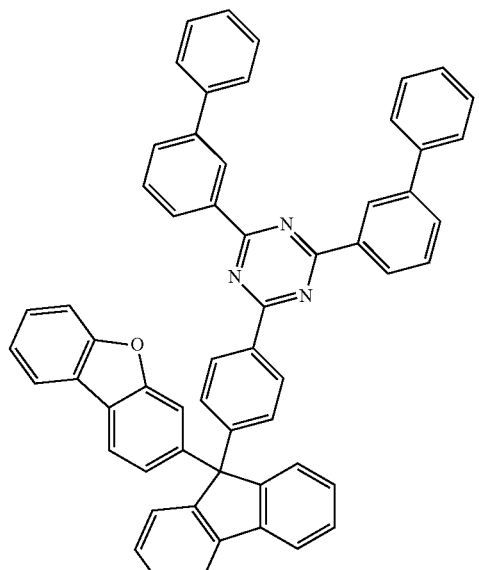
Inv 55
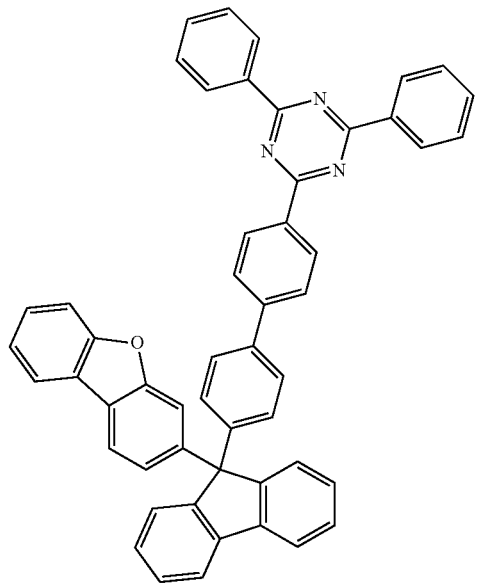
Inv 56
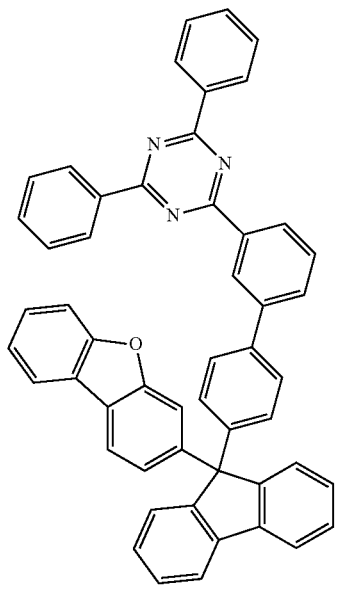
Inv 57
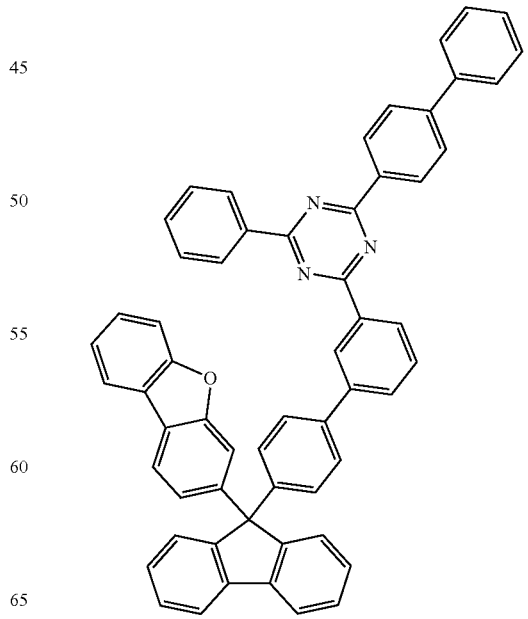

Inv 58
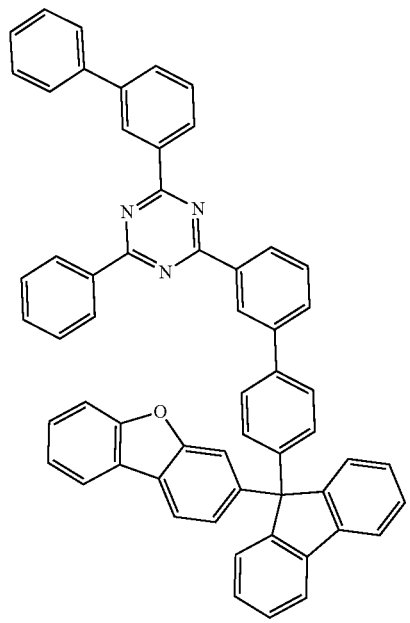
Inv 60
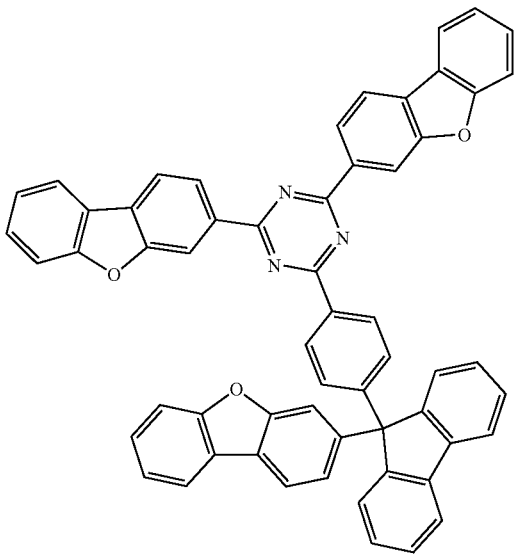
Inv 61
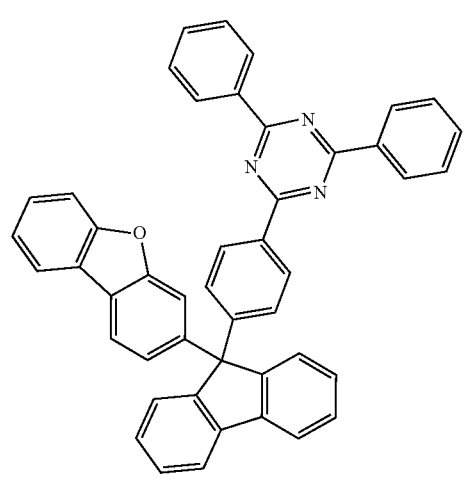
Inv 59
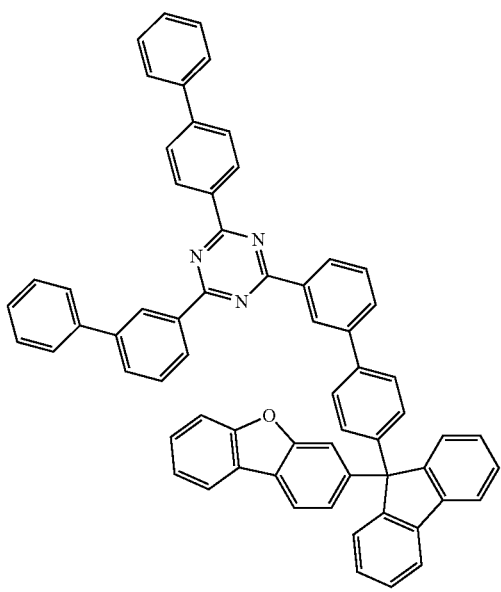
Inv 62
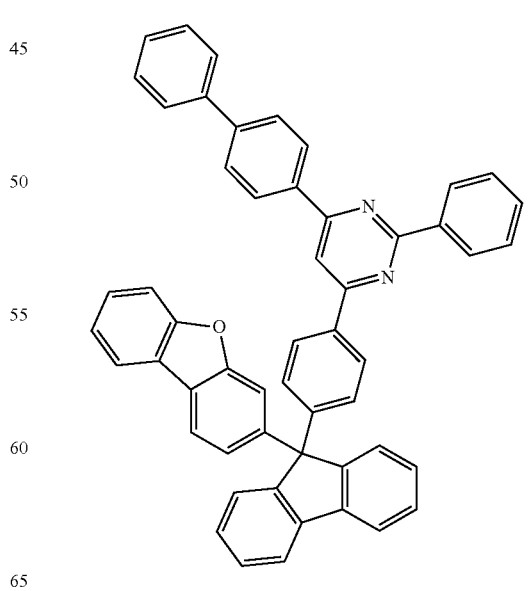

Inv 63
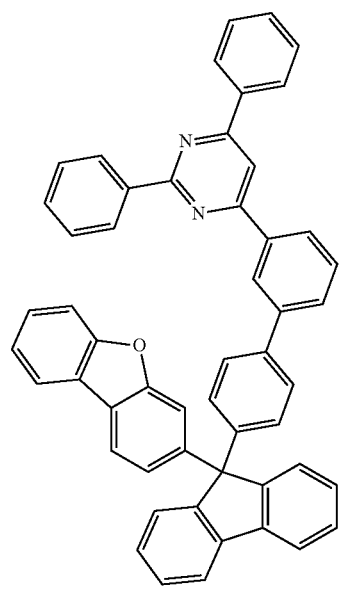
Inv 64
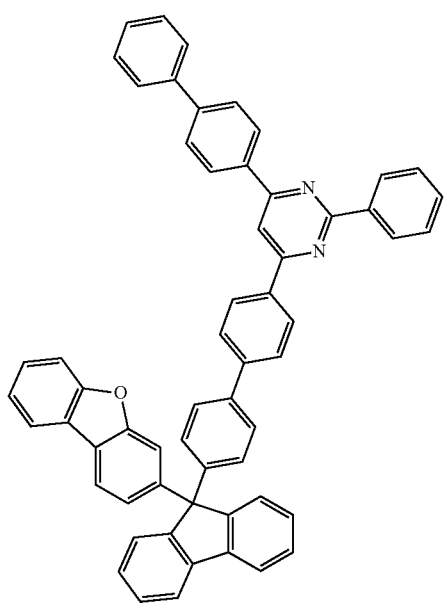
Inv 65
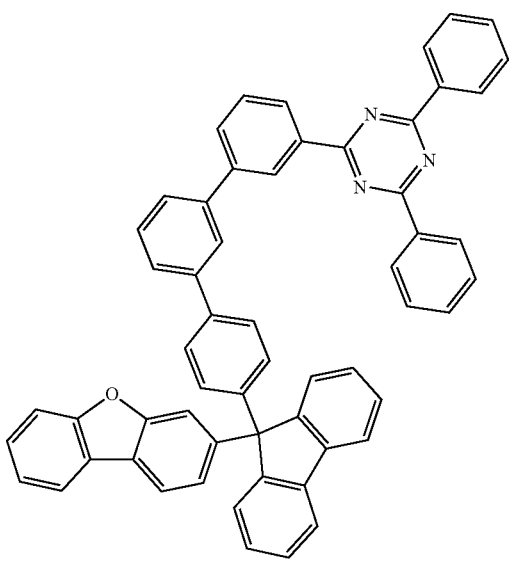
Inv 66
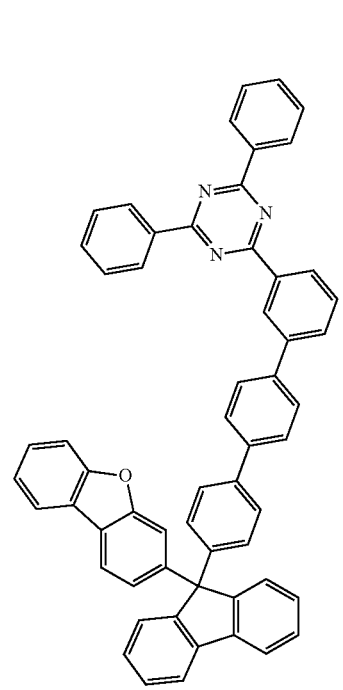

Inv 67
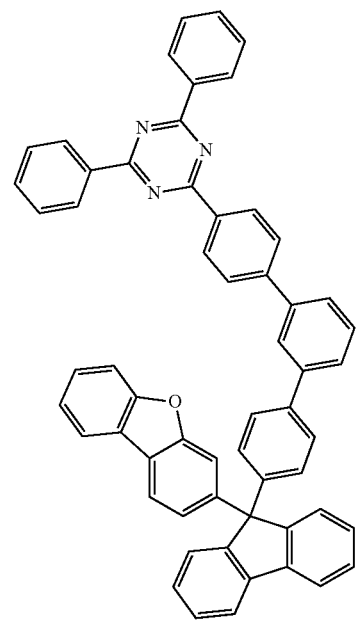
Inv 68
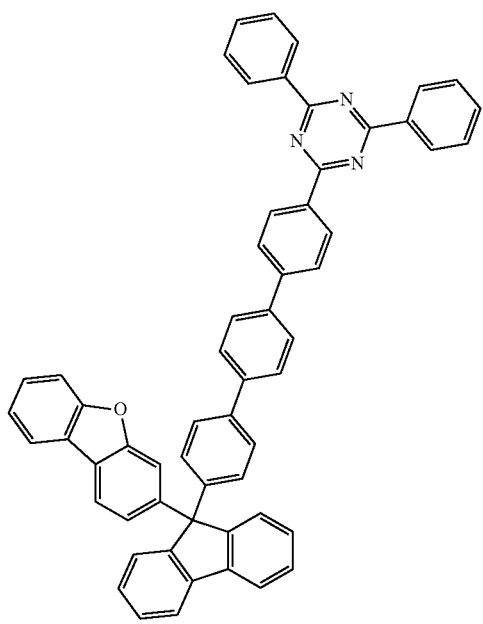
Inv 69
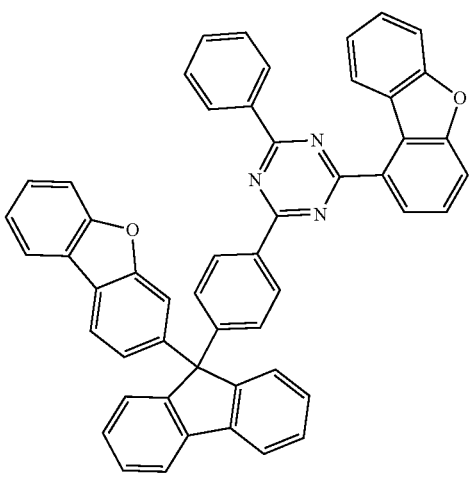
Inv 70
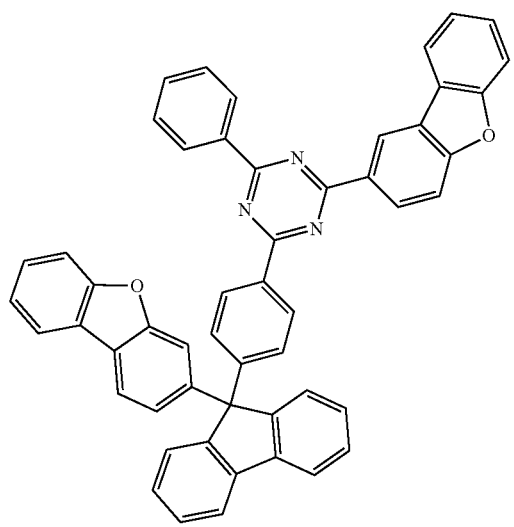
Inv 71
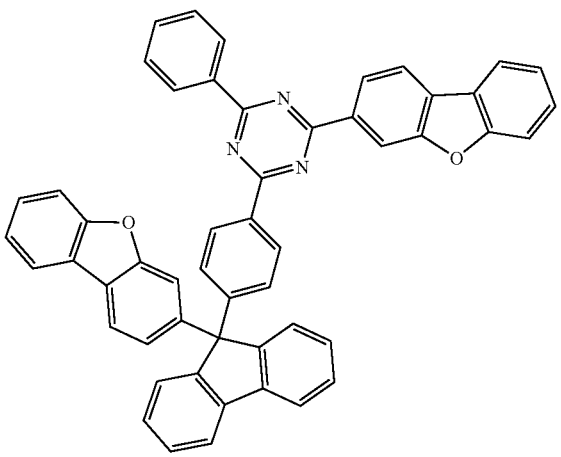

Inv 72
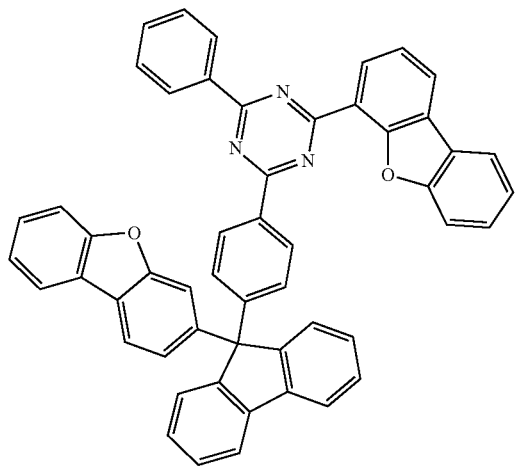
Inv 73
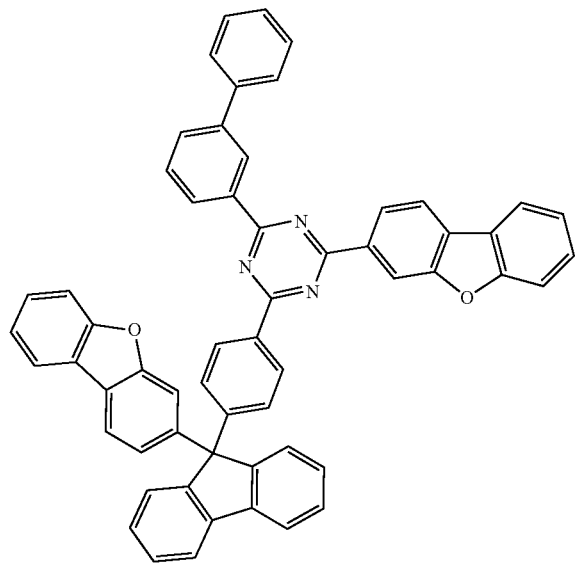
Inv 74
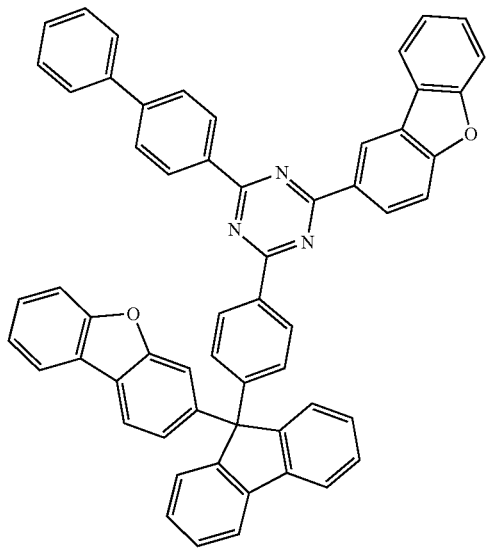
Inv 75
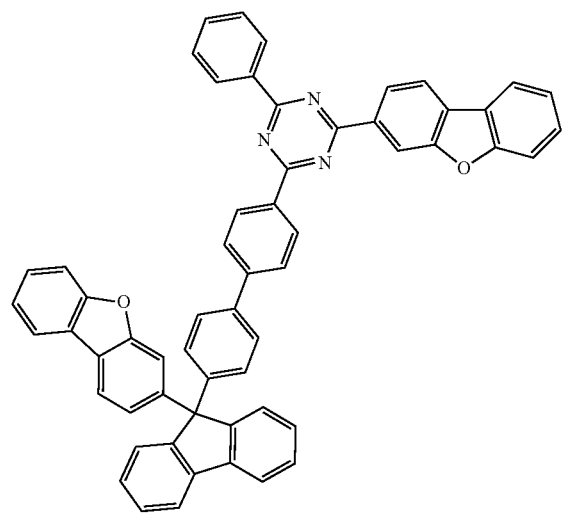
Inv 76
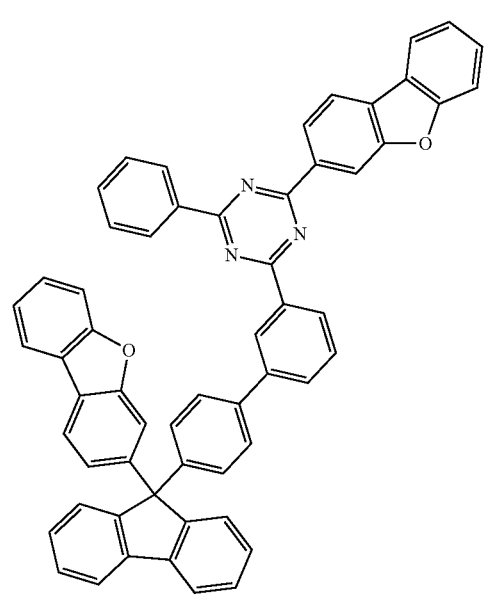
Inv 77
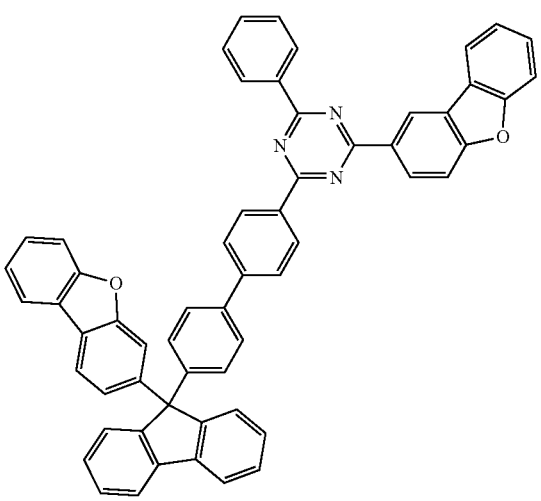

Inv 78
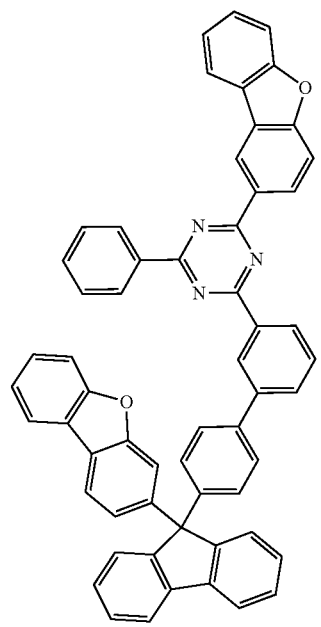
Inv 80
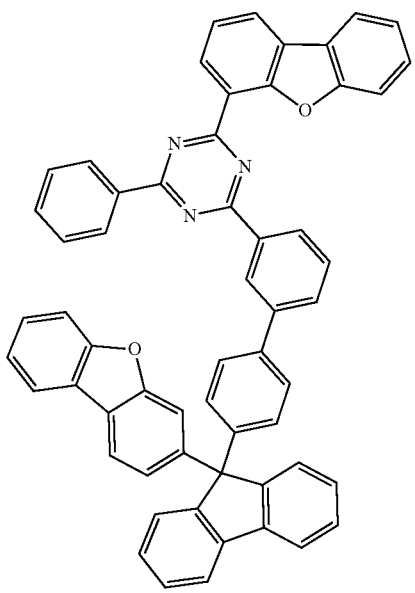
Inv 79
Inv 81
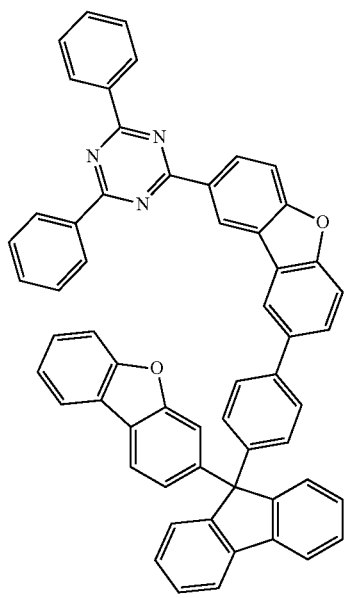

Inv 82
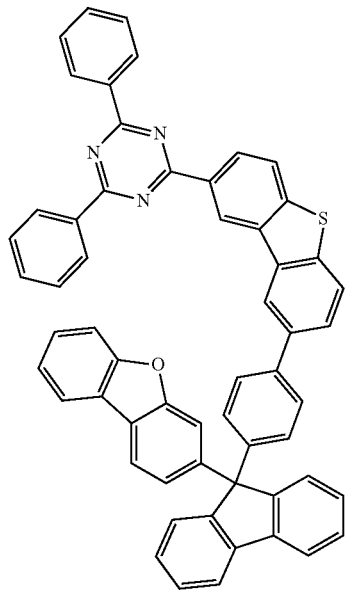
Inv 84
Inv 85
Inv 83
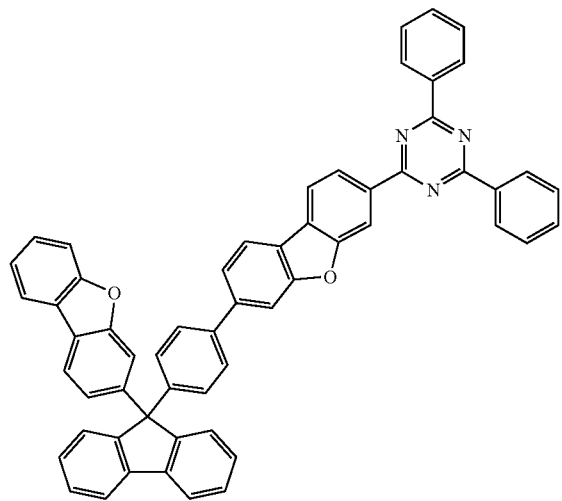
Inv 86
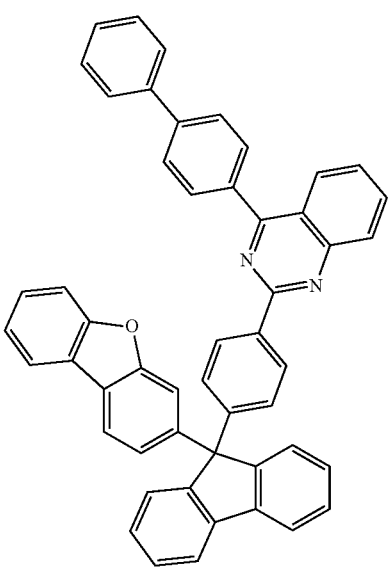

Inv 87
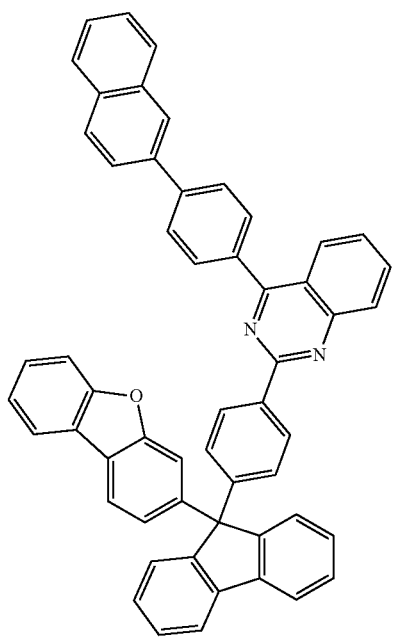
Inv 88
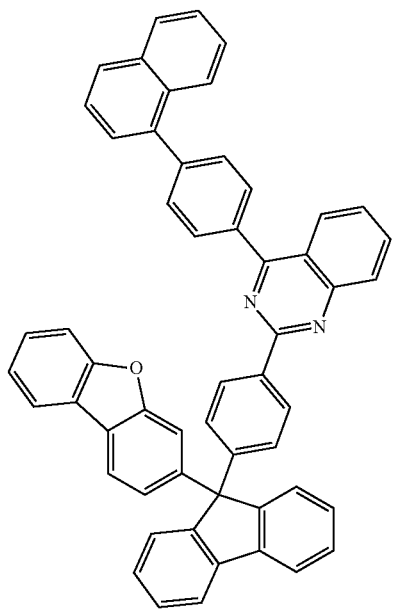
Inv 89
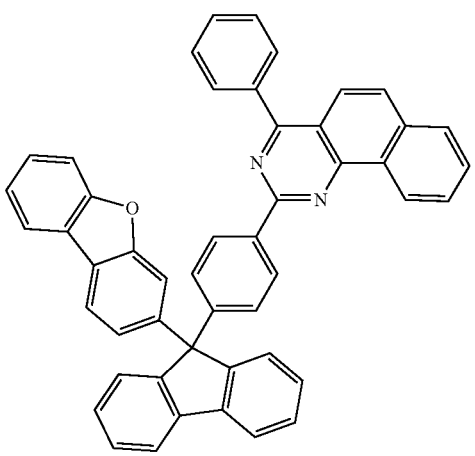
Inv 90
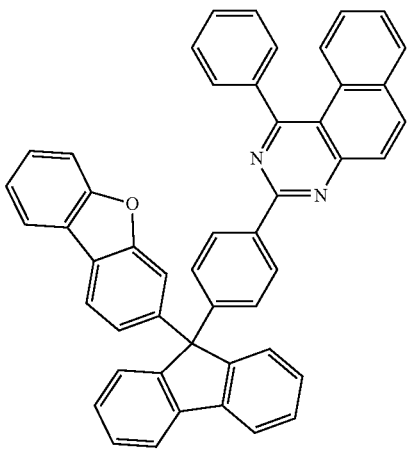
Inv 91
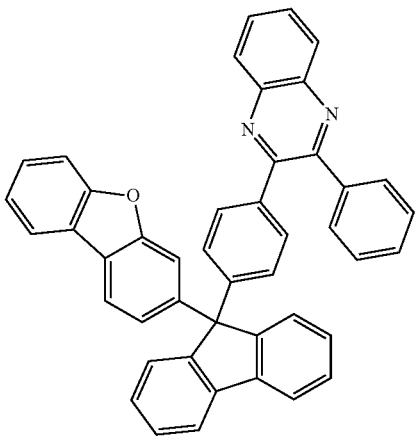

-continued
Inv 92
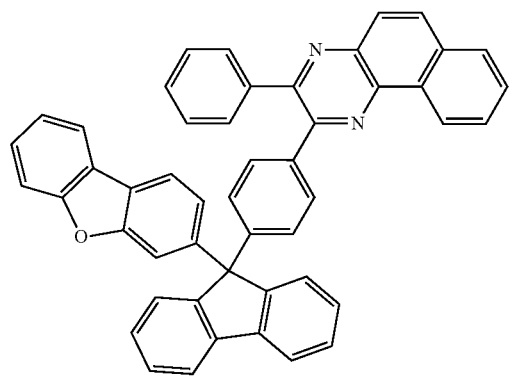
Inv 93
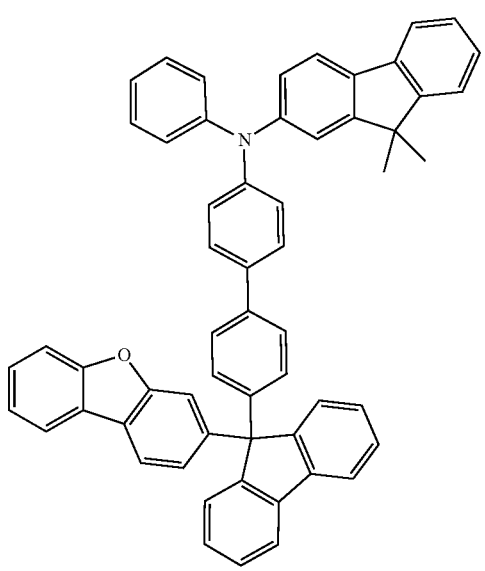
Inv 94
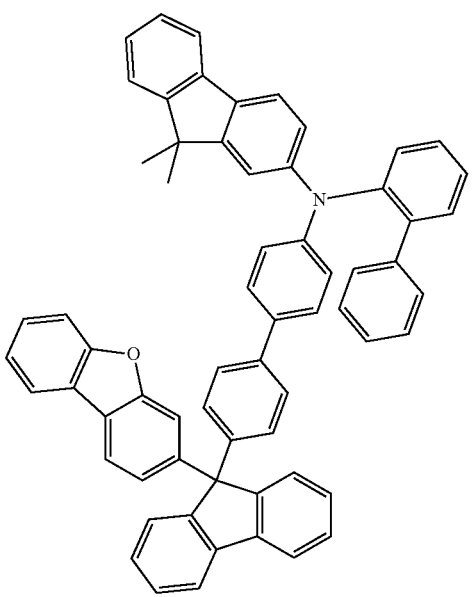
-continued
Inv 95
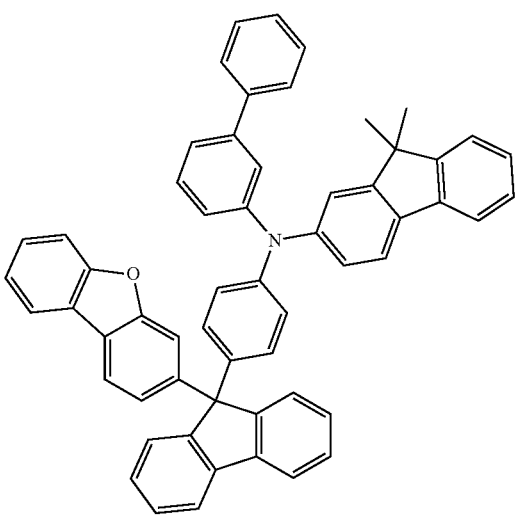
Inv 96
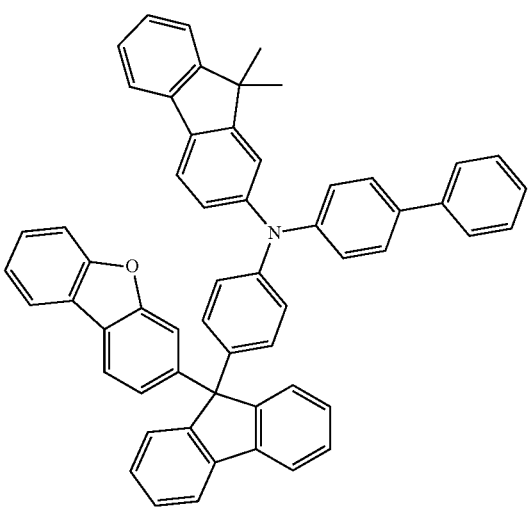
Inv 97
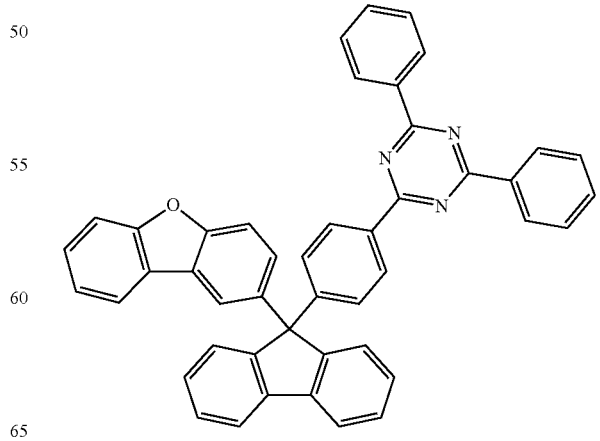

Inv 98
Inv 99
Inv 100
Inv 101
Inv 102
Inv 103

Inv 104
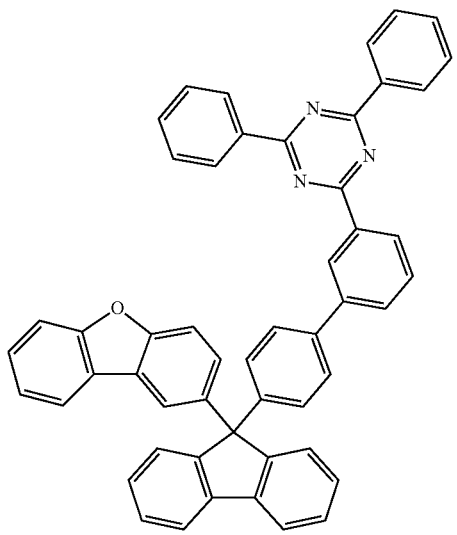
Inv 106
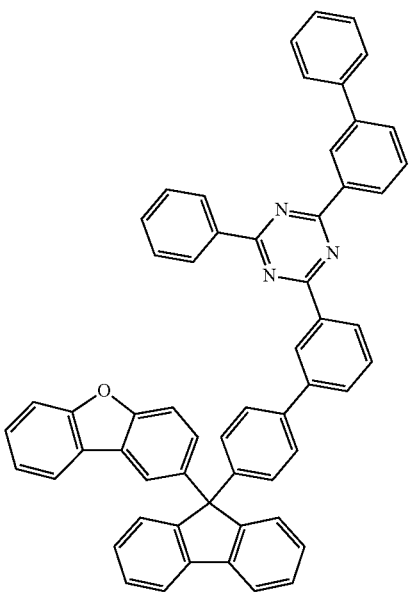
Inv 105
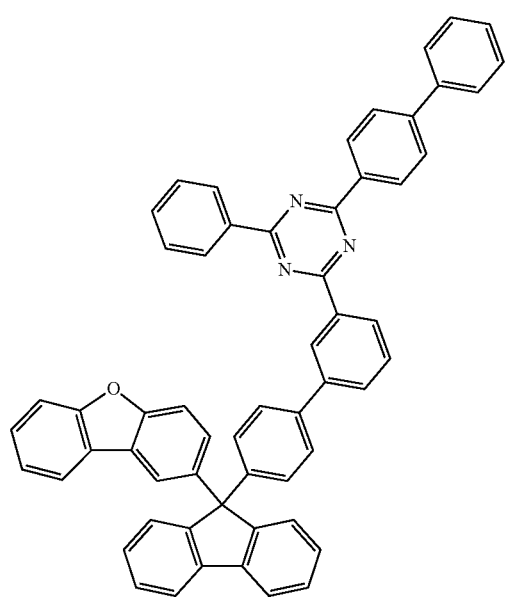
Inv 107
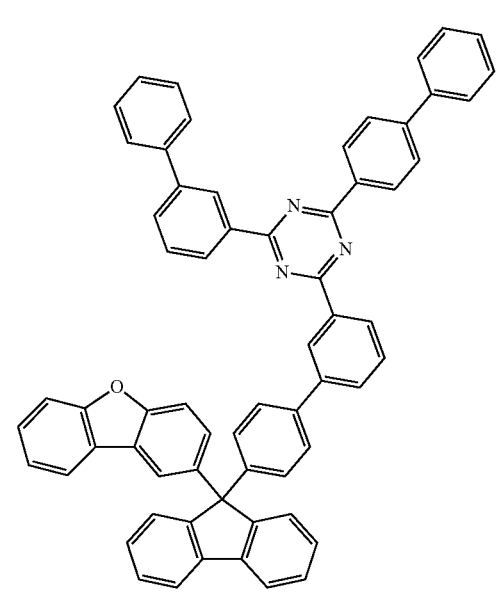

Inv 108
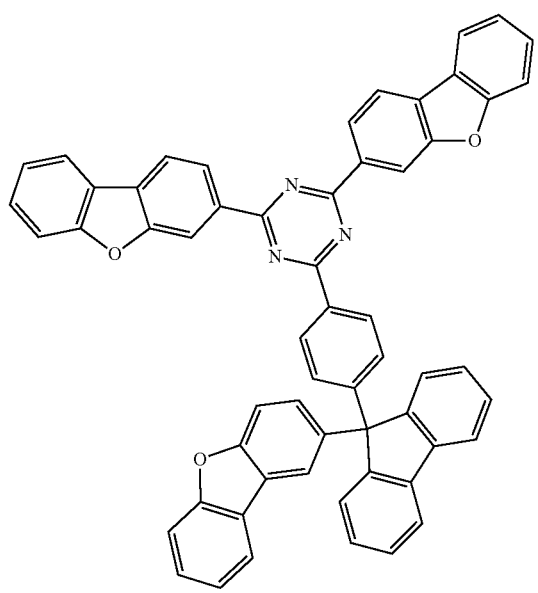
Inv 109
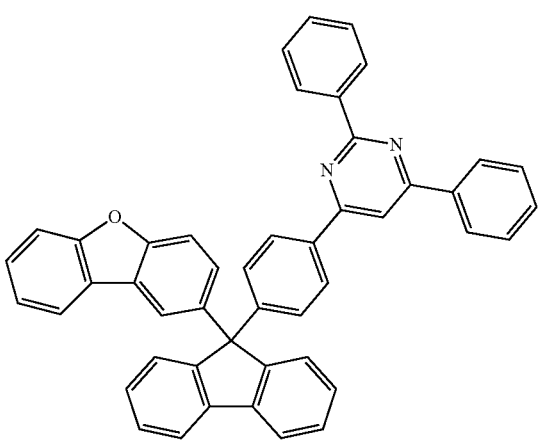
Inv 110
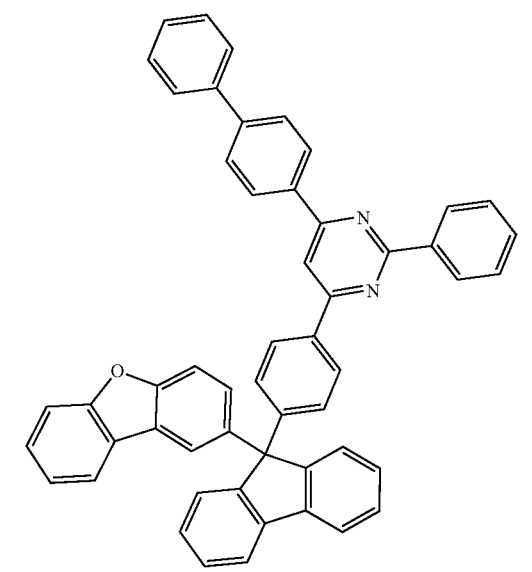
Inv 111
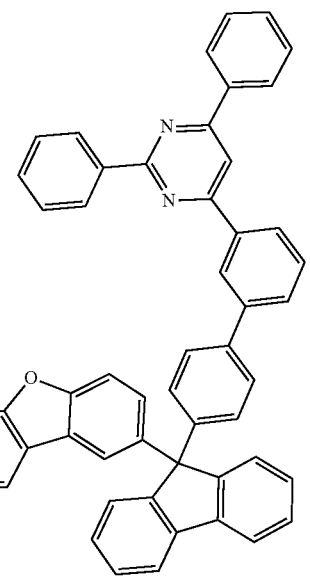
Inv 112
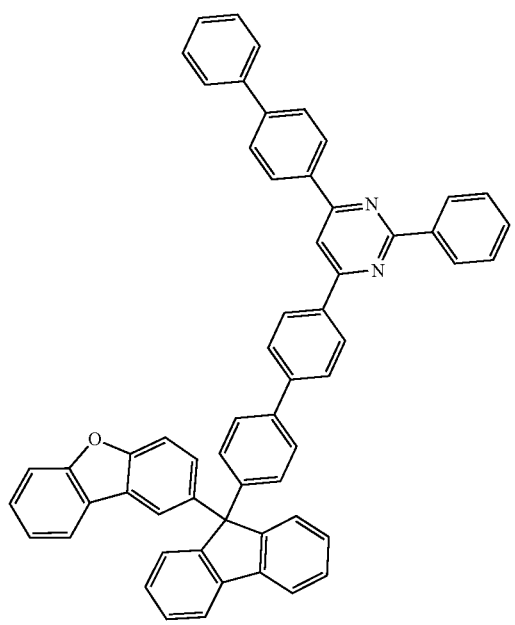

Inv 113
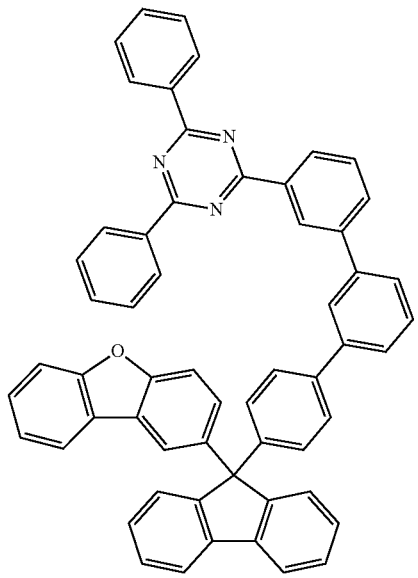
Inv 114
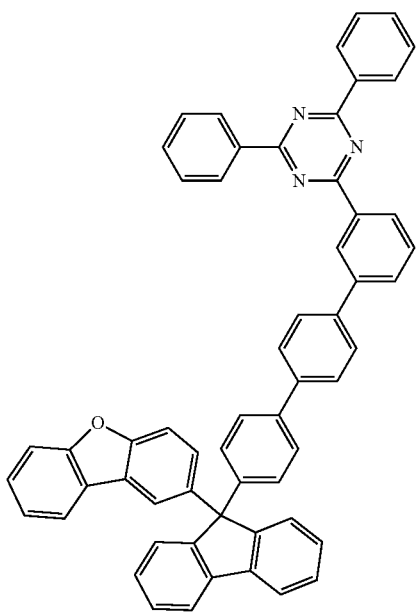
Inv 115
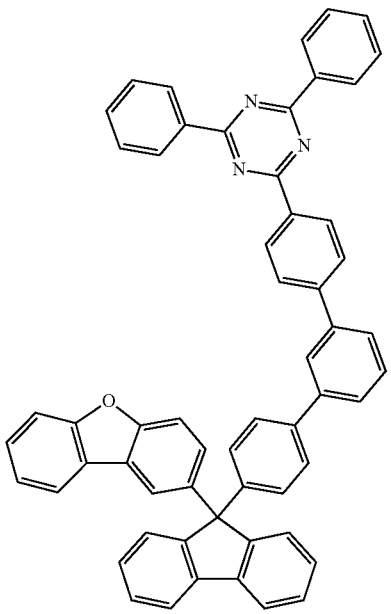
Inv 116
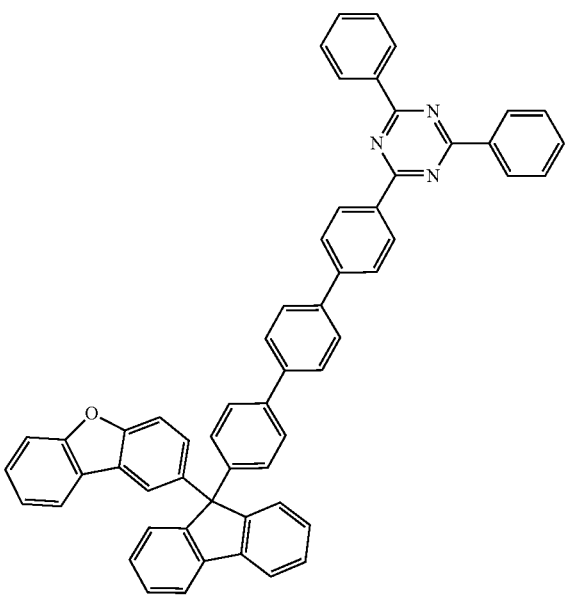

Inv 117
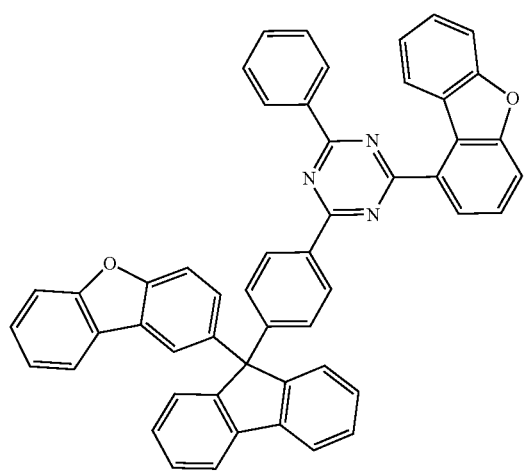
Inv 118
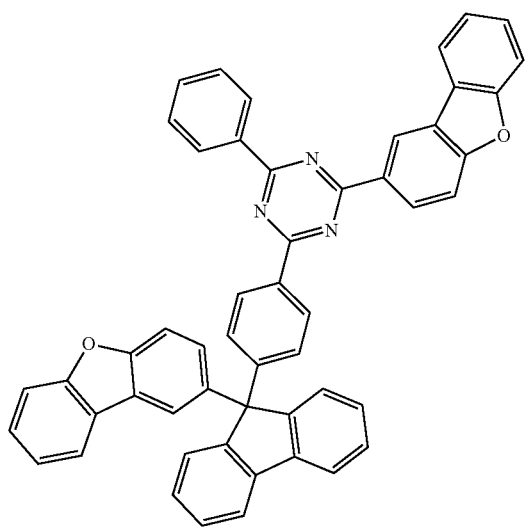
Inv 119
Inv 120
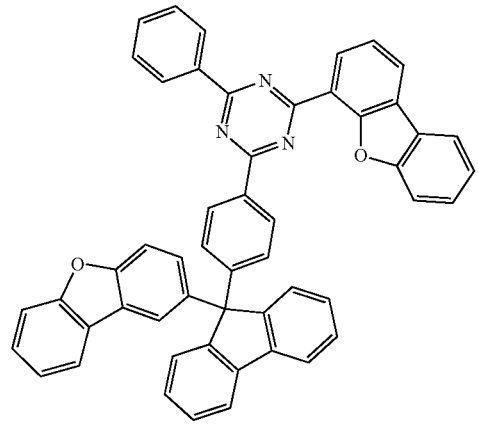
Inv 121
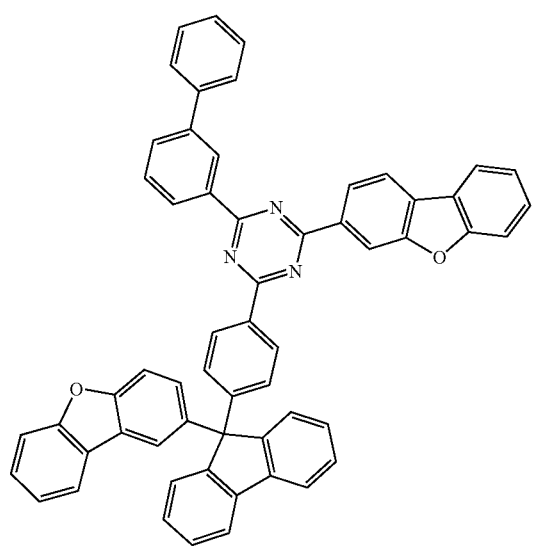
Inv 122
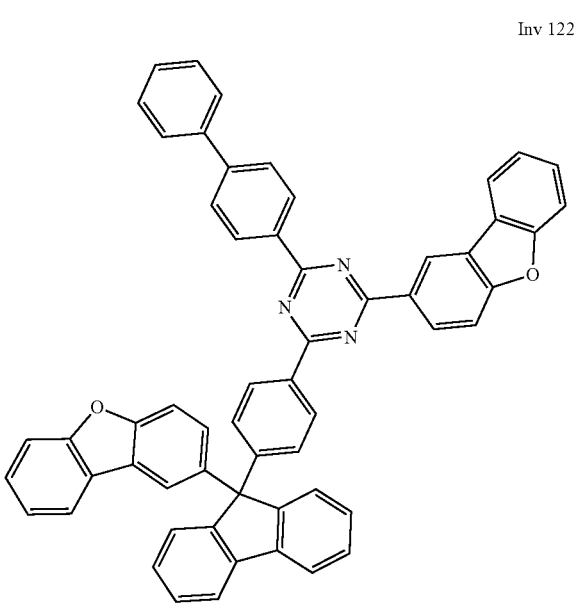

Inv 123
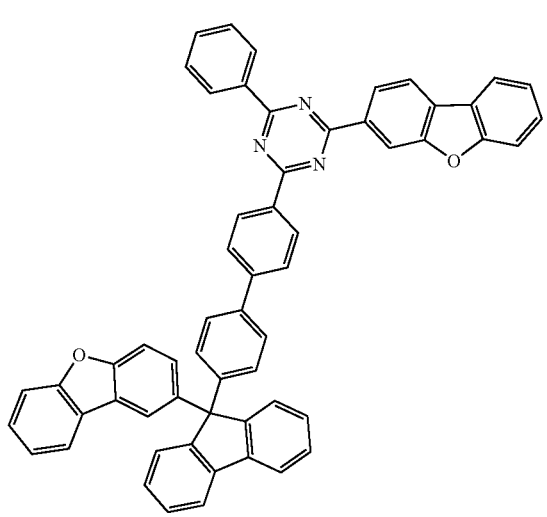
Inv 125
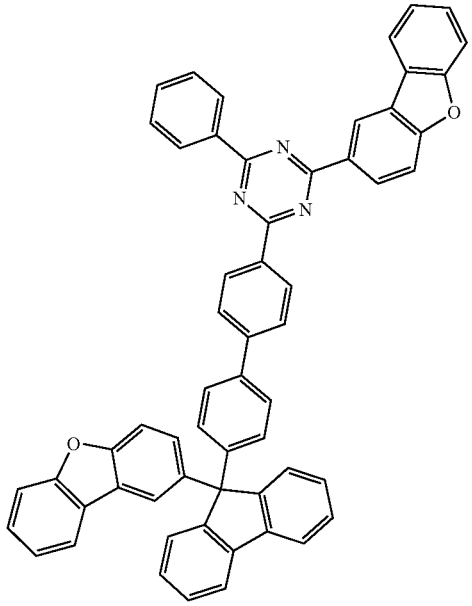
Inv 124
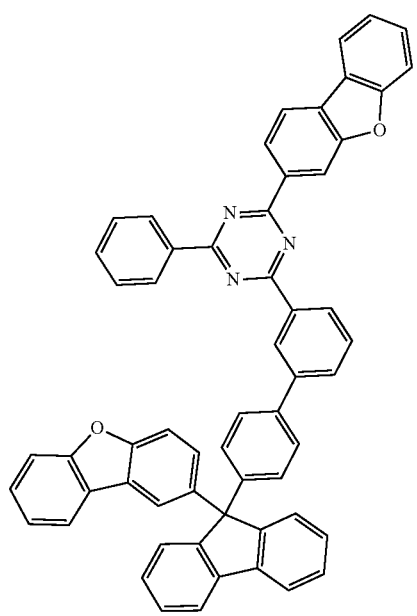
Inv 126
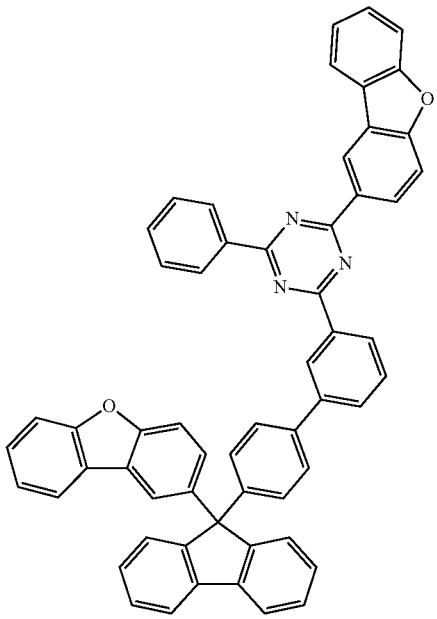

-continued
Inv 127
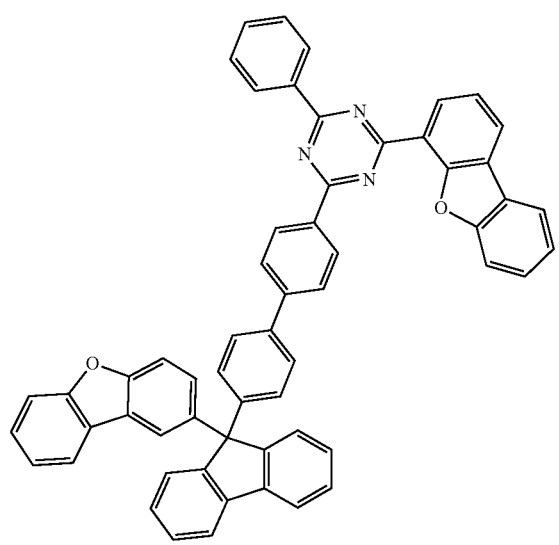
Inv 129
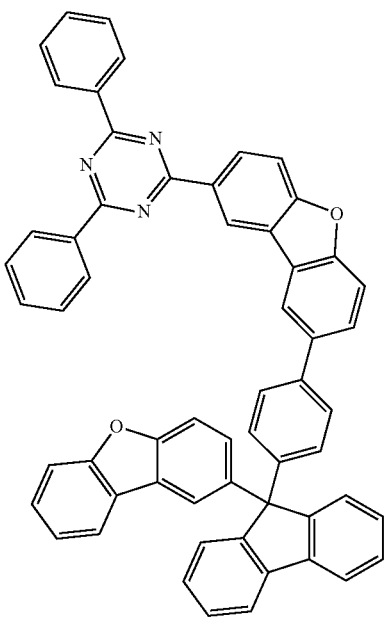
Inv 128
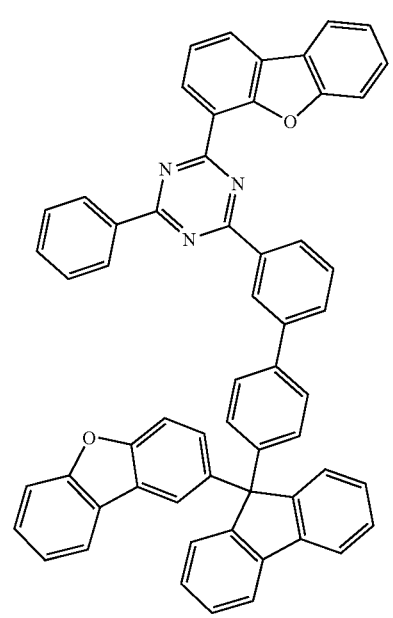
Inv 130
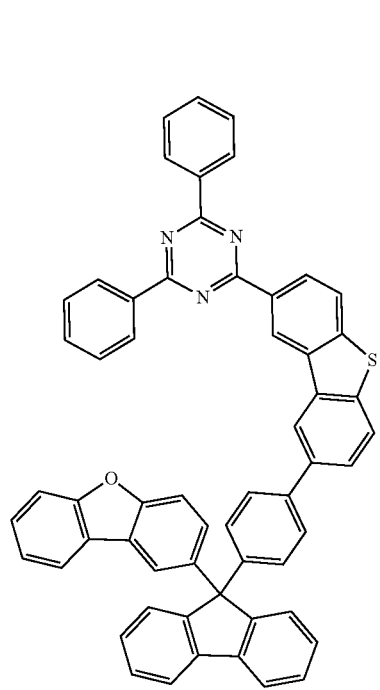

Inv 131
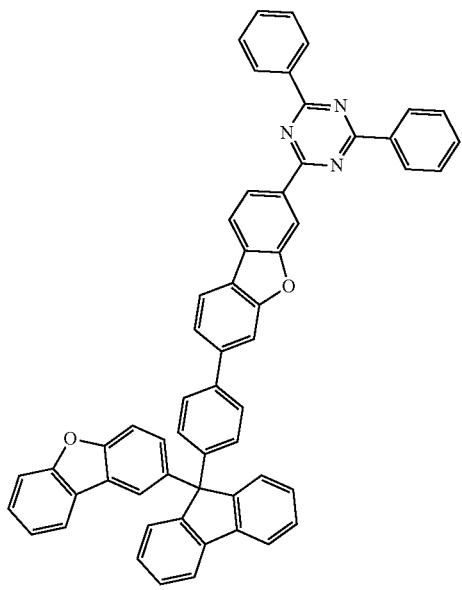
Inv 132
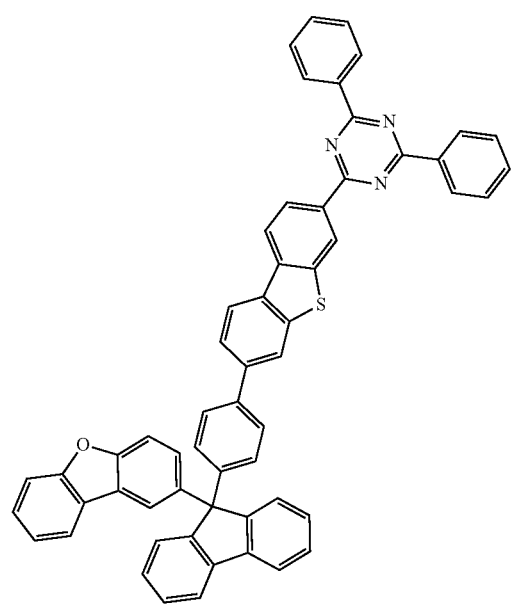
Inv 133
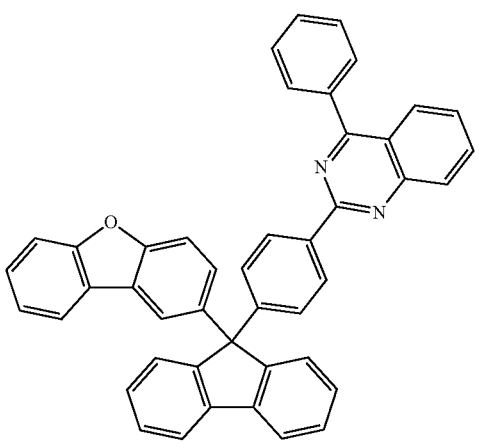
Inv 134
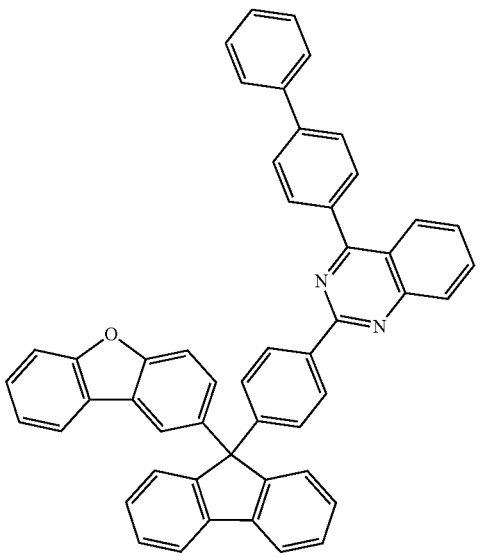
Inv 135
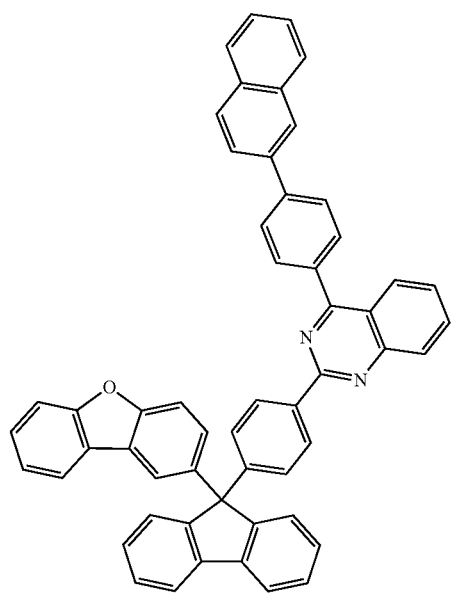

Inv 136
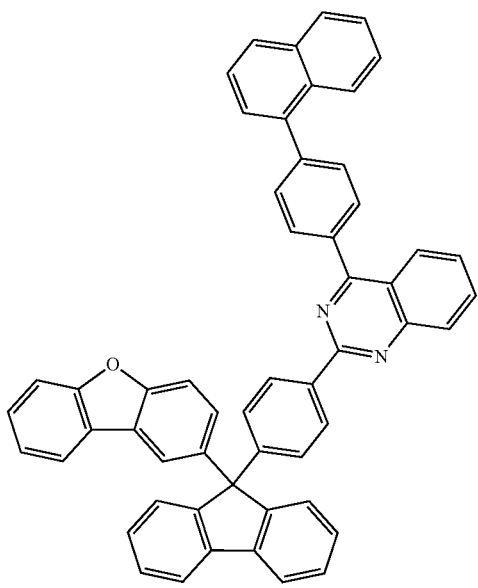
Inv 137
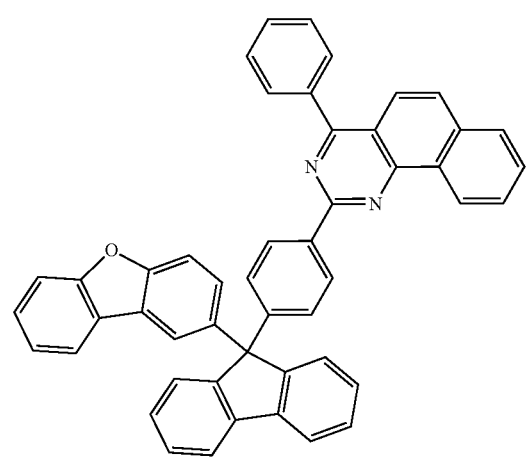
Inv 138
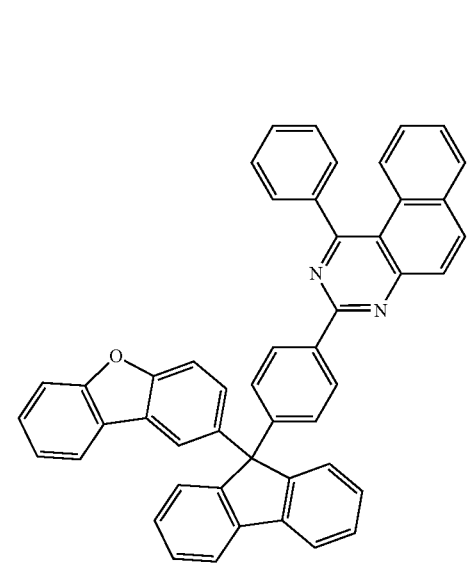
Inv 139
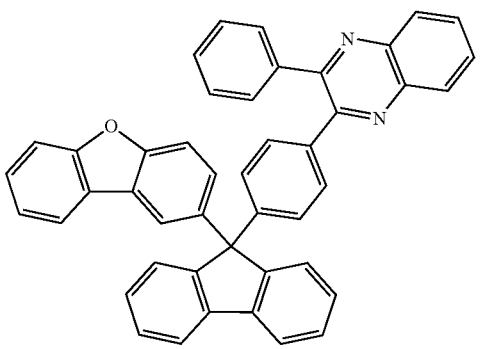
Inv 140
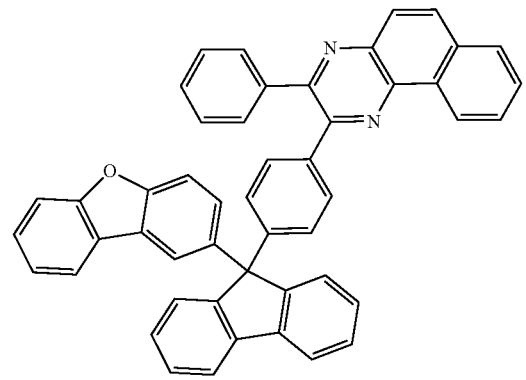
Inv 141
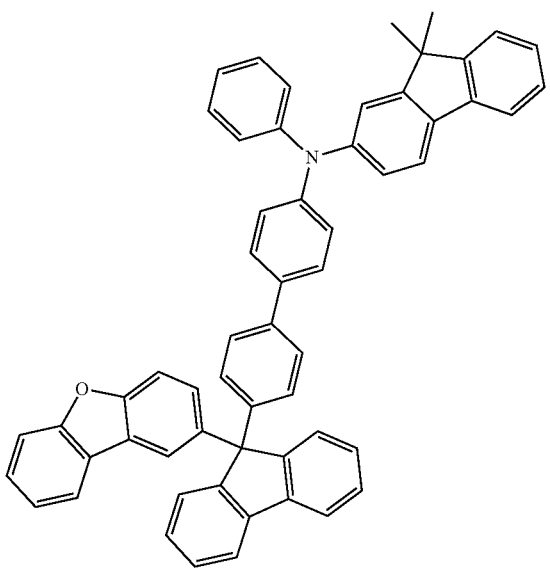

Inv 142
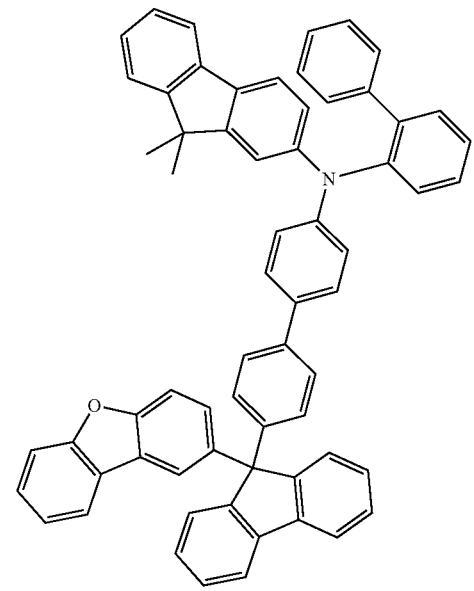
Inv 143
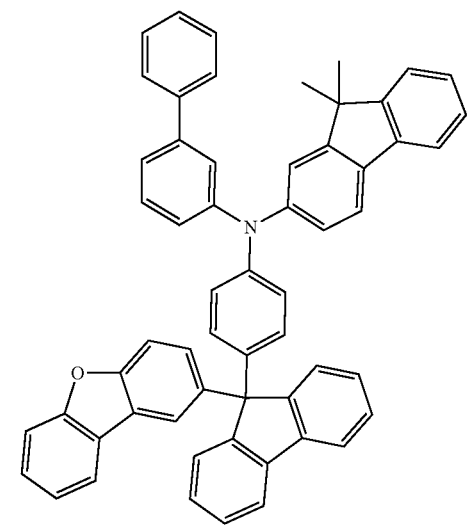
Inv 144
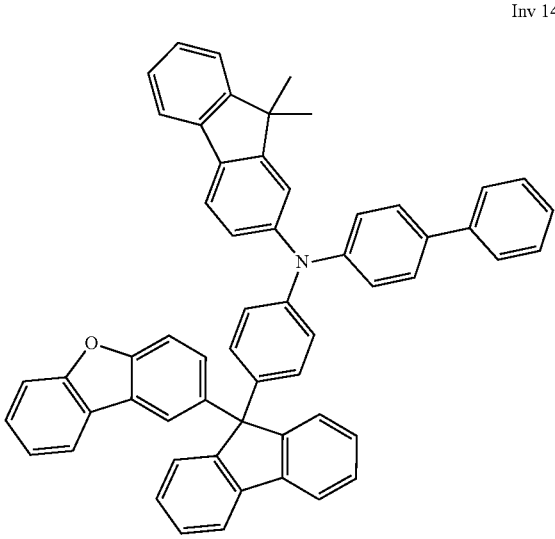
Inv 145
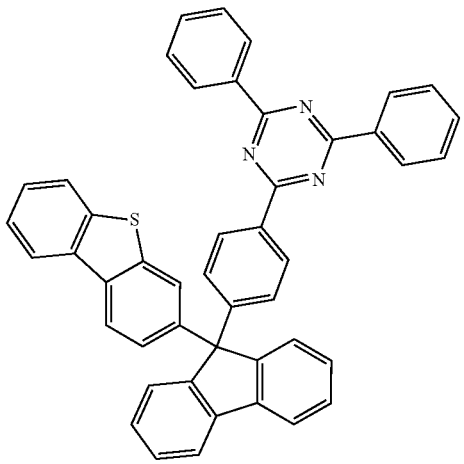
Inv 146
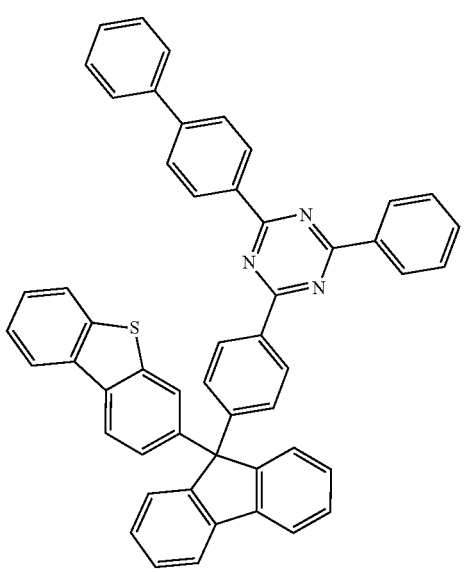
Inv 147
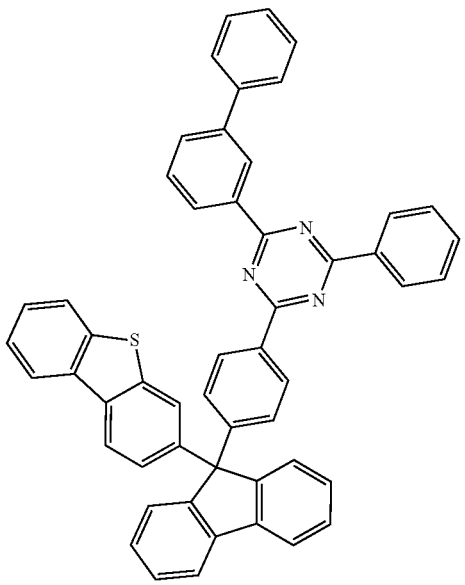

Inv 148
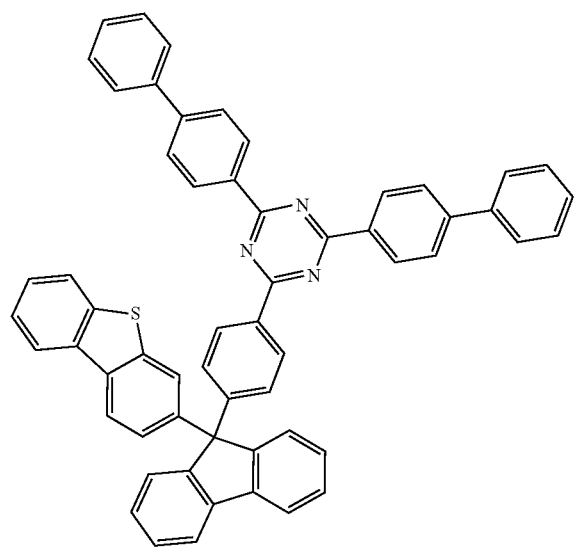
Inv 149
Inv 150
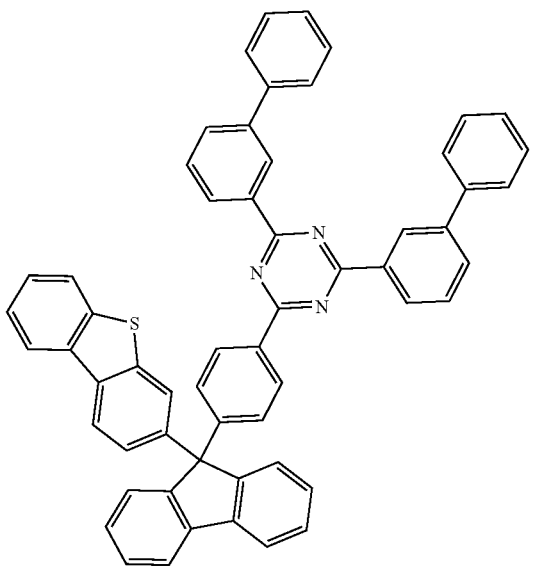
Inv 151
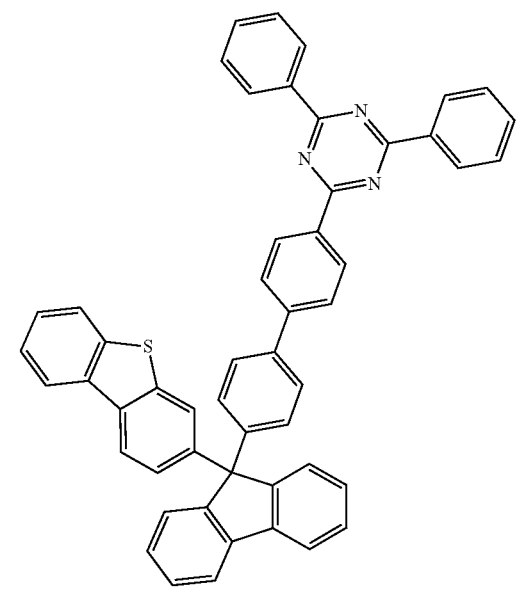

-continued
Inv 152
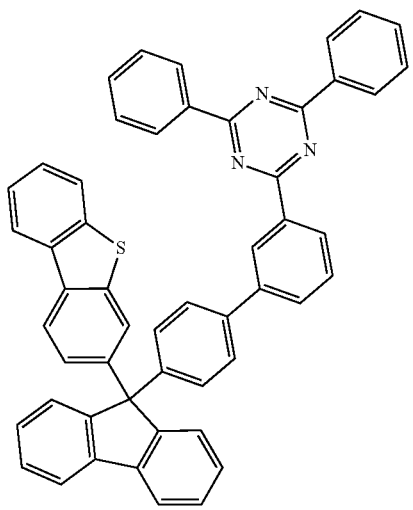
Inv 154
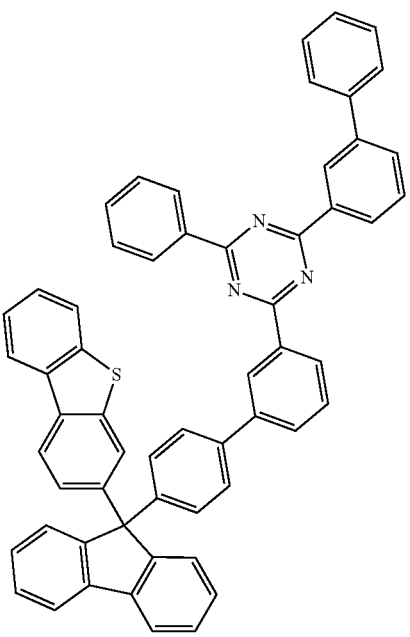
Inv 153
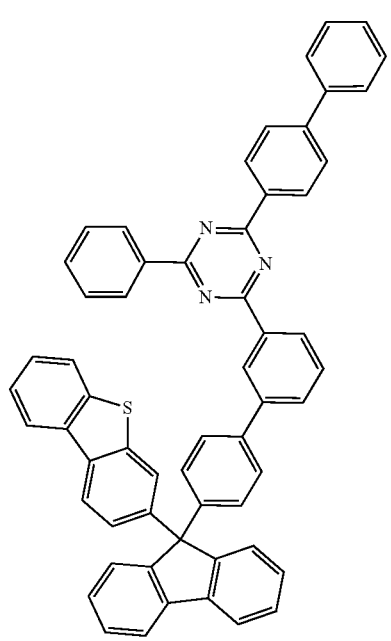
Inv 155
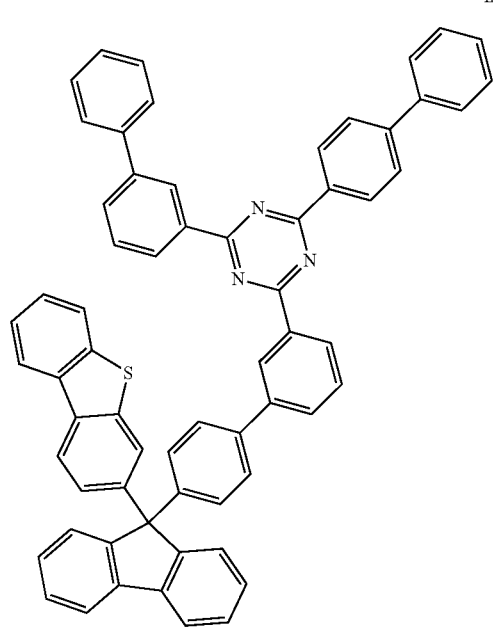

Inv 156
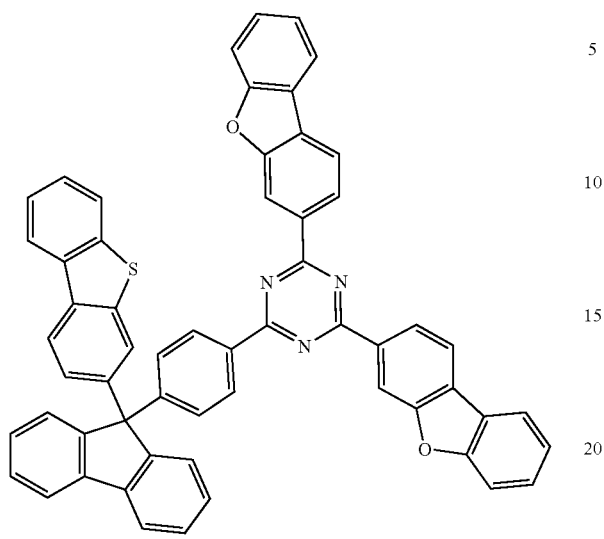
Inv 157
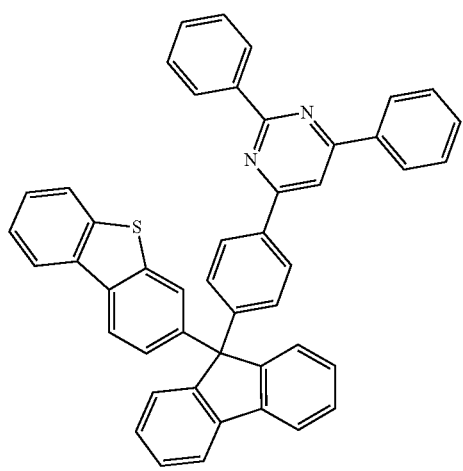
Inv 158
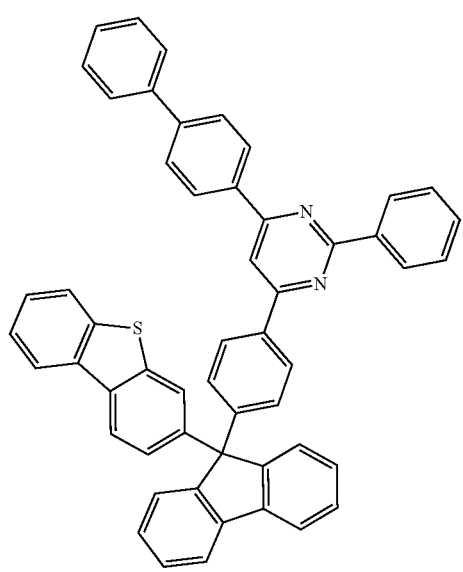
Inv 159
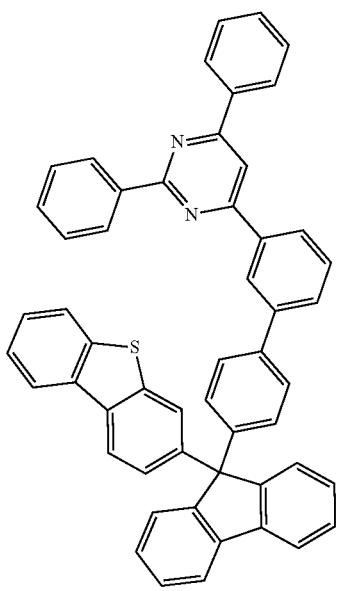
Inv 160
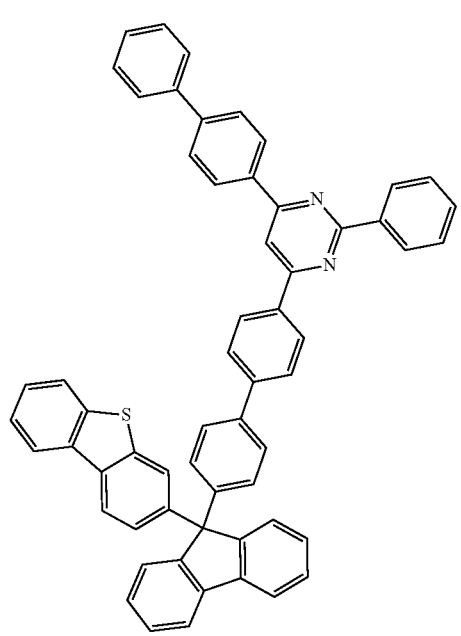

-continued
Inv 161
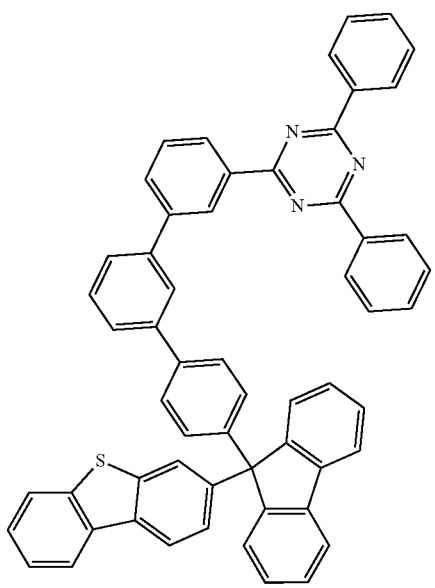
Inv 162
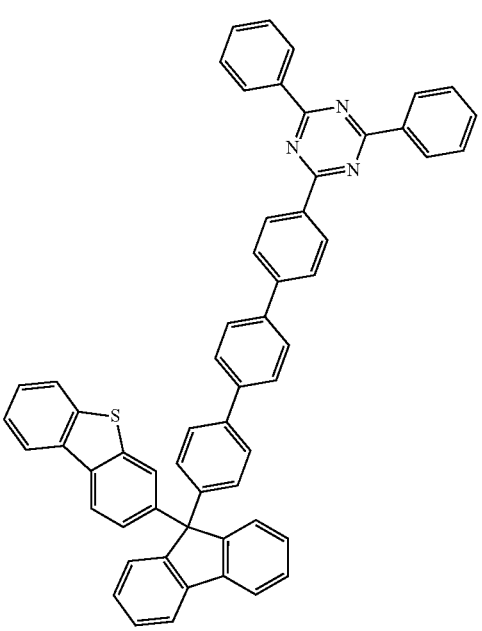
-continued
Inv 163
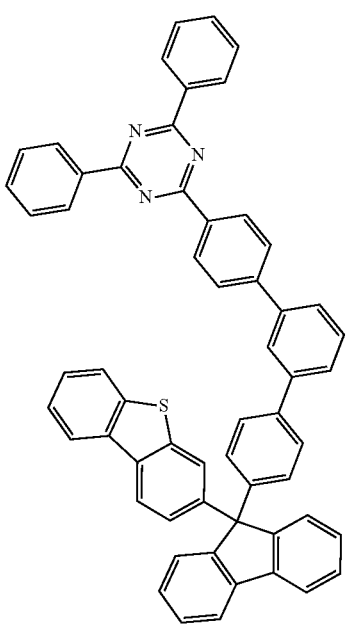
Inv 164

Inv 165
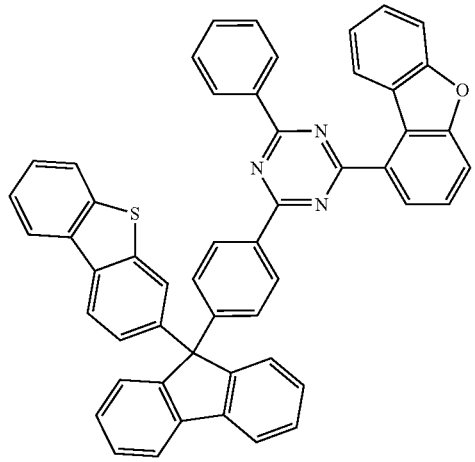
Inv 166
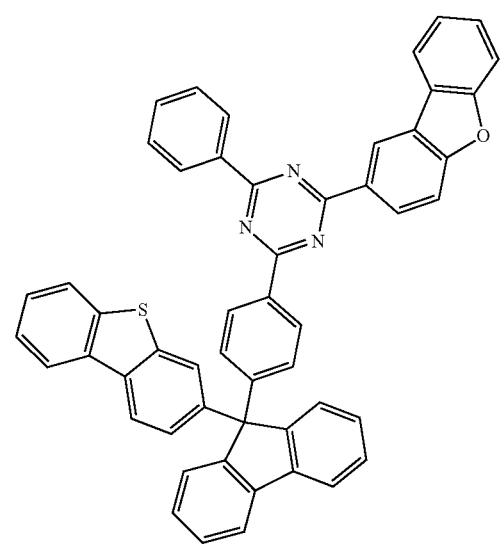
Inv 167
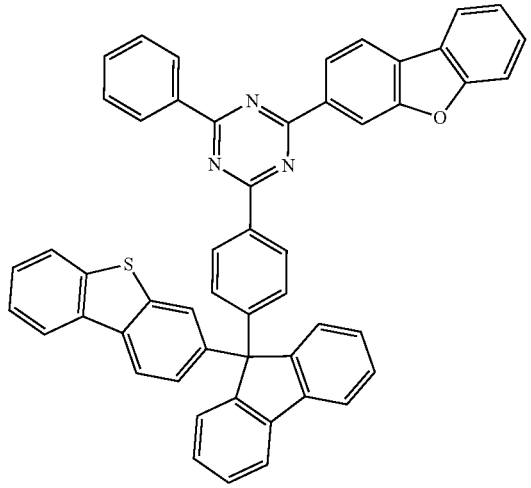
Inv 168
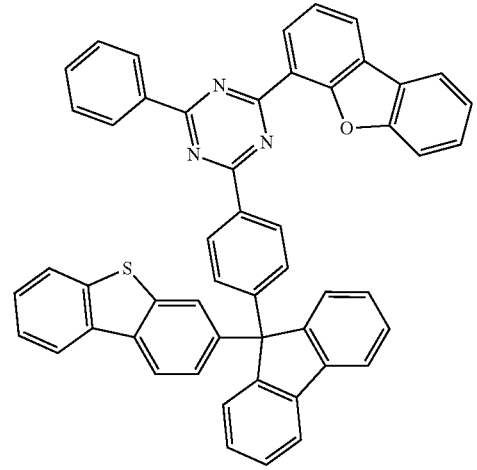
Inv 169
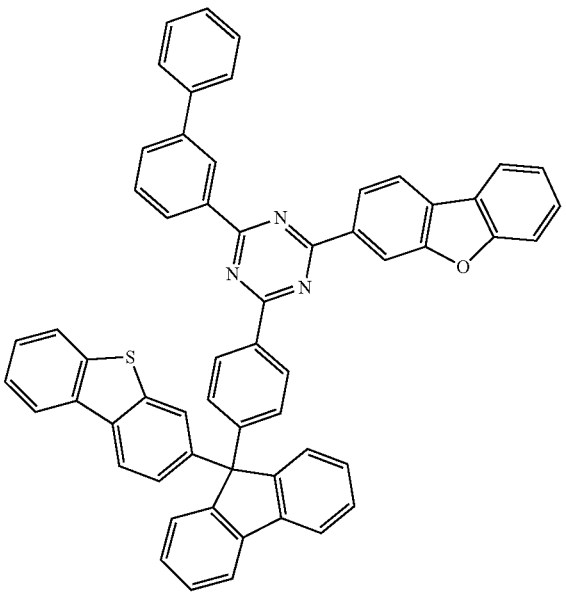
Inv 170
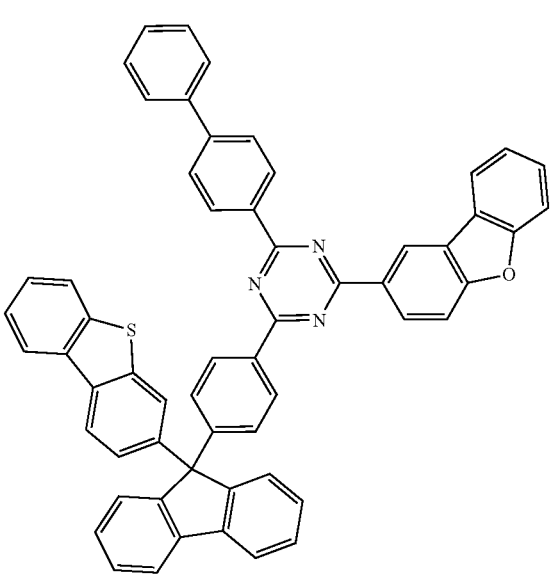

Inv 171
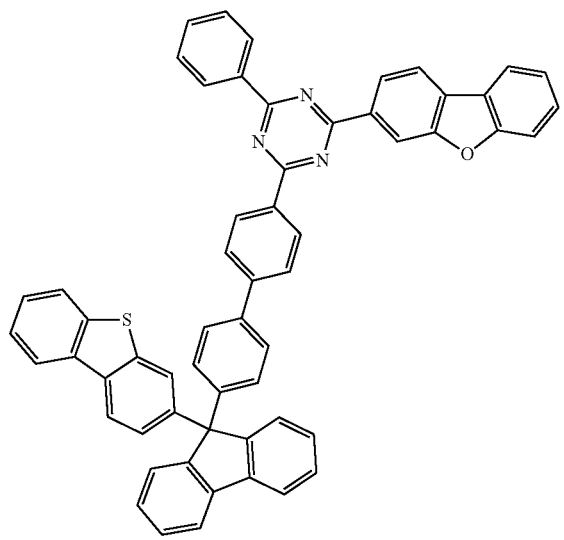
Inv 172
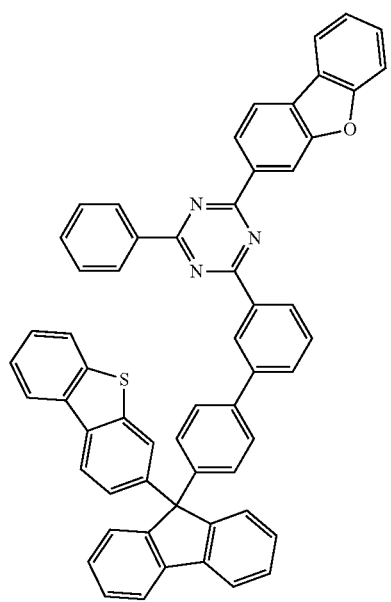
Inv 173
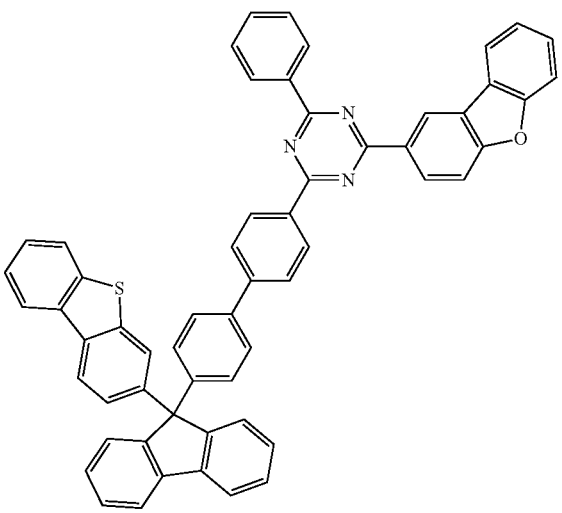
Inv 174
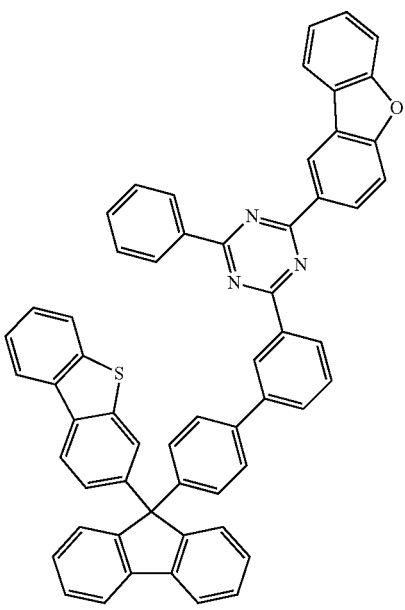

Inv 175
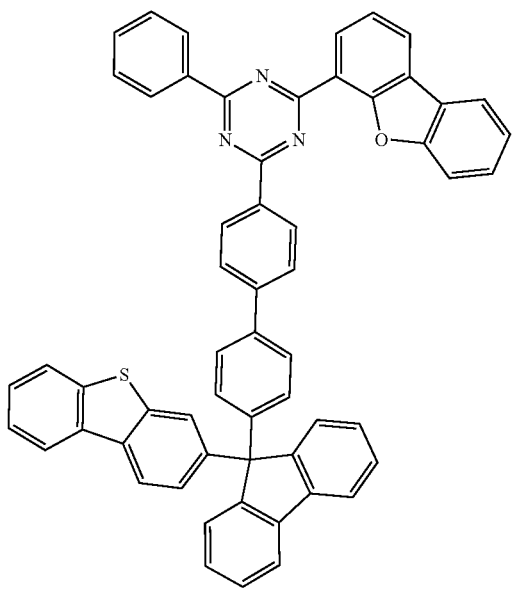
Inv 176
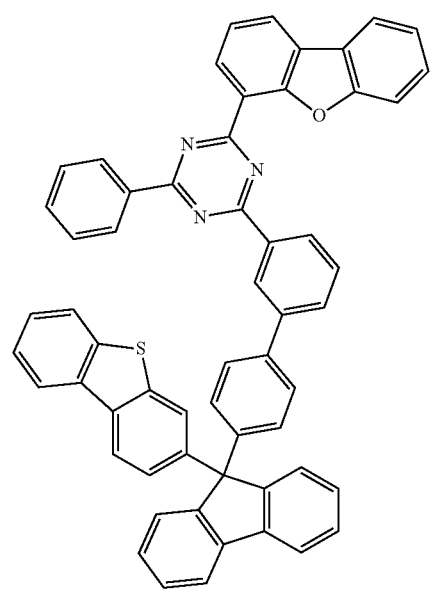
Inv 177
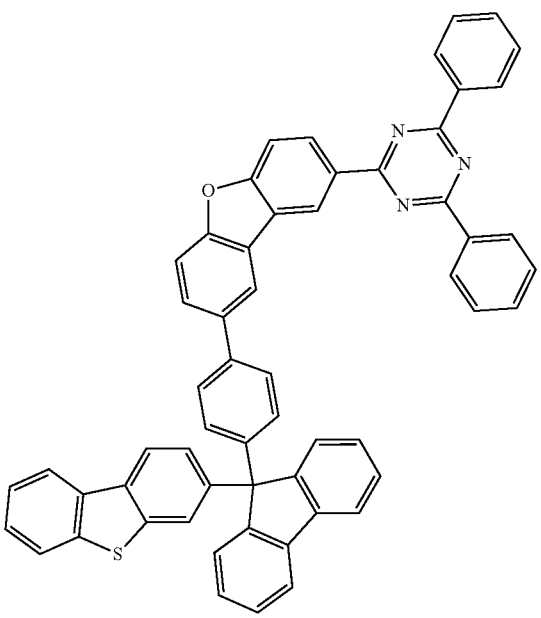
Inv 178
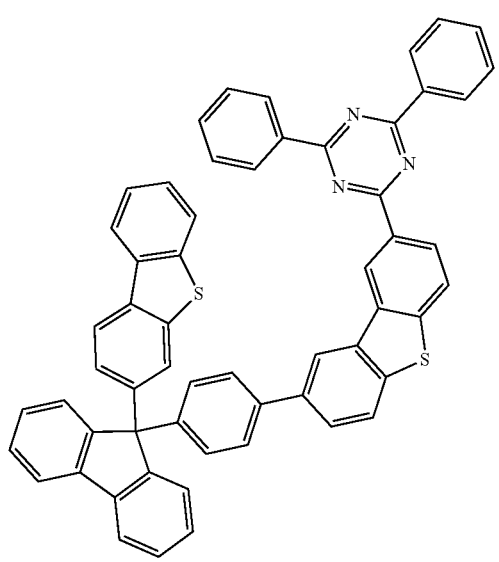

Inv 179
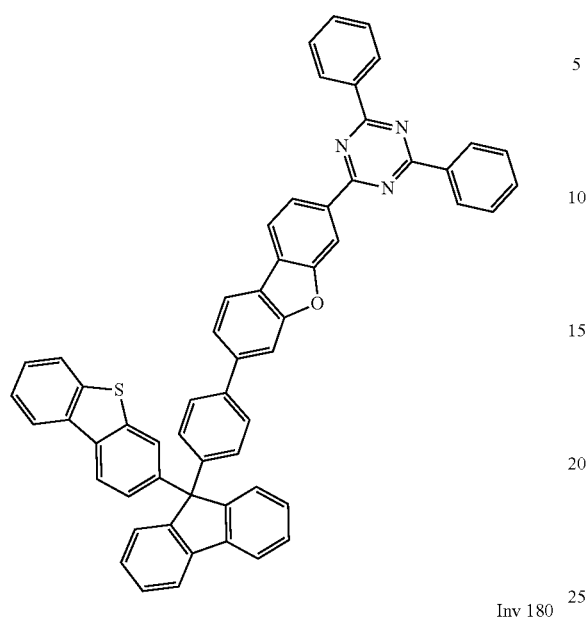
Inv 180
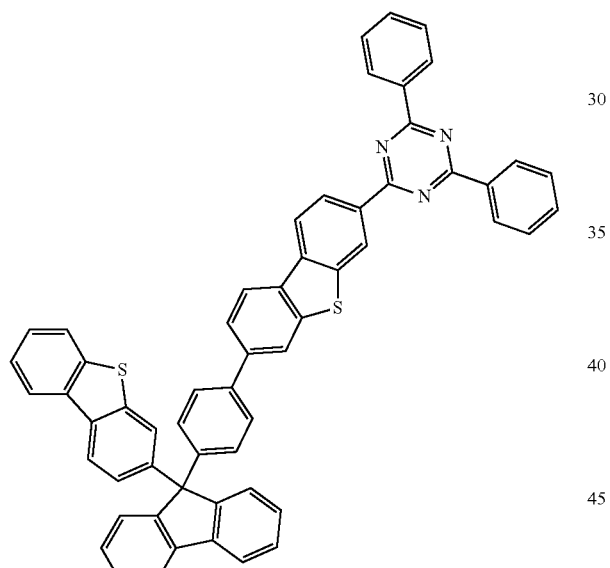
Inv 181
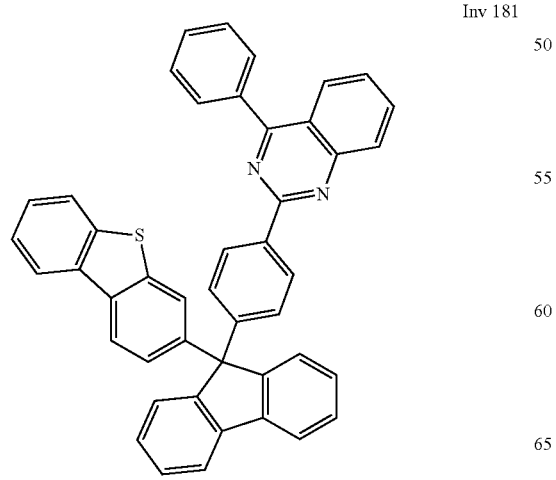
Inv 182
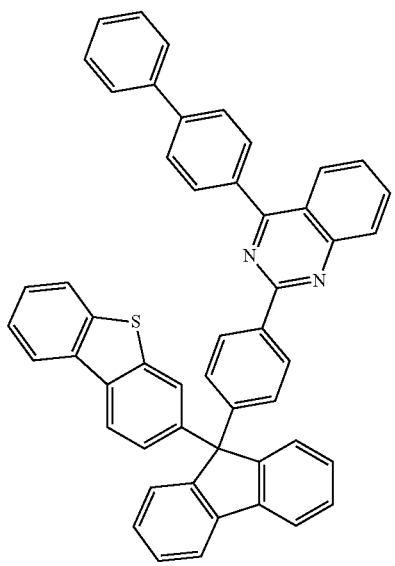
Inv 183
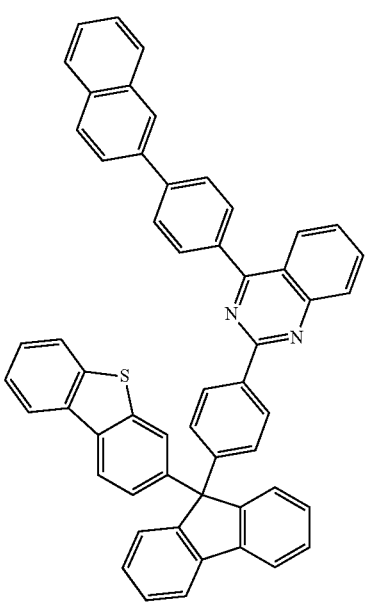

Inv 184
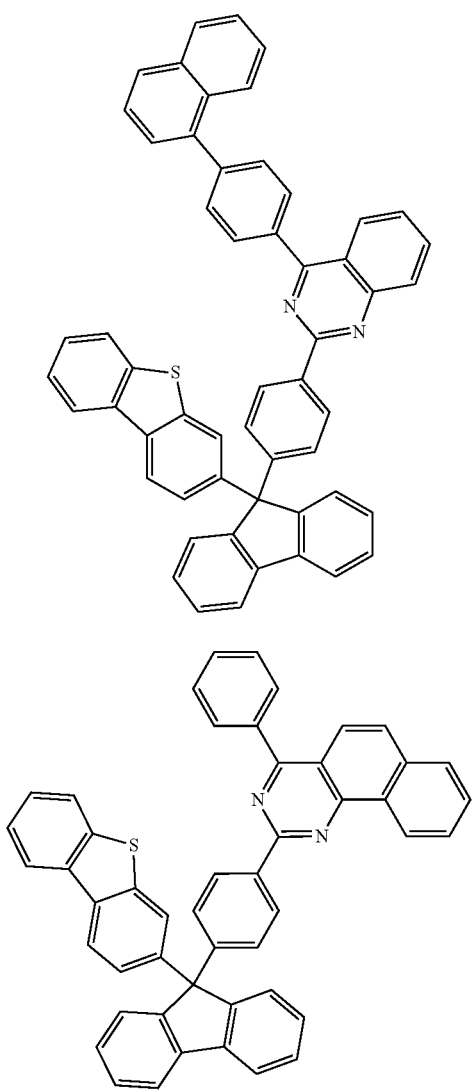
Inv 185
Inv 186
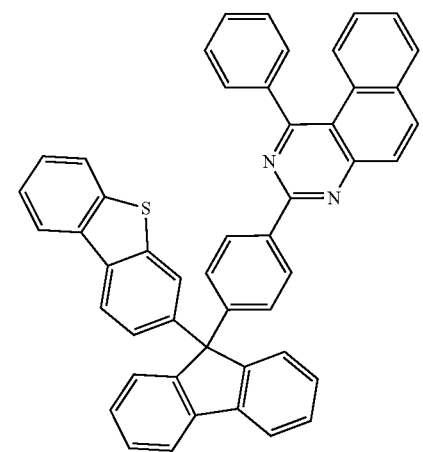
Inv 187
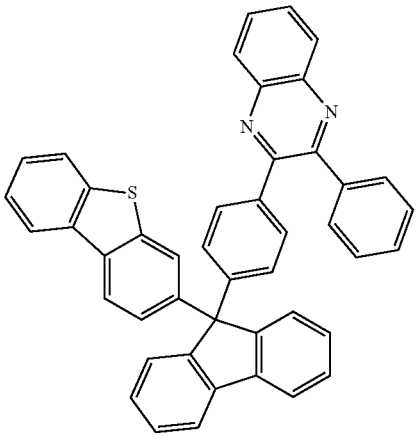
Inv 188
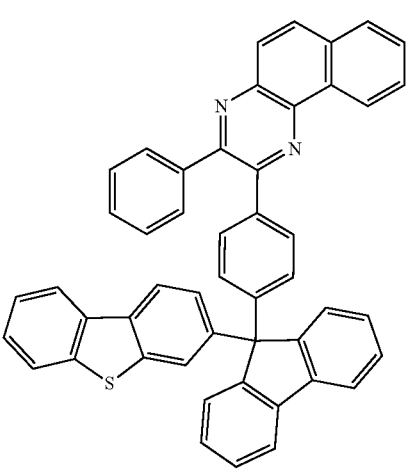
Inv 189
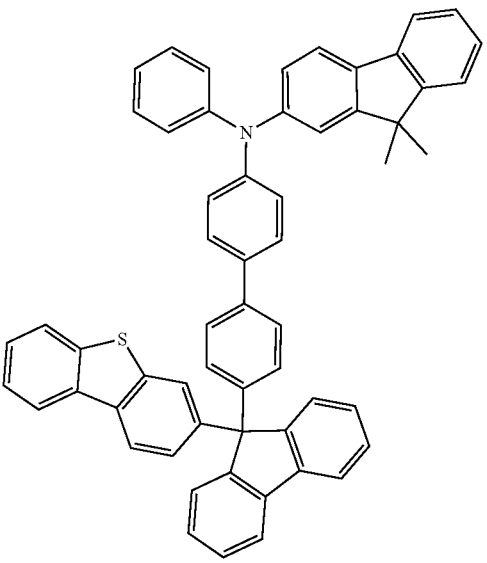

Inv 190
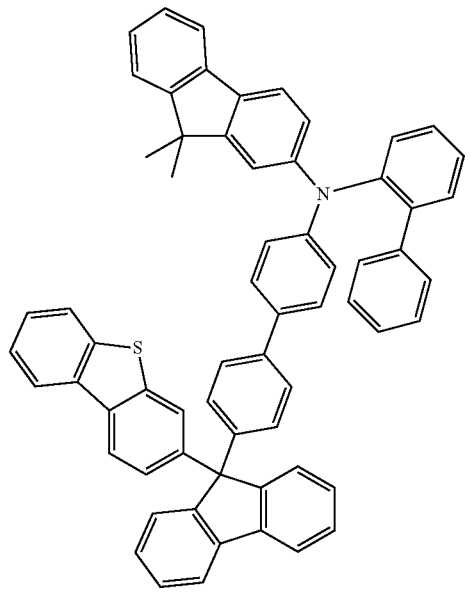
Inv 191
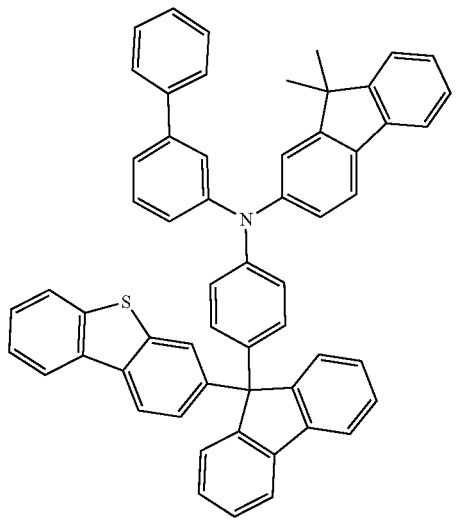
Inv 192
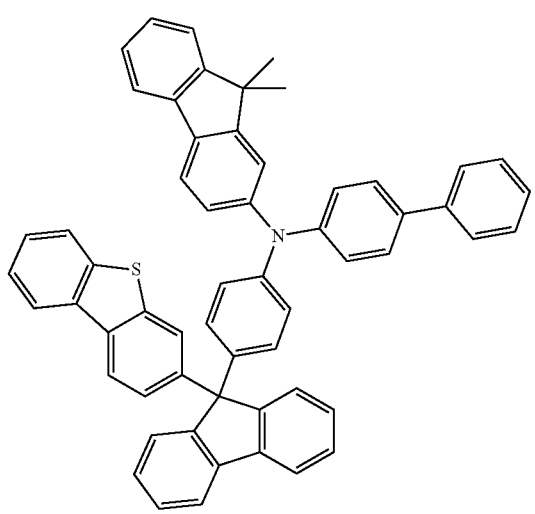
Inv 193
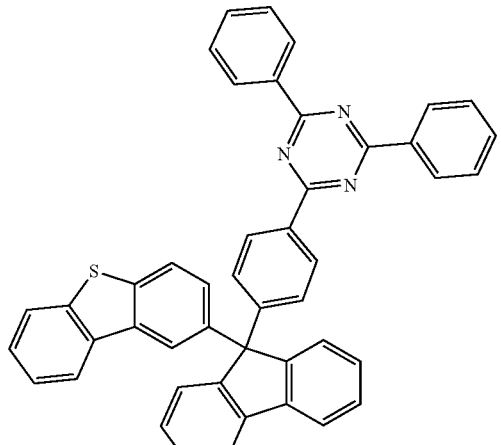
Inv 194
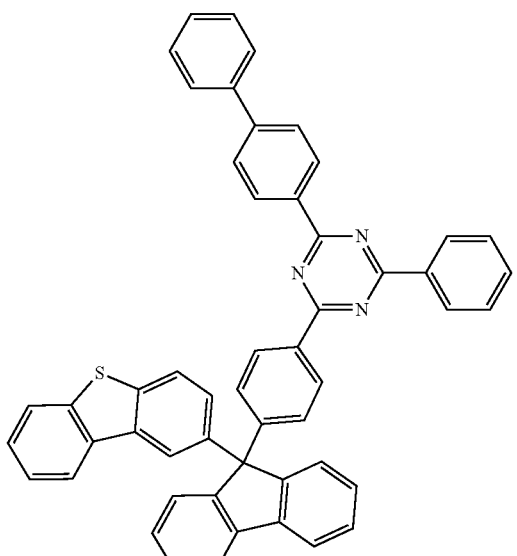
Inv 195
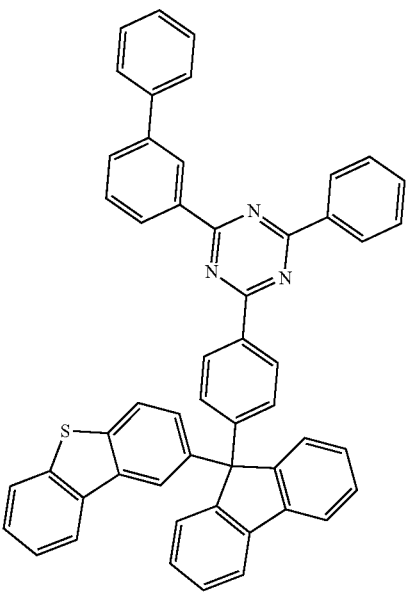

Inv 196
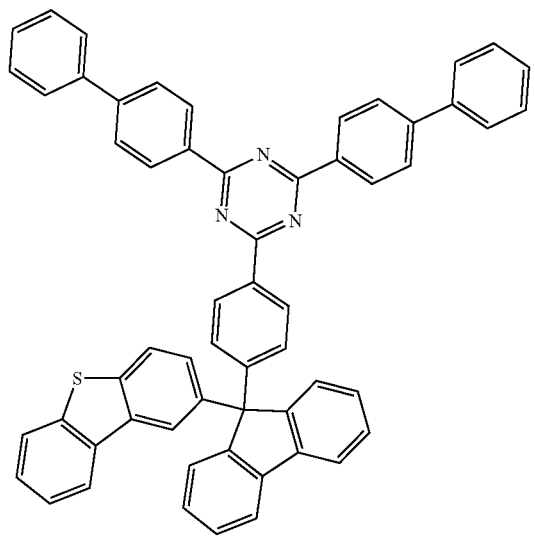
Inv 198
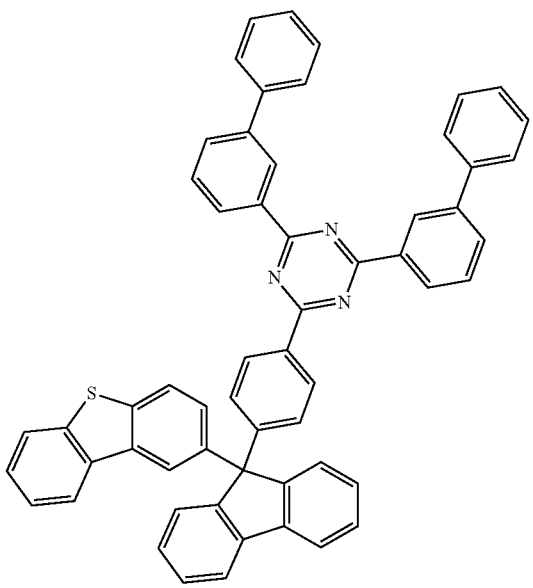
Inv 197
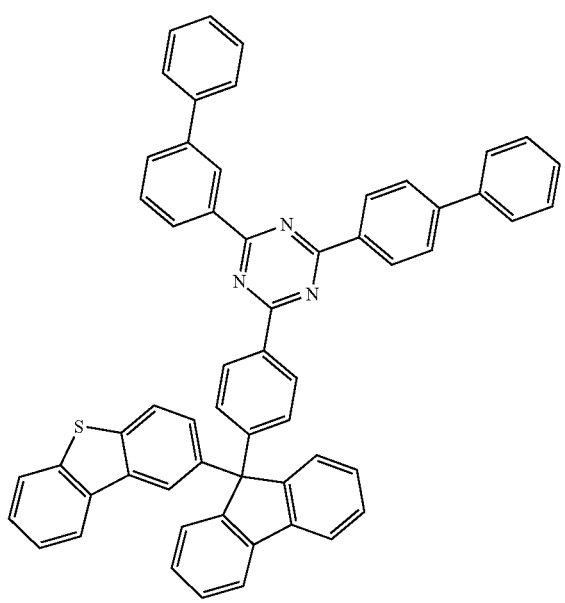
Inv 199
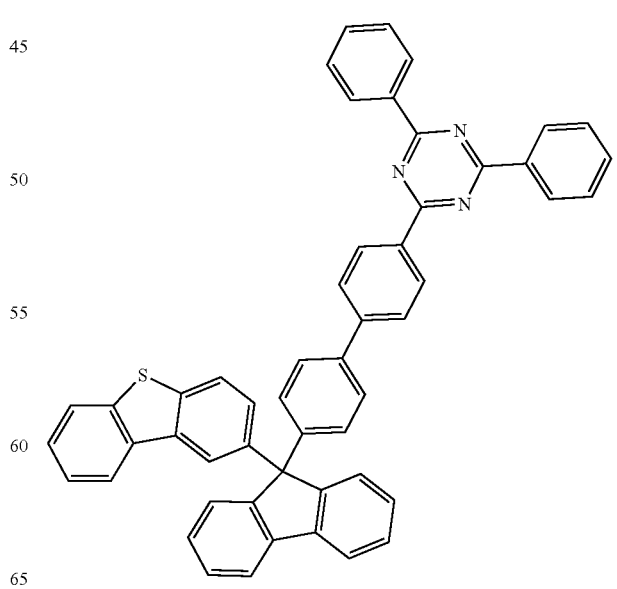

Inv 200
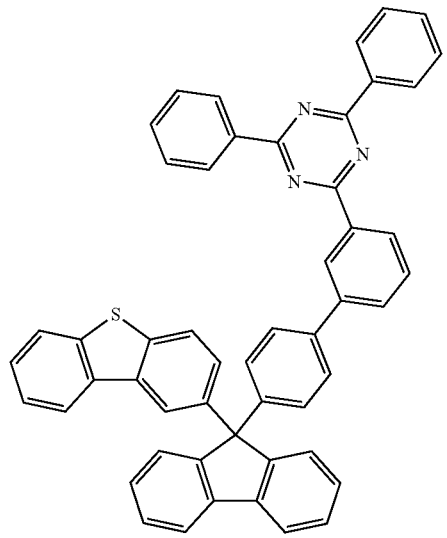
Inv 202
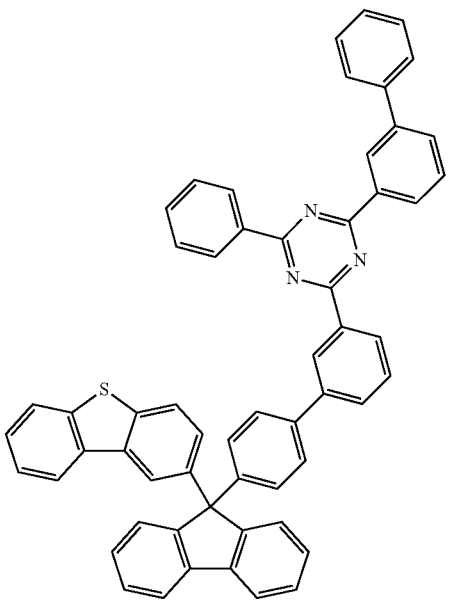
Inv 201
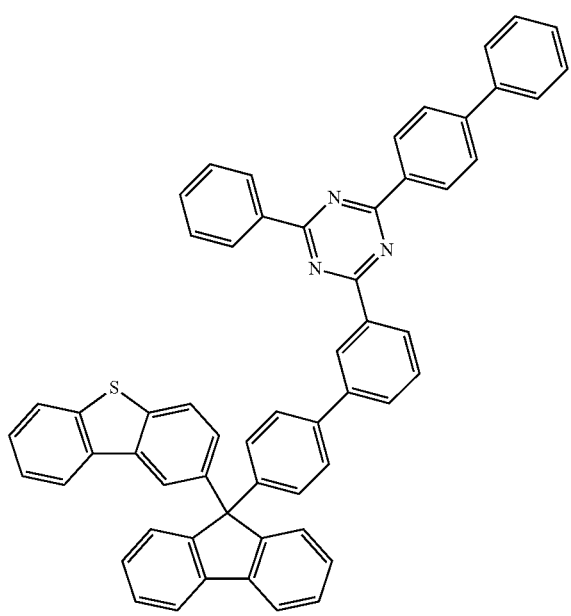
Inv 203
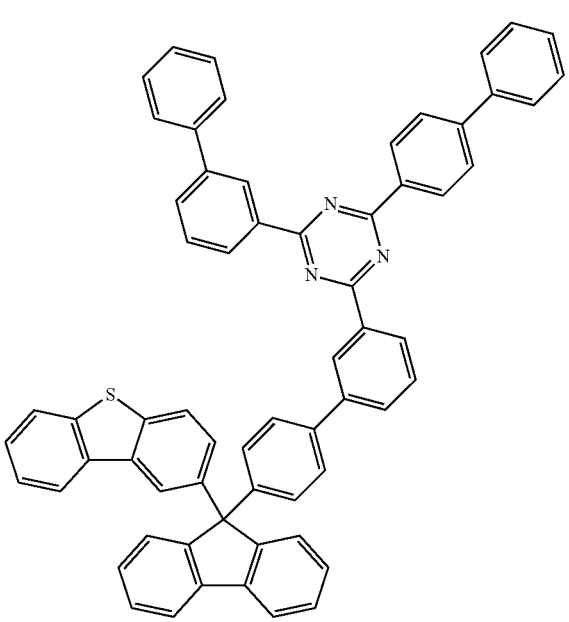

Inv 204
Inv 205
Inv 206
Inv 207
Inv 208
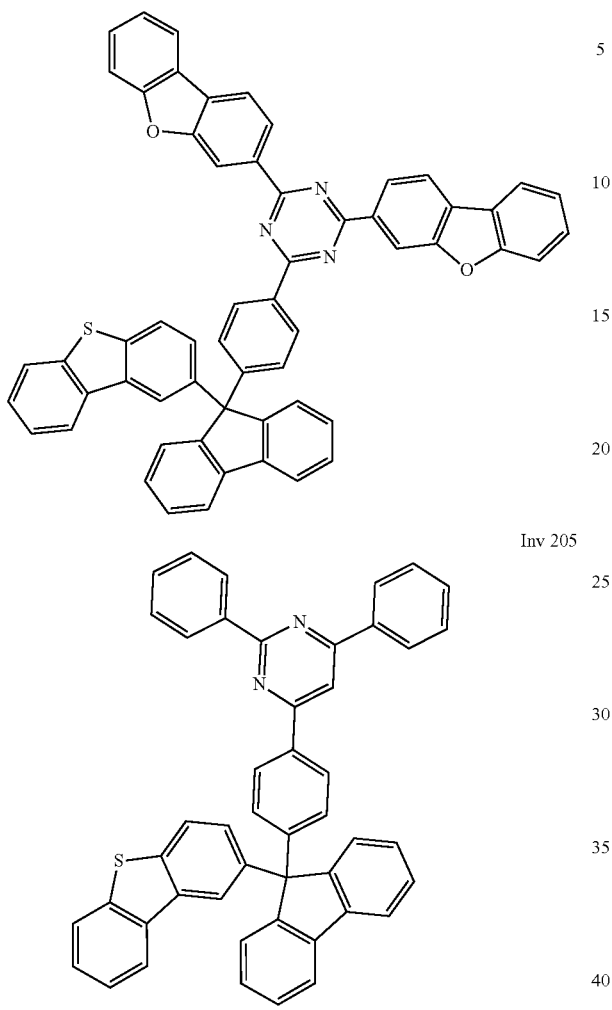
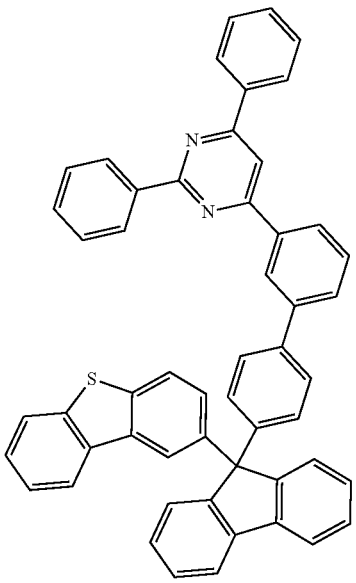
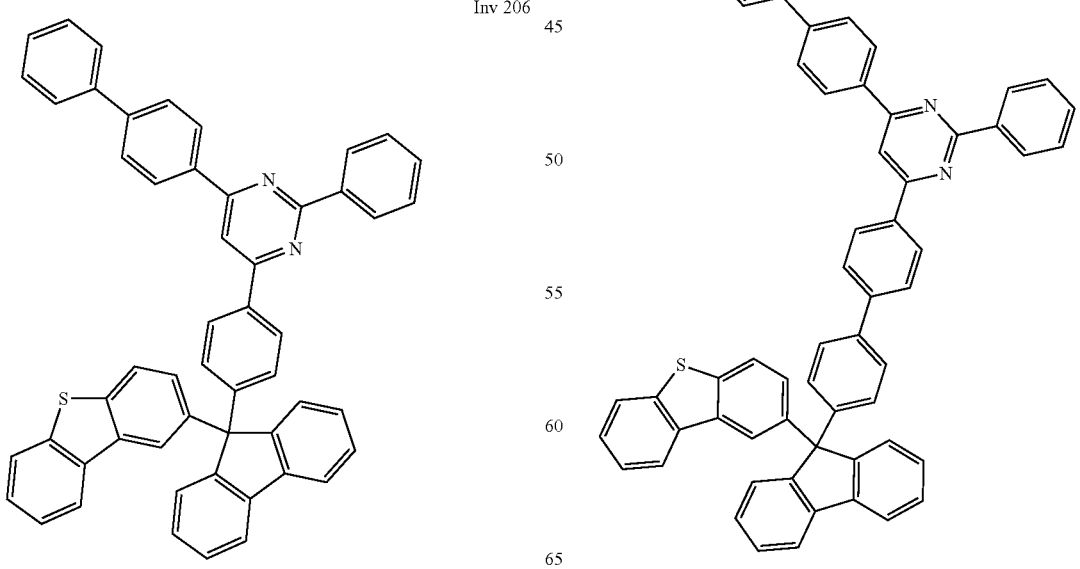

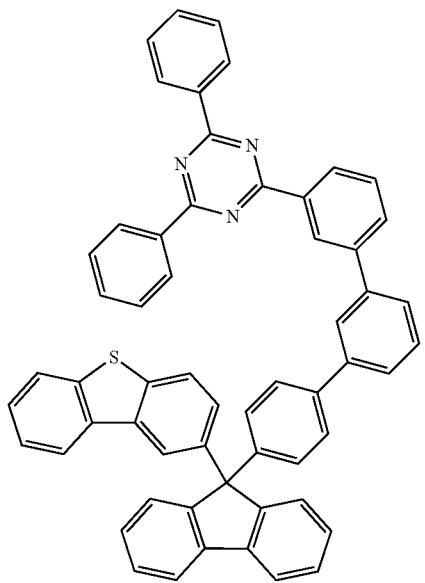
Inv 209
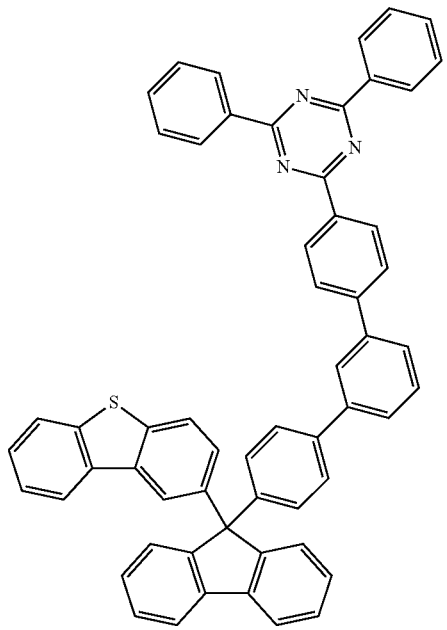
Inv 211
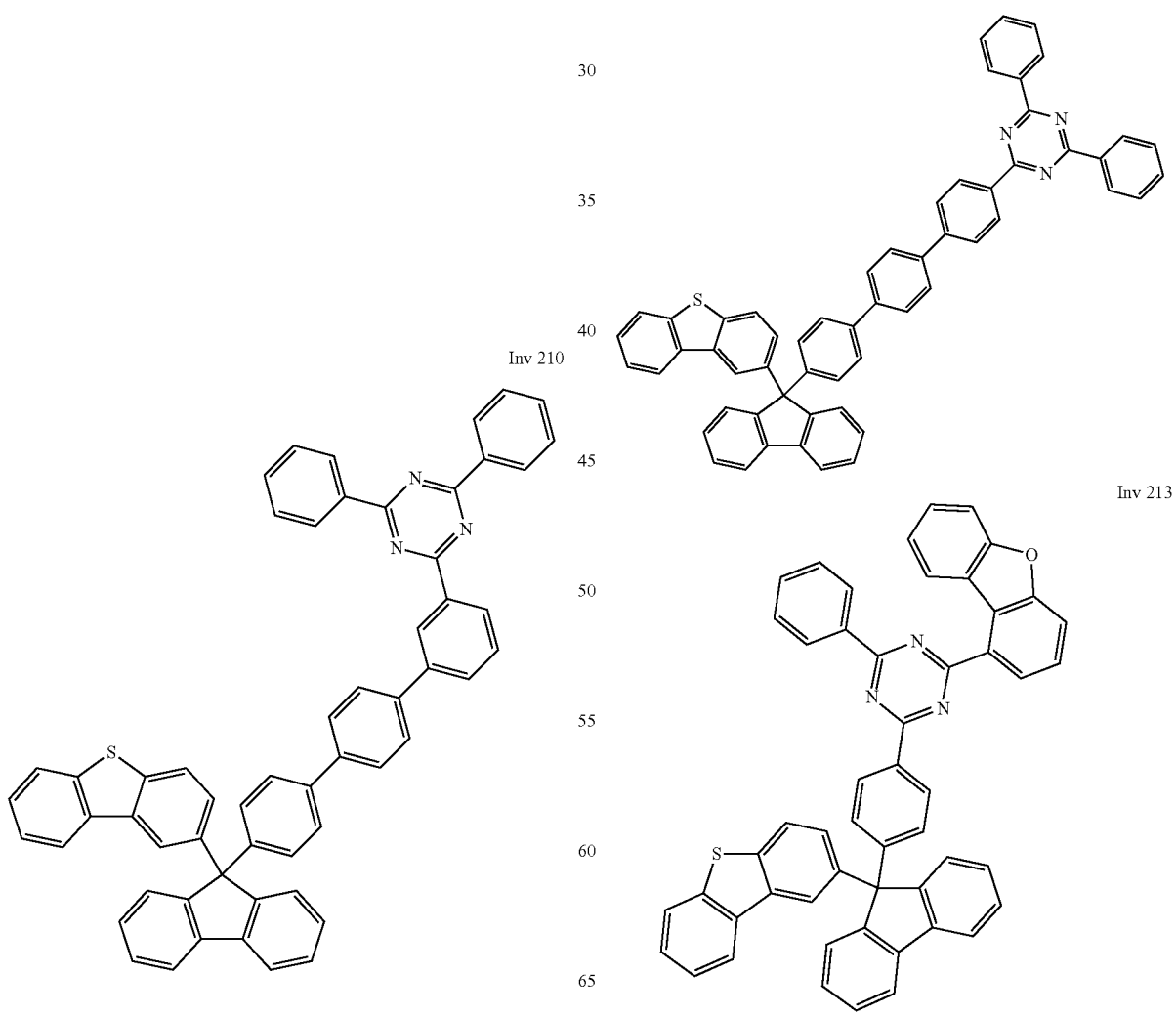
Inv 210
Inv 212
Inv 213

Inv 214
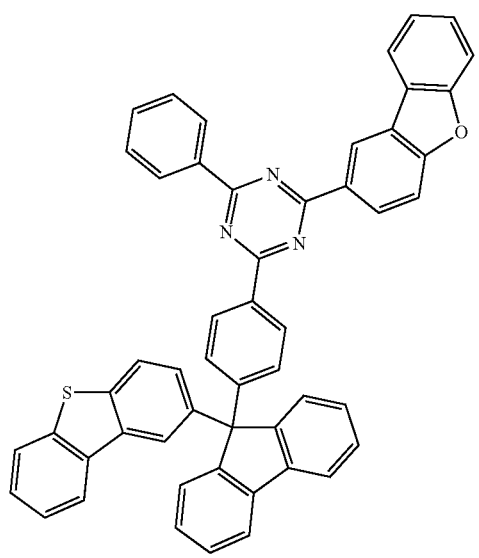
Inv 215
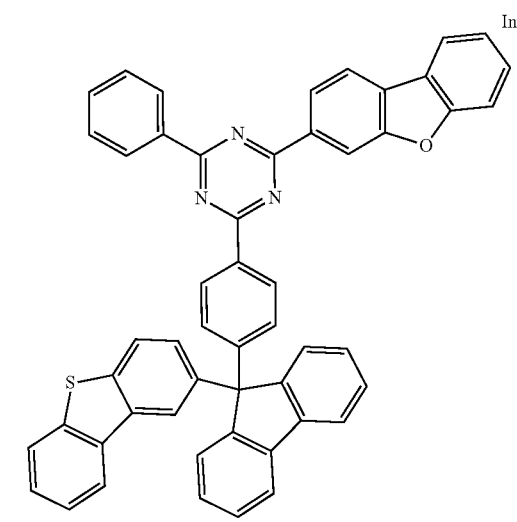
Inv 216
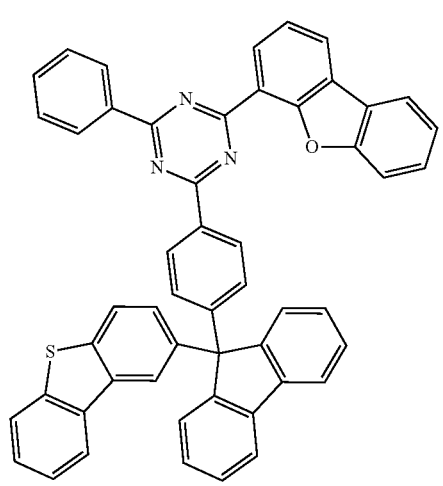
Inv 217
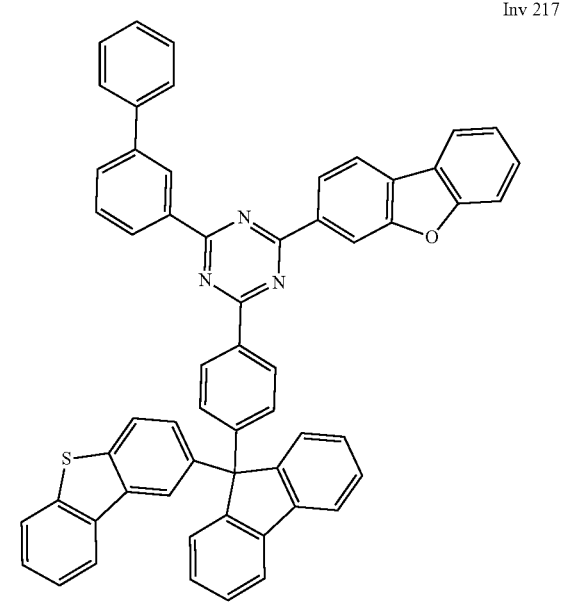
Inv 218
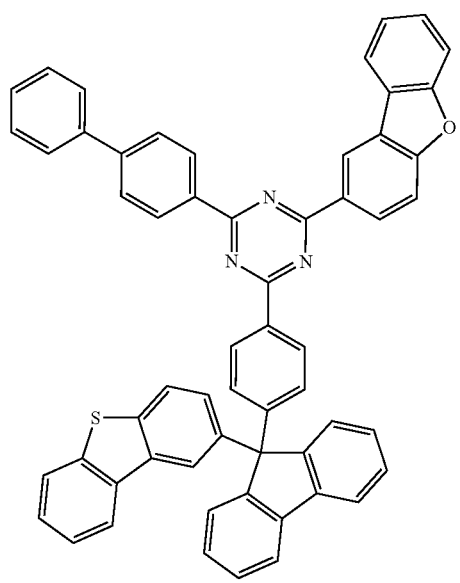

Inv 219
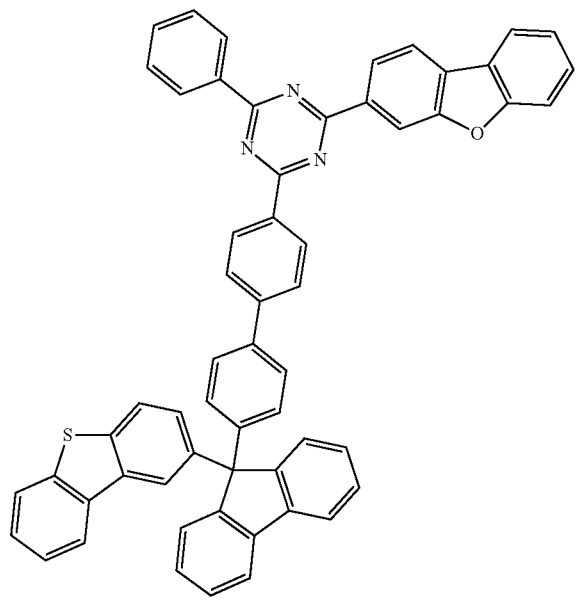
Inv 220
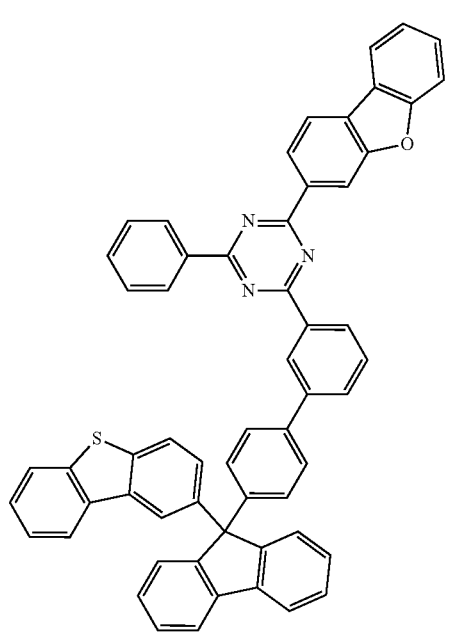
Inv 221
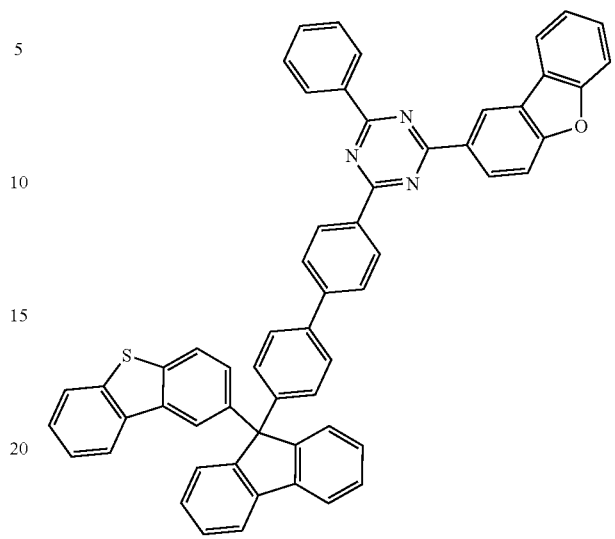
Inv 222
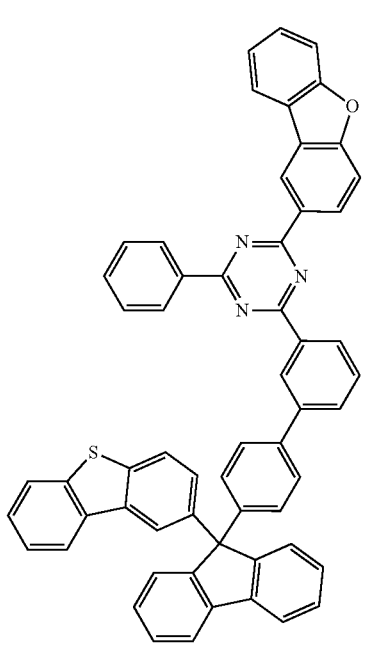

Inv 223
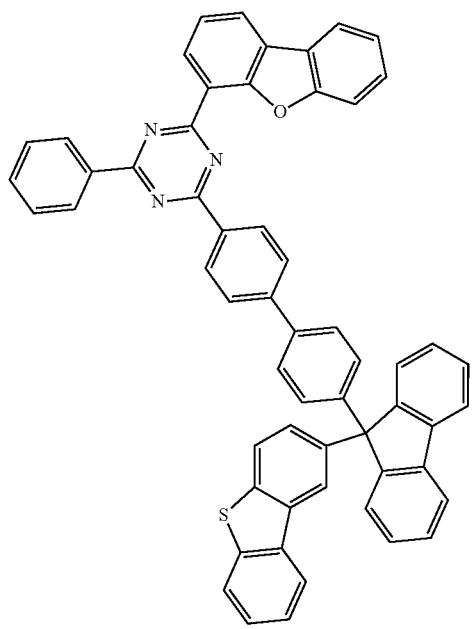
Inv 224
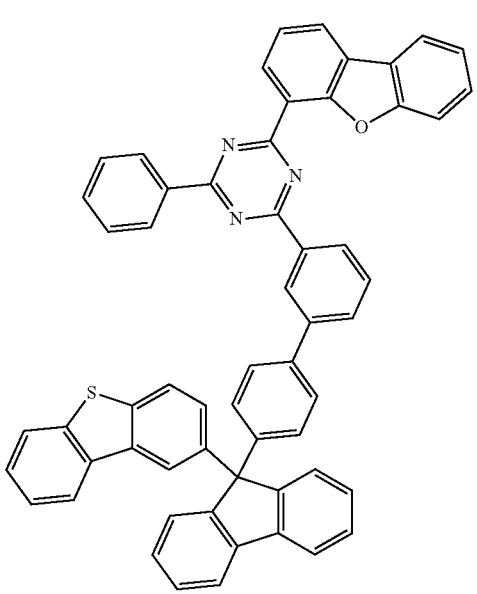
Inv 225
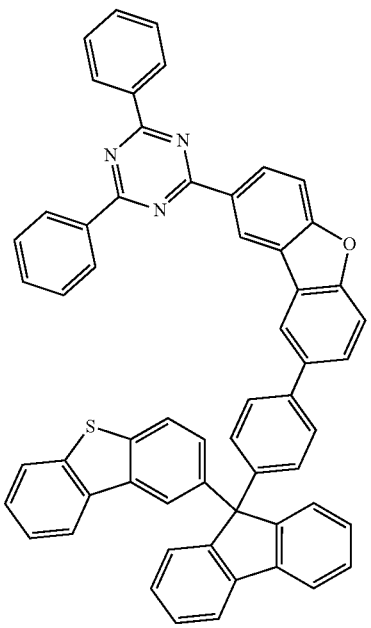
Inv 226
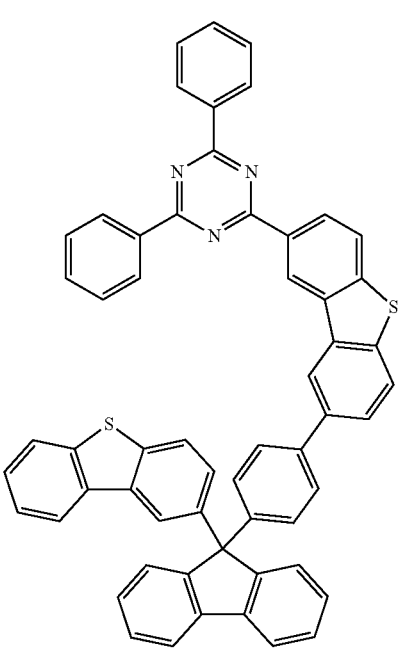

Inv 227
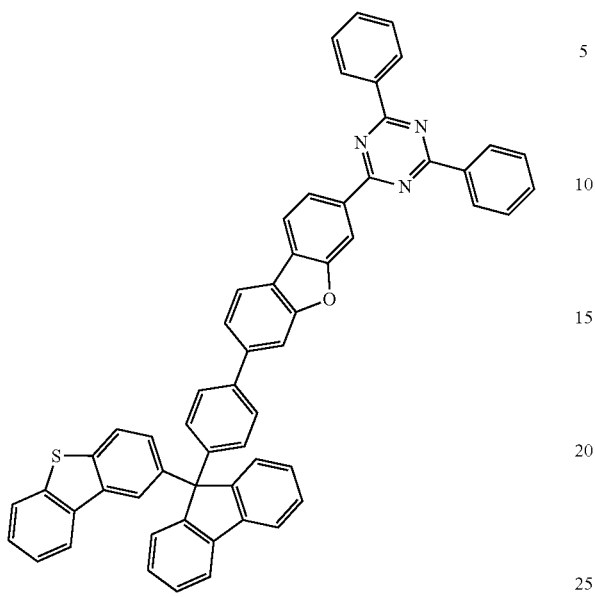
Inv 229
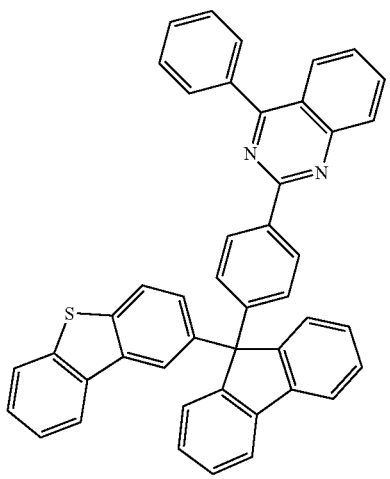
Inv 228
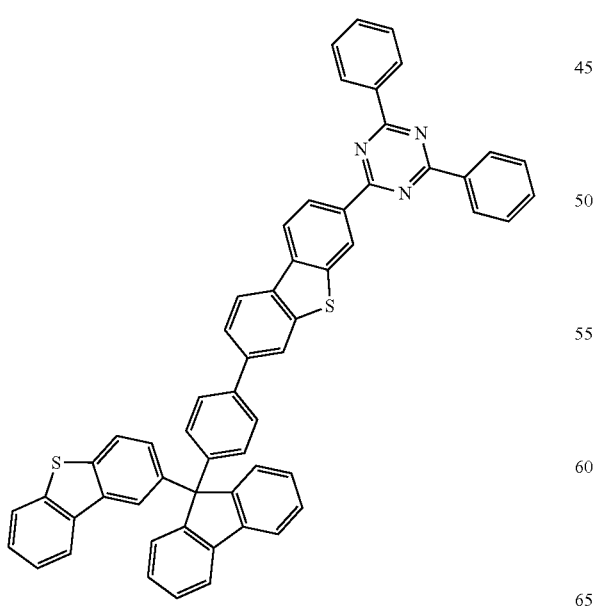
Inv 230
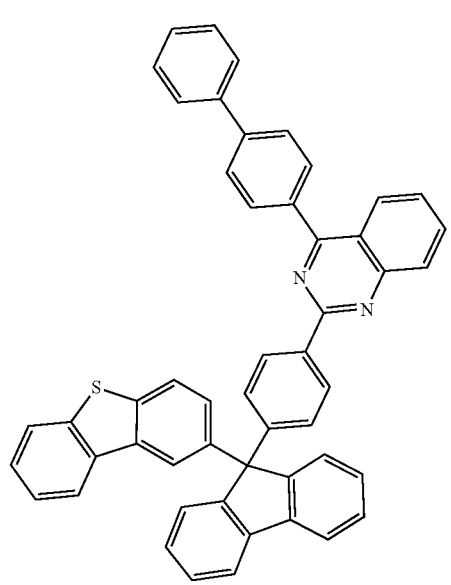

Inv 231
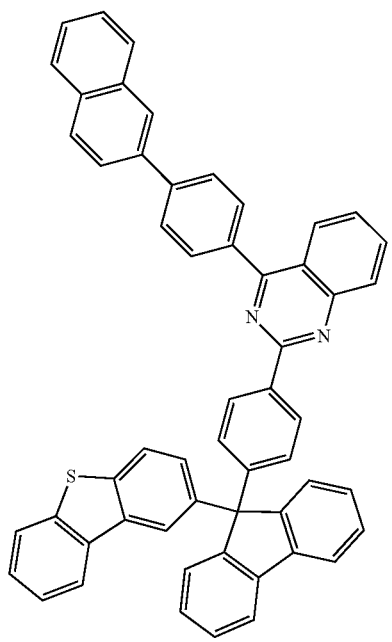
Inv 232
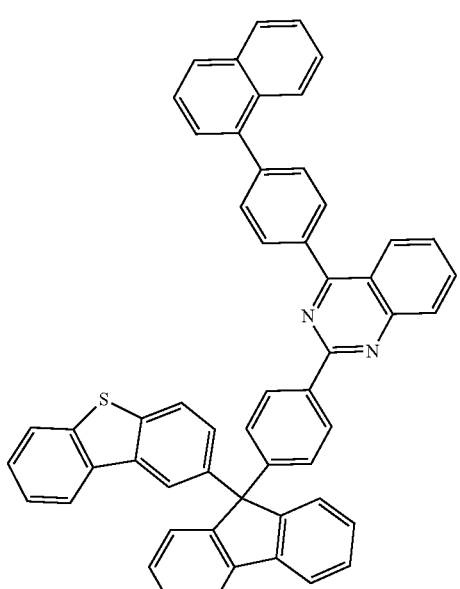
Inv 233
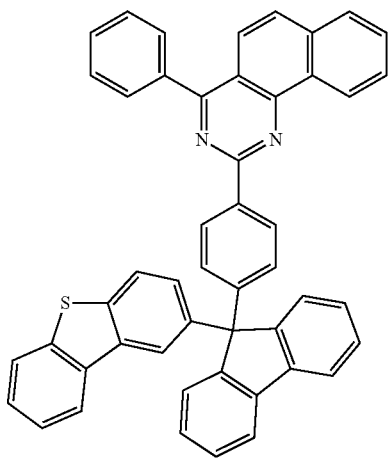
Inv 234
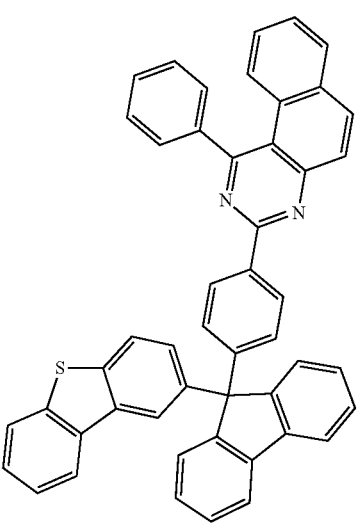
Inv 235
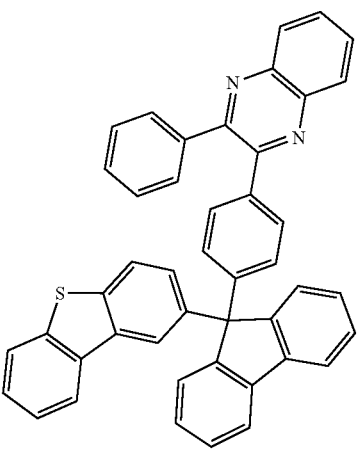

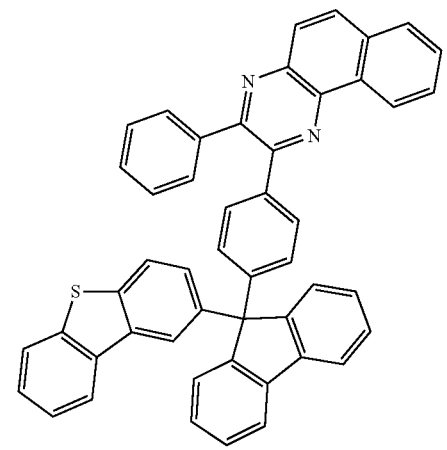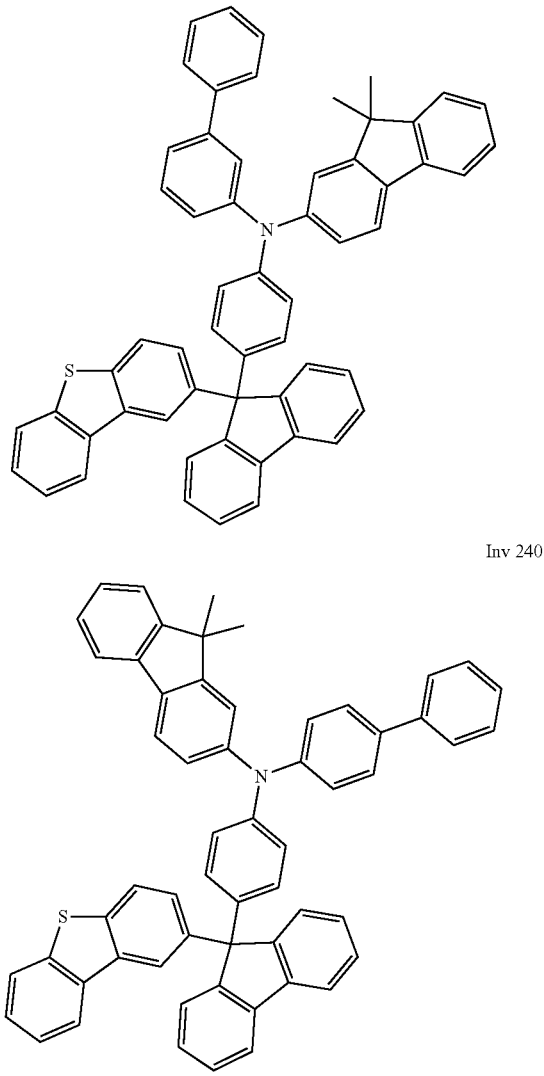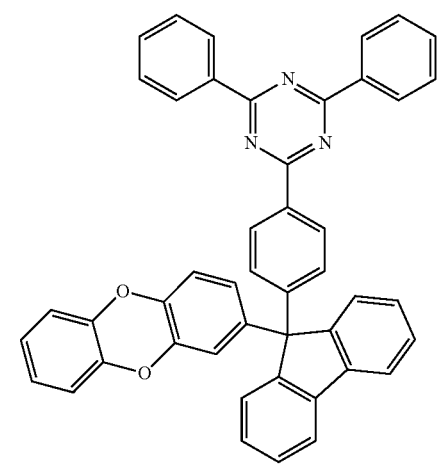

121
-continued
Inv 242
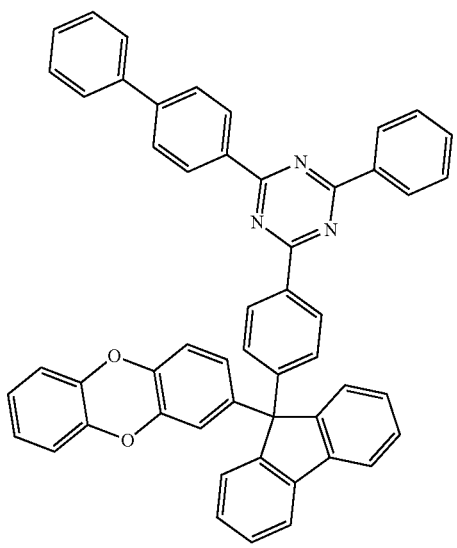
Inv 243
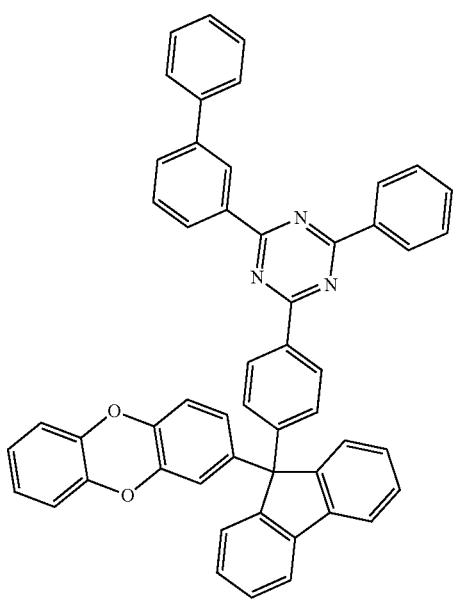
122
-continued
Inv 244
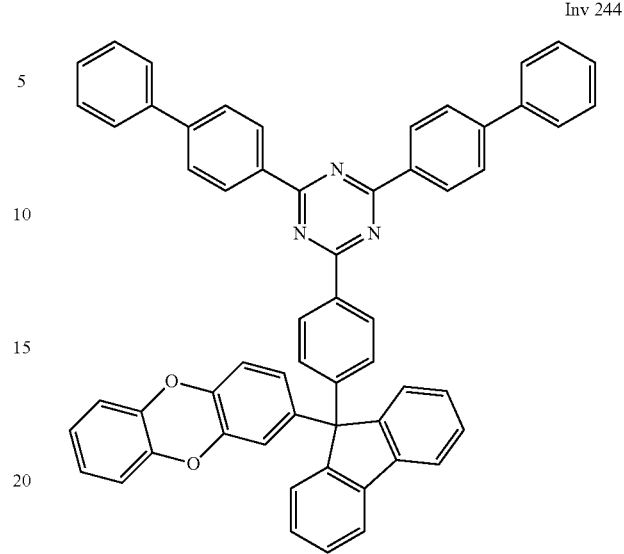
Inv 245
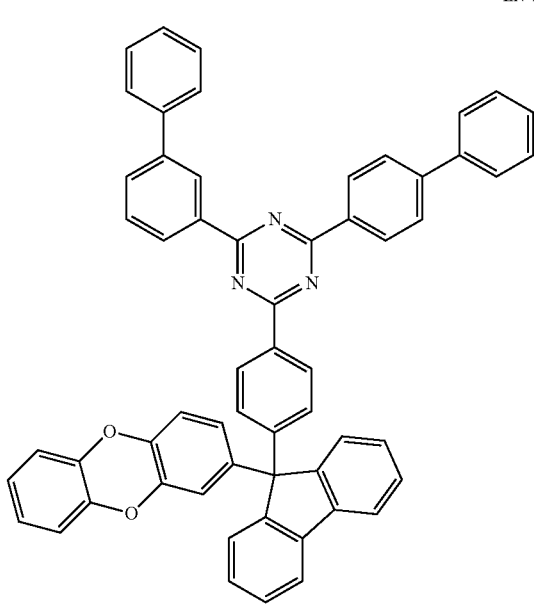

123
-continued
Inv 246
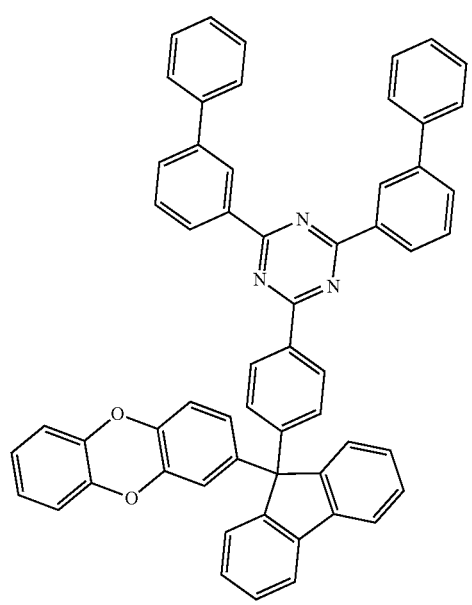
Inv 247
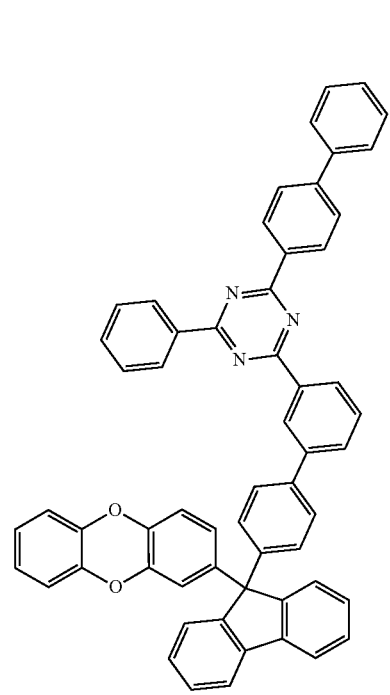
124
-continued
Inv 248
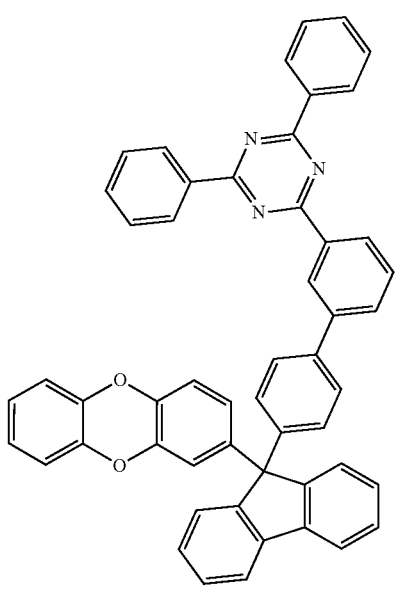
Inv 249

Inv 250
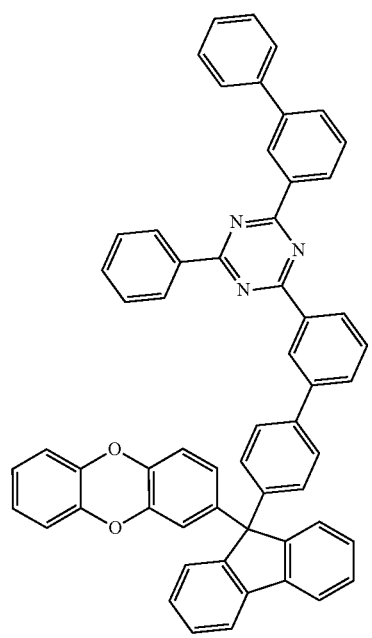
Inv 251
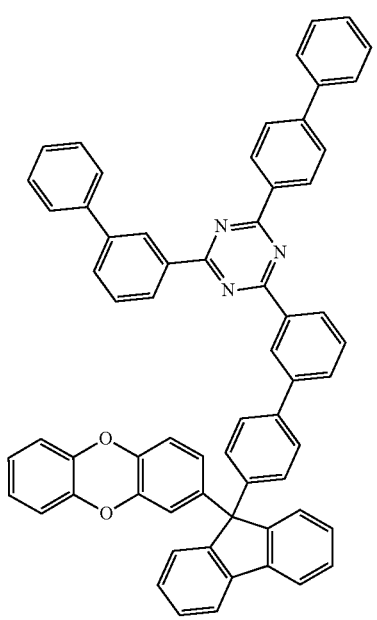
Inv 252
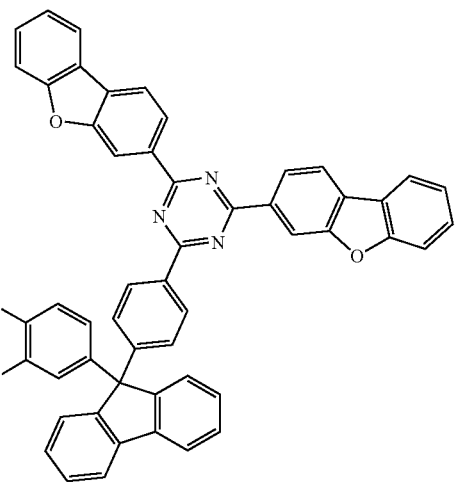
Inv 253
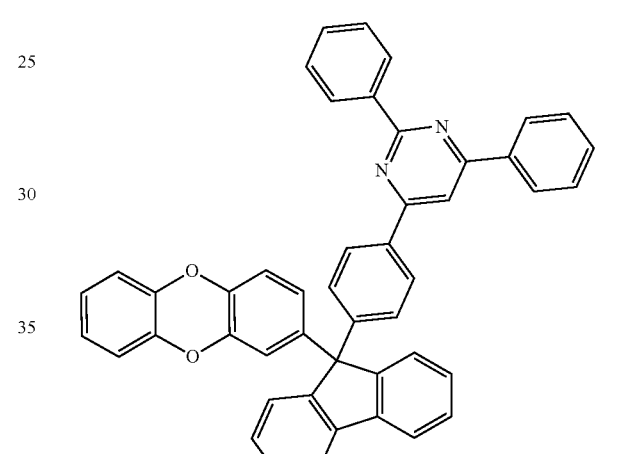
Inv 254
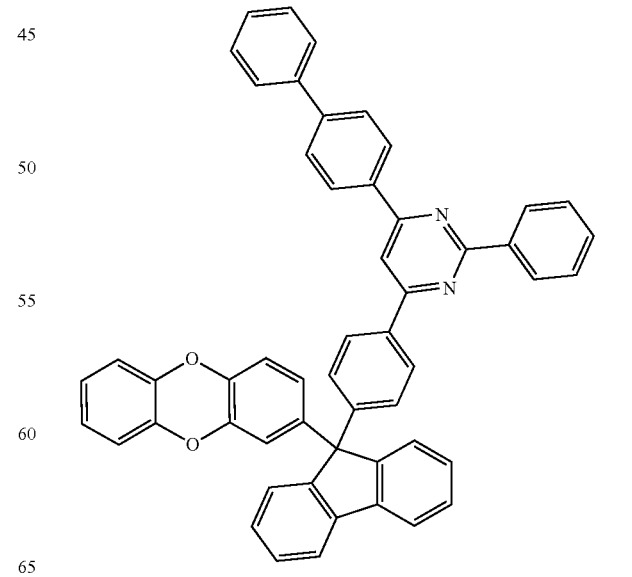

Inv 255
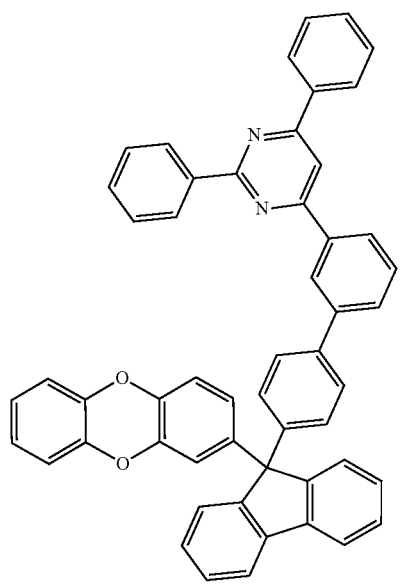
Inv 256
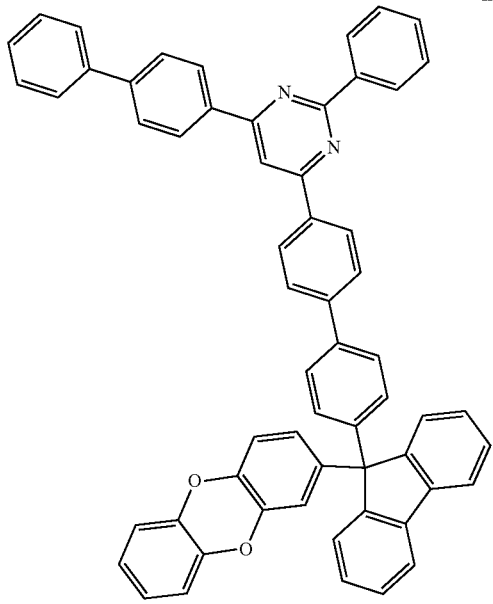
Inv 257
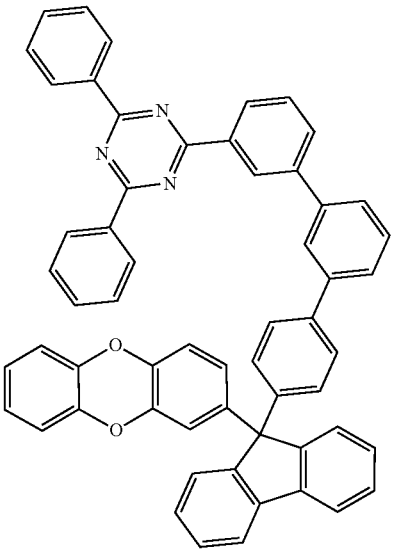
Inv 258
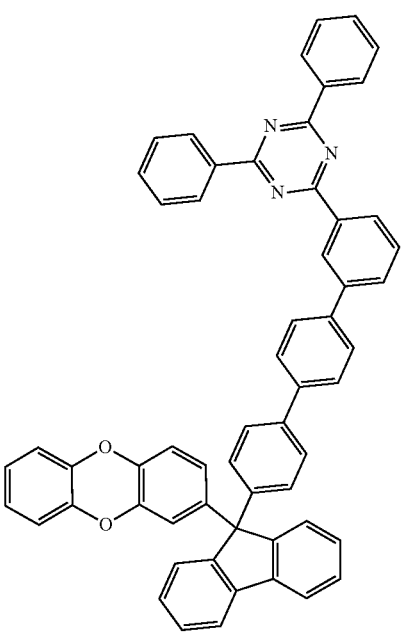

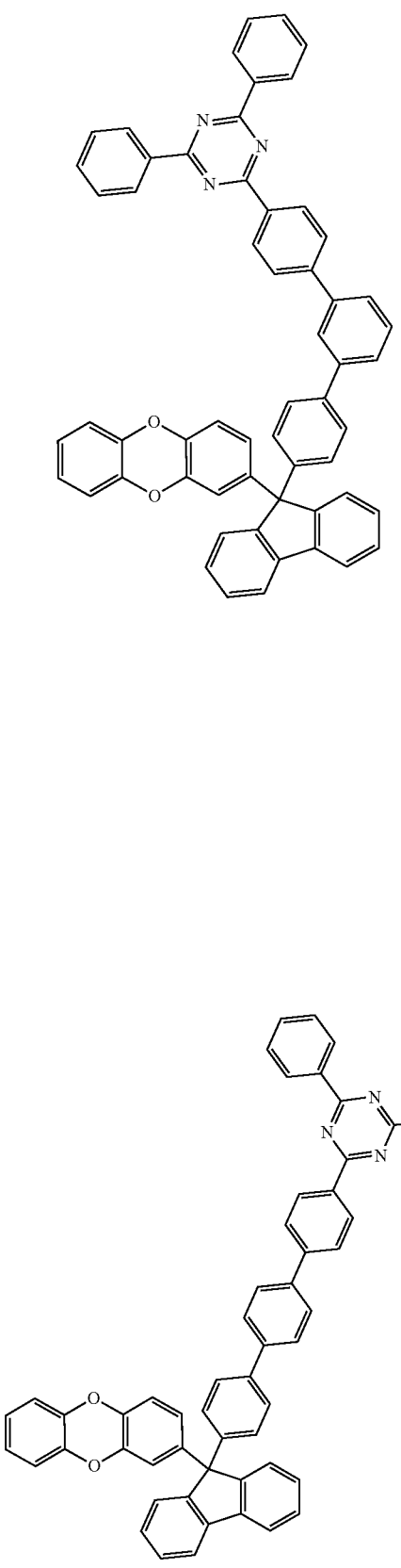
Inv 259
Inv 260
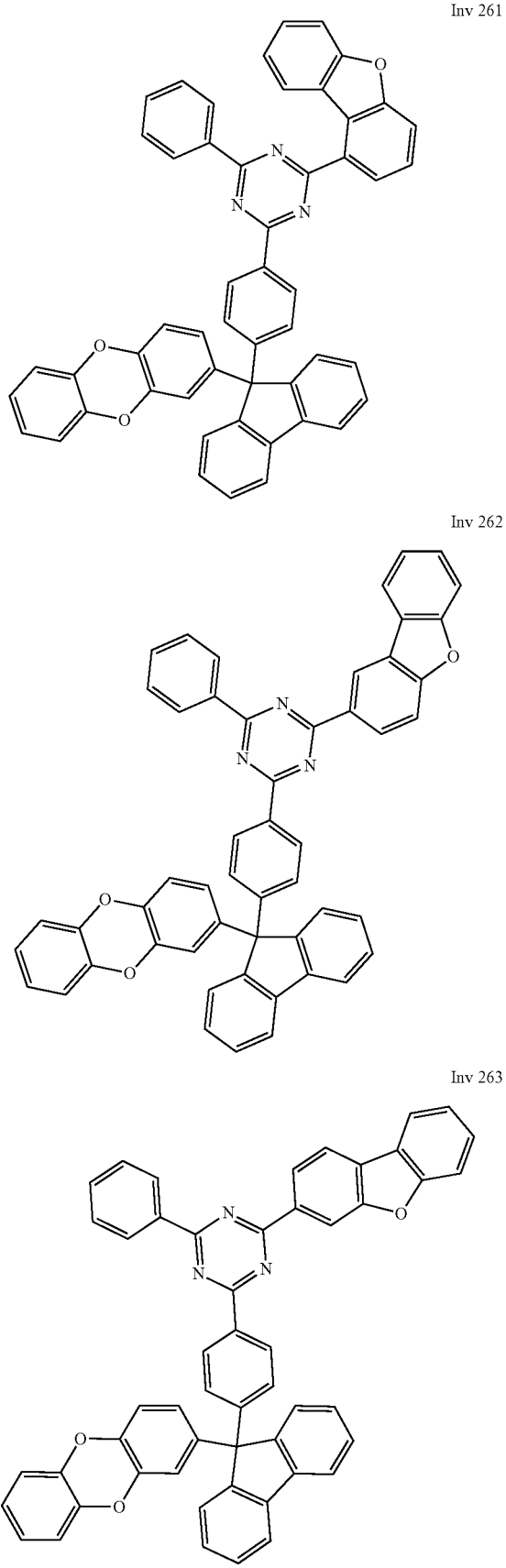
Inv 261
Inv 262
Inv 263

Inv 264
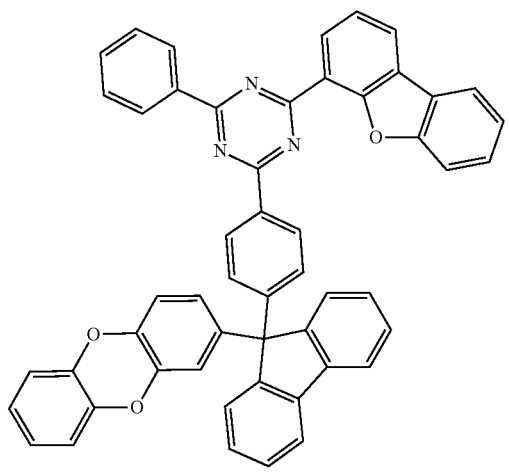
Inv 265
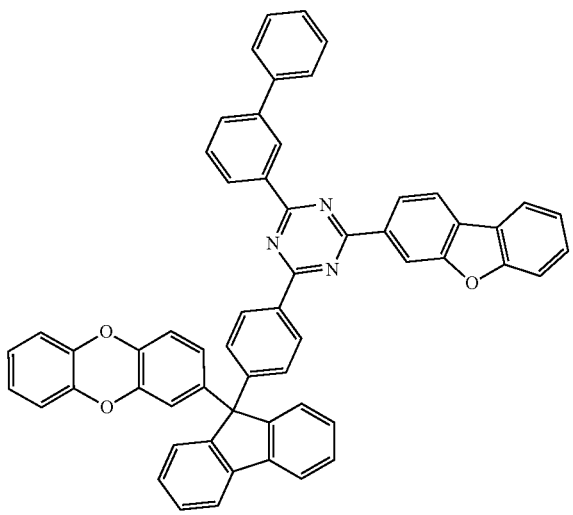
Inv 266
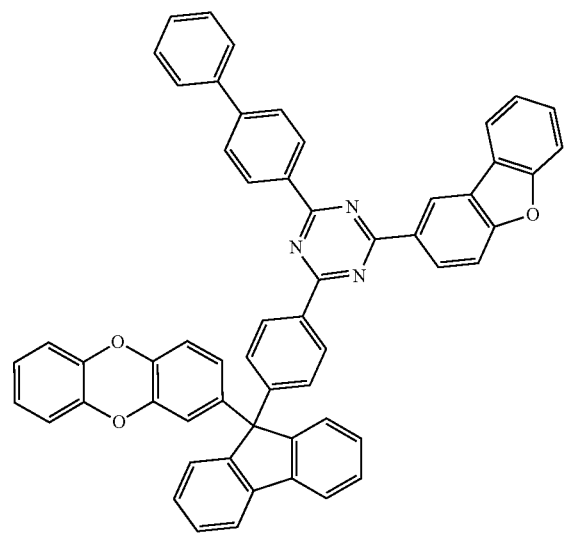
Inv 267
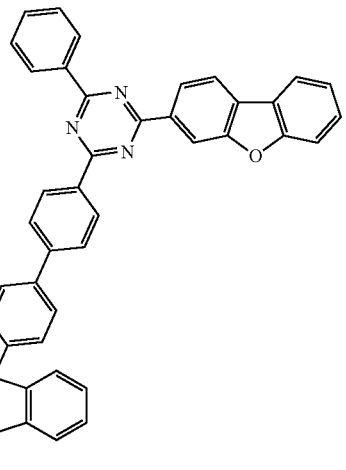
Inv 268
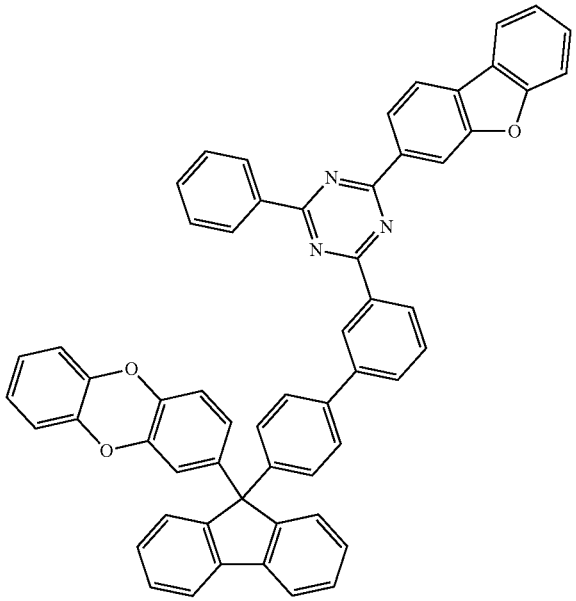
Inv 269
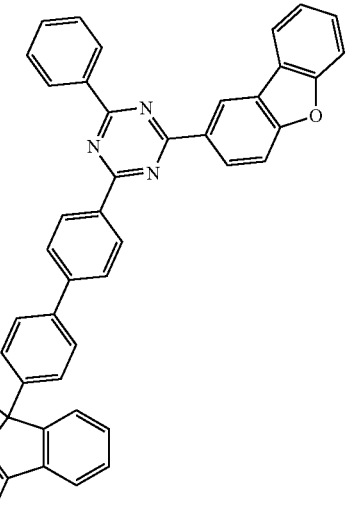

Inv 270
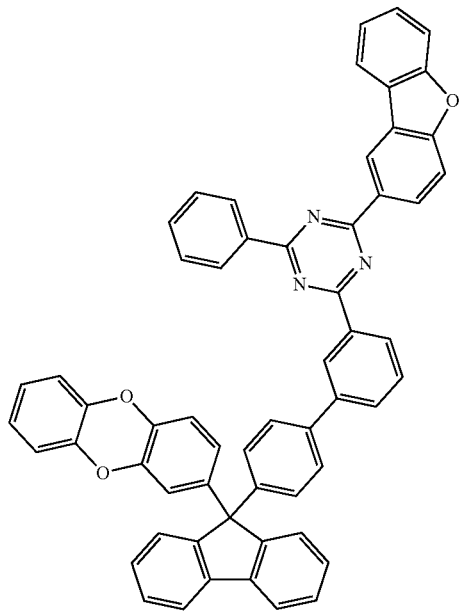
Inv 272
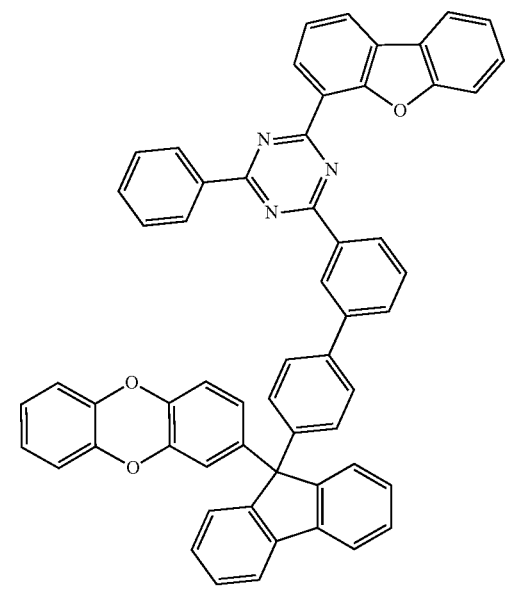
Inv 271
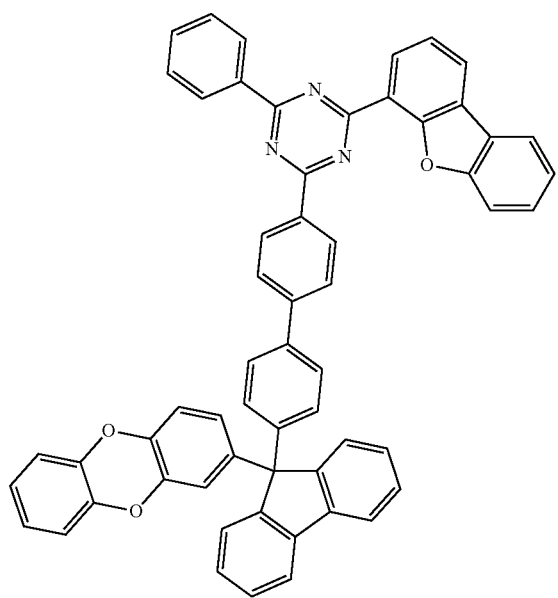
Inv 273
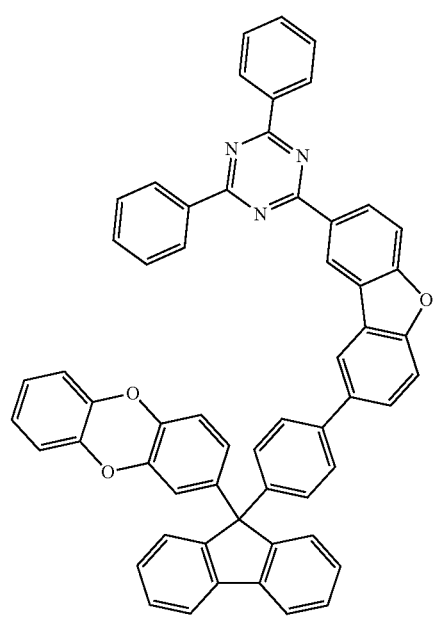

Inv 274
Inv 276
Inv 275
Inv 277
Inv 278
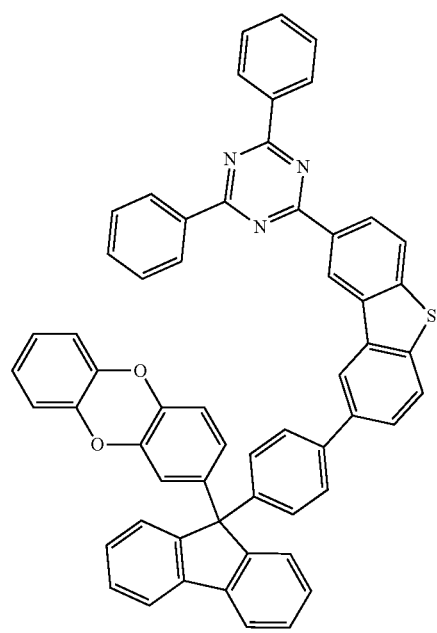
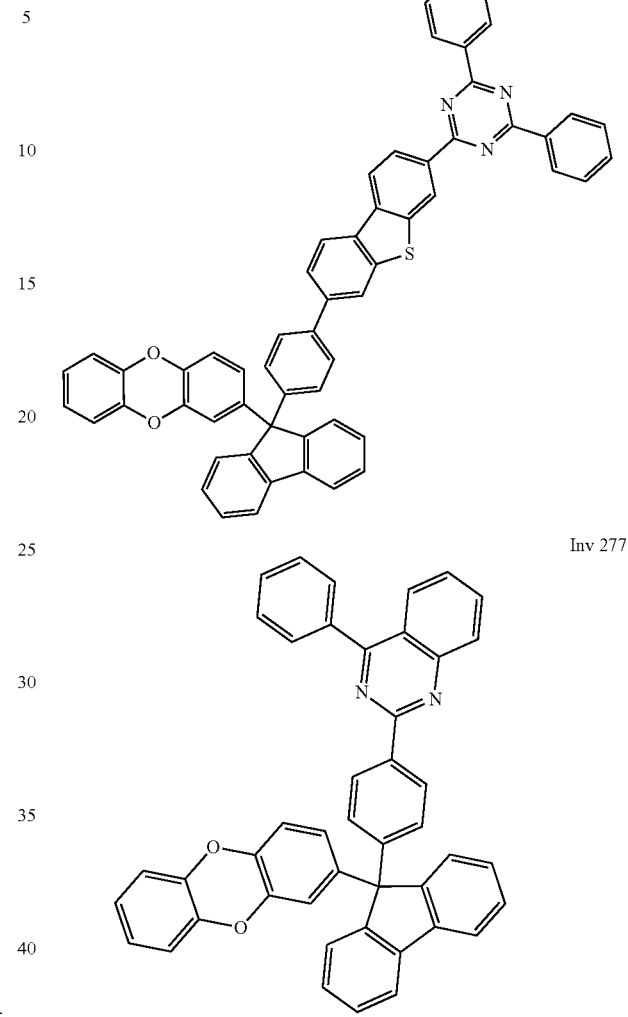
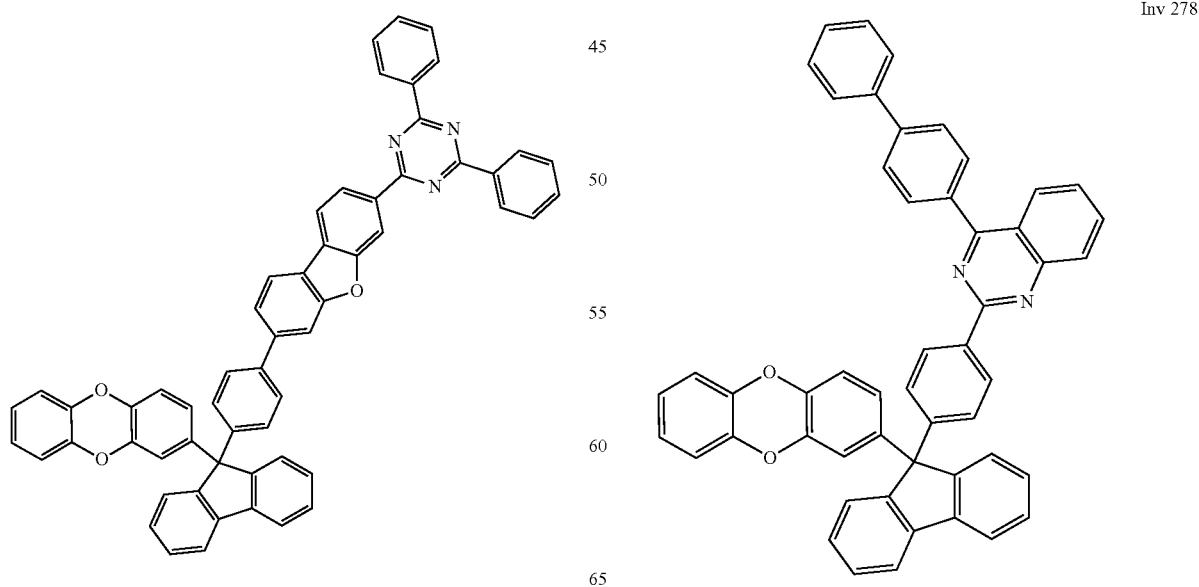

Inv 279
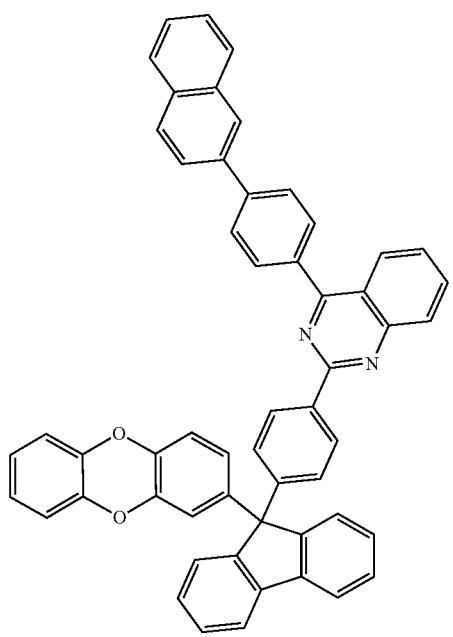
Inv 280
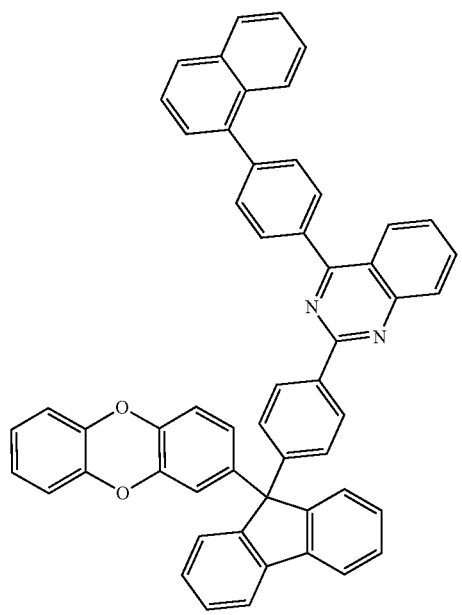
Inv 281
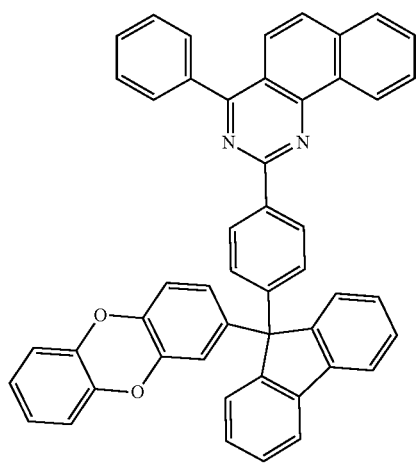
Inv 282
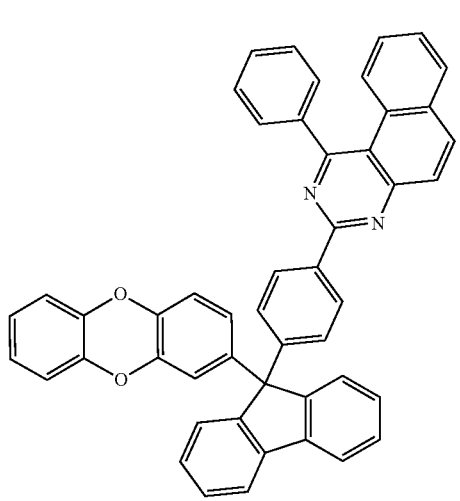
Inv 283
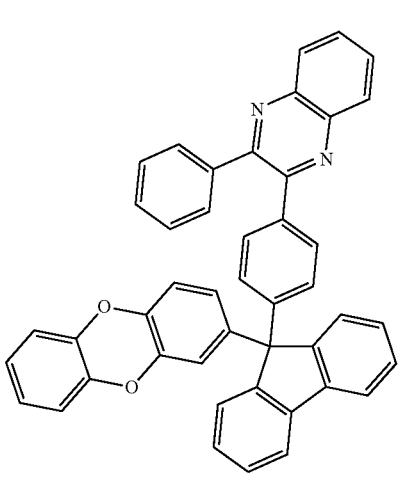

Inv 284
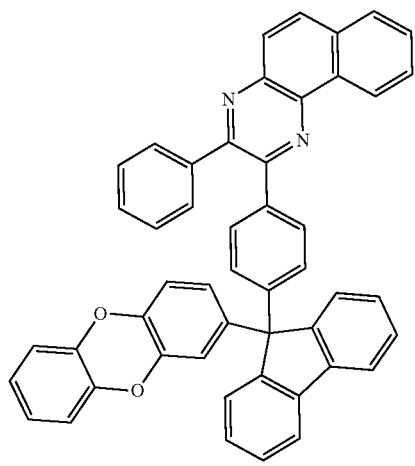
Inv 285
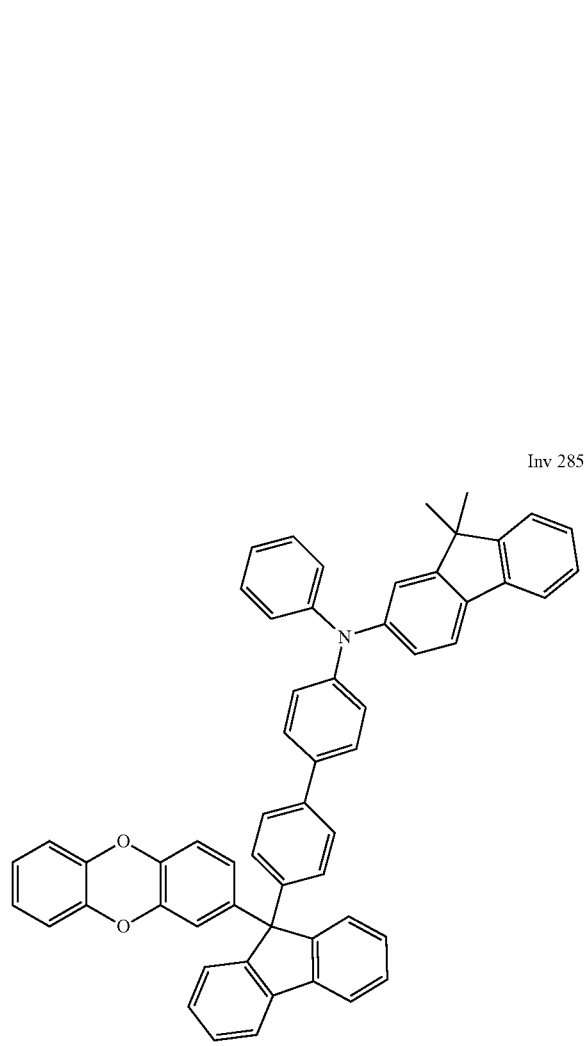
Inv 286
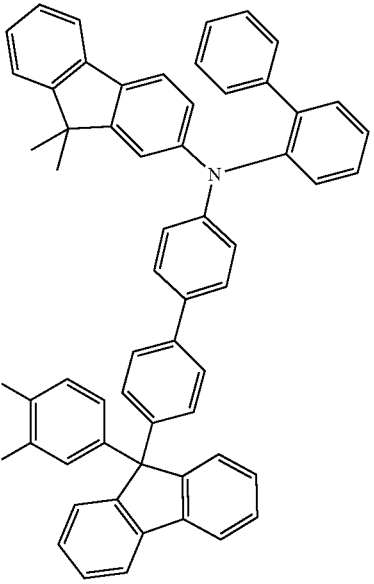
Inv 287
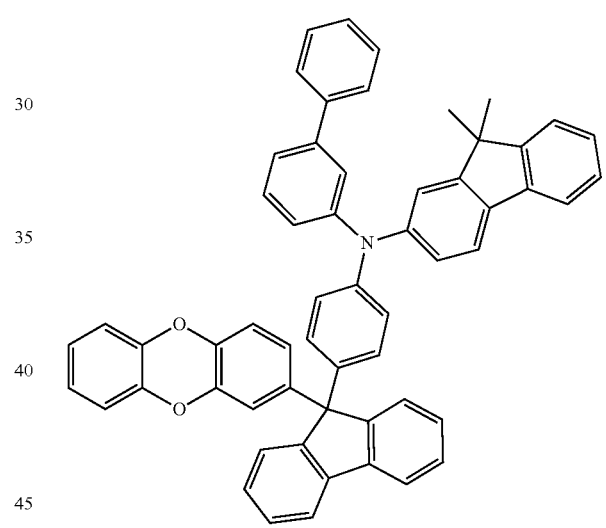
Inv 288
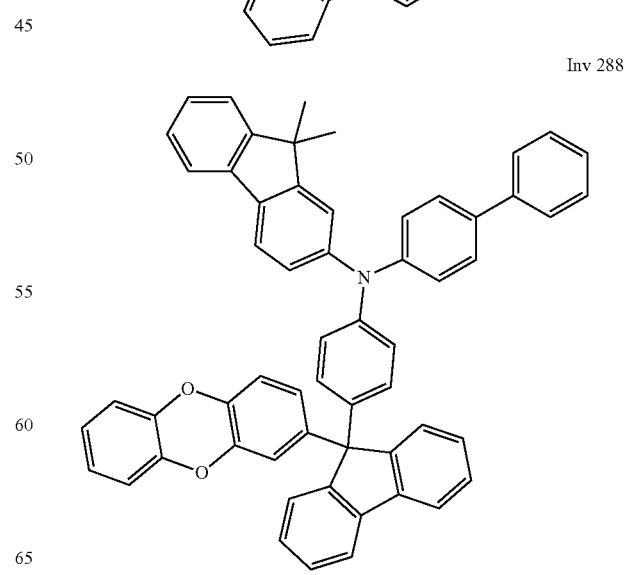

The compound of Chemical Formula 1 of the present invention may be synthesized using general synthesis methods (refer to Chem. Rev., 60: 313 (1960); *J. Chem. SOC.* 4482 (1955); Chem. Rev. 95: 2457 (1995) or the like). Detailed synthesis processes of the compounds of the present invention will be specifically described in synthesis examples to be described later.

2. Organic Electroluminescent Device

Meanwhile, another aspect of the present invention relates to an organic electroluminescent device (organic EL device) including the compound represented by Chemical Formula 1 according to the present invention.

Specifically, the present invention relates to an organic electroluminescent device including an anode, a cathode, and one or more organic material layers provided between the anode and the cathode, and at least one of the one or more organic material layers includes the compound represented by Chemical Formula 1. Herein, the compound may be used either alone or as a mixture of two or more.

The one or more organic material layers may be any one or more of a hole injection layer, a hole transport layer, a light emitting layer, a light emitting auxiliary layer, a lifetime improving layer, an electron transport layer, an electron transport auxiliary layer and an electron injection layer, and at least one organic material layer among these may include the compound represented by Chemical Formula 1.

The structure of the organic electroluminescent device according to the present invention described above is not particularly limited, but, when referring to FIG. 1 as one example, includes an anode (10) and a cathode (20) facing each other, and an organic layer (30) located between the anode (10) and the cathode (20). Herein, the organic layer (30) may include a hole transport layer (31), a light emitting layer (32) and an electron transport layer (34). In addition, a hole transport auxiliary layer (33) may be included between the hole transport layer (31) and the light emitting layer (32), and an electron transport auxiliary layer (35) may be included between the electron transport layer (34) and the light emitting layer (32).

When referring to FIG. 2 as another example of the present invention, the organic layer (30) may further include a hole injection layer (37) between the hole transport layer (31) and the anode (10), and may further include an electron injection layer (36) between the electron transport layer (34) and the cathode (20).

The hole injection layer (37) laminated between the hole transport layer (31) and the anode (10) in the present invention is a layer having a function of, as well as improving interfacial properties between ITO used as the anode and an organic material used as the hole transport layer (31), smoothing the ITO surface by being coated on the top of the ITO of which surface is not smooth, and those commonly used in the art may be used without particular limit, and for example, amine compounds may be used. However, the hole injection layer is not limited thereto.

In addition, the electron injection layer (36) is a layer laminated on the top of the electron transport layer (34) and having a function of facilitating electron injection from the cathode and eventually improving power efficiency, and is not particularly limited as long as it is commonly used in the art. For example, materials such as LiF, Liq, NaCl, CsF, $Li_2O$ or BaO may be used.

Although not shown in the drawings in the present invention, a light emitting auxiliary layer may be further included between the hole transport auxiliary layer (33) and the light emitting layer (32). The light emitting auxiliary layer may perform a role of adjusting a thickness of the organic layer (30) while performing a role of transporting holes to the light emitting layer (32). The light emitting auxiliary layer may include a hole transport material, and may be formed with the same material as the hole transport layer (31).

In addition, although not shown in the drawings in the present invention, a lifetime improving layer may be further included between the electron transport auxiliary layer (35) and the light emitting layer (32). Holes migrating to the light emitting layer (32) by getting on an ionization potential level in an organic light emitting device are not able to diffuse or migrate to the electron transport layer by being blocked by a high energy barrier of the lifetime improving layer, and consequently, the lifetime improving layer has a function of limiting the holes in the light emitting layer. Such a function of limiting the holes in the light emitting layer prevents the holes from diffusing to the electron transport layer migrating electrons by reduction, and therefore, suppresses a lifetime decrease phenomenon caused through an irreversible decomposition reaction by oxidation, and thereby contributes to improving a lifetime of the organic light emitting device.

Specifically, the novel organic compound according to the present invention has a structure in which a specific moiety is fixed at a number 9 position of phenyl fluorene and an EWG having an excellent electron transport ability bonds to the other side to form a basic skeleton, and various substituents bond to such a basic skeleton.

Among organic material layers generally included in an organic electroluminescent device, a phosphorescent light emitting layer includes a host and a dopant in order to increase color purity and increase luminous efficiency. Herein, the host needs to have a higher triplet energy gap than the dopant. In other words, in order to effectively provide phosphorescent light emission from the dopant, energy of the host in the lowest excited state needs to be higher than energy of the dopant in the lowest emitted state.

However, the compound represented by Chemical Formula 1 provided in the present invention has a wide singlet energy level and a high triplet energy level. Furthermore, by introducing a specific substituent to such a structure, a higher energy level than a dopant may be obtained when used as a host of a light emitting layer.

In addition, the compound has high triplet energy as described above, and therefore, may prevent excitons produced in the light emitting layer from diffusing (migrating) to an adjacent electron transport layer or hole transport layer. Accordingly, the compound according to the present invention may be used as a material of an organic material layer of an organic electroluminescent device, and preferably, may be used as a material of a light emitting layer (blue, green and/or red phosphorescent host material).

In addition, in the compound of Chemical Formula 1, the compound molecular weight significantly increases by introducing various substituents, particularly an aryl group and/or a heteroaryl group, to the basic skeleton, which enhances a glass transition temperature leading to high thermal stability compared to existing light emitting materials (for example, CBP). In addition, the compound is effective in suppressing crystallization of an organic material layer.

As described above, when using the compound represented by Chemical Formula 1 as a material of an organic material layer, preferably a light emitting layer material (blue, green and/or red phosphorescent host material), an electron transport layer/injection layer material, a hole transport layer/injection layer material, a light emitting auxiliary layer material, a lifetime improving layer material, of an organic electroluminescent device in the present invention, performance and lifetime properties of the organic electroluminescent device may be greatly enhanced. Such an organic electroluminescent device may resultantly maximize performance of a full color organic light emitting panel.

In addition, the organic electroluminescent device in the present invention has, as described above, an anode, one or more organic material layers and a cathode consecutively laminated, and in addition thereto, may further include an insulating layer or an adhesive layer at an interface between the electrode and the organic material layer.

Except that at least one or more of the organic material layers (for example, electron transport auxiliary layer) are formed to include the compound represented by Chemical Formula 1, the organic electroluminescent device of the present invention may be manufactured by forming other organic material layers and electrodes using materials and methods known in the art.

The organic material layer may be formed using a vacuum deposition method or a solution coating method. Examples of the solution coating method may include spin coating, dip coating, doctor blading, inkjet printing, thermal transfer method or the like, but are not limited thereto.

A substrate capable of being used in the present invention is not particularly limited, and silicon wafers, quartz, glass plates, metal plates, plastic films, sheets and the like may be used.

The anode material may be prepared using, for example, a conductor having high work function so as to have smooth hole injection, and examples thereof may include metals such as vanadium, chromium, copper, zinc or gold, or alloys thereof; metal oxides such as zinc oxide, indium oxide, indium tin oxide (ITO) or indium zinc oxide (IZO); combinations of metals and oxides such as ZnO:Al or SnO$_2$:Sb; conductive polymers such as polythiophene, poly(3-methylthiophene), poly[3,4-(ethylene-1,2-dioxy)thiophene] (PEDT), polypyrrole or polyaniline; carbon black, and the like, but are not limited thereto.

The cathode material may be prepared using, for example, a conductor having low work function so as to have smooth electron injection, and examples thereof may include metals such as magnesium, calcium, sodium, potassium, titanium, indium, yttrium, lithium, gadolinium, aluminum, silver, tin or lead, or alloys thereof; and multilayer-structured materials such as LiF/Al or LiO$_2$/Al, but are not limited thereto.

Hereinafter, the present invention will be described in detail with reference to examples as follows. However, the following examples are for illustrative purposes only, and the present invention is not limited to the following examples.

EXAMPLE

[Preparation Example 1] Synthesis of Core 1

<Step 1> Synthesis of (4-chlorophenyl)(2-phenylbenzo[d]oxazol-6-yl)methanone

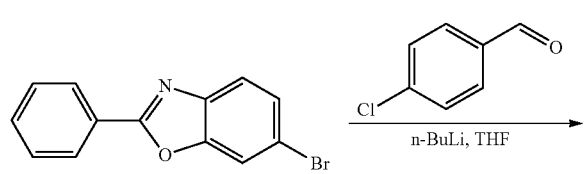

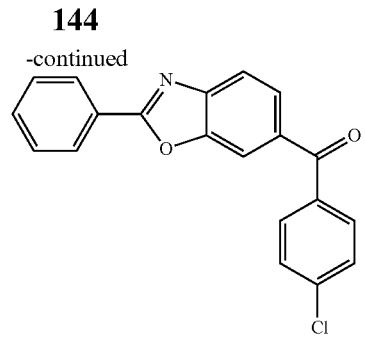

To a reactor, 6-bromo-2-phenylbenzo[d]oxazole (100 g, 364.8 mmol) was introduced, and after injecting THF (1000 ml) thereto, the result was introduced to a dry ice bath while stirring, and the inner temperature was set at −78□. 2.5 M n-BuLi (133.7 ml, 334.4 mmol) was slowly injected thereto using a syringe, and then the result was stirred for 30 minutes. 4-Chlorobenzaldehyde (42.7 g, 304 mmol) dissolved in THF (100 ml) was slowly added dropwise thereto. The temperature was slowly raised to room temperature. After concentrating the reaction material, I$_2$ (203.7 g, 802.6 mmol), K$_2$CO$_3$ (166.4 g, 1203.8 mmol) and t-BuOH (800 ml) were introduced thereto, and the result was heated under reflux for 7 hours. After the reaction was terminated, the result was extracted with ethyl acetate, and then filtered using MgSO$_4$.

After the reaction was terminated, the result was extracted with methylene chloride, and filtered using MgSO$_4$. After removing the solvent of the filtered organic layer, (4-chlorophenyl)(2-phenylbenzo[d]oxazol-6-yl)methanone (85.2 g, yield 70%), a target compound, was obtained using column chromatography.

$^1$H-NMR: δ 7.55 (m, 5H) 7.82 (m, 5H), 8.25 (m, 2H) [LCMS]: 333.7

<Step 2> Synthesis of [1,1'-biphenyl]-2-yl(4-chlorophenyl)(2-phenylbenzo[d]oxazol-6-yl)methanol

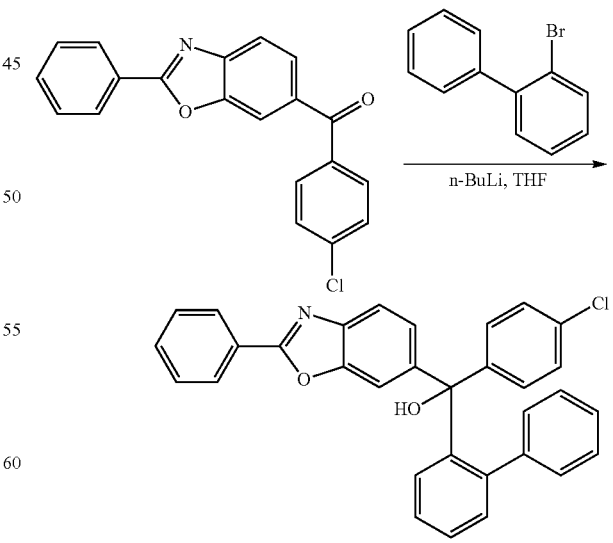

To a reactor, 2-bromo-1,1'-biphenyl (71.4 g, 306.3 mmol) was introduced, and after injecting THF (500 ml) thereto, the result was introduced to a dry ice bath while stirring, and the inner temperature was set at −78□. 2.5 M n-BuLi (112.3 ml, 280.8 mmol) was slowly injected thereto using a syringe, and then the result was stirred for 30 minutes. (4-Chlorophenyl)(2-phenylbenzo[d]oxazol-6-yl)methanone (85.2 g, 255.26 mmol) synthesized in <Step 1> of Preparation Example 1 was dissolved in THF (500 ml) and then slowly added dropwise thereto. The temperature was slowly raised to room temperature to terminate the reaction. After the reaction was terminated, the result was extracted with ethyl acetate, and then filtered using MgSO₄. After removing the solvent of the filtered organic layer, [1,1'-biphenyl]-2-yl(4-chlorophenyl)(2-phenylbenzo[d]oxazol-6-yl)methanol (79.7 g, yield 64%), a target compound, was obtained using column chromatography.

¹H-NMR: δ 6.72 (s, 1H), 7.23 (m, 4H), 7.48 (m, 10H), 7.65 (m, 4H) 7.8 (d, 1H), 8.22 (m, 2H) [LCMS]: 487.9

<Step 3> Synthesis of 6-(9-(4-chlorophenyl)-9H-fluoren-9-yl)-2-phenylbenzo[d]oxazole

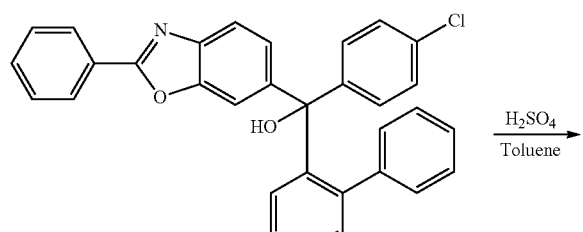

In a reactor, [1,1'-biphenyl]-2-yl(4-chlorophenyl)(2-phenylbenzo[d]oxazol-6-yl)methanol (79.7 g, 163.3 mmol) synthesized in <Step 2> was dissolved in toluene (1000 ml), and sulfuric acid (20 ml) was added thereto while vigorously stirring. The result was stirred for 8 hours after raising the temperature to 1000, and then cooled to room temperature. After the reaction was terminated, the result was extracted with methylene chloride, and then filtered using MgSO₄. After removing the solvent of the filtered organic layer, 6-(9-(4-chlorophenyl)-9H-fluoren-9-yl)-2-phenylbenzo[d]oxazole (55.2 g, yield 72%), a target compound, was obtained using column chromatography.

¹H-NMR: δ 7.18 (m, 4H), 7.35 (m, 7H), 7.62 (m, 5H), 7.9 (m, 2H), 8.26 (m, 2H)]
[LCMS]: 469.9

<Step 4> Synthesis of Core 1

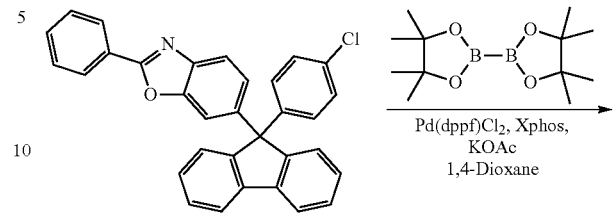

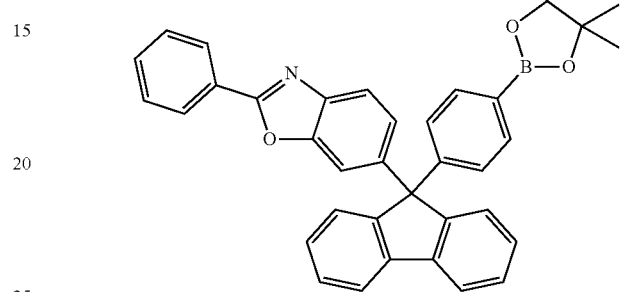

6-(9-(4-Chlorophenyl)-9H-fluoren-9-yl)-2-phenylbenzo[d]oxazole (55.2 g, 117.4 mmol) synthesized in <Step 3> of Preparation Example 1, 4,4,4',4',5,5,5',5'-octamethyl-2,2'-bi(1,3,2-dioxaborolane) (35.8 g, 140.96 mmol), Pd(dppf)Cl₂ (2.57 g, 3.52 mmol), KOAc (34.5 g, 352.2 mmol) and Xphos (5.6 g, 11.74 mmol) were introduced to 1,4-dioxane (1000 ml), and the result was heated under reflux for 12 hours. After the reaction was terminated, the result was extracted with methylene chloride, and filtered using MgSO₄. After removing the solvent of the filtered organic layer, Core 1 (45.5 g, yield 69%), a target compound, was obtained using column chromatography.

¹H-NMR: δ 1.55 (s, 12H), 7.15 (m, 4H), 7.32 (m, 2H), 7.4 (m, 2H), 7.48 (s, 1H), 7.62 (m, 5H), 7.81 (d, 2H), 7.95 (m, 2H), 8.25 (m, 2H)
[LCMS]: 561.4

[Preparation Example 2] Synthesis of Core 2

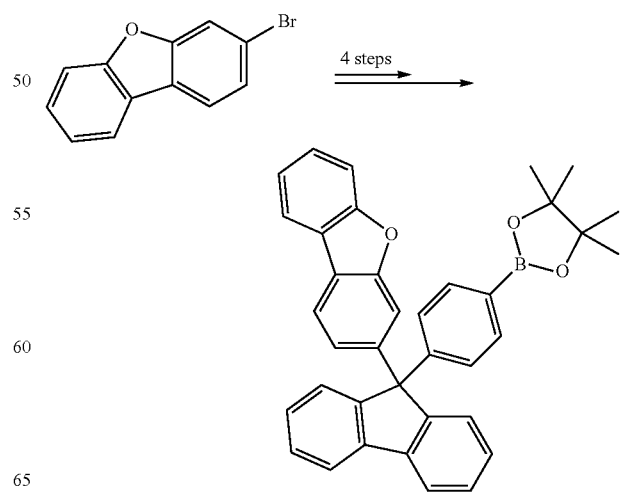

Core 2 (48 g, yield 22%) was obtained in the same manner as in [Preparation Example 1] except that 3-bromodibenzo[b,d]furan was used as the reaction material of <Step 4>.

¹H-NMR: δ 1.52 (s, 12H), 6.98 (d, 1H), 7.25 (m, 2H), 7.39 (m, 7H), 7.57 (m, 3H), 7.75 (m, 2H), 7.83 (d, 1H), 7.9 (m, 2H), 8.02 (d, 1H)

[LCMS]: 534.4

[Preparation Example 3] Synthesis of Core 3

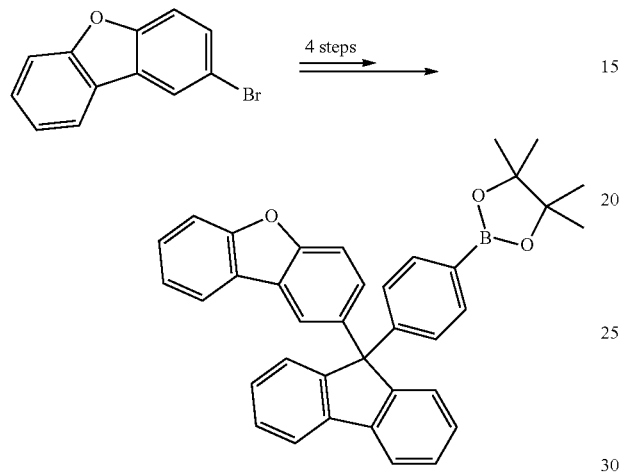

Core 3 (46 g, yield 21%) was obtained in the same manner as in [Preparation Example 1] except that 2-bromodibenzo[b,d]furan was used as the reaction material of <Step 4>.

¹H-NMR: δ 1.48 (s, 12H), 7.09 (d, 1H), 7.18 (m, 2H), 7.35 (m, 7H), 7.54 (m, 4H), 7.75 (d, 2H), 7.92 (m, 2H), 7.98 (d, 1H)

[LCMS]: 534.4

[Preparation Example 4] Synthesis of Core 4

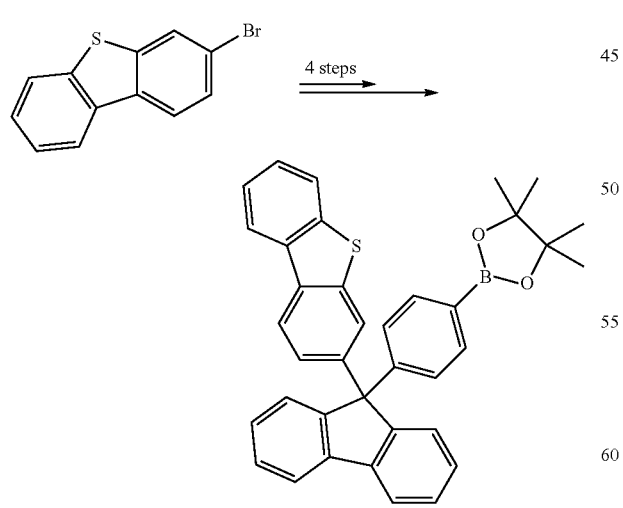

Core 4 (42 g, yield 20%) was obtained in the same manner as in [Preparation Example 1] except that 3-bromodibenzo[b,d]thiophene was used as the reaction material of <Step 1>.

¹H-NMR: δ 1.50 (s, 12H), 7.18 (m, 2H), 7.37 (m, 5H), 7.56 (m, 4H), 7.75 (m, 3H), 7.93 (m, 3H), 8.05 (d, 1H), 8.45 (d, 1H)

[LCMS]: 550.5

[Preparation Example 5] Synthesis of Core 5

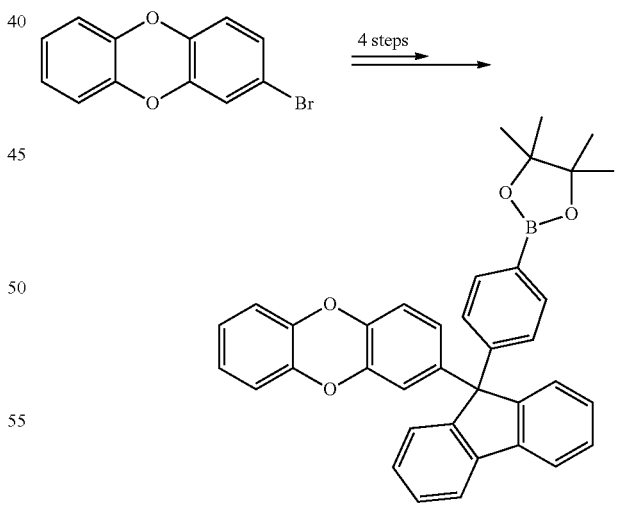

Core 5 (44 g, yield 21%) was obtained in the same manner as in [Preparation Example 4] except that 2-bromodibenzo[b,d]thiophene was used as the reaction material of <Step 4>.

¹H-NMR: δ 1.52 (s, 12H), 7.15 (m, 2H), 7.27 (m, 3H), 7.38 (m, 2H), 7.55 (m, 4H), 7.63 (s, 1H), 7.8 (m, 3H), 7.93 (m, 3H), 8.45 (d, 1H)

[LCMS]: 550.5

[Preparation Example 6] Synthesis of Core 6

Core 6 (41 g, yield 19%) was obtained in the same manner as in [Preparation Example 4] except that 2-bromodibenzo[b,e][1,4]dioxin was used as the reaction material of <Step 4>.

¹H-NMR: δ 1.5 (s, 12H), 6.82 (m, 4H), 6.94 (m, 3H), 7.2 (m, 2H), 7.32 (m, 2H), 7.38 (m, 2H), 7.55 (m, 2H), 7.75 (m, 2H), 8.20 (m, 2H)

[LCMS]: 550.4

SYNTHESIS EXAMPLE

[Synthesis Example 1] Synthesis of Compound Inv 1

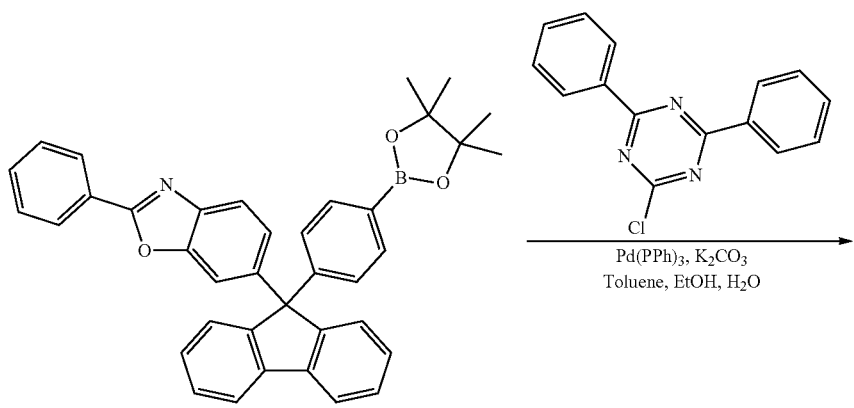

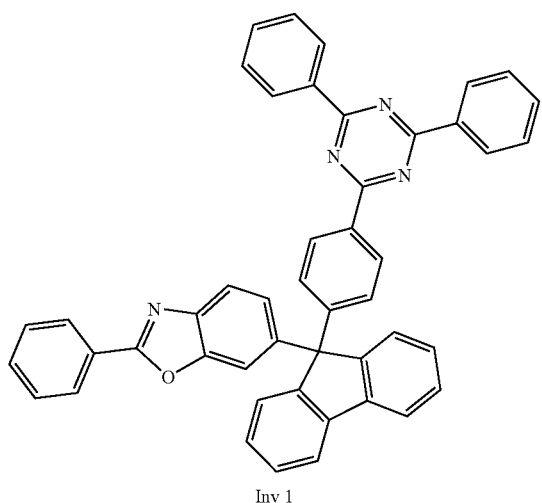

Inv 1

Core 1 (5 g, 8.9 nmmol) of [Preparation Example 1], 2-chloro-4,6-diphenyl-1,3,5-triazine (2.86 g, 8.9 nmmol), Pd(PPh$_3$)$_4$ (0.3 g, 0.26 nmmol) and K$_2$CO$_3$ (3.7 g, 26.7 nmmol) were introduced to toluene (80 ml), EtOH (20 ml) and H$_2$O (20 ml), and the result was heated under reflux for 12 hours. After the reaction was terminated, the result was extracted with methylene chloride, and filtered using MgSO$_4$. After removing the solvent of the filtered organic layer, Inv 1 (4.3 g, yield 72%), a target compound, was obtained using column chromatography.

[LCMS]: 666.7

[Synthesis Example 2] Synthesis of Compound Inv 12
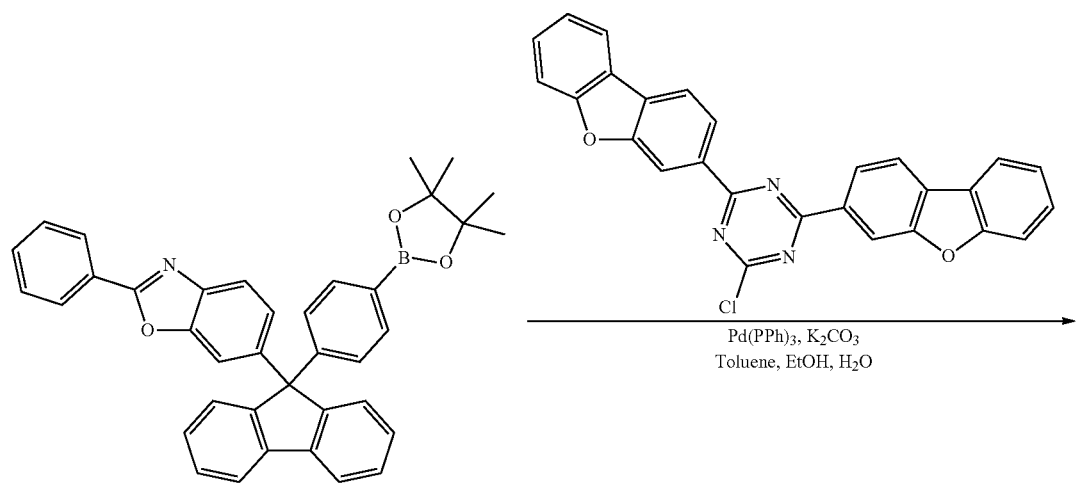
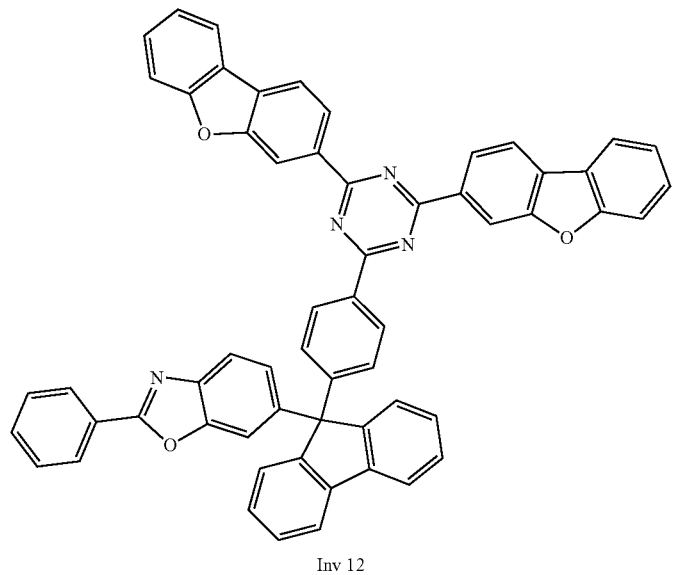
Inv 12
Inv 12 (5.6 g, yield 74%), a target compound, was obtained in the same manner as in [Synthesis Example 1] except that 2-chloro-4,6-bis(dibenzo[b,d]furan-3-yl)-1,3,5-triazine (4.7 g, 10.68 mmol) was used instead of 2-chloro-4,6-diphenyl-1,3,5-triazine.
[LCMS]: 846.9

[Synthesis Example 3] Synthesis of Compound Inv 18

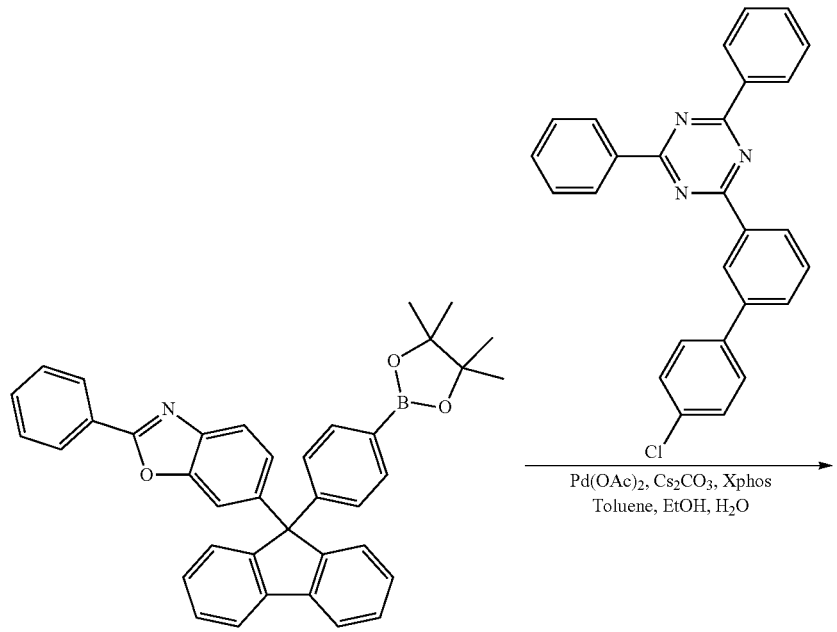

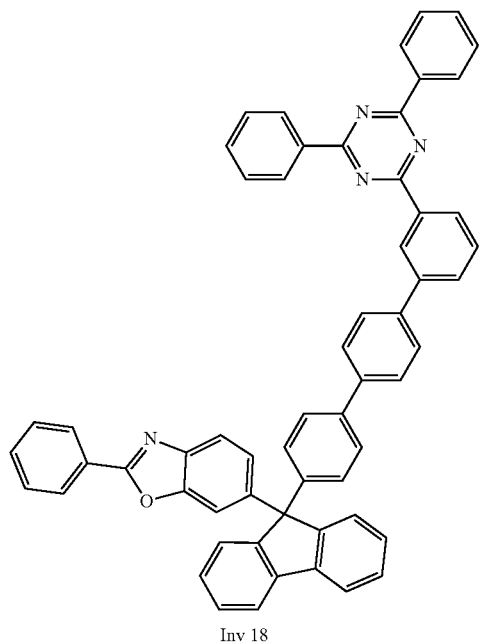

Inv 18

Core 1 (5 g, 8.9 mmol), 2-(4'-chloro-[1,1'-biphenyl]-3-yl)-4,6-diphenyl-1,3,5-triazine (4.5 g, 10.68 mmol), Pd(OAc)$_2$ (0.06 g, 0.26 mmol), Cs$_2$CO$_3$ (5.8 g, 17.8 mmol) and Xphos (0.42 g, 0.9 mmol) were introduced to toluene (80 ml), EtOH (20 ml) and H$_2$O (20 ml), and the result was heated under reflux for 12 hours. After the reaction was terminated, the result was extracted with methylene chloride, and filtered using MgSO$_4$. After removing the solvent of the filtered organic layer, Inv 18 (5.1 g, yield 70%), a target compound, was obtained using column chromatography.

[LCMS]: 818.9

[Synthesis Example 4] Synthesis of Compound Inv 41
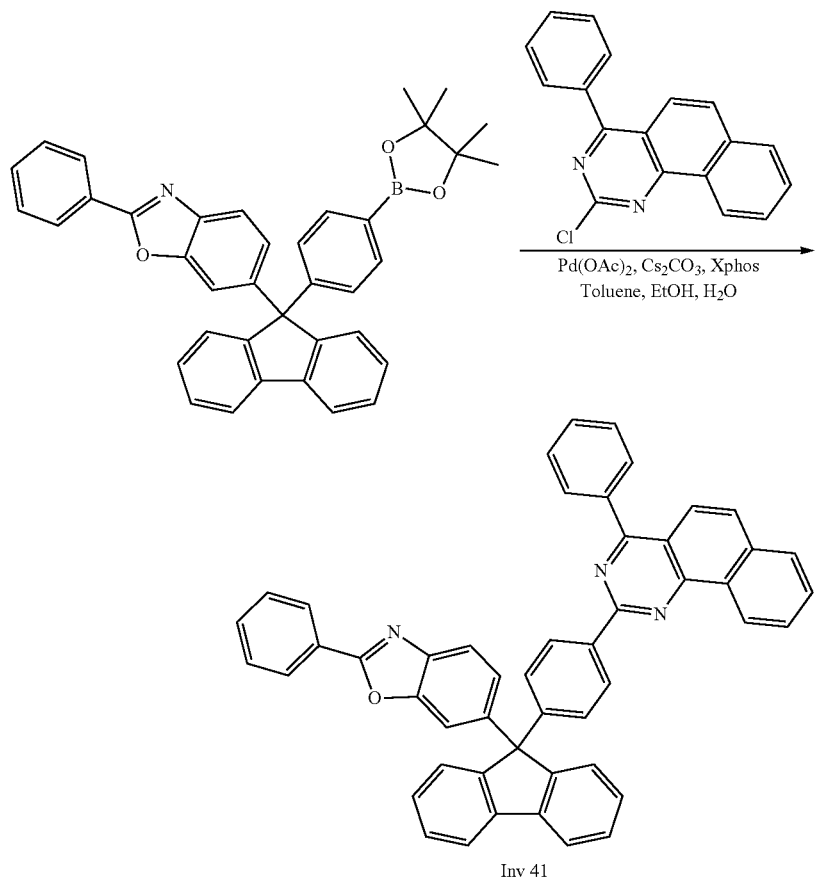
Inv 41
Inv 41 (4.2 g, yield 68%), a target compound, was obtained in the same manner as in [Synthesis Example 3] except that 2-chloro-4-phenylbenzo[h]quinazoline (3.1 g, 10.68 mmol) was used instead of 2-(4'-chloro-[1,1'-biphenyl]-3-yl)-4,6-diphenyl-1,3,5-triazine.
[LCMS]: 689.8
[Synthesis Example 5] Synthesis of Compound Inv 48
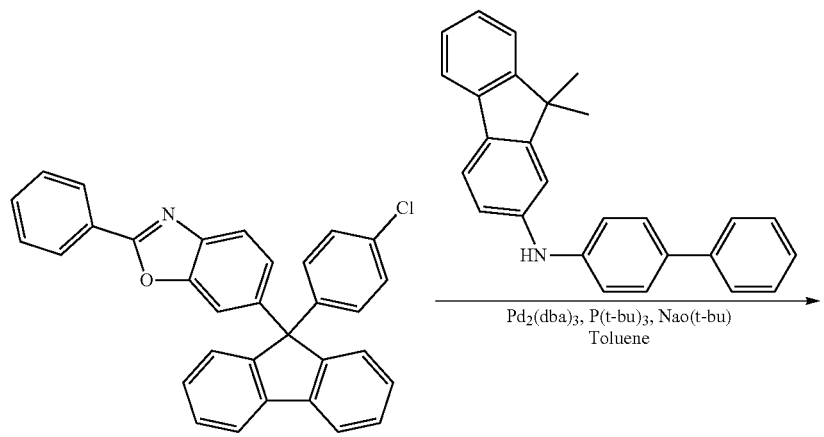

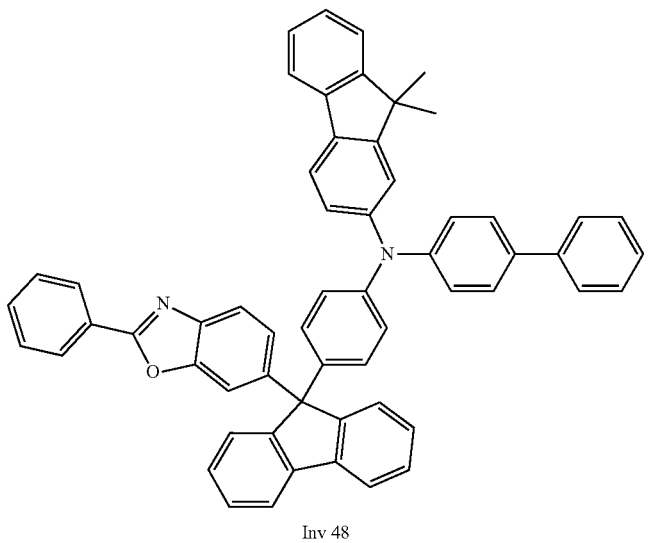

Inv 48

6-(9-(4-Chlorophenyl)-9H-fluoren-9-yl)-2-phenylbenzo[d]oxazole (5.0 g, 10.64 mmol) obtained in <Step 3> of [Preparation Example 1], N-([1,1'-biphenyl]-4-yl)-9,9-dimethyl-9H-fluoren-2-amine (4.61 g, 12.76 mmol), Pd$_2$(dba)$_3$ (0.29 g, 0.32 mmol), P(t-Bu)$_3$ (0.21 g, 10.64 mmol) and sodium tert-butoxide (2.04 g, 21.27 mmol) were introduced to toluene (80 ml), and the result was stirred for 12 hours at 110. After the reaction was terminated, the result was extracted with methylene chloride, and filtered using MgSO$_4$. After removing the solvent of the filtered organic layer, Inv 48 (5.5 g, yield 65%), a target compound, was obtained using column chromatography.

[LCMS]: 795

[Synthesis Example 6] Synthesis of Compound Inv 50

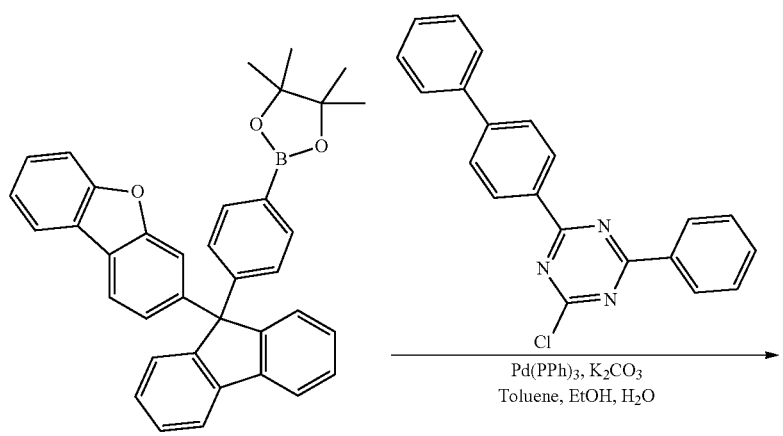

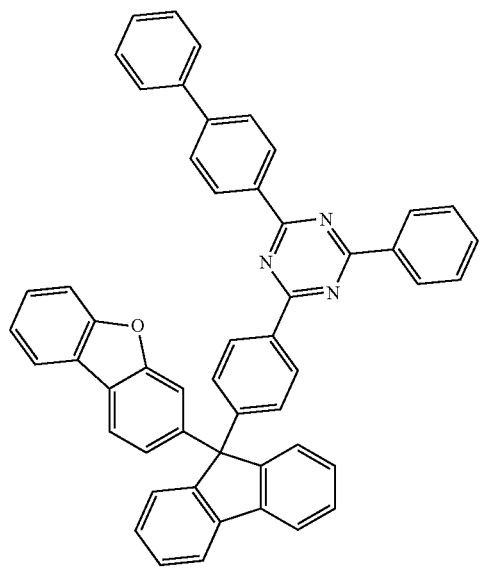

Inv 50

Inv 50 (4.8 g, yield 71%), a target compound, was obtained in the same manner as in [Synthesis Example 1] except that Core 2 (5 g, 9.35 mmol) of [Preparation Example 2] was used instead of Core 1, and 2-([1,1'-biphenyl]-4-yl)-4-chloro-6-phenyl-1,3,5-triazine (3.86 g, 11.22 mmol) was used instead of 2-chloro-4,6-diphenyl-1,3,5-triazine.

[LCMS]: 715.8

[Synthesis Example 7] Synthesis of Compound Inv 56

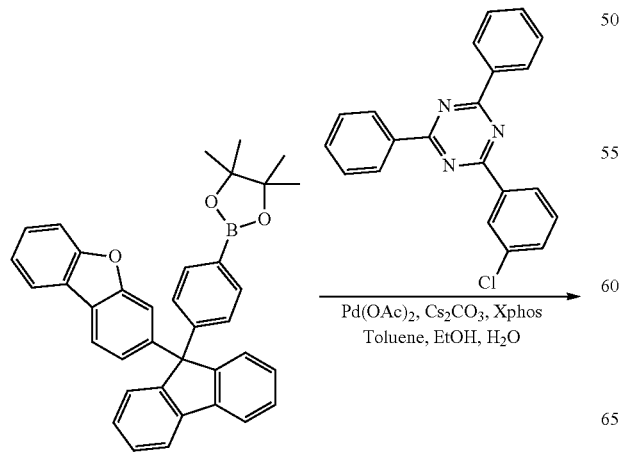

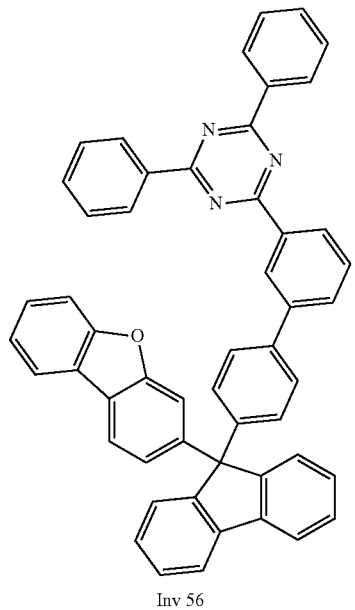

Inv 56

Inv 56 (5.0 g, yield 74%), a target compound, was obtained in the same manner as in [Synthesis Example 3] except that Core 2 (5 g, 9.35 mmol) was used instead of Core 1, and 2-(3-chlorophenyl)-4,6-diphenyl-1,3,5-triazine (3.86 g, 11.22 mmol) was used instead of 2-(4'-chloro-[1,1'-biphenyl]-3-yl)-4,6-diphenyl-1,3,5-triazine.

[LCMS]: 715.8

[Synthesis Example 8] Synthesis of Compound Inv 64
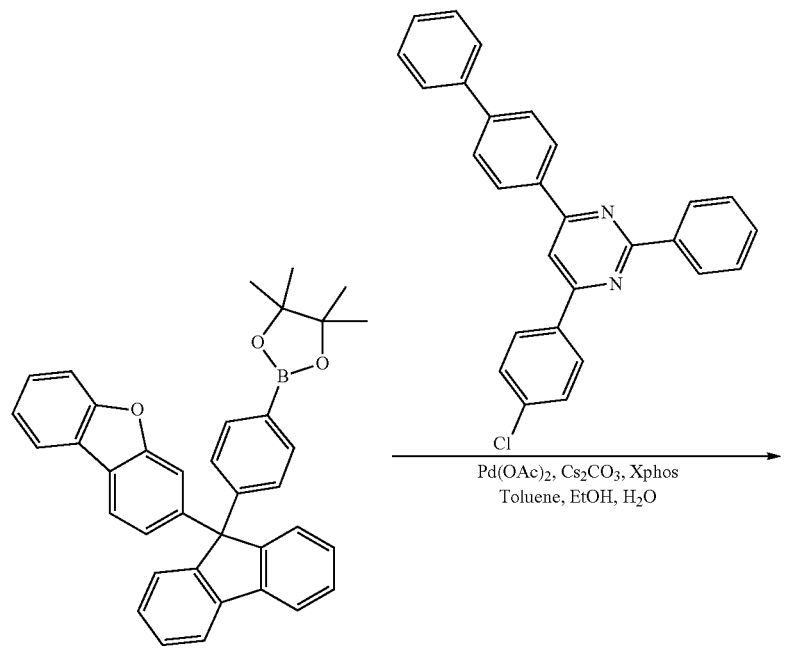
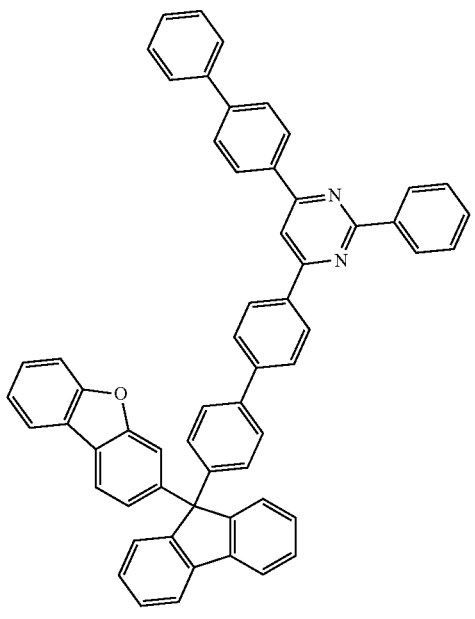
Inv 64
Inv 64 (5 g, yield 71%), a target compound, was obtained in the same manner as in [Synthesis Example 7] except that 4-([1,1'-biphenyl]-4-yl)-6-(4-chlorophenyl)-2-phenylpyrimidine (4.7 g, 11.22 mmol) was used instead of 2-(3-chlorophenyl)-4,6-diphenyl-1,3,5-triazine.
[LCMS]: 790.97

[Synthesis Example 9] Synthesis of Compound Inv 87

[Synthesis Example 10] Synthesis of Compound Inv 94

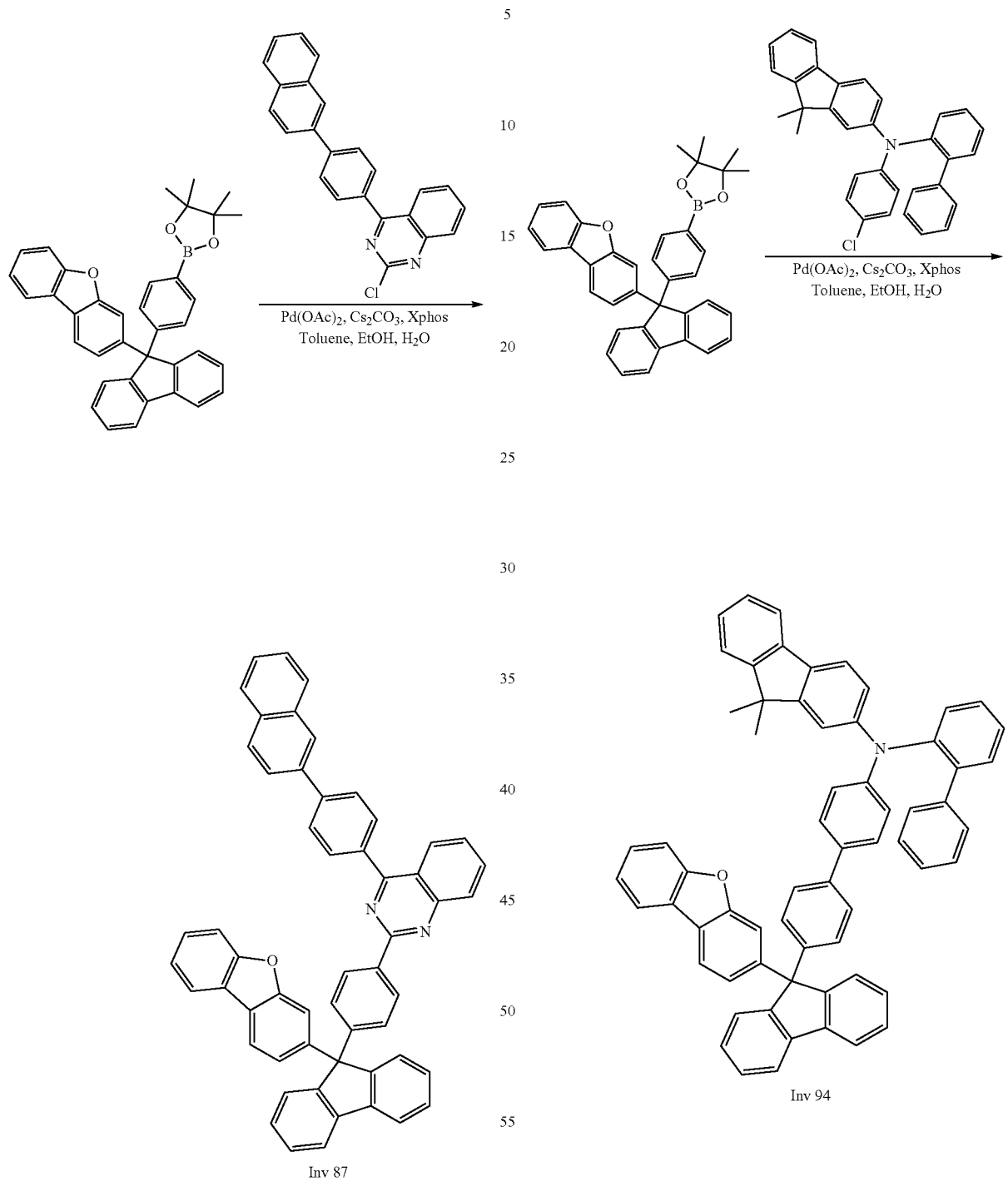

Inv 87

Inv 94

Inv 87 (4.6 g, yield 66%), a target compound, was obtained in the same manner as in [Synthesis Example 7] except that 2-chloro-4-(4-(naphthalen-2-yl)phenyl)quinazoline (4.11 g, 11.22 mmol) was used instead of 2-(3-chlorophenyl)-4,6-diphenyl-1,3,5-triazine.

[LCMS]: 738.8

Inv 94 (5.2 g, yield 65%), a target compound, was obtained in the same manner as in [Synthesis Example 7] except that N-([1,1'-biphenyl]-2-yl)-N-(4-chlorophenyl)-9,9-dimethyl-9H-fluoren-2-amine (5.3 g, 11.22 mmol) was used instead of 2-(3-2-(3-chlorophenyl)-4,6-diphenyl-1,3,5-triazine.

[LCMS]: 844

[Synthesis Example 11] Synthesis of Compound Inv 100
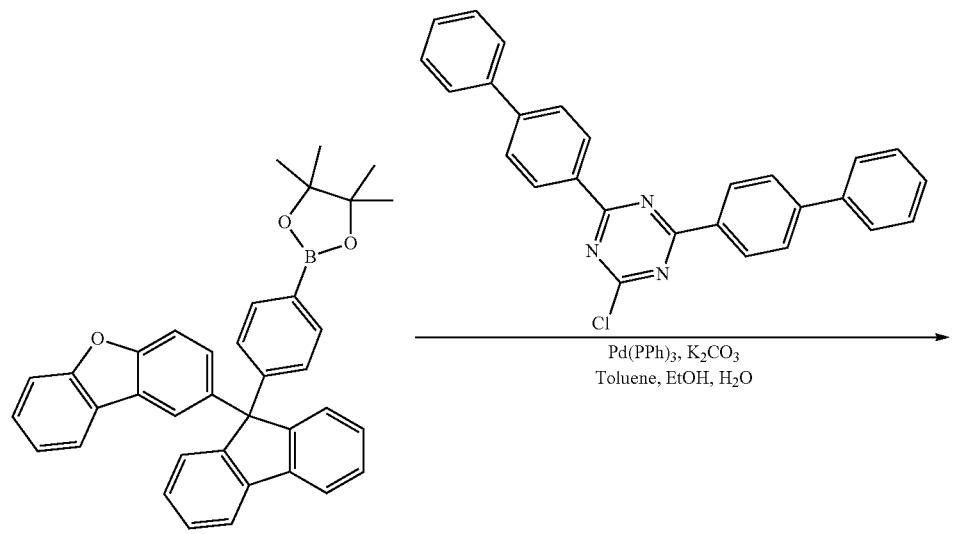
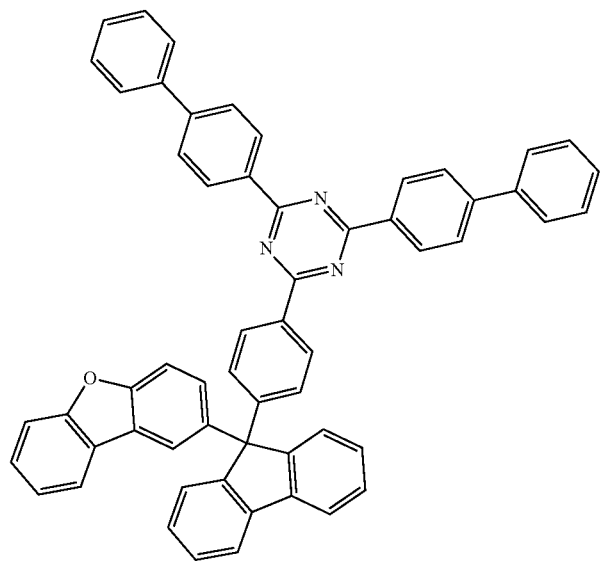
Inv 100
Inv 100 (5.4 g, yield 73%), a target compound, was obtained in the same manner as in [Synthesis Example 1] except that Core 3 (5 g, 9.35 mmol) of [Preparation Example 3] was used instead of Core 1, and 2,4-di([1,1'-biphenyl]-4-yl)-6-chloro-1,3,5-triazine (4.71 g, 11.22 mmol) was used instead of 2-chloro-4,6-diphenyl-1,3,5-triazine.
[LCMS]: 791.9

[Synthesis Example 12] Synthesis of Compound Inv 106
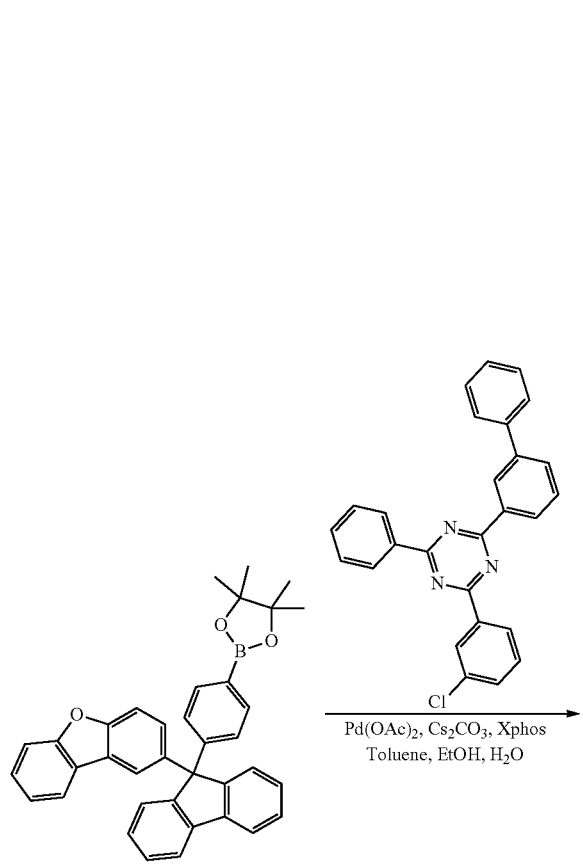
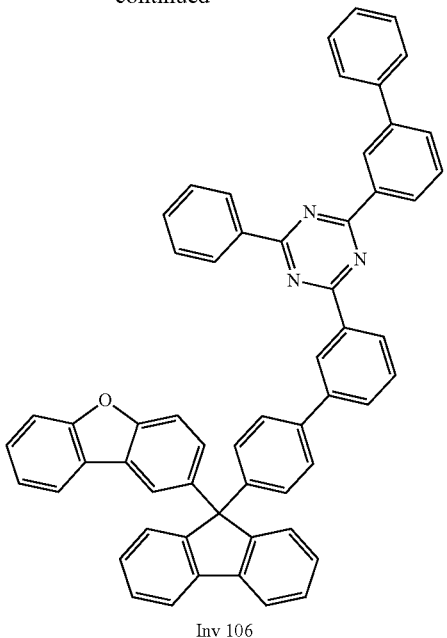
Inv 106
Inv 106 (5.0 g, yield 74%), a target compound, was obtained in the same manner as in [Synthesis Example 3] except that Core 3 (5 g, 9.35 mmol) was used instead of Core 1, and 2-([1,1'-biphenyl]-3-yl)-4-(3-chlorophenyl)-6-phenyl-1,3,5-triazine (3.86 g, 11.22 mmol) was used instead of 2-(4'-chloro-[1,1'-biphenyl]-3-yl)-4,6-diphenyl-1,3,5-triazine.
[LCMS]: 818.9
[Synthesis Example 13] Synthesis of Compound Inv 127
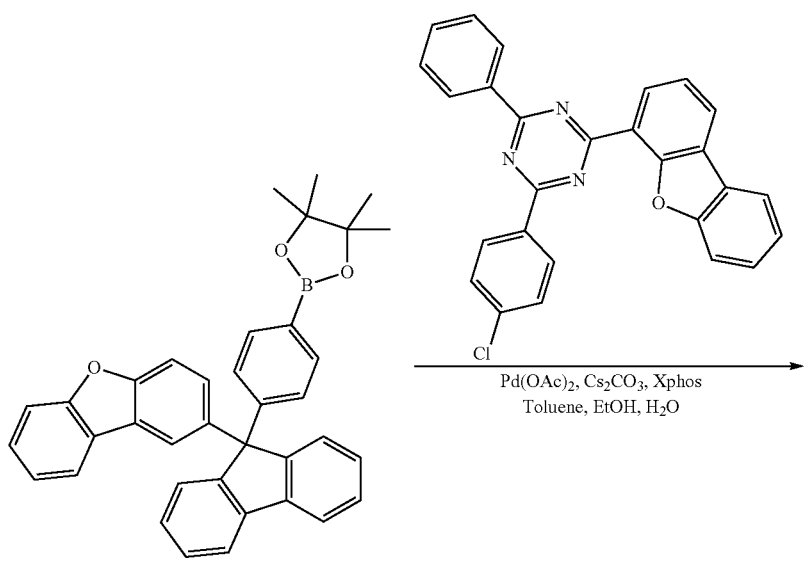

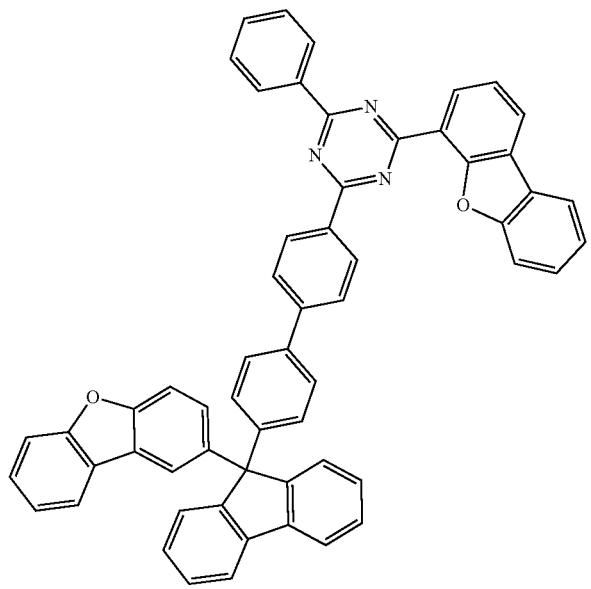

Inv 127

Inv 127 (5.5 g, yield 73%), a target compound, was obtained in the same manner as in [Synthesis Example 12] except that 2-(4-chlorophenyl)-4-(dibenzo[b,d]furan-4-yl)-6-phenyl-1,3,5-triazine (4.87 g, 11.22 mmol) was used instead of 2-([1,1'-biphenyl]-3-yl)-4-(3-chlorophenyl)-6-phenyl-1,3,5-triazine.

[LCMS]: 805.9

[Synthesis Example 14] Synthesis of Compound Inv 138

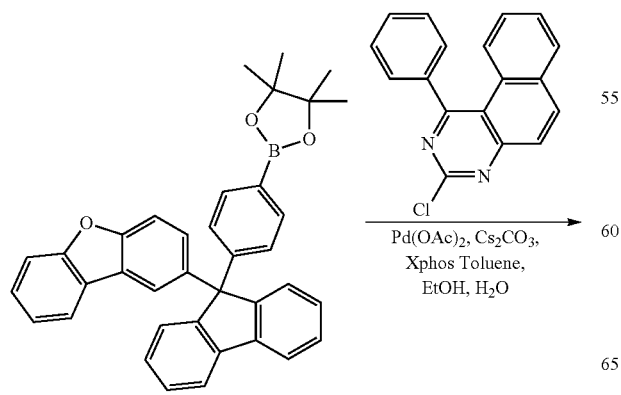

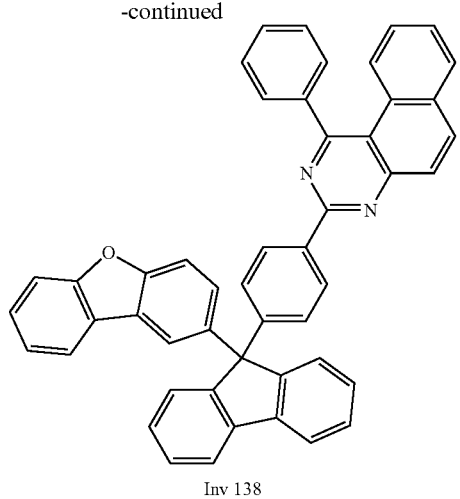

Inv 138

Inv 138 (4.2 g, yield 67%), a target compound, was obtained in the same manner as in [Synthesis Example 12] except that 3-chloro-1-phenylbenzo[f]quinazoline (3.26 g, 11.22 mmol) was used instead of 2-([1,1'-biphenyl]-3-yl)-4-(3-chlorophenyl)-6-phenyl-1,3,5-triazine.

[LCMS]: 662.7

[Synthesis Example 15] Synthesis of Compound Inv 141
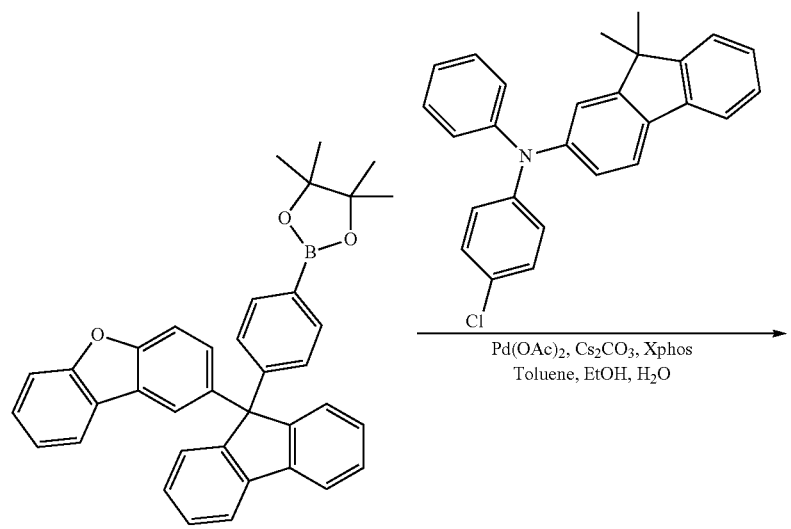
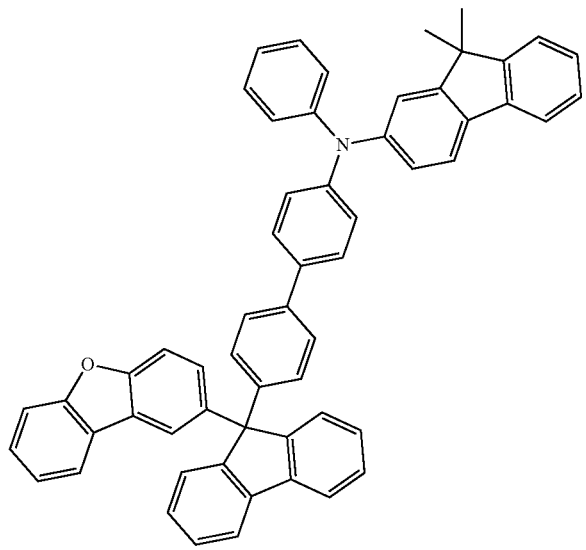
Inv 141
Inv 141 (4.9 g, yield 68%), a target compound, was obtained in the same manner as in [Synthesis Example 12] except that N-(4-chlorophenyl)-9,9-dimethyl-N-phenyl-9H-fluoren-2-amine (4.44 g, 11.22 mmol) was used instead of 2-([1,1'-biphenyl]-3-yl)-4-(3-chlorophenyl)-6-phenyl-1,3,5-triazine.
[LCMS]: 767.97

[Synthesis Example 16] Synthesis of Compound Inv 147
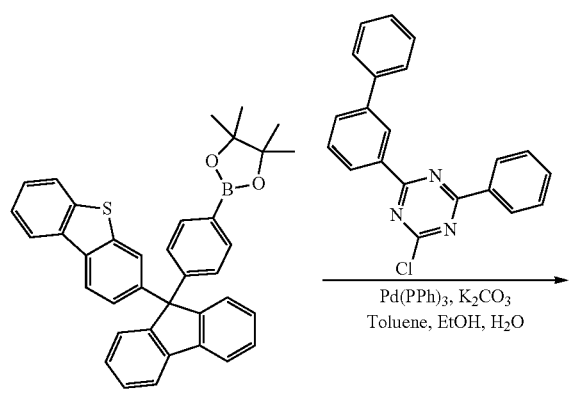
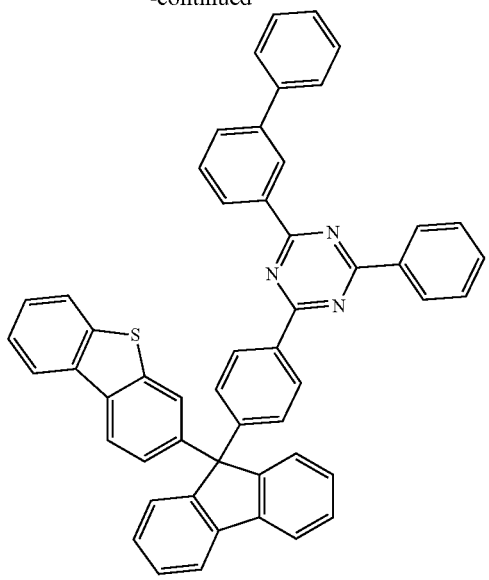
Inv 147
Inv 147 (4.8 g, yield 72%), a target compound, was obtained in the same manner as in [Synthesis Example 1] except that Core 4 (5 g, 9.08 mmol) of [Preparation Example 4] was used instead of Core 1, and 2-([1,1'-biphenyl]-3-yl)-4-chloro-6-phenyl-1,3,5-triazine (3.74 g, 10.89 mmol) was used instead of 2-chloro-4,6-diphenyl-1,3,5-triazine.
[LCMS]: 731.9
[Synthesis Example 17] Synthesis of Compound Inv 158
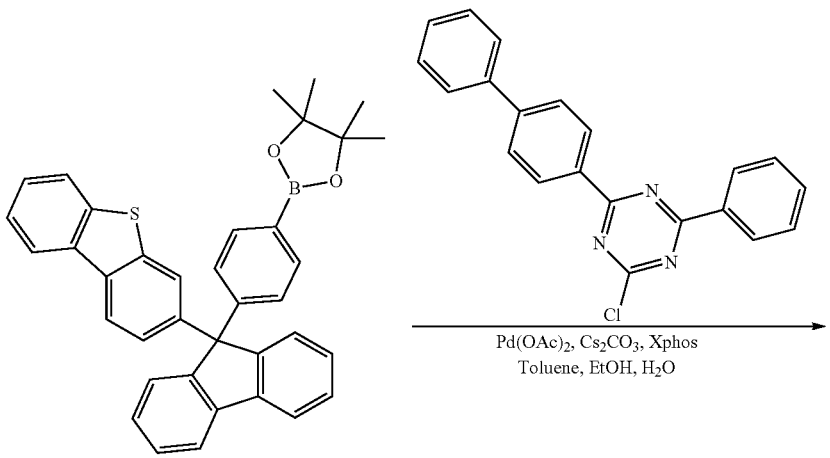

-continued
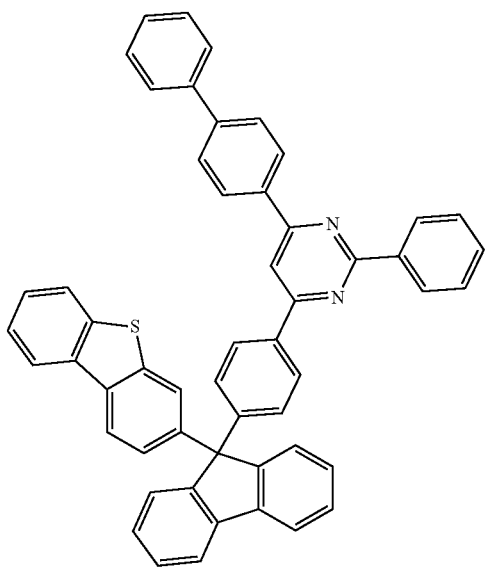
Inv 158
Inv 158 (5.0 g, yield 75%), a target compound, was obtained in the same manner as in [Synthesis Example 3] except that Core 4 (5 g, 9.08 mmol) was used instead of Core 1, and 4-([1,1'-biphenyl]-4-yl)-6-chloro-2-phenylpyrimidine (3.73 g, 10.89 mmol) was used instead of 2-(4'-chloro-[1,1'-biphenyl]-3-yl)-4,6-diphenyl-1,3,5-triazine.
[LCMS]: 730.9
[Synthesis Example 18] Synthesis of Compound Inv 167
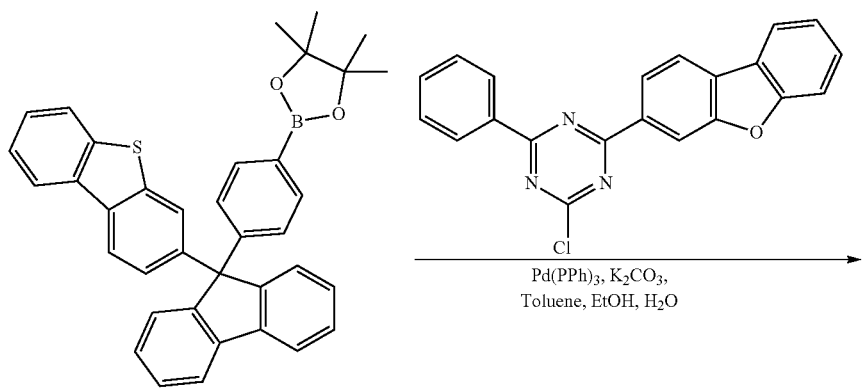

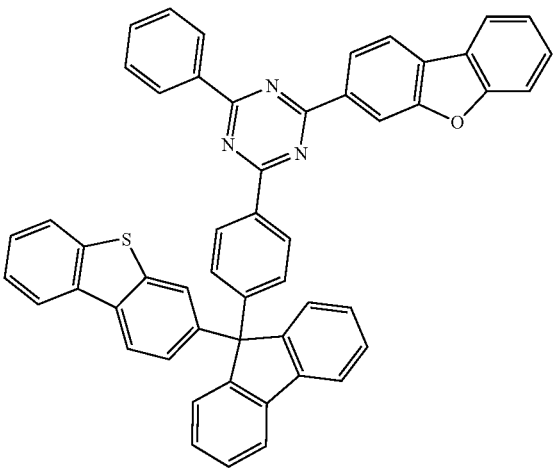

Inv 167

Inv 167 (4.8 g, yield 70%), a target compound, was obtained in the same manner as in [Synthesis Example 16] except that 2-chloro-4-(dibenzo[b,d]furan-3-yl)-6-phenyl-1,3,5-triazine was used instead of 2-([1,1'-biphenyl]-3-yl)-4-chloro-6-phenyl-1,3,5-triazine (3.89 g, 10.89 mmol).

[LCMS]: 745.9

[Synthesis Example 19] Synthesis of Compound Inv 184

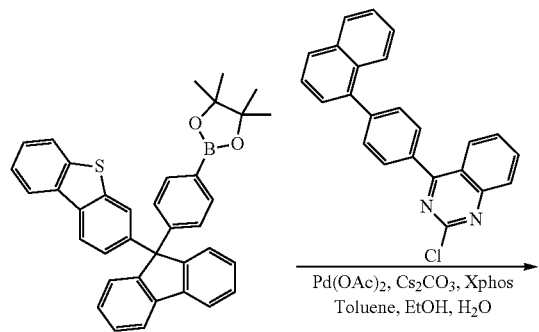

-continued

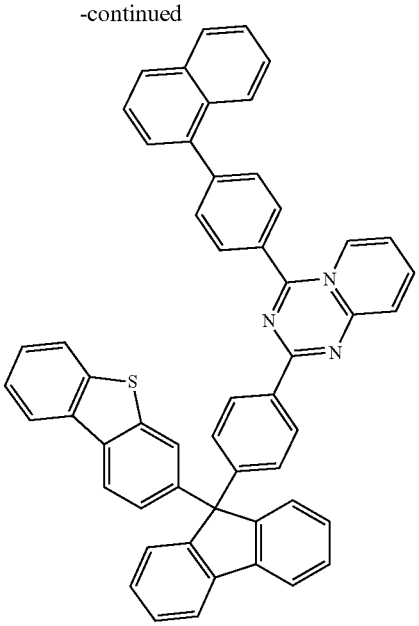

Inv 184

Inv 184 (4.3 g, yield 62%), a target compound, was obtained in the same manner as in [Synthesis Example 17] except that 2-chloro-4-(4-(naphthalen-1-yl)phenyl)quinazoline (4.0 g, 10.89 mmol) was used instead of 4-([1,1'-biphenyl]-4-yl)-6-chloro-2-phenylpyrimidine.

[LCMS]: 754.9

[Synthesis Example 20] Synthesis of Compound Inv 191

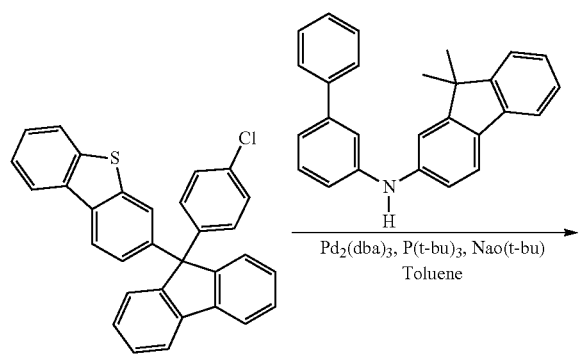

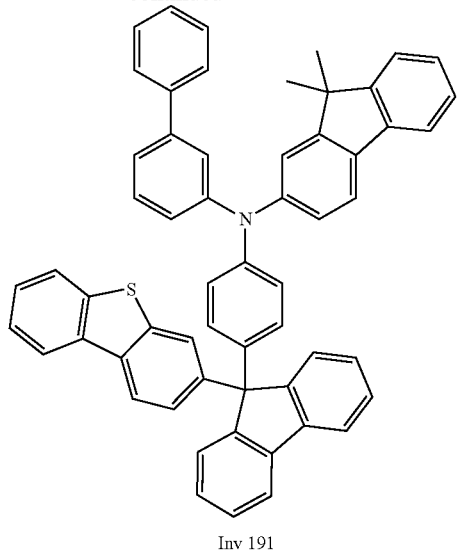

Inv 191

Inv 191 (5.2 g, yield 60%), a target compound, was obtained in the same manner as in [Synthesis Example 5] except that 3-(9-(4-chlorophenyl)-9H-fluoren-9-yl)dibenzo[b,d]thiophene (5.0 g, 10.89 mmol) was used instead of 6-(9-(4-chlorophenyl)-9H-fluoren-9-yl)-2-phenylbenzo[d]oxazole, and N-([1,1'-biphenyl]-3-yl)-9,9-dimethyl-9H-fluoren-2-amine (4.72 g, 13.07 mmol) was used instead of N-([1,1'-biphenyl]-4-yl)-9,9-dimethyl-9H-fluoren-2-amine.
[LCMS]: 784

[Synthesis Example 21] Synthesis of Compound Inv 197

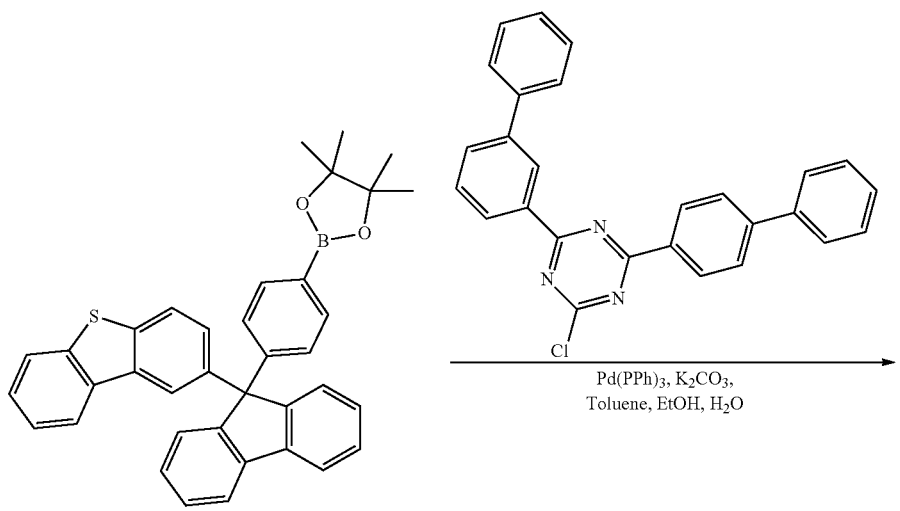

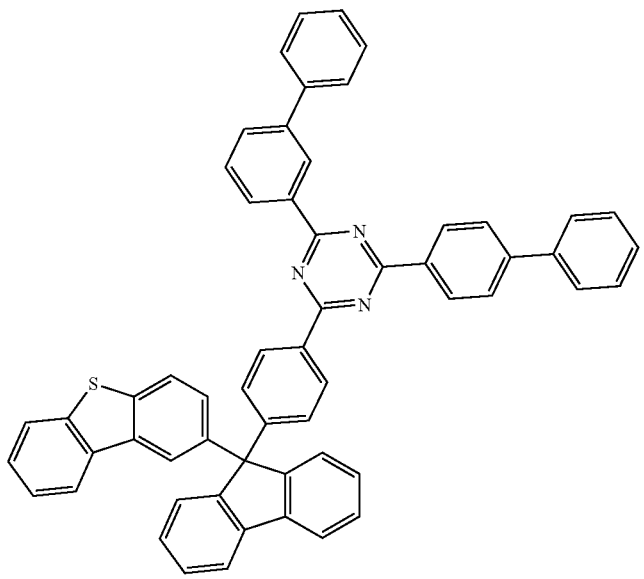
Inv 197
Inv 197 (5.1 g, yield 69%), a target compound, was obtained in the same manner as in [Synthesis Example 1] except that Core 5 (5 g, 9.08 mmol) of [Preparation Example 5] was used instead of Core 1, and 2-([1,1'-biphenyl]-3-yl)-4-([1,1'-biphenyl]-4-yl)-6-chloro-1,3,5-triazine (4.57 g, 10.89 mmol) was used instead of 2-chloro-4,6-diphenyl-1,3,5-triazine.
[LCMS]: 808
[Synthesis Example 22] Synthesis of Compound Inv 214
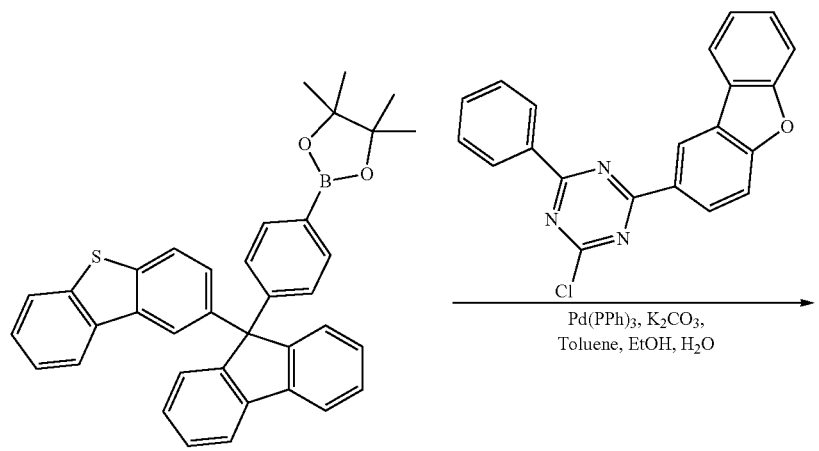

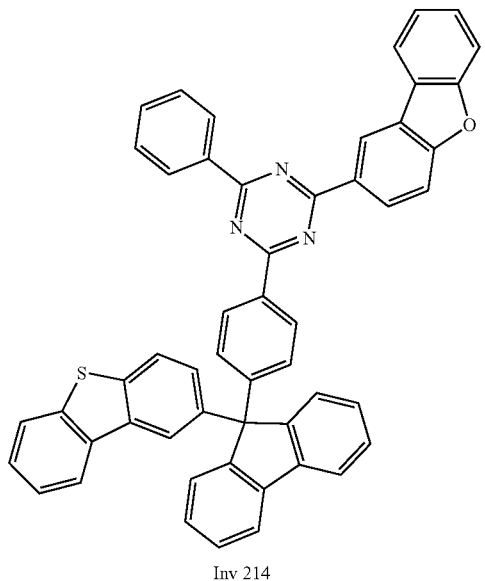
Inv 214
Inv 214 (5.0 g, yield 73%), a target compound, was obtained in the same manner as in [Synthesis Example 21] except that 2-chloro-4-(dibenzo[b,d]furan-2-yl)-6-phenyl-1,3,5-triazine (3.89 g, 10.89 mmol) was used instead of 2-([1,1'-biphenyl]-3-yl)-4-([1,1'-biphenyl]-4-yl)-6-chloro-1,3,5-triazine.
[LCMS]: 745.9
[Synthesis Example 23] Synthesis of Compound Inv 223
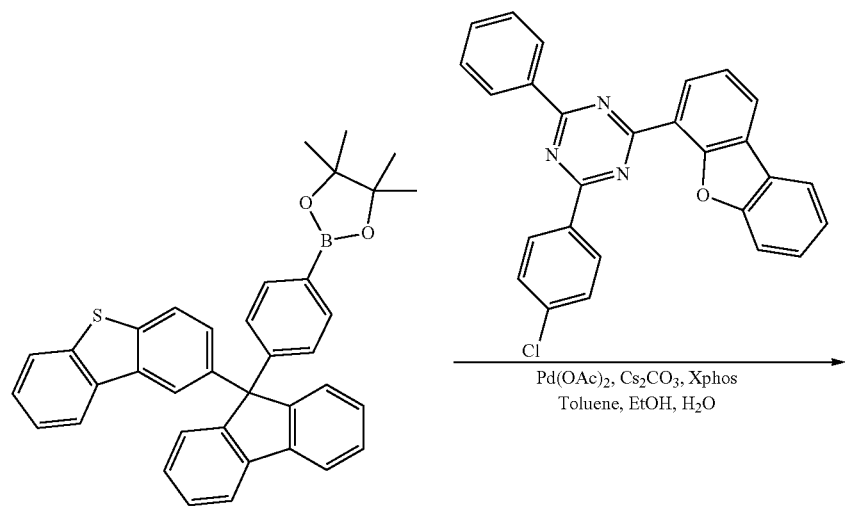

-continued

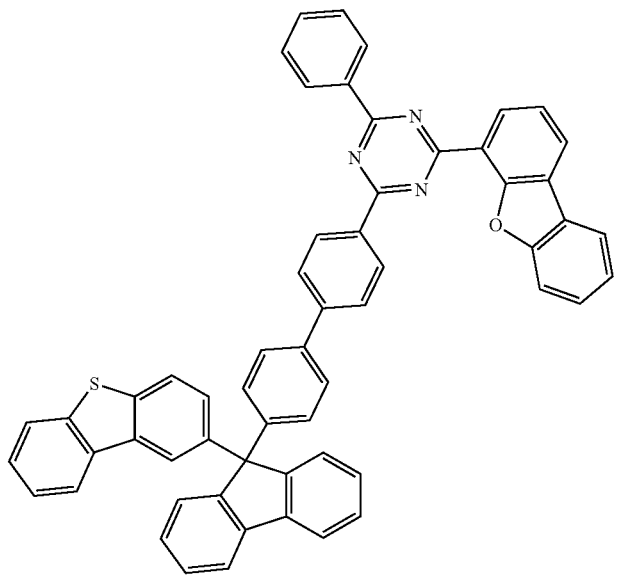

Inv 223

Inv 223 (5.4 g, yield 72%), a target compound, was obtained in the same manner as in [Synthesis Example 3] except that Core 5 (5 g, 9.08 mmol) was used instead of Core 1, and 2-(4-chlorophenyl)-4-(dibenzo[b,d]furan-4-yl)-6-phenyl-1,3,5-triazine (4.72 g, 10.89 mmol) was used instead of 2-(4'-chloro-[1,1'-biphenyl]-3-yl)-4,6-diphenyl-1,3,5-triazine.

[LCMS]: 822

[Synthesis Example 24] Synthesis of Compound Inv 229

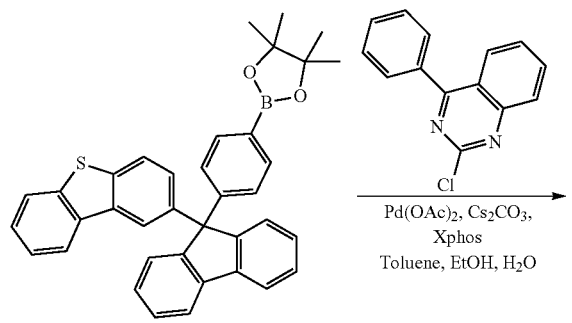

-continued

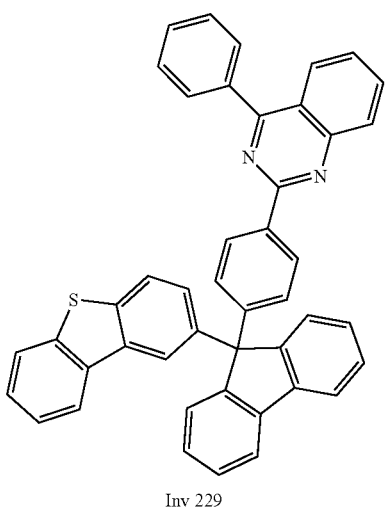

Inv 229

Inv 229 (3.8 g, yield 66%), a target compound, was obtained in the same manner as in [Synthesis Example 23] except that 2-chloro-4-phenylquinazoline (2.62 g, 10.89 mmol) was used instead of 2-(4-chlorophenyl)-4-(dibenzo[b,d]furan-4-yl)-6-phenyl-1,3,5-triazine.

[LCMS]: 628.7

[Synthesis Example 25] Synthesis of Compound Inv 238
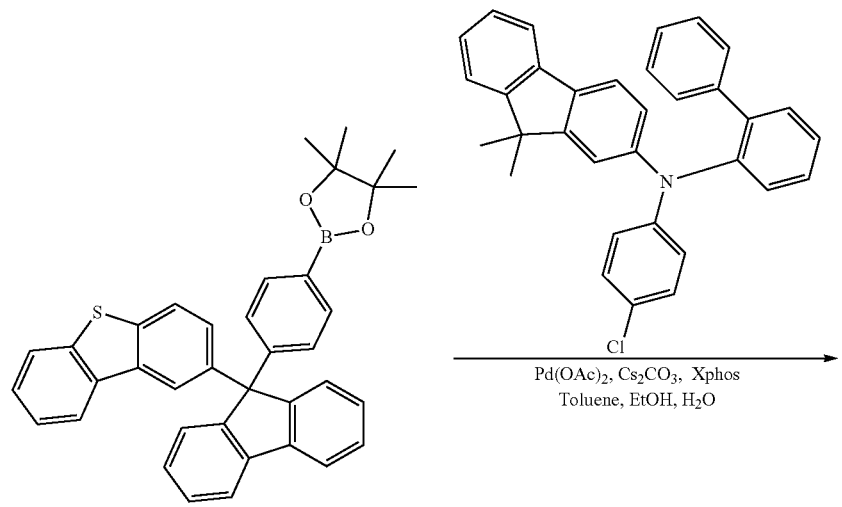
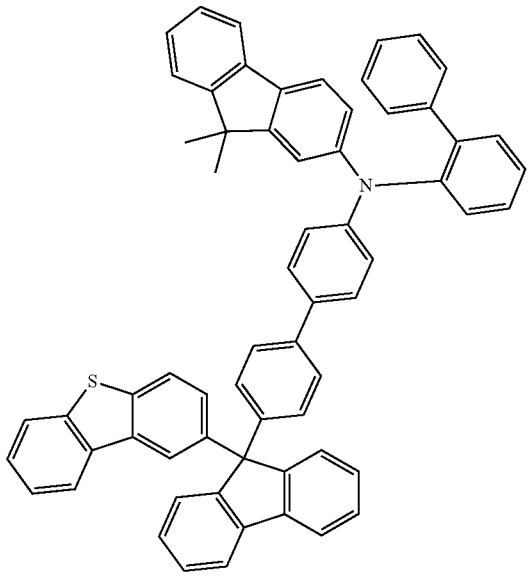
Inv 238
Inv 238 (5.3 g, yield 67%), a target compound, was obtained in the same manner as in [Synthesis Example 23] except that N-([1,1'-biphenyl]-2-yl)-N-(4-chlorophenyl)-9,9-dimethyl-9H-fluoren-2-amine (5.14 g, 10.89 mmol) was used instead of 2-(4-chlorophenyl)-4-(dibenzo[b,d]furan-4-yl)-6-phenyl-1,3,5-triazine.
[LCMS]: 752.9

[Synthesis Example 26] Synthesis of Compound Inv 243
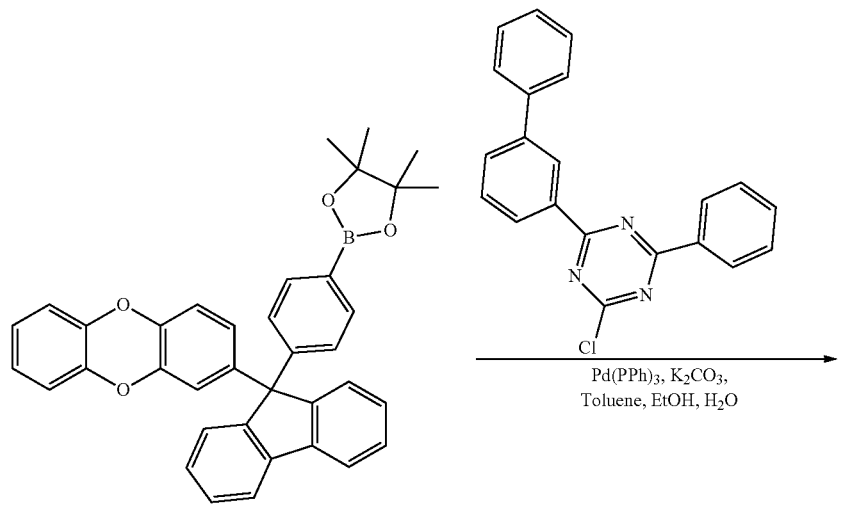
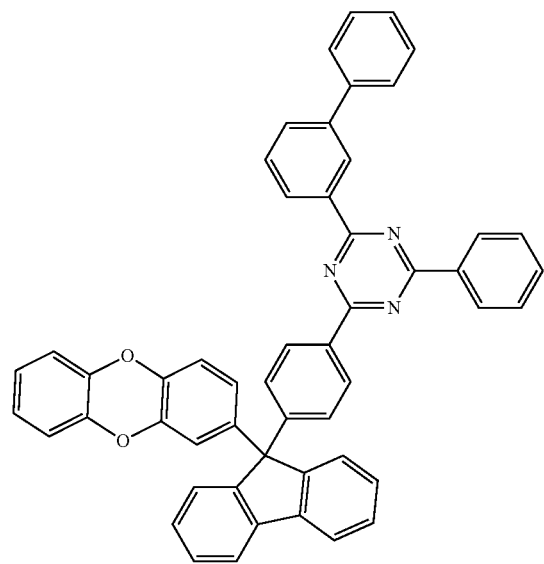
Inv 243
Inv 243 (4.7 g, yield 70%), a target compound, was obtained in the same manner as in [Synthesis Example 1] except that Core 6 (5 g, 9.08 mmol) of [Preparation Example 6] was used instead of Core 1, and 2-([1,1'-biphenyl]-3-yl)-4-chloro-6-phenyl-1,3,5-triazine (3.74 g, 10.9 mmol) was used instead of 2-chloro-4,6-diphenyl-1,3,5-triazine.
[LCMS]: 731.8

[Synthesis Example 27] Synthesis of Compound Inv 252
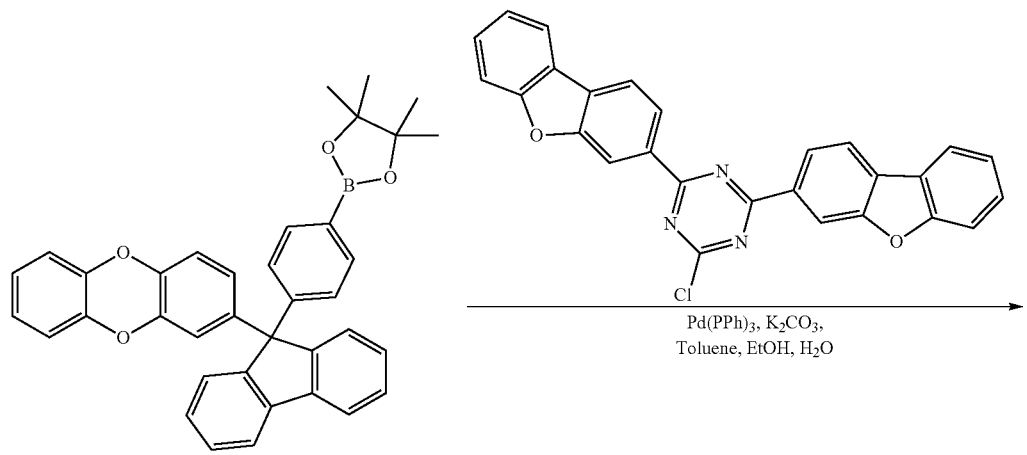
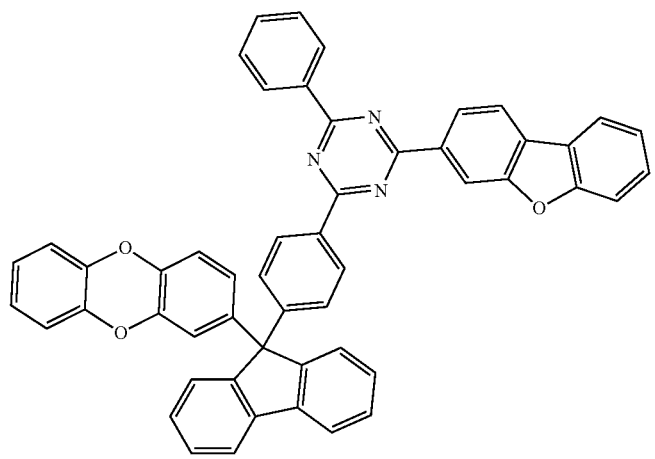
Inv 252
Inv 252 (5.2 g, yield 68%), a target compound, was obtained in the same manner as in [Synthesis Example 2] except that Core 6 (5 g, 9.08 mmol) was used instead of Core 1.
[LCMS]: 835.9

[Synthesis Example 28] Synthesis of Compound Inv 259
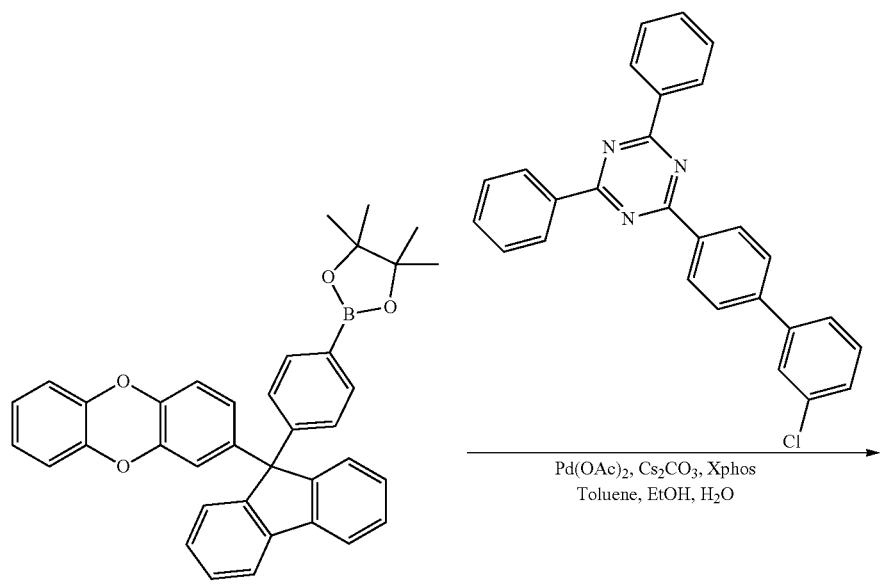
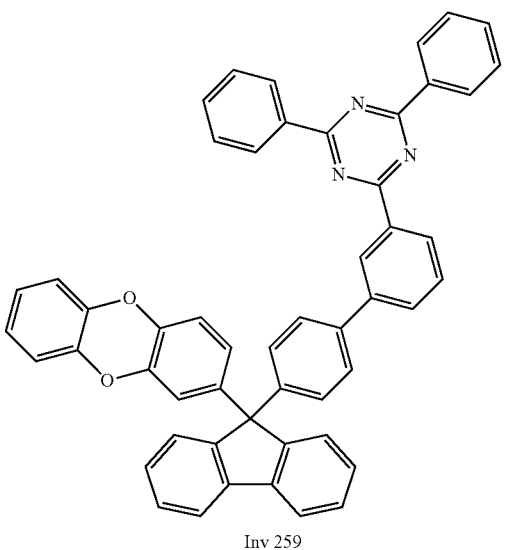
Inv 259 (5.2 g, yield 68%), a target compound, was obtained in the same manner as in [Synthesis Example 3] except that Core 5 (5 g, 9.08 mmol) was used instead of Core 1, and 2-(3'-chloro-[1,1'-biphenyl]-4-yl)-4,6-diphenyl-1,3,5-triazine (4.57 g, 10.9 mmol) was used instead of 2-(4'-chloro-[1,1'-biphenyl]-3-yl)-4,6-diphenyl-1,3,5-triazine.
[LCMS]: 807.9

[Synthesis Example 29] Synthesis of Compound Inv 282
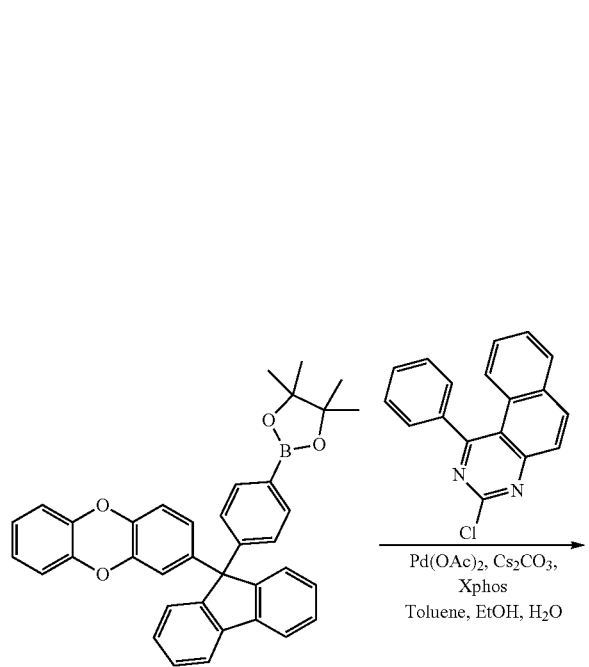
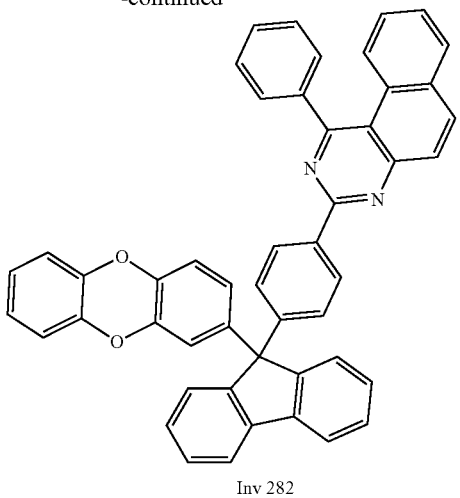
Inv 282
Inv 282 (4.2 g, yield 68%), a target compound, was obtained in the same manner as in [Synthesis Example 28] except that 3-chloro-1-phenylbenzo[f]quinazoline (3.17 g, 10.89 mmol) was used instead of 2-(3'-chloro-[1,1'-biphenyl]-4-yl)-4,6-diphenyl-1,3,5-triazine.
[LCMS]: 678.7
[Synthesis Example 30] Synthesis of Compound Inv 285
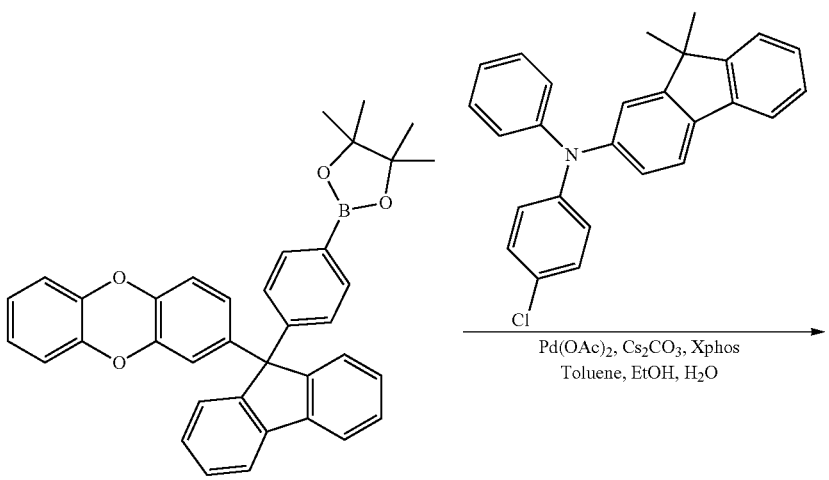

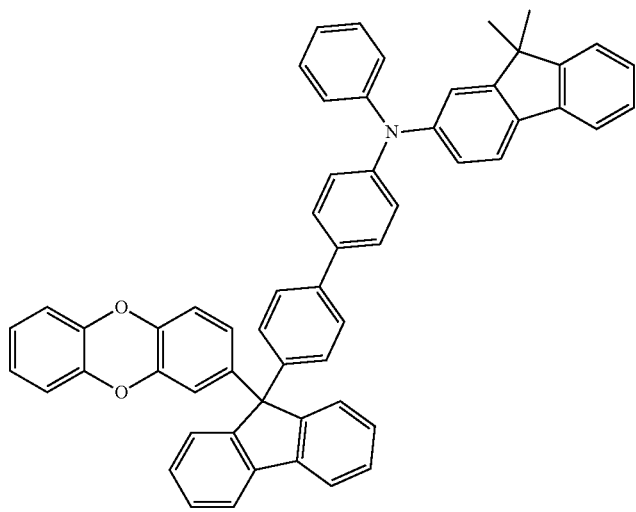

Inv 285

Inv 285 (5.1 g, yield 71%), a target compound, was obtained in the same manner as in [Synthesis Example 28] except that N-(4-chlorophenyl)-9,9-dimethyl-N-phenyl-9H-fluoren-2-amine (4.31 g, 10.9 mmol) was used instead of 2-(3'-chloro-[1,1'-biphenyl]-4-yl)-4,6-diphenyl-1,3,5-triazine.

[LCMS]: 783.9

[Examples 1 to 12] Manufacture of Green Organic EL Device

After high purity sublimation purifying Compounds Inv 1 to Inv 252 using commonly known methods, green organic EL devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, m-MTDATA (60 nm)/TCTA (80 nm)/each compound of Compounds Inv 1 to Inv 252+10% Ir(ppy)₃ (30 nm)/BCP (10 nm)/Alq₃ (30 nm)/LiF (1 nm)/Al (200 nm) were laminated in this order to manufacture an organic EL device.

Structures of m-MTDATA, TCTA, Ir(ppy)₃, CBP and BCP are as follows.

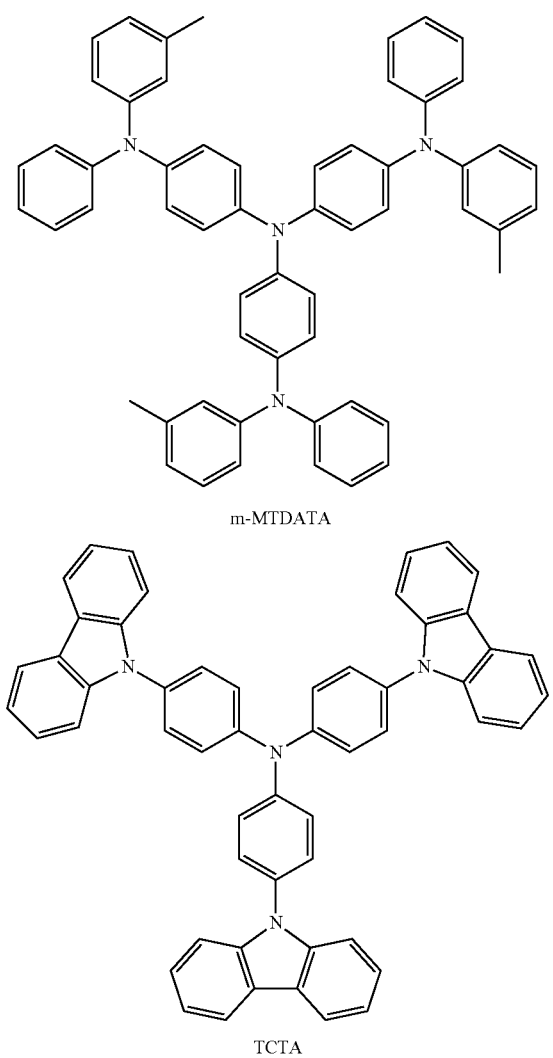

m-MTDATA

TCTA

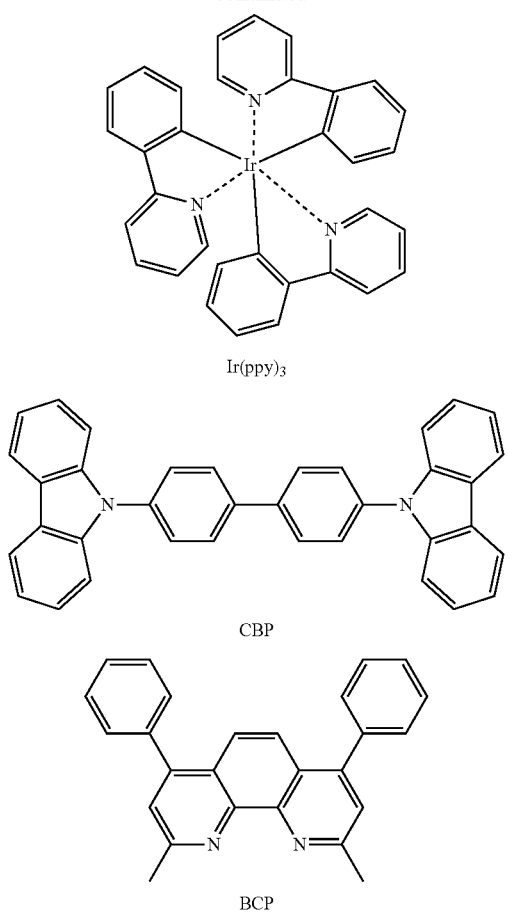

Ir(ppy)₃

CBP

BCP

[Comparative Example 1] Manufacture of Green Organic EL Device

A green organic EL device was manufactured in the same manner as in Example 1 except that CBP was used instead of Compound Inv 1 as the light emitting host material when forming the light emitting layer.

Evaluation Example 1

For each of the green organic EL devices manufactured in Examples 1 to 12 and Comparative Example 1, driving voltage, current efficiency and light emission peak at current density of (10) mA/cm² were measured, and the results are shown in the following Table 1.

TABLE 1

| Sample | Host | Driving Voltage (V) | EL Peak (nm) | Current Efficiency (cd/A) |
|---|---|---|---|---|
| Example 1 | Inv 1 | 5.64 | 516 | 42.2 |
| Example 2 | Inv 12 | 5.35 | 517 | 47.4 |
| Example 3 | Inv 50 | 5.62 | 518 | 49.2 |

TABLE 1-continued

| Sample | Host | Driving Voltage (V) | EL Peak (nm) | Current Efficiency (cd/A) |
|---|---|---|---|---|
| Example 4 | Inv 56 | 5.53 | 516 | 44.8 |
| Example 5 | Inv 100 | 5.36 | 517 | 43.1 |
| Example 6 | Inv 106 | 5.88 | 516 | 43.6 |
| Example 7 | Inv 147 | 5.44 | 516 | 47.4 |
| Example 8 | Inv 167 | 5.62 | 516 | 43.4 |
| Example 9 | Inv 197 | 5.46 | 517 | 49.2 |
| Example 10 | Inv 214 | 5.39 | 516 | 47.4 |
| Example 11 | Inv 243 | 5.74 | 516 | 47.6 |
| Example 12 | Inv 252 | 5.81 | 518 | 43.2 |
| Comparative Example 1 | CBP | 6.52 | 516 | 38.2 |

As shown in Table 1, it was seen that using Compounds Inv 1 to Inv 252 according to the present invention in a light emitting layer of the green organic EL device (Examples 1 to 12) resulted in more superior performance in terms of efficiency and driving voltage compared to the green organic EL device using existing CBP (Comparative Example 1).

[Examples 13 to 18] Manufacture of Red Organic EL Device

After high purity sublimation purifying Compounds Inv 41 to Inv 282 using commonly known methods, red organic electroluminescent devices were manufactured using the following procedure.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, m-MTDATA (60 nm)/TCTA (80 nm)/each compound of Compounds Inv 41 to Inv 282+10% (piq)₂Ir(acac) (300 nm)/BCP (10 nm)/Alq₃ (30 nm)/LiF (1 nm)/Al (200 nm) were laminated in this order to manufacture an organic electroluminescent device.

Comparative Example 2

A red organic electroluminescent device was manufactured in the same manner as in Example 13 except that CBP was used instead of Compound Inv 41 as the light emitting host material when forming the light emitting layer.

Structures of m-MTDATA, (piq)₂Ir(acac), CBP and BCP used in Examples 13 to 18 and Comparative Example 2 are as follows.

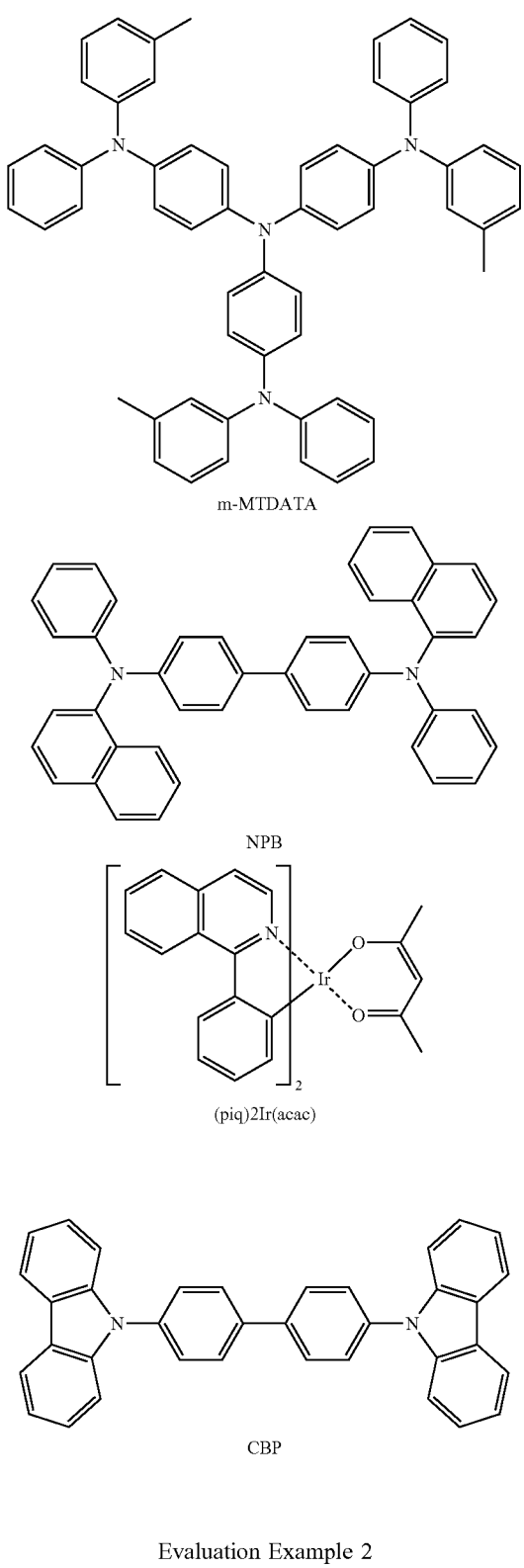

Evaluation Example 2

For each of the organic electroluminescent devices manufactured in Examples 13 to 18 and Comparative Example 2, driving voltage and current efficiency at current density of 10 mA/cm² were measured, and the results are shown in the following Table 2.

TABLE 2

| Sample | Host | Driving Voltage (V) | Current Efficiency (cd/A) |
|---|---|---|---|
| Example 13 | Inv 41 | 4.92 | 12.6 |
| Example 14 | Inv 87 | 4.84 | 13.6 |
| Example 15 | Inv 138 | 4.28 | 14.8 |
| Example 16 | Inv 184 | 4.14 | 15.8 |
| Example 17 | Inv 229 | 4.32 | 14.7 |
| Example 18 | Inv 282 | 4.25 | 14.6 |
| Comparative Example 2 | CBP | 5.35 | 8.2 |

As shown in Table 2, it was seen that using the compounds according to the present invention as a material of a light emitting layer of the red organic electroluminescent device (Examples 13 to 18) resulted in more superior performance in terms of efficiency and driving voltage compared to the red organic electroluminescent device using existing CBP as a material of a light emitting layer (Comparative Example 2).

[Examples 19 to 24] Manufacture of Blue Organic Electroluminescent Device

After high purity sublimation purifying Compounds Inv 18 to Inv 259 using commonly known methods, blue organic electroluminescent devices were manufactured as follows.

First, a glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, DS-205 (Doosan Corporation Electro-Materials, 80 nm)/NPB (15 nm)/ADN+5% DS-405 (Doosan Corporation Electro-Materials, 30 nm)/each compound of Compounds Inv 18 to Inv 259 (30 nm)/LiF (1 nm)/Al (200 nm) were laminated in this order to manufacture an organic electroluminescent device.

[Comparative Example 3] Manufacture of Blue Organic Electroluminescent Device

A blue organic electroluminescent device was manufactured in the same manner as in Example 19 except that Alq₃ was used instead of Compound Inv 18 as the electron transport layer material.

[Comparative Example 4] Manufacture of Blue Organic Electroluminescent Device

A blue organic electroluminescent device was manufactured in the same manner as in Example 19 except that Compound Inv 18 was not used as the electron transport layer material.

Structures of NPB, AND and Alq₃ used in Examples 19 to 24 and Comparative Examples 3 and 4 are as follows.

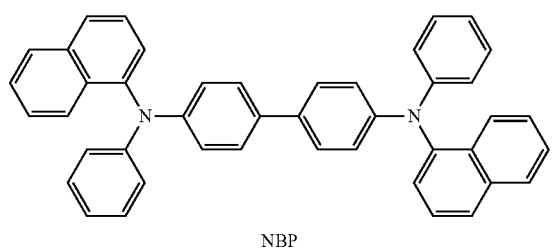

NBP

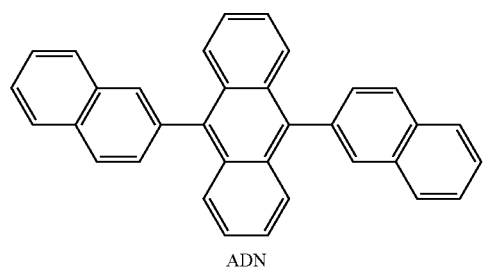

ADN

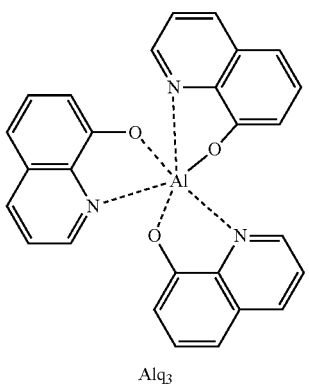

Alq₃

Evaluation Example 3

For each of the blue organic electroluminescent devices manufactured in Examples 19 to 24 and Comparative Examples 3 and 4, driving voltage, current efficiency and light emission peak at current density of (10) mA/cm² were measured, and the results are shown in the following Table 3.

TABLE 3

| Sample | Material | Driving Voltage (V) | EL Peak (nm) | Current Efficiency (cd/A) |
|---|---|---|---|---|
| Example 19 | Inv 18 | 3.4 | 458 | 7.0 |
| Example 20 | Inv 64 | 4.0 | 459 | 7.1 |
| Example 21 | Inv 127 | 3.8 | 458 | 6.8 |
| Example 22 | Inv 158 | 4.0 | 455 | 7.2 |
| Example 23 | Inv 223 | 3.9 | 456 | 6.7 |

TABLE 3-continued

| Sample | Material | Driving Voltage (V) | EL Peak (nm) | Current Efficiency (cd/A) |
|---|---|---|---|---|
| Example 24 | Inv 259 | 3.6 | 457 | 6.9 |
| Comparative Example 3 | Alq₃ | 4.8 | 458 | 6.2 |
| Comparative Example 4 | — | 5.2 | 460 | 5.6 |

As shown in Table 3, it was seen that the blue organic electroluminescent devices using the compounds of the present invention in an electron transport layer (Examples 19 to 24) exhibited superior performance in terms of driving voltage, light emission peak and current efficiency compared to the blue organic electroluminescent device using existing Alq₃ in an electron transport layer (Comparative Example 3), and the blue organic electroluminescent device without an electron transport layer (Comparative Example 4).

[Examples 25 to 30] Manufacture of Organic EL Device

After high purity sublimation purifying Compounds Inv 48 to Inv 285 using commonly known methods, blue organic electroluminescent devices were manufactured as follows.

A glass substrate on which indium tin oxide (ITO) was coated as a thin film to a thickness of 1500 Å was ultrasonic cleaned using distilled water. After the cleaning with distilled water was finished, the substrate was ultrasonic cleaned with solvents of isopropyl alcohol, acetone, methanol and the like, dried, then transferred to a UV OZONE washer (Power sonic 405, manufactured by Hwashin Tech. Co., Ltd.), and then, after cleaning the substrate for 5 minutes using UV, the substrate was transferred to a vacuum deposition apparatus.

On the transparent ITO electrode prepared as above, m-MTDATA (60 nm)/each compound of Compounds Inv 48 to Inv 285 (80 nm)/DS-H522+5% DS-501 (300 nm)/BCP (10 nm)/Alq₃ (30 nm)/LiF (1 nm)/Al (200 nm) were laminated in this order to manufacture an organic EL device.

DS-H522 and DS-501 used for manufacturing the device were products manufactured by Doosan Corporation Electro-Materials BG, and structures of m-MTDATA, TCTA, CBP, Ir(ppy)₃, and BCP are as follows.

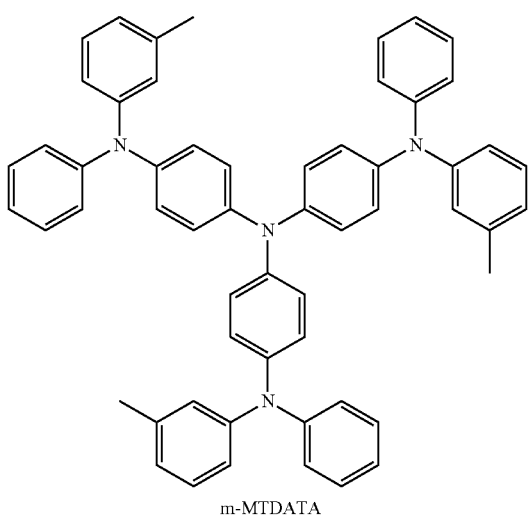

m-MTDATA

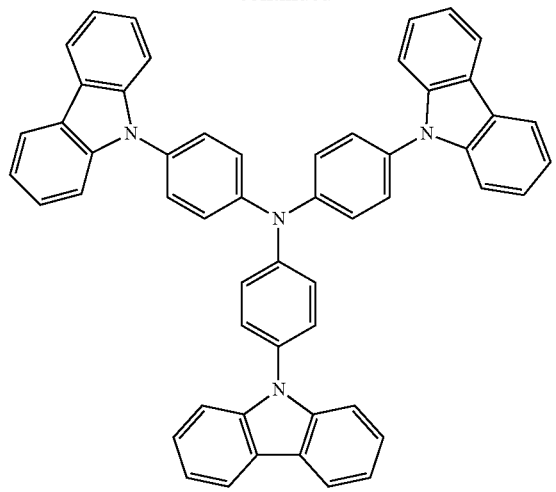

TCTA

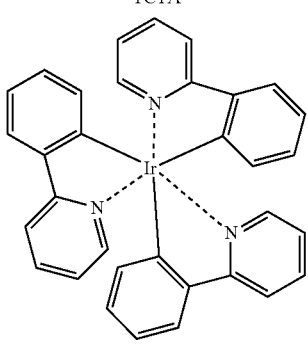

Ir(ppy)₃

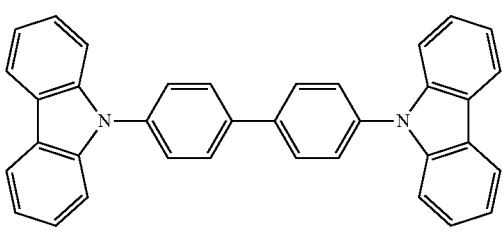

CBP

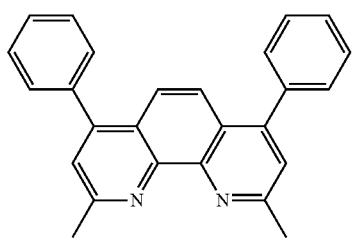

BCP

[Comparative Example 5] Manufacture of Organic EL Device

An organic EL device was manufactured in the same manner as in Example 25 except that NPB was used as the hole transport layer material instead of Compound Inv 48 used as the hole transport layer material when forming the hole transport layer. A structure of the used NPB is as follows.

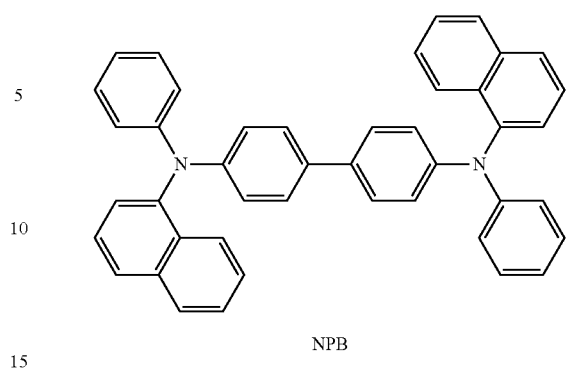

NPB

Evaluation Example 4

For each of the organic EL devices manufactured in Examples 25 to 30 and Comparative Example 5, driving voltage and current efficiency at current density of 10 mA/cm² were measured, and the results are shown in the following Table 4.

TABLE 4

| Sample | Hole Transport Layer | Driving Voltage (V) | Current Efficiency (cd/A) |
|---|---|---|---|
| Example 25 | Inv 48 | 4.2 | 22.2 |
| Example 26 | Inv 94 | 4.3 | 24.1 |
| Example 27 | Inv 141 | 4.1 | 23.3 |
| Example 28 | Inv 191 | 4.0 | 25.6 |
| Example 29 | Inv 238 | 4.2 | 23.5 |
| Example 30 | Inv 285 | 4.3 | 22.1 |
| Comparative Example 5 | NPB | 5.2 | 18.1 |

As shown in Table 4, it was seen that the organic EL devices using the compounds (Inv 48 to Inv 285) according to the present invention in a hole transport layer (organic EL devices each manufactured in Examples 25 to 30) exhibited more superior performance in terms of current efficiency and driving voltage compared to the organic EL device using existing NPB (organic EL device of Comparative Example 5).

REFERENCE NUMERAL

10: Anode
20: Cathode
30: Organic Layer
31: Hole Transport Layer
32: Light Emitting Layer
33: Hole Transport Auxiliary Layer
34: Electron Transport Layer
35: Electron Transport Auxiliary Layer
36: Electron Injection Layer
37: Hole Injection Layer

The invention claimed is:

1. A compound of the following Chemical Formula 1:

[Chemical Formula 1]

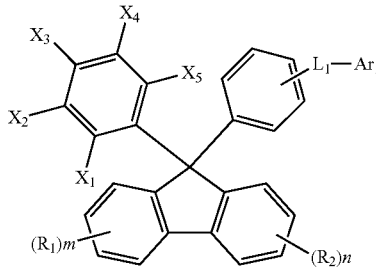

wherein, in Chemical Formula 1, $L_1$ is selected from the group consisting of a single bond, a $C_6$~$C_{18}$ arylene group and a heteroarylene group having 5 to 18 nuclear atoms;

$Ar_1$ is a substituent represented by any one of the following Chemical Formula 13, Chemical Formula 14, and Chemical Formula C-1 to Chemical Formula C-6,

[Chemical Formula 13]

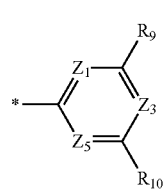

[Chemical Formula 14]

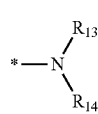

[Chemical Formulas C-1-C6]

C-1

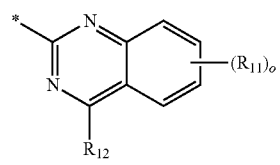

C-2

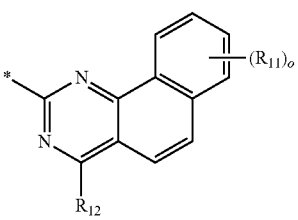

C-3

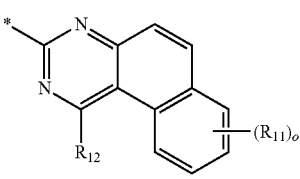

C-4

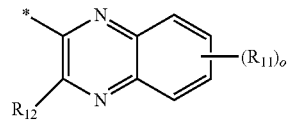

C-5

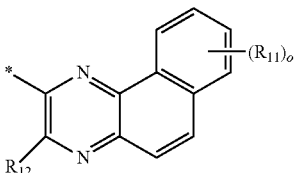

C-6

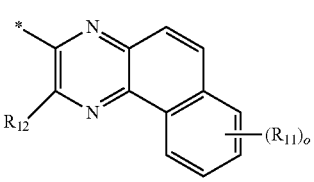

in Chemical Formulas 13, 14, and C1-C6,

* means a part where a bond is formed;

$Z_1$, $Z_3$ and $Z_5$ are each independently N or C ($R_8$), wherein at least one of $Z_1$, $Z_3$ and $Z_5$ is N;

o is an integer of 0 to 4;

$R_8$ to $R_{14}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bond to adjacent groups to form a fused ring; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_8$, to $R_{14}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other;

any one of $X_1$ and $X_2$, $X_2$ and $X_3$, $X_3$ and $X_4$, and $X_4$ and $X_5$ bonds to a ring of the following Chemical Formula 2 or 4 to form a fused ring;

m and n are an integer of 4;

$R_1$ and $R_2$ are hydrogen;

$X_1$ to $X_5$ not forming a fused ring with a ring of the following Chemical Formula 2 or 4 are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$, $R_2$, and $X_1$ to $X_5$ not forming a fused ring with a ring represented by the following Chemical Formula 2 or 4 are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other;

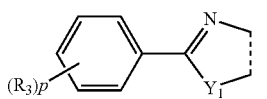

[Chemical Formula 2]

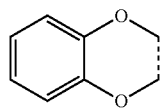

[Chemical Formula 4]

wherein in Chemical Formula 2 or 4,
wherein in Chemical Formula 2 or 4,
a dotted line means a part that is fused to Chemical Formula 1;
p is an integer of 0 to 5;
$Y1$ is O;
$R_3$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$ to $R_6$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylsulfonyl group, a $C_6$~$C_{60}$ arylsulfonyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group, a $C_1$~$C_{40}$ alkylcarbonyl group, a $C_6$~$C_{60}$ arylcarbonyl group and a $C_6$~$C_{60}$ arylsilyl group, and when substituted with a plurality of the substituents, these are the same as or different from each other.

2. A compound of the following Chemical Formula 1:

[Chemical Formula 1]

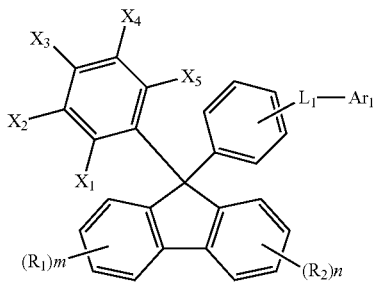

wherein in Chemical Formula 1,
$L_1$ is selected from the group consisting of a single bond, a $C_6$~$C_{18}$ arylene group and a heteroarylene group having 5 to 18 nuclear atoms;
any one of $X_1$ and $X_2$, $X_2$ and $X_3$, $X_3$ and $X_4$, and $X_4$ and $X_5$ bonds to a ring of the following Chemical Formula 3 to form a fused ring;
m and n are each independently an integer of 0 to 4;
$R_1$, $R_2$, and $X_1$ to $X_5$ not forming a fused ring with a ring of the following Chemical Formula 3 is each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3\sim C_{40}$ cycloalkyl group, a heterocycloalkyl group having 3 to 40 nuclear atoms, a $C_6\sim C_{60}$ aryl group, a heteroaryl group having 5 to 60 nuclear atoms, a $C_1\sim C_{40}$ alkyloxy group, a $C_6\sim C_{60}$ aryloxy group, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_1$, $R_2$, and $X_1$ to $X_5$ not forming a fused ring with a ring of the following Chemical Formula 3 is each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group and a $C_6\sim C_{60}$ arylsilyl group, and when substituted with a plurality of the substituents, these are the same as or different from each other;

[Chemical Formula 3]

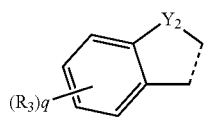

wherein in Chemical Formula 3,
a dotted line means a part that is fused to Chemical Formula 1;
q is an integer of 0 to 4;
$Y_2$ is O, S or C $(R_5)(R_6)$;
$R_3$, $R_5$, and $R_6$ are each independently selected from the group consisting of hydrogen, deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_3\sim C_{40}$ cycloalkyl group, a heterocycloalkyl group having 3 to 40 nuclear atoms, a $C_6\sim C_{60}$ aryl group, a heteroaryl group having 5 to 60 nuclear atoms, a $C_1\sim C_{40}$ alkyloxy group, a $C_6\sim C_{60}$ aryloxy group, a $C_3\sim C_{40}$ alkylsilyl group, a $C_6\sim C_{60}$ arylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylsulfonyl group, the arylsulfonyl group, the alkylboron group, the arylboron group, the arylphosphanyl group, the mono or diarylphosphinyl group, the alkylcarbonyl group, the arylcarbonyl group and the arylsilyl group of $R_3$, $R_5$, and $R_6$ are each independently unsubstituted or substituted with one or more types of substituents selected from the group consisting of deuterium, halogen, a cyano group, a nitro group, a $C_1\sim C_{40}$ alkyl group, a $C_2\sim C_{40}$ alkenyl group, a $C_2\sim C_{40}$ alkynyl group, a $C_6\sim C_{60}$ aryl group, a heteroaryl group having 5 to 60 nuclear atoms, a $C_6\sim C_{60}$ aryloxy group, a $C_1\sim C_{40}$ alkyloxy group, a $C_6\sim C_{60}$ arylamine group, a $C_3\sim C_{40}$ cycloalkyl group, a heterocycloalkyl group having 3 to 40 nuclear atoms, a $C_1\sim C_{40}$ alkylsilyl group, a $C_1\sim C_{40}$ alkylsulfonyl group, a $C_6\sim C_{60}$ arylsulfonyl group, a $C_1\sim C_{40}$ alkylboron group, a $C_6\sim C_{60}$ arylboron group, a $C_6\sim C_{60}$ arylphosphanyl group, a $C_6\sim C_{60}$ mono or diarylphosphinyl group, a $C_1\sim C_{40}$ alkylcarbonyl group, a $C_6\sim C_{60}$ arylcarbonyl group and a $C_6\sim C_{60}$ arylsilyl group, and when substituted with a plurality of the substituents, these are the same as or different from each other;

$Ar_1$ is a substituent represented by any one of the following Chemical Formula 13, Chemical Formula C-1 to Chemical Formula C-6,

[Chemical Formula 13]

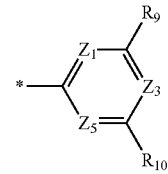

[Chemical Formulas C1-C6]

C-1

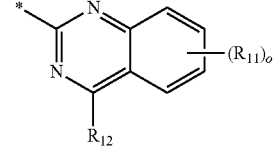

C-2

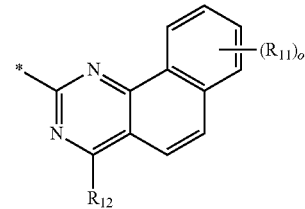

C-3

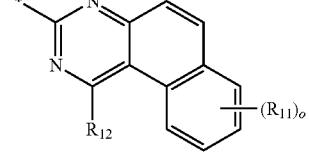

C-4

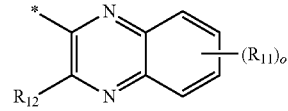

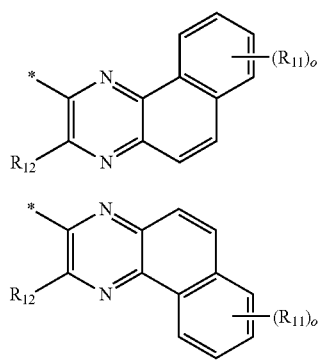

$Z_1$, $Z_3$ and $Z_5$ are each independently N or C ($R_8$), wherein at least one of $Z_1$, $Z_3$ and $Z_5$ is N;

o is an integer of 0 to 4;

$R_8$ is selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group, or bonds to adjacent groups to form a fused ring, and when $R_8$ is present in plural numbers, these are the same as or different from each other; and $R_9$ and $R_{10}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group;

the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_8$ and $R_{10}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other; and $R_{11}$ and $R_{12}$ are each independently selected from the group consisting of hydrogen, deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_3$~$C_{40}$ cycloalkyl group, a heterocycloalkyl group having 3 to 40 nuclear atoms, a $C_6$~$C_{60}$ aryl group, a heteroaryl group having 5 to 60 nuclear atoms, a $C_1$~$C_{40}$ alkyloxy group, a $C_6$~$C_{60}$ aryloxy group, a $C_3$~$C_{40}$ alkylsilyl group, a $C_6$~$C_{60}$ arylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylamine group; and the alkyl group, the alkenyl group, the alkynyl group, the aryl group, the heteroaryl group, the aryloxy group, the alkyloxy group, the cycloalkyl group, the heterocycloalkyl group, the arylamine group, the alkylsilyl group, the alkylboron group, the arylboron group, the arylphosphanyl group, the mono or diarylphosphinyl group and the arylsilyl group of $R_{11}$ and $R_{12}$ are each independently unsubstituted or substituted with one or more types of substituents selected from the group consisting of deuterium, halogen, a cyano group, a nitro group, a $C_1$~$C_{40}$ alkyl group, a $C_2$~$C_{40}$ alkenyl group, a $C_2$~$C_{40}$ alkynyl group, a $C_6$~$C_{60}$ aryl group, a heteroaryl group having 5 to 60 nuclear atoms, a $C_6$~$C_{60}$ aryloxy group, a $C_1$~$C_{40}$ alkyloxy group, a $C_6$~$C_{60}$ arylamine group, a $C_3$~$C_{40}$ cycloalkyl group, a heterocycloalkyl group having 3 to 40 nuclear atoms, a $C_1$~$C_{40}$ alkylsilyl group, a $C_1$~$C_{40}$ alkylboron group, a $C_6$~$C_{60}$ arylboron group, a $C_6$~$C_{60}$ arylphosphanyl group, a $C_6$~$C_{60}$ mono or diarylphosphinyl group and a $C_6$~$C_{60}$ arylsilyl group, and when substituted with a plurality of the substituents, these are the same as or different from each other;

provided that when $Ar_1$ is represented by Chemical Formula C-1, $R_{12}$ is not hydrogen or deuterium;

provided that when $Ar_1$ is represented by Chemical Formula 13, compounds meet conditions that at least one of $R_9$ and $R_{10}$ is a heteroaryl group having 5 to 60 nuclear atoms, or that $L_1$ is a heteroarylene group having 5 to 18 nuclear atoms.

3. The compound of claim 1, which is represented by the following Chemical Formula 5 or 10:

[Chemical Formula 5]

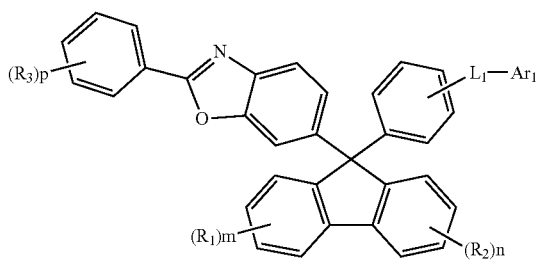

-continued

[Chemical Formula 10]

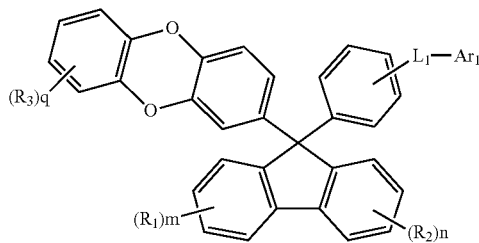

wherein, in Chemical Formula 5 or 10, p, q, m, n, $R_1$ to $R_3$, $L_1$ and $Ar_1$ have the same definitions as in claim 1.

4. The compound of claim 1, wherein $L_1$ is a direct bond, or a linker selected from the group consisting of the following Chemical Formula A-1 to A-6:

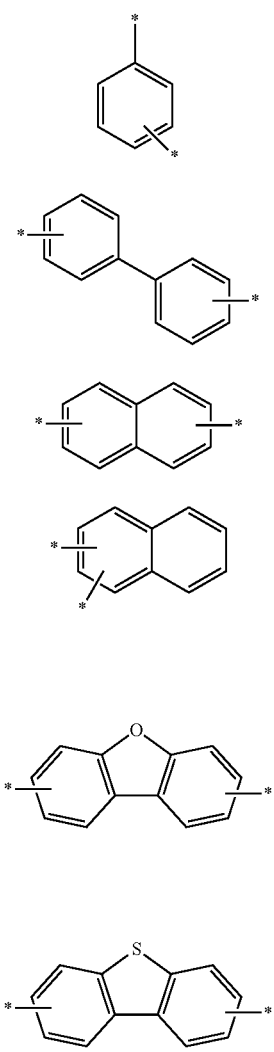

wherein in Chemical Formula A-1 to A-6,

* means a part where a bond is formed.

5. The compound of claim 2, wherein $R_{12}$ is selected from the group consisting of a $C_1$~$C_{40}$ alkyl group, a $C_6$~$C_{60}$ aryl group and a heteroaryl group having 5 to 60 nuclear atoms; and the alkyl group, the aryl group and the heteroaryl group of $R_{12}$ are each independently unsubstituted or substituted with one or more types of substituents selected from the group consisting of a $C_1$~$C_{40}$ alkyl group, a $C_6$~$C_{60}$ aryl group and a heteroaryl group having 5 to 60 nuclear atoms, and when substituted with a plurality of the substituents, these are the same as or different from each other.

6. The compound of claim 1, wherein $R_{13}$ and $R_{14}$ are each independently selected from the group consisting of a $C_1$~$C_{30}$ alkyl group, a $C_6$~$C_{30}$ aryl group and a heteroaryl group having 5 to 30 nuclear atoms.

7. The compound of claim 1, which is selected from the group consisting of the following compounds:

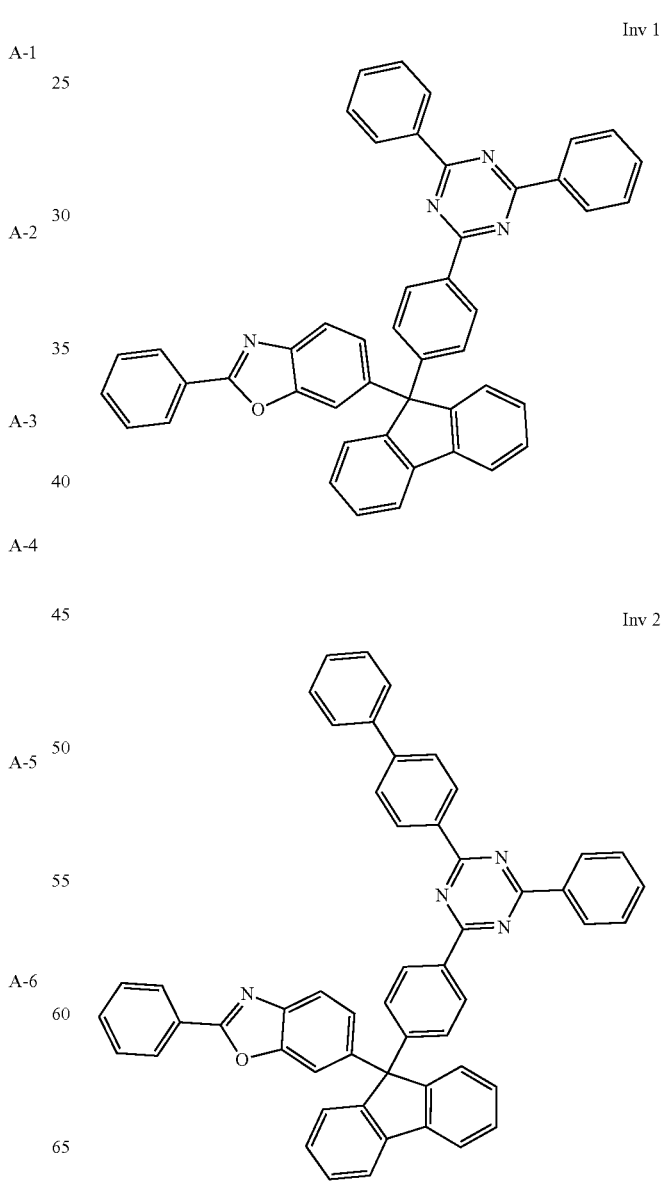

Inv 3
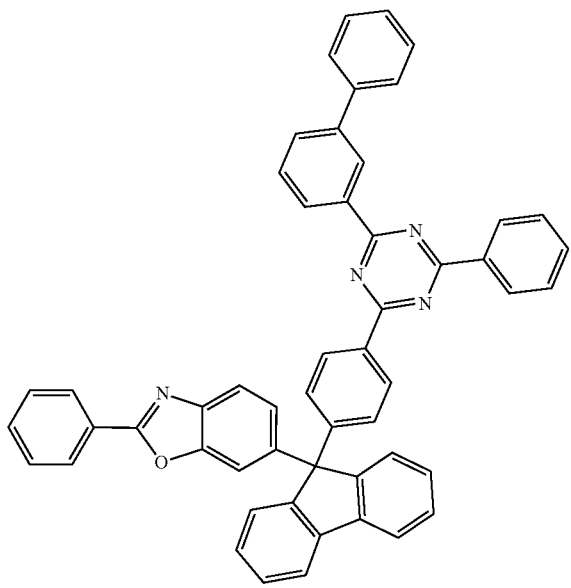
Inv 4
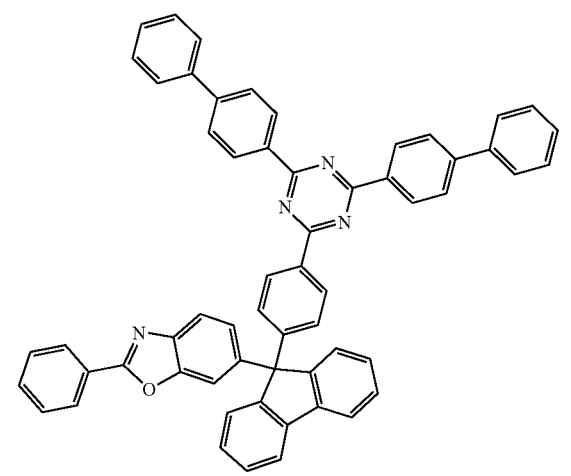
Inv 5
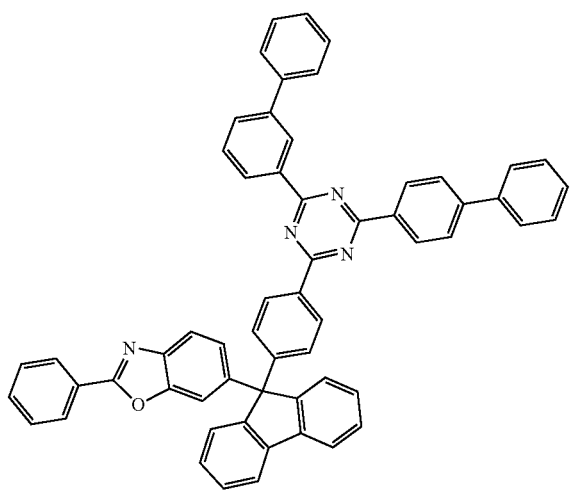
Inv 6
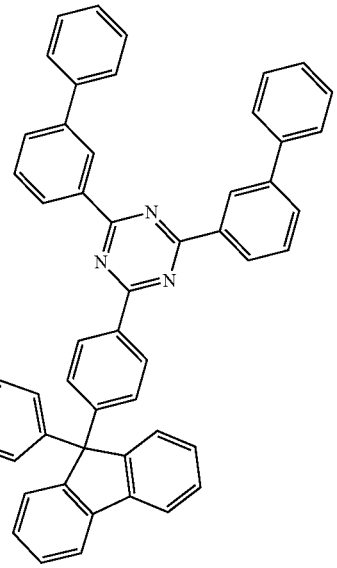
Inv 7
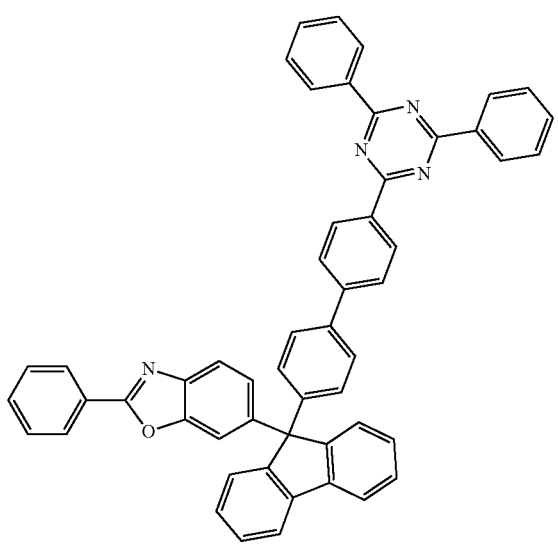

Inv 8
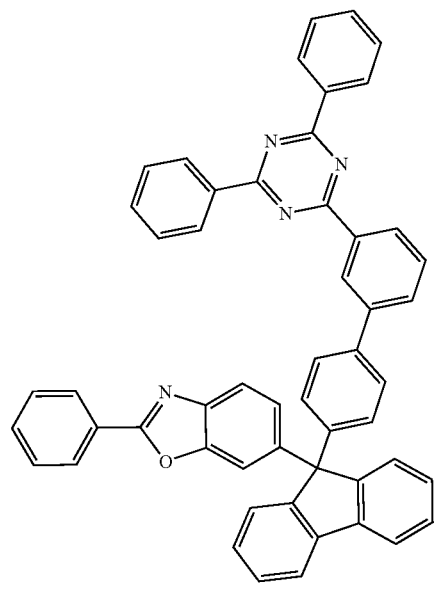
Inv 9
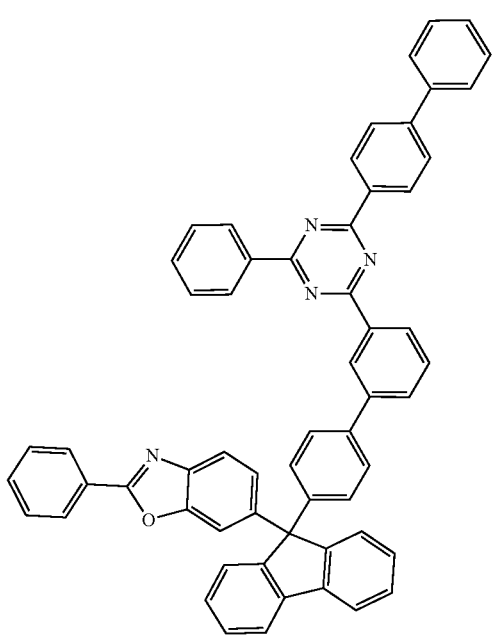
Inv 10
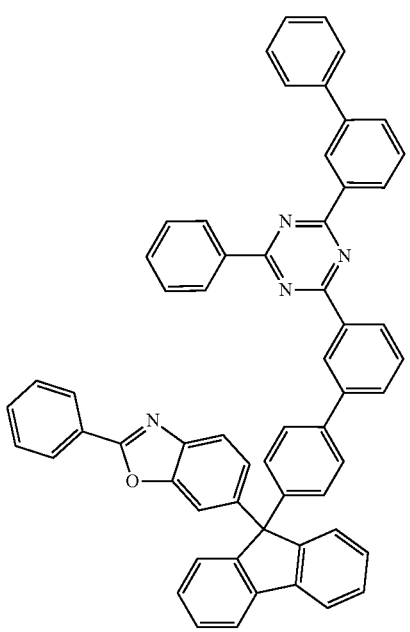
Inv 11
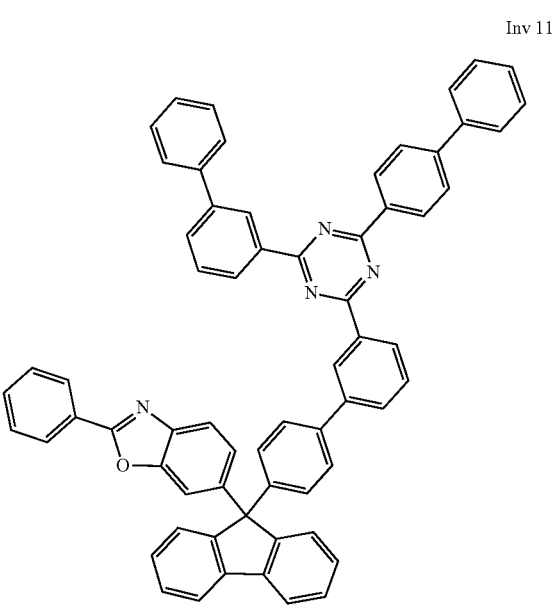

Inv 12
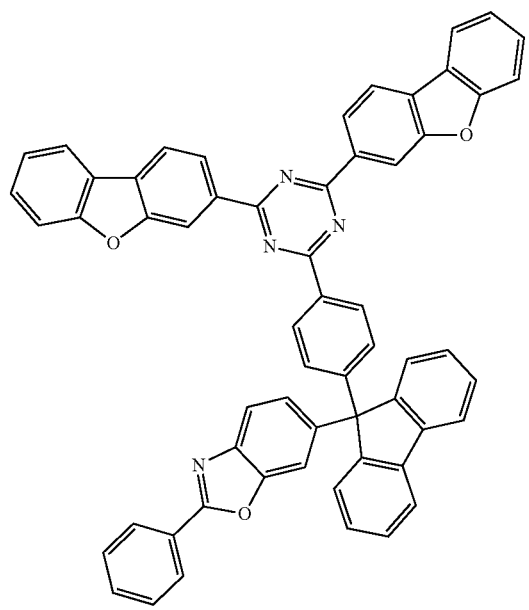
Inv 13
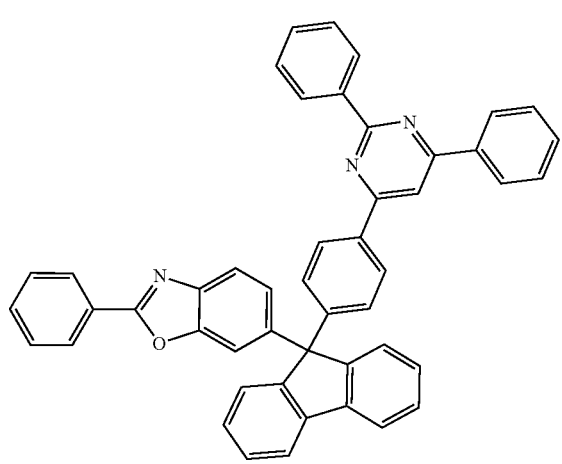
Inv 14
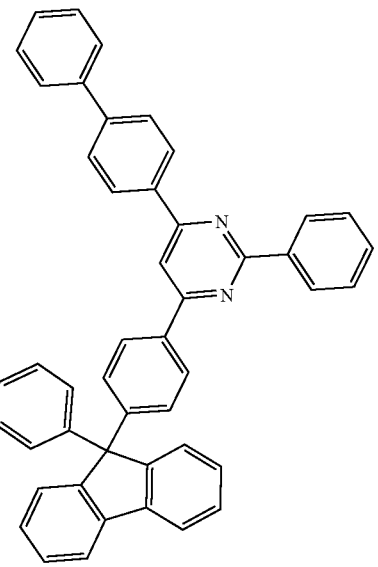
Inv 15
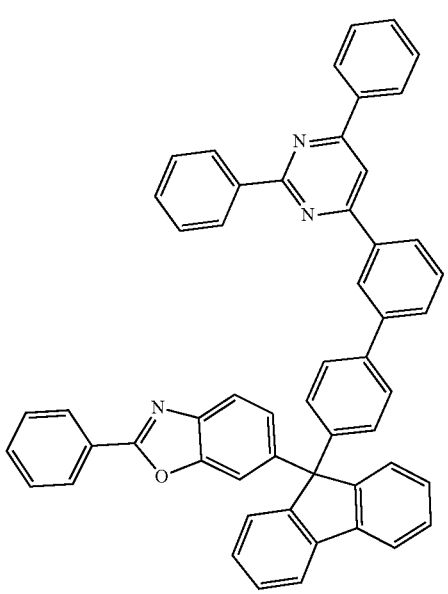

-continued
Inv 16
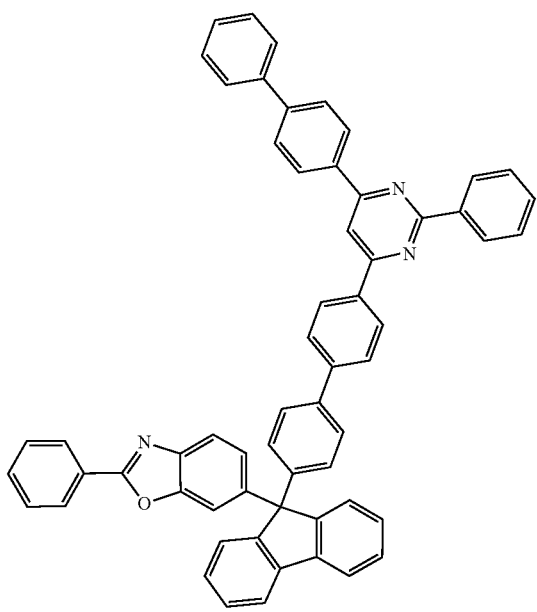
Inv 17
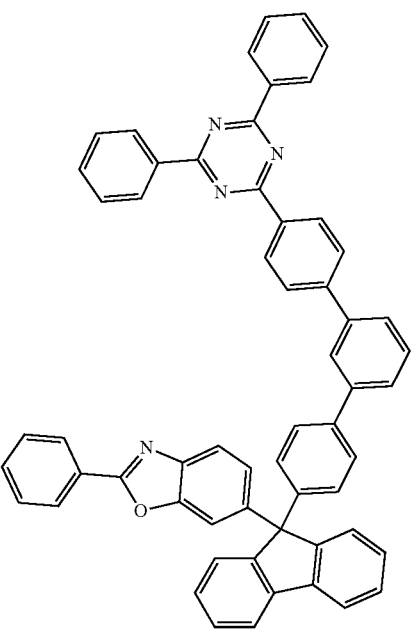
-continued
Inv 18
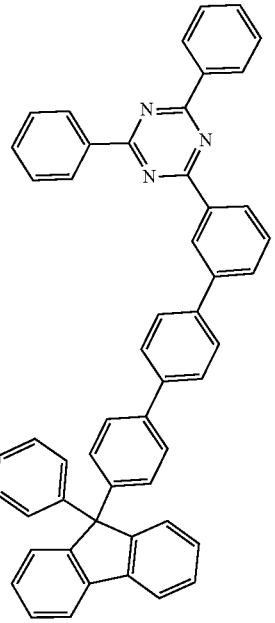
Inv 19

Inv 20
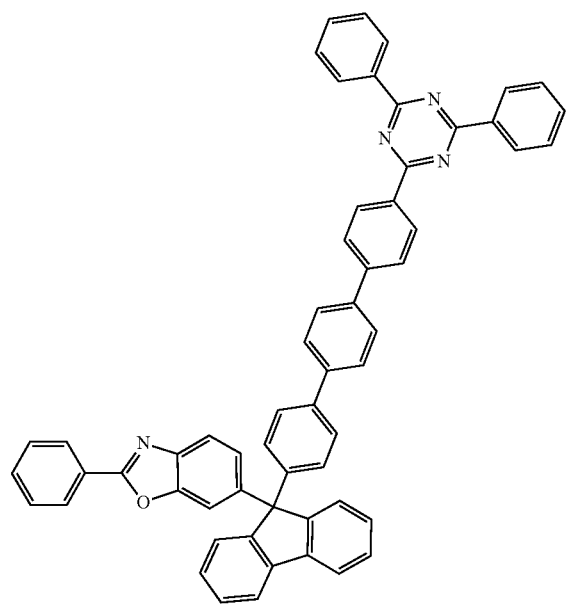
Inv 21
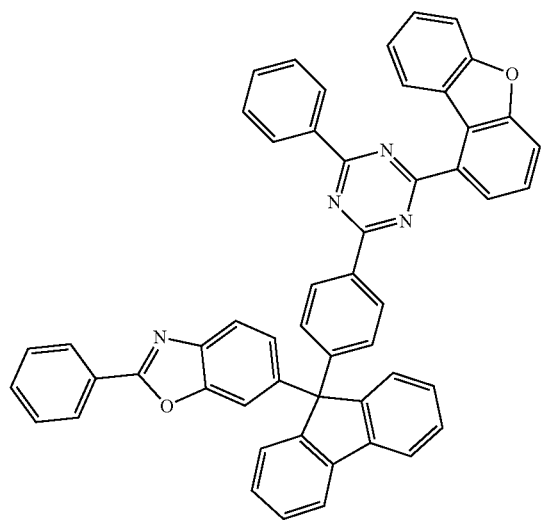
Inv 22
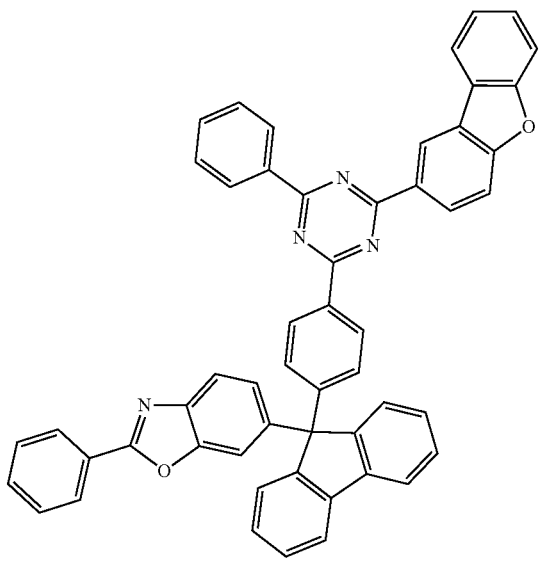
Inv 23
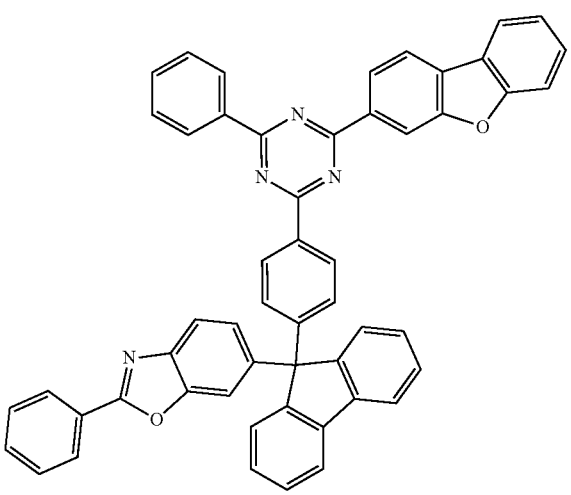
Inv 24
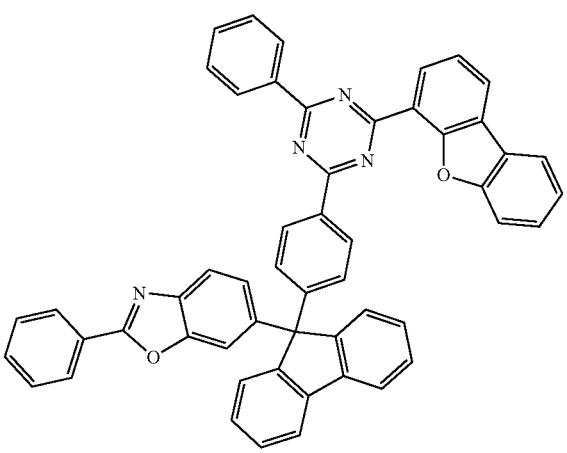

Inv 25
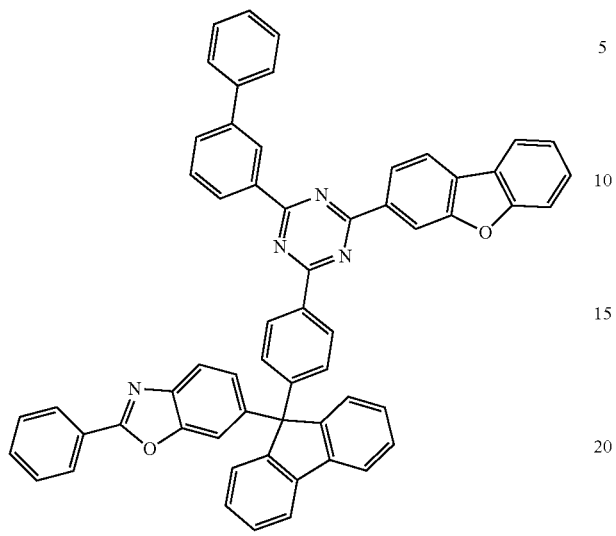
Inv 26
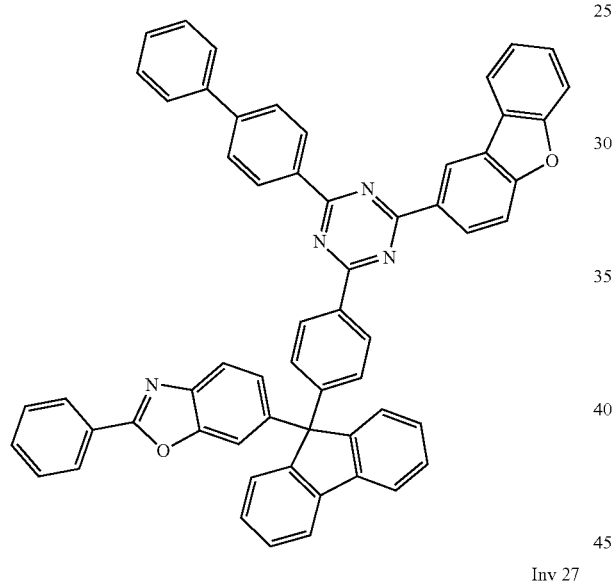
Inv 27
Inv 28
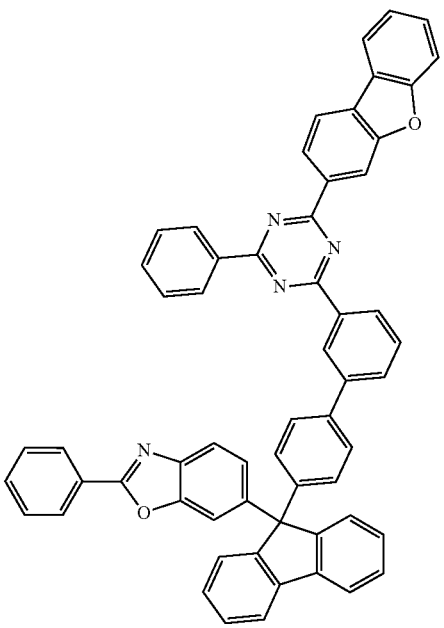
Inv 29
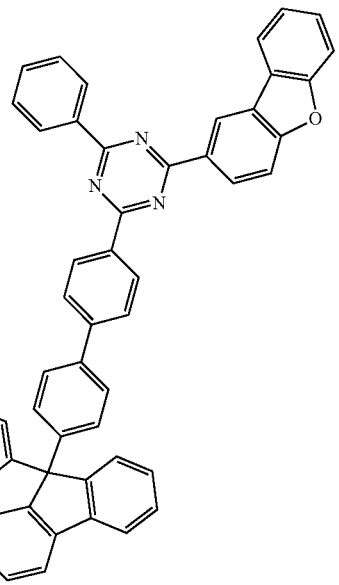

-continued
Inv 30
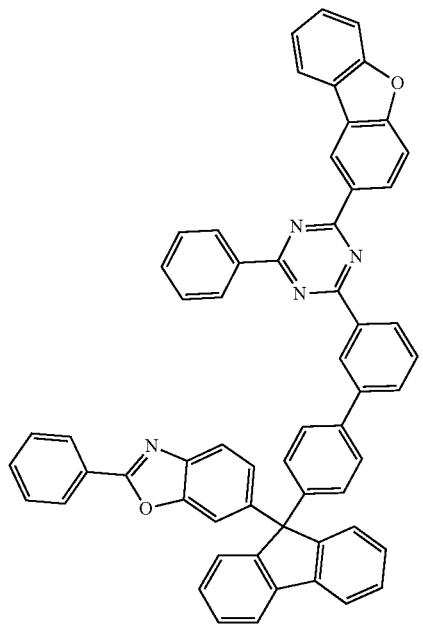
Inv 31
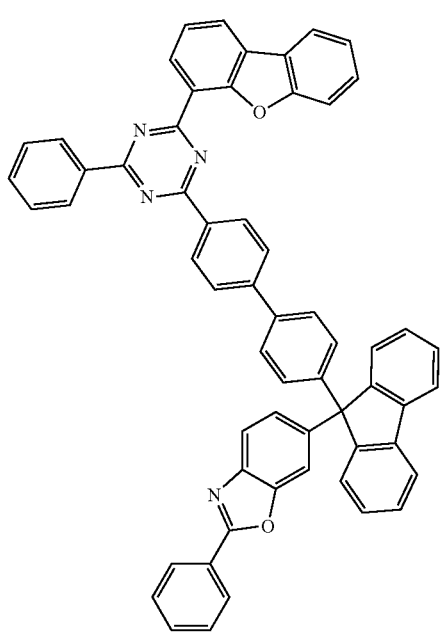
-continued
Inv 32
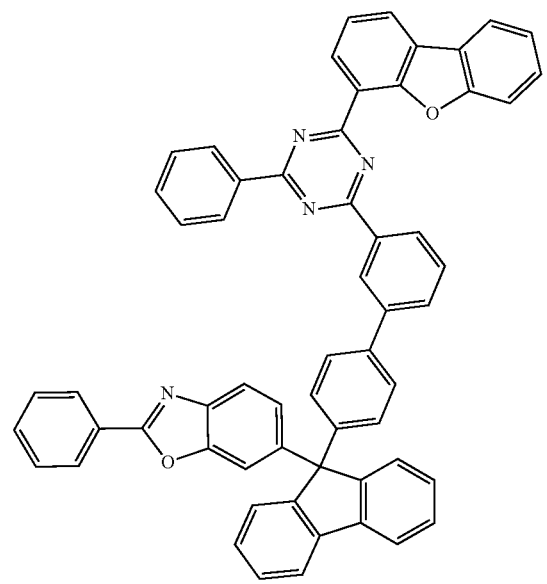
Inv 33
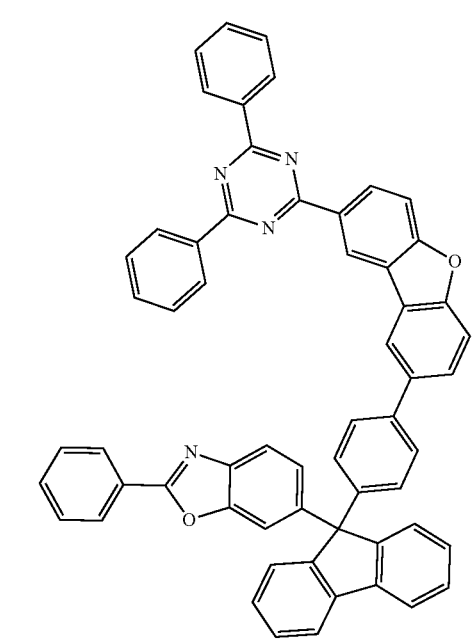

-continued
Inv 34
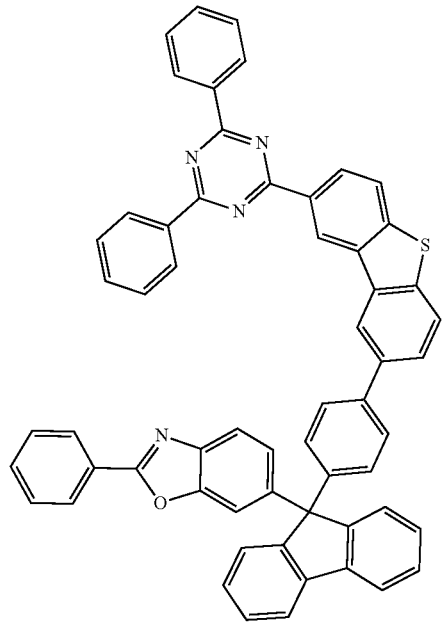
Inv 35
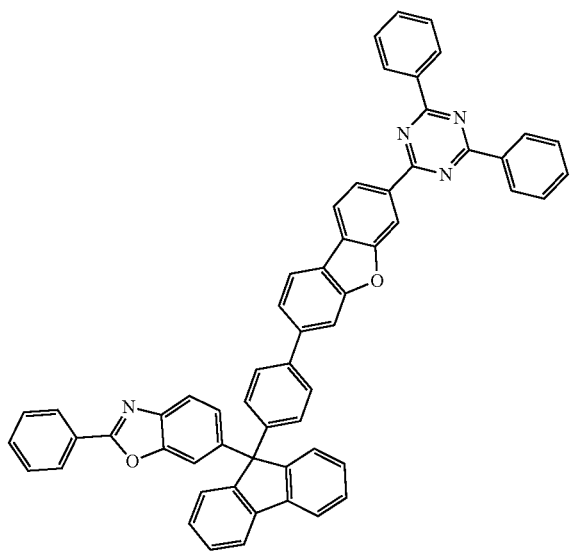
-continued
Inv 36
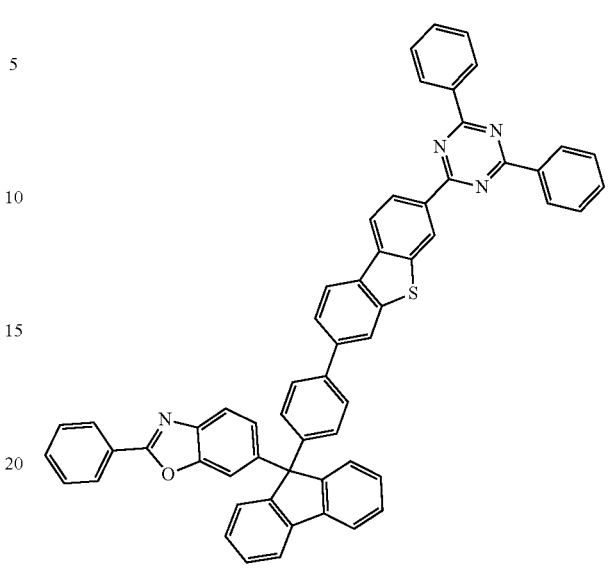
Inv 37
Inv 38
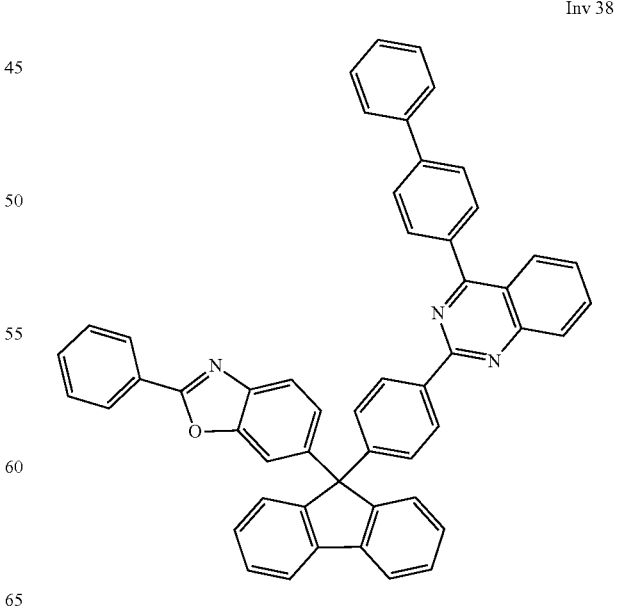

-continued
Inv 39
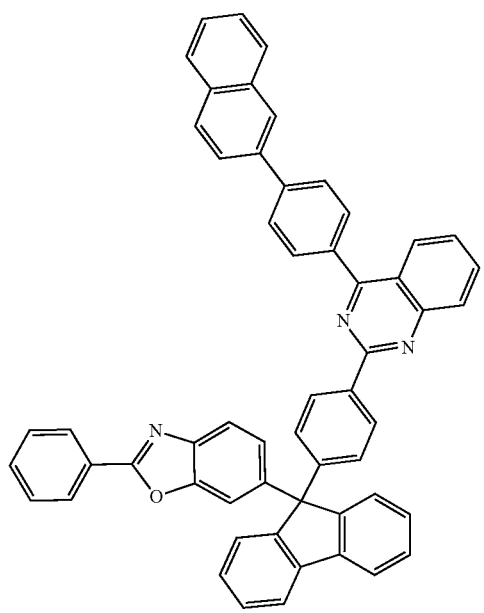
Inv 40
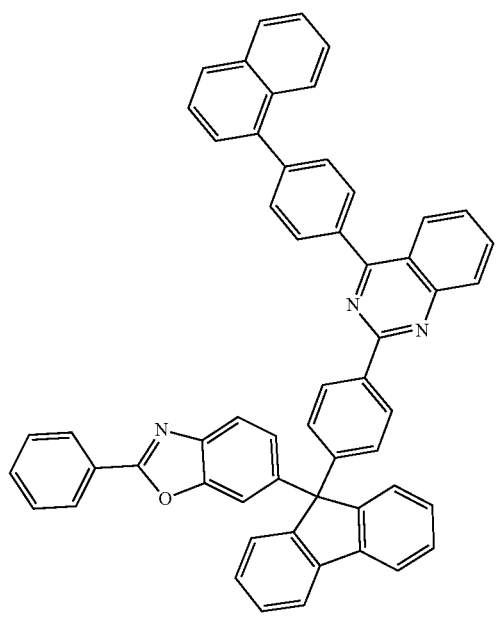
Inv 41
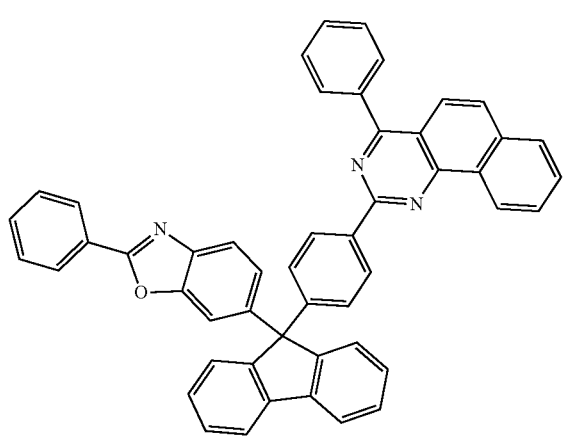
-continued
Inv 42
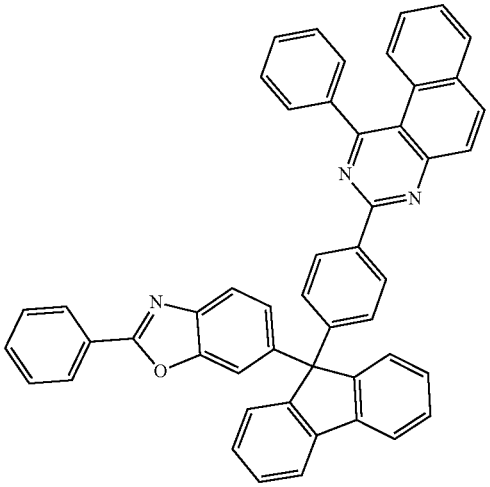
Inv 43
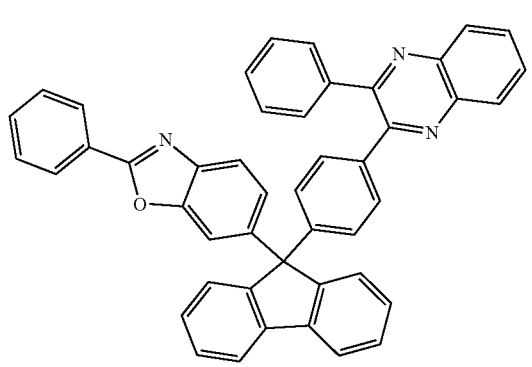
Inv 44
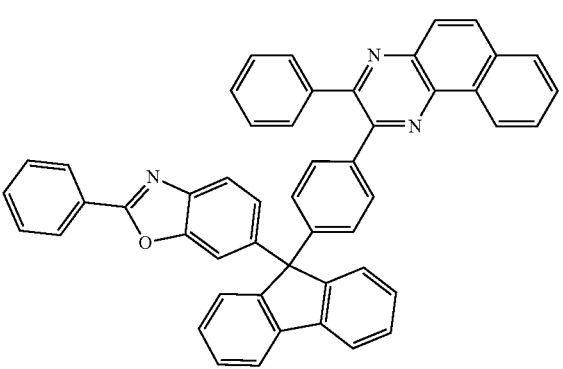

-continued
Inv 45
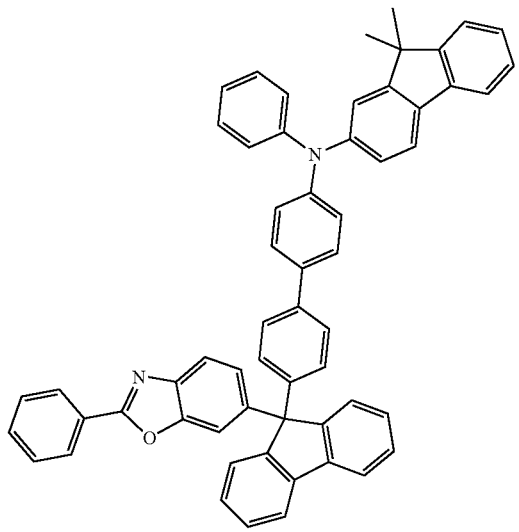
Inv 46
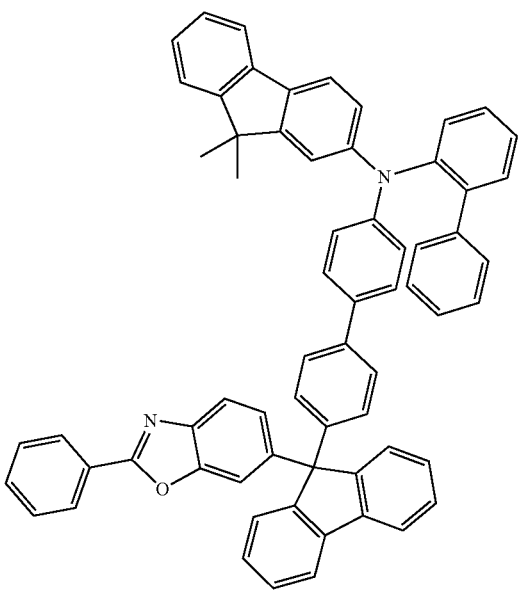
-continued
Inv 47
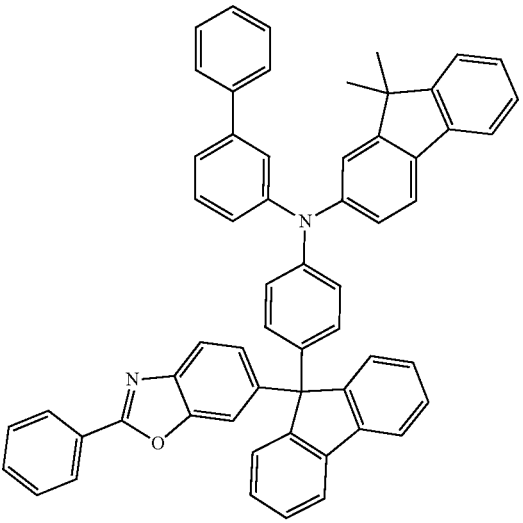
Inv 48
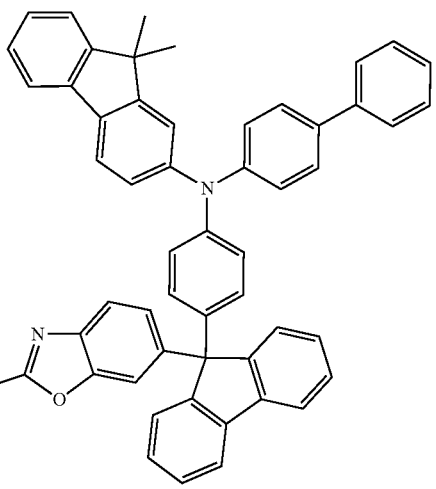
Inv 241
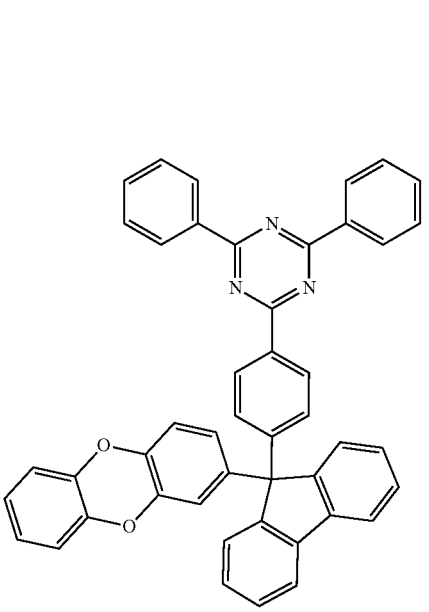

Inv 242
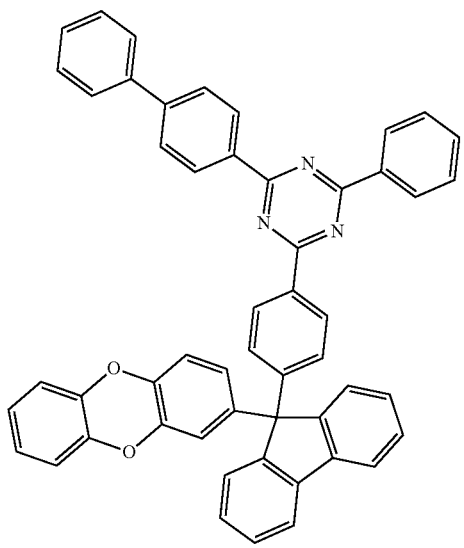
Inv 244
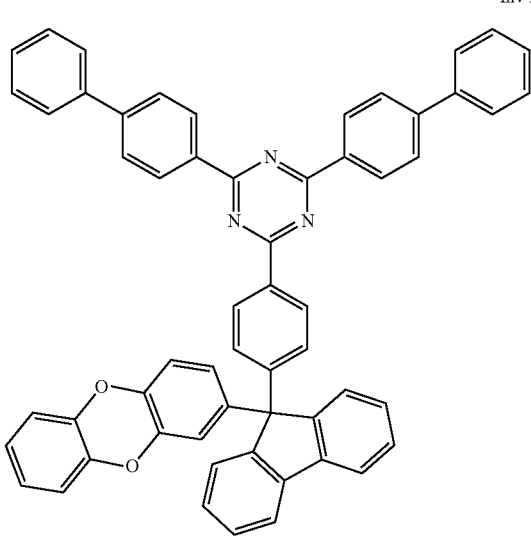
Inv 243
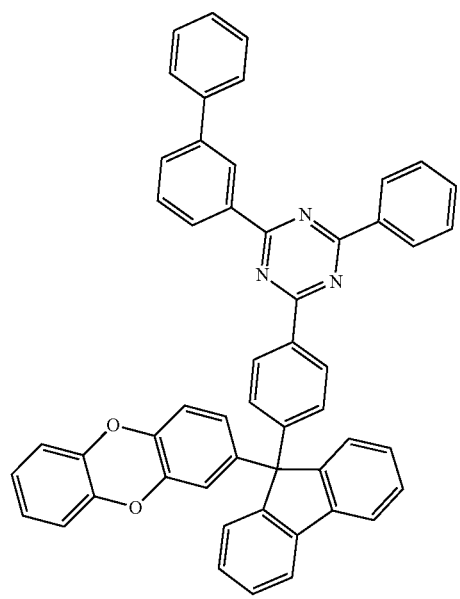
Inv 245
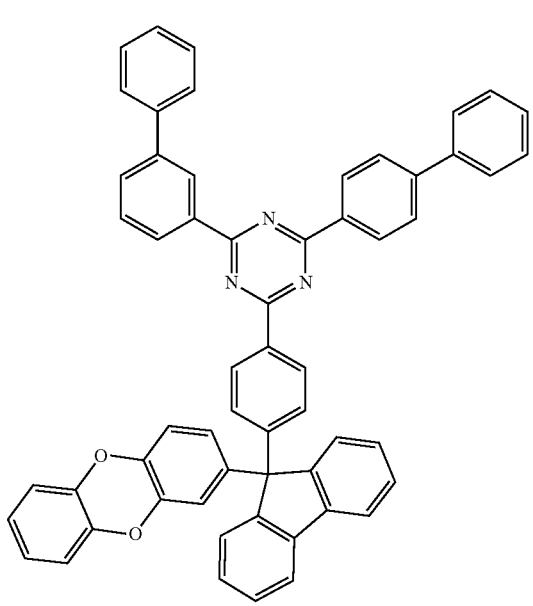

-continued
Inv 246
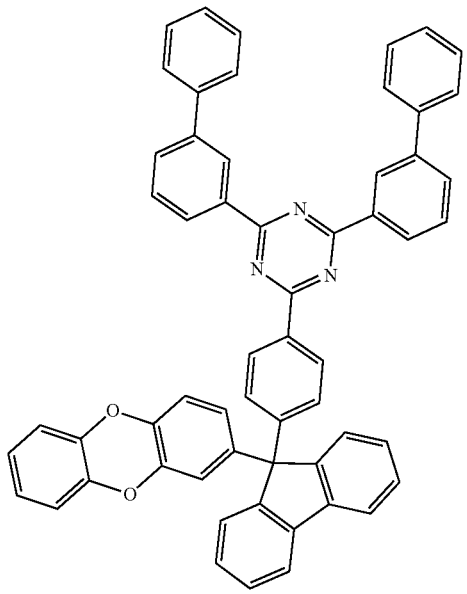
Inv 247
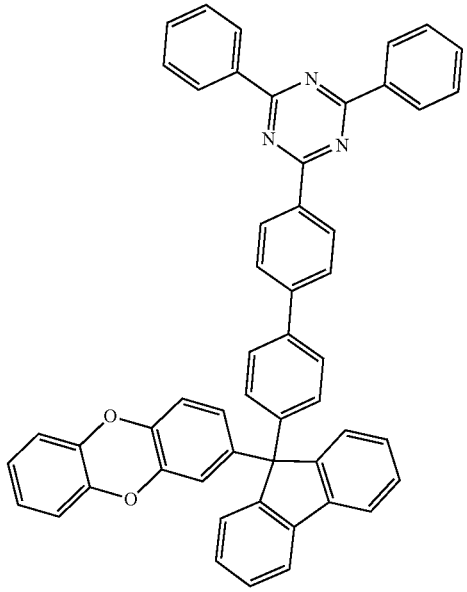
-continued
Inv 248
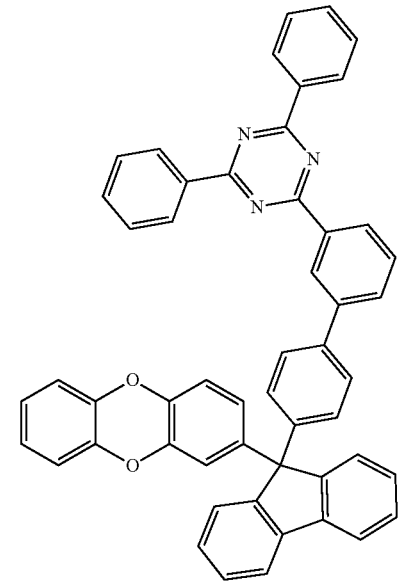
Inv 249
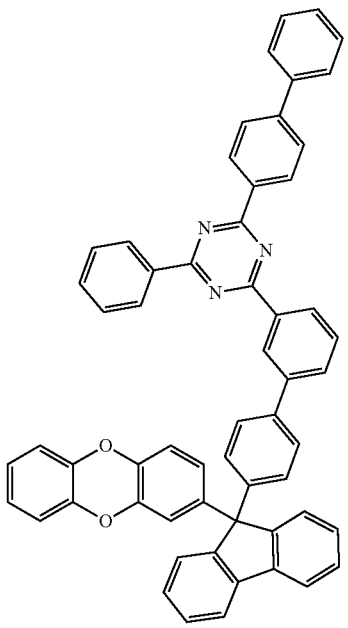

Inv 250
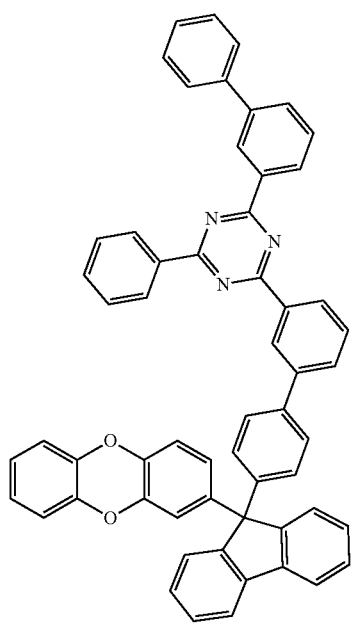
Inv 251
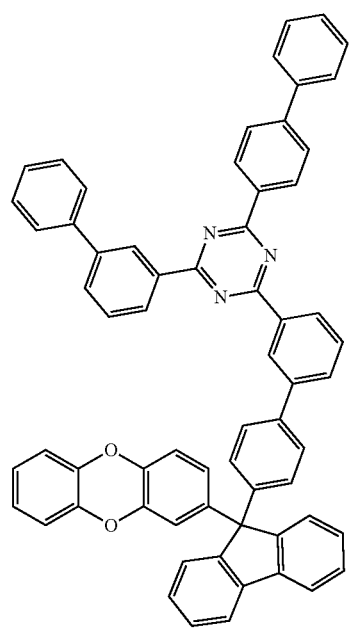
Inv 252
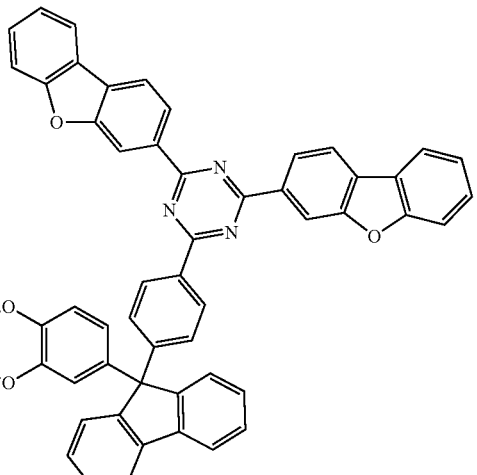
Inv 253
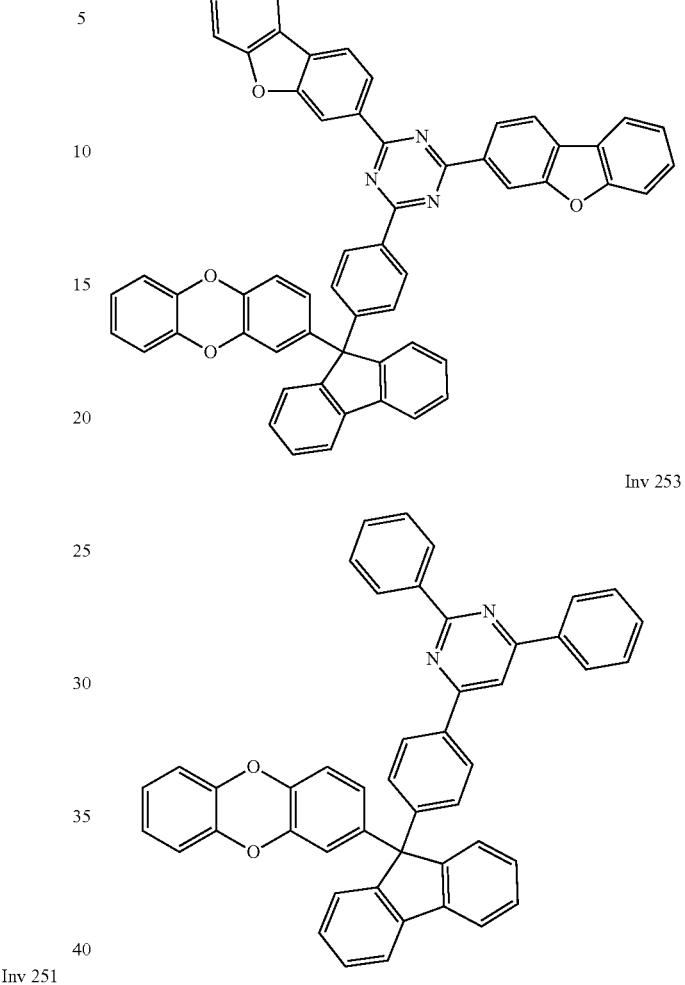
Inv 254
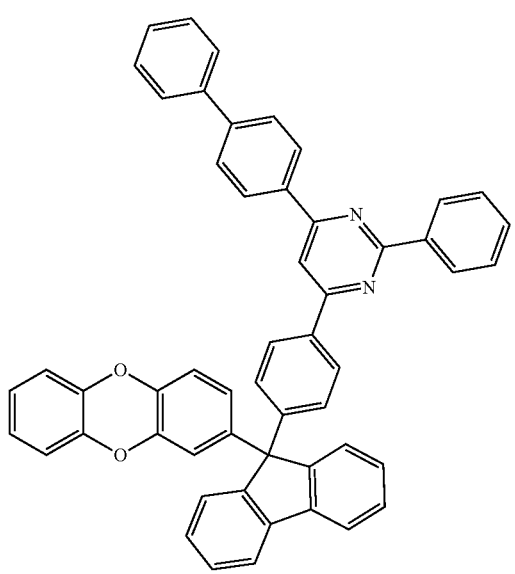

-continued
Inv 255
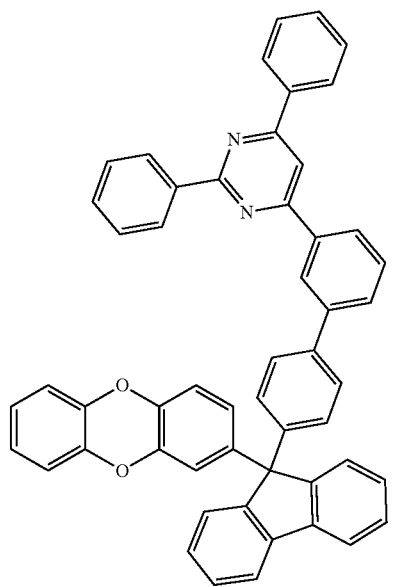
Inv 256
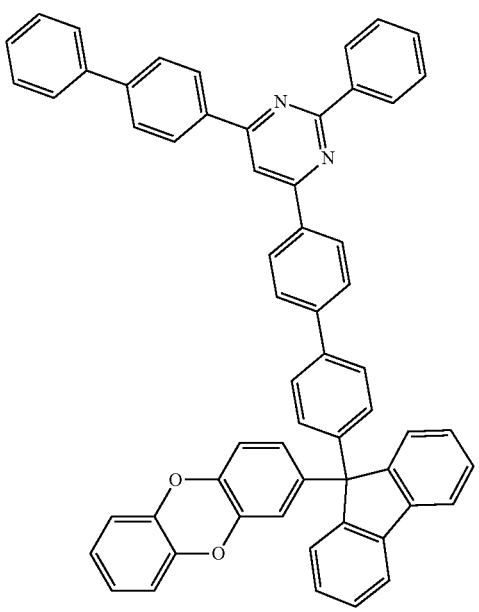
-continued
Inv 257
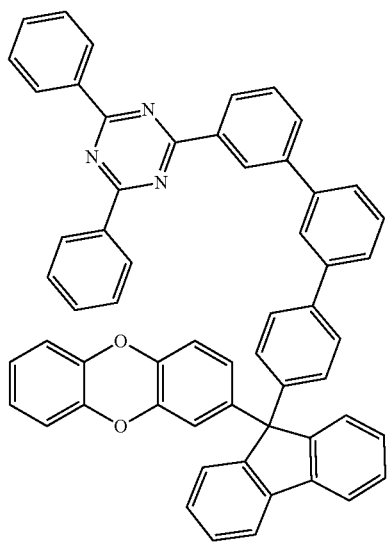
Inv 258
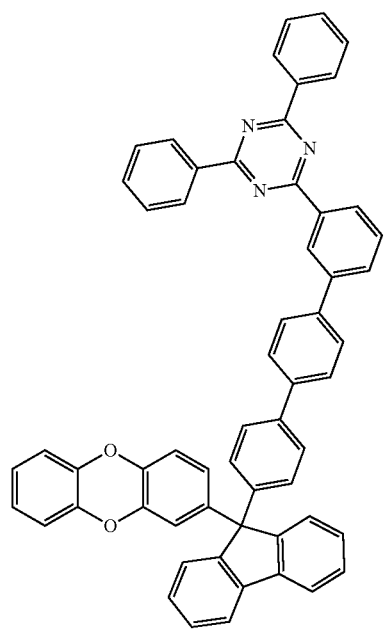

Inv 259
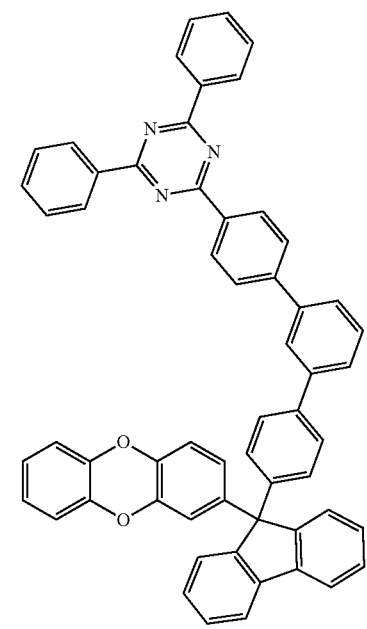
Inv 260
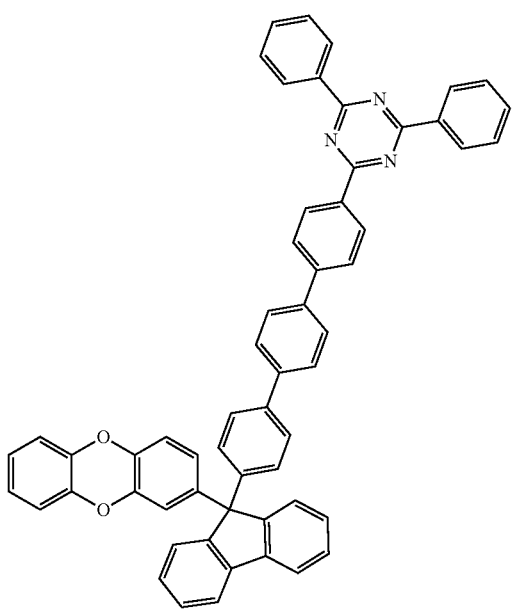
Inv 261
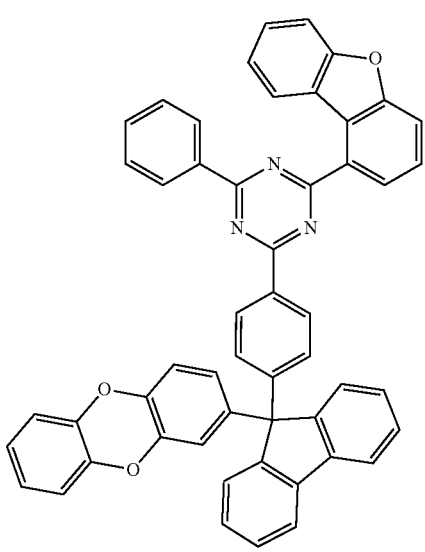
Inv 262
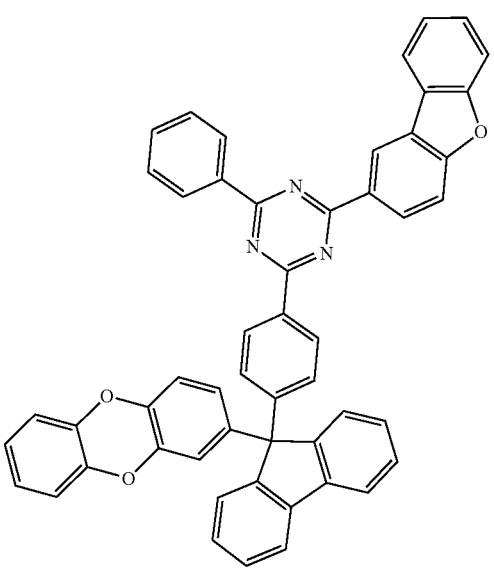
Inv 263
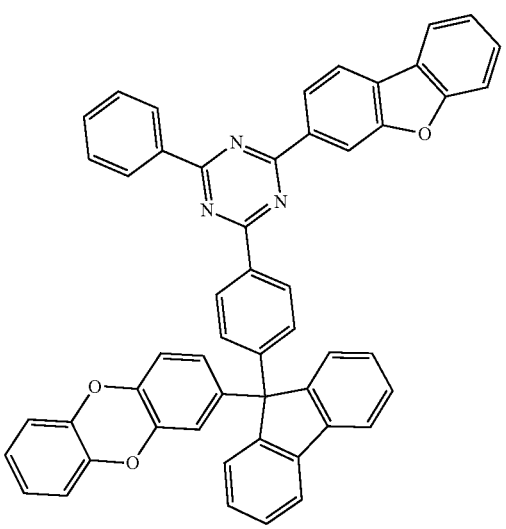

Inv 264
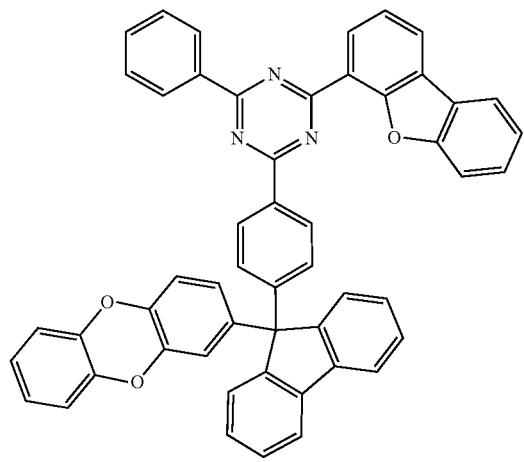
Inv 265
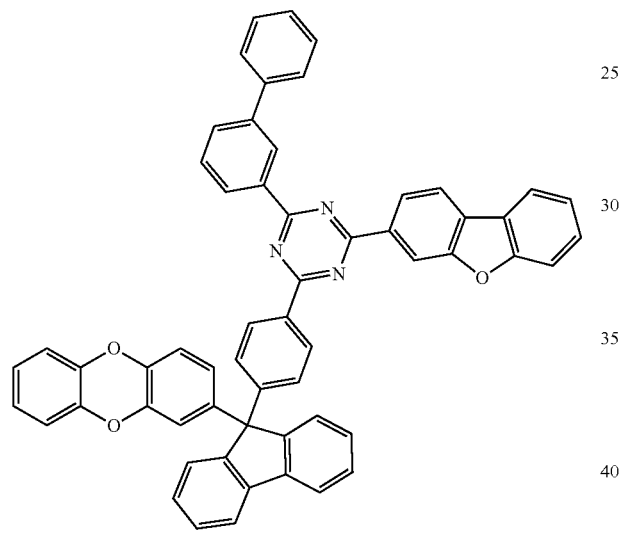
Inv 266
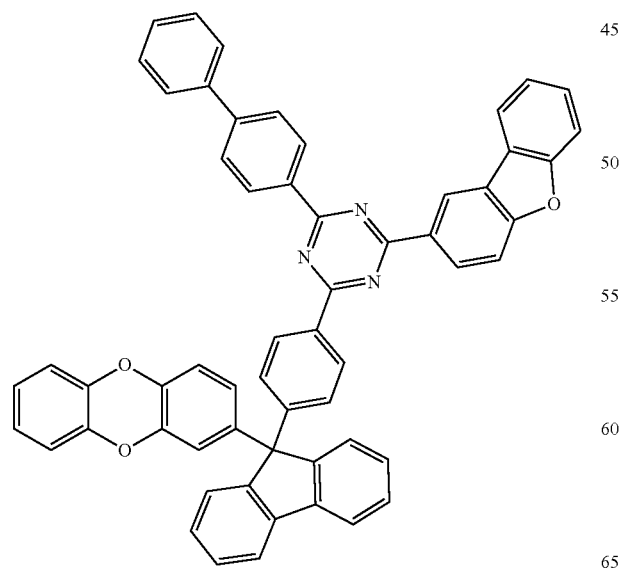
Inv 267
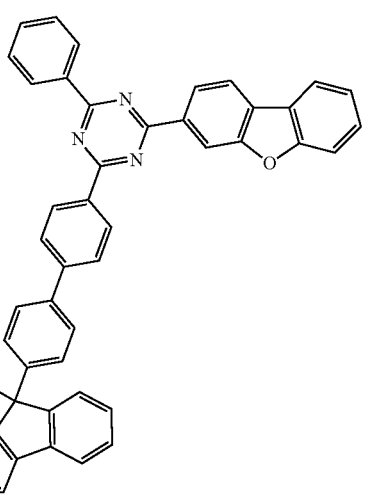
Inv 268
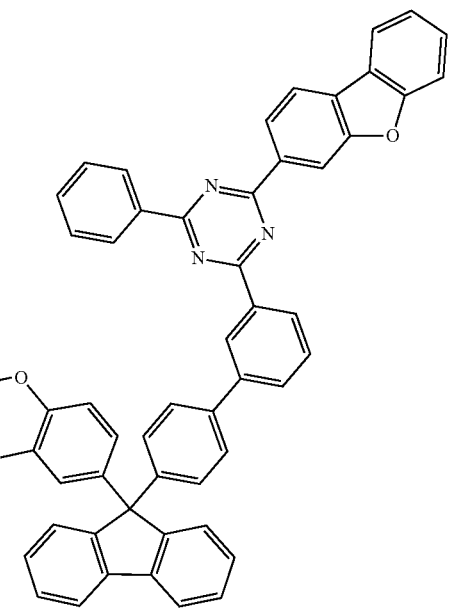

-continued
Inv 269
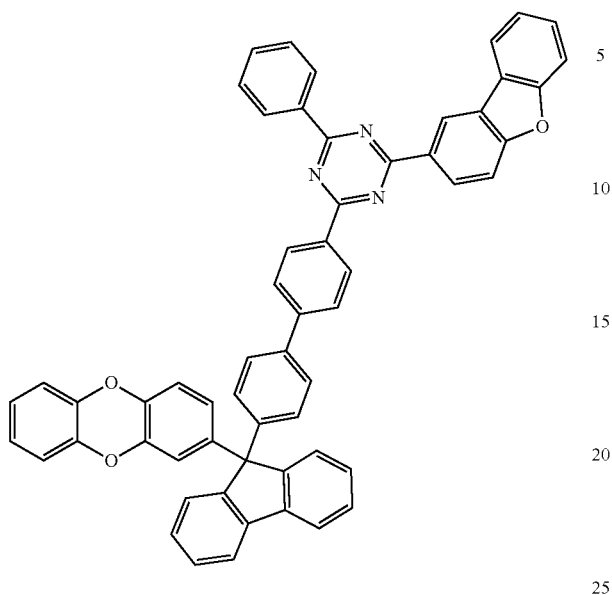
Inv 270
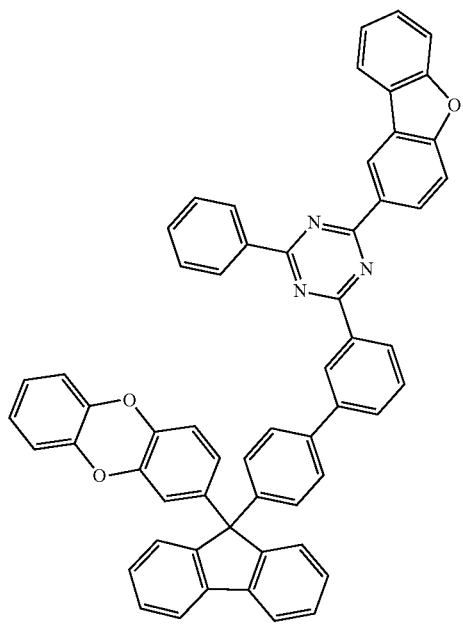
-continued
Inv 271
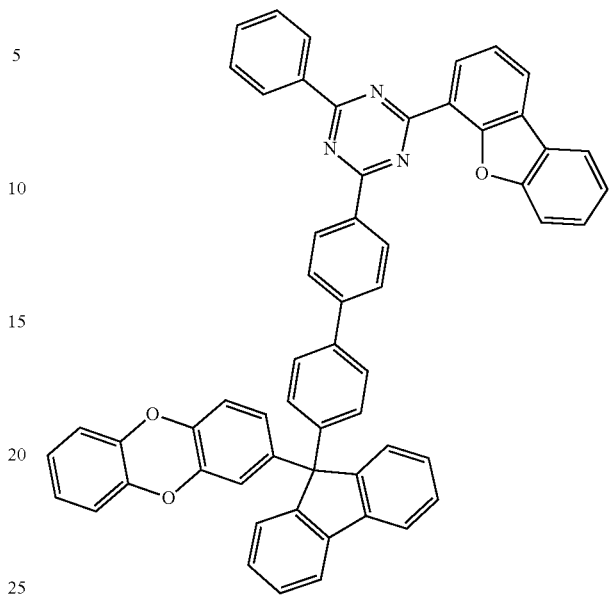
Inv 272
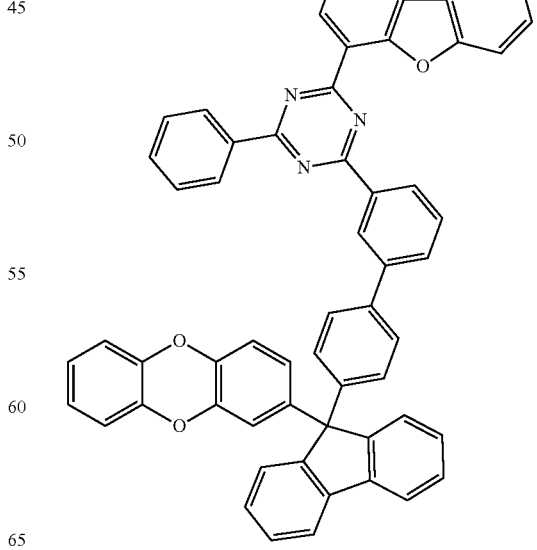

Inv 273
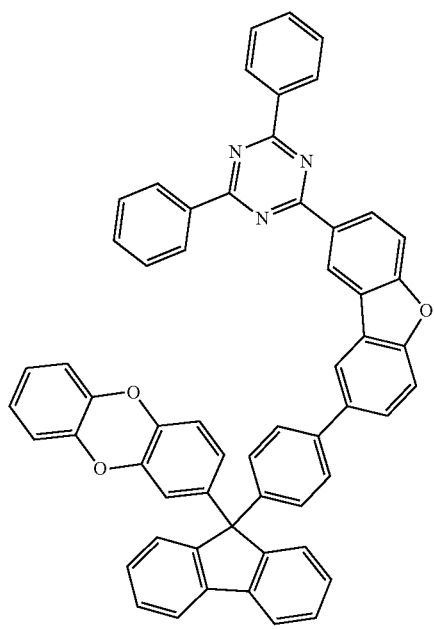
Inv 274
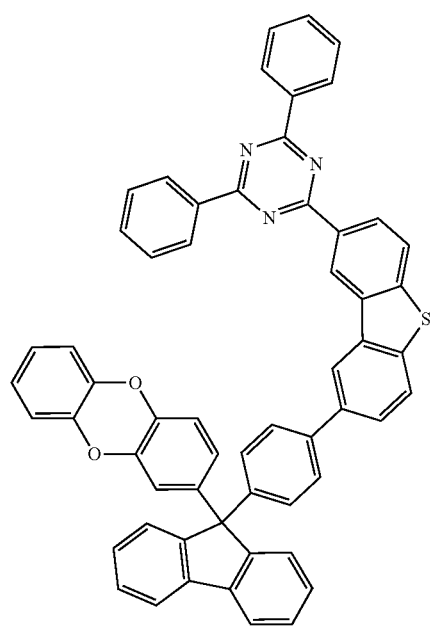
Inv 275
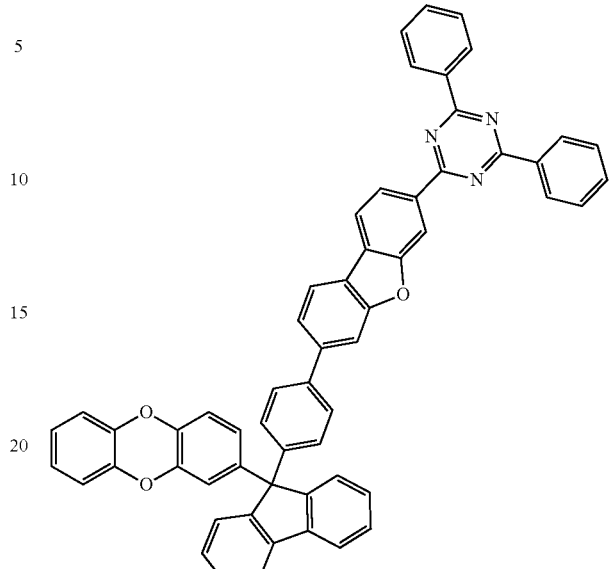
Inv 276
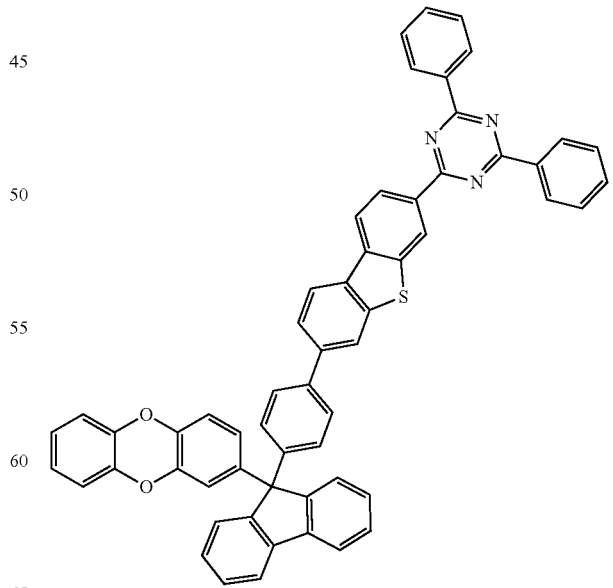

-continued
Inv 277
Inv 278
Inv 279
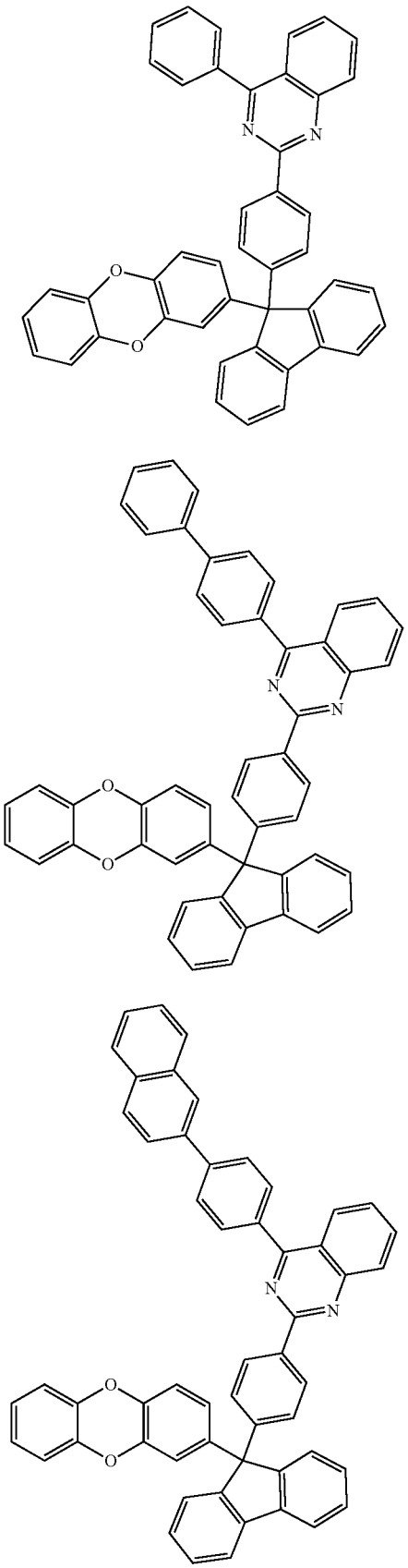
-continued
Inv 280
Inv 281
Inv 282
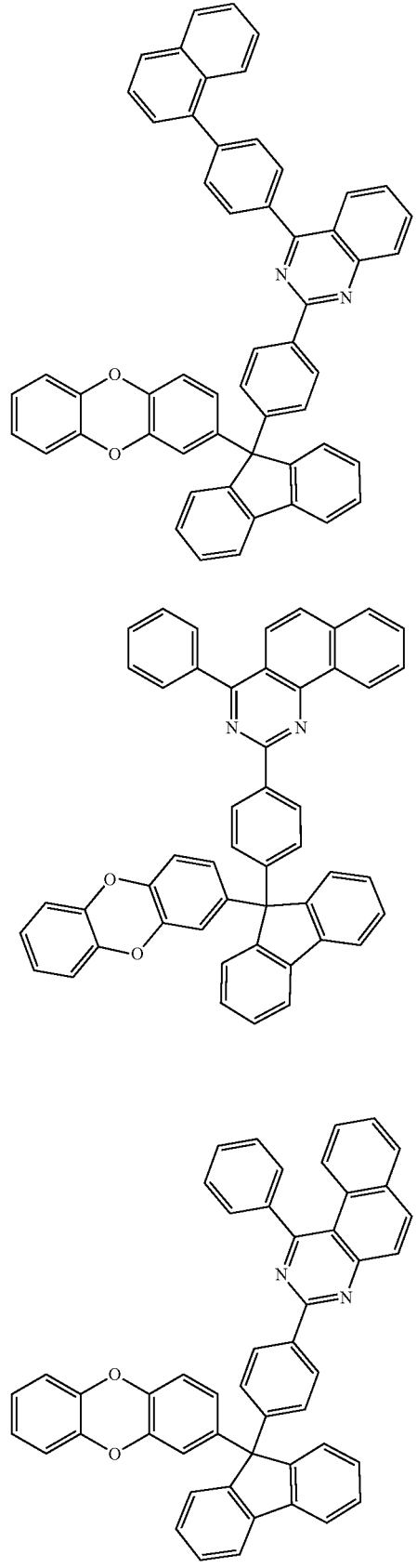

Inv 283
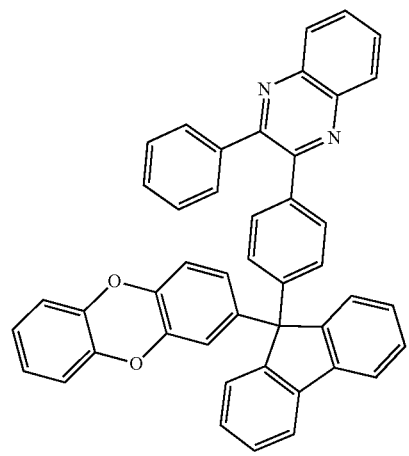
Inv 284
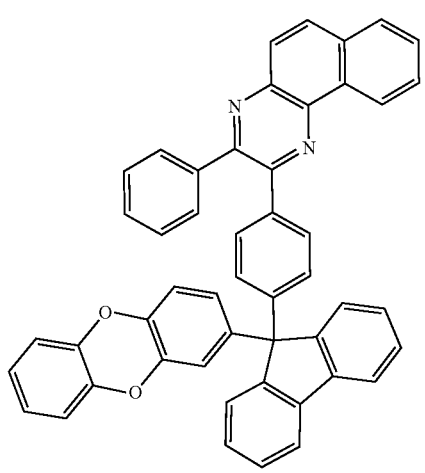
Inv 285
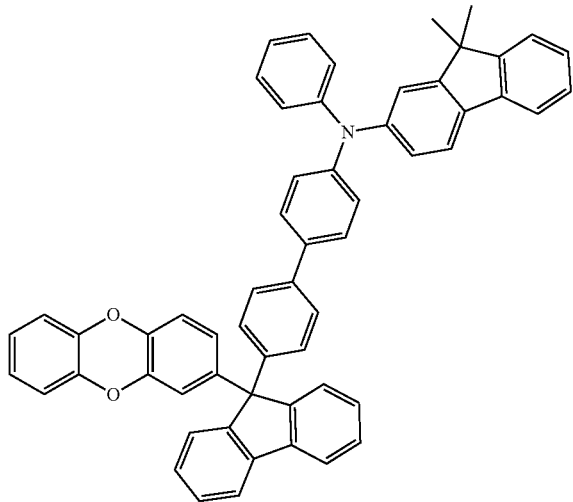
Inv 286
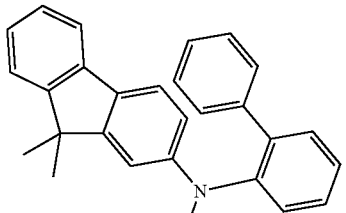
Inv 287
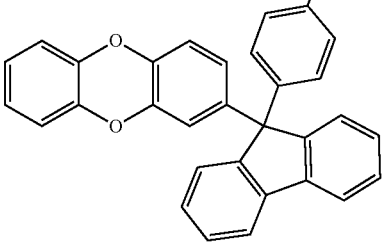
Inv 288
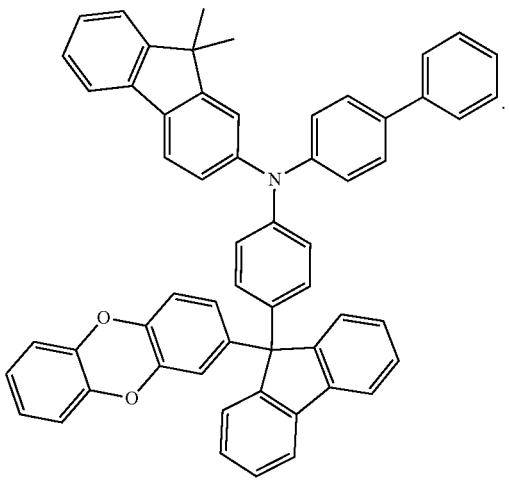

8. An organic electroluminescent device comprising:
an anode;
a cathode; and
one or more organic material layers provided between the anode and the cathode,
wherein at least one of the one or more organic material layers includes the compound of the Chemical Formula 1 of claim 1.

9. The organic electroluminescent device of claim 8, wherein the organic material layer includes one or more layers selected from the group consisting of a hole injection layer, a hole transport layer, a hole transport auxiliary layer, an electron transport layer, an electron transport auxiliary layer and a light emitting layer.

10. The compound of claim 2, which is represented by any one of the following Chemical Formula 6 to 9:

[Chemical Formula 6]

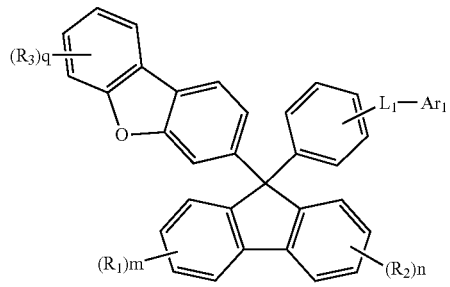

[Chemical Formula 7]

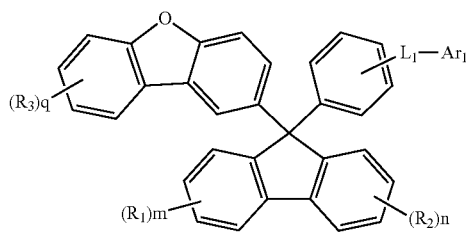

[Chemical Formula 8]

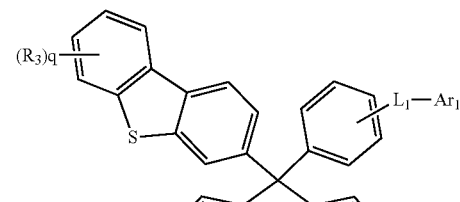

[Chemical Formula 9]

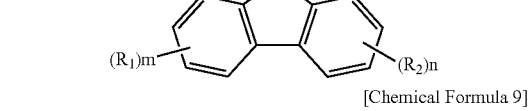

wherein, in Chemical Formula 6 to 9,
p is an integer of 0 to 5;
$L_1$, $Ar_1$, q, m, n, $R_1$, $R_2$, and $R_3$ have the same definitions as in claim 2.

11. The compound of claim 2, which is selected from the group consisting of the following compounds:

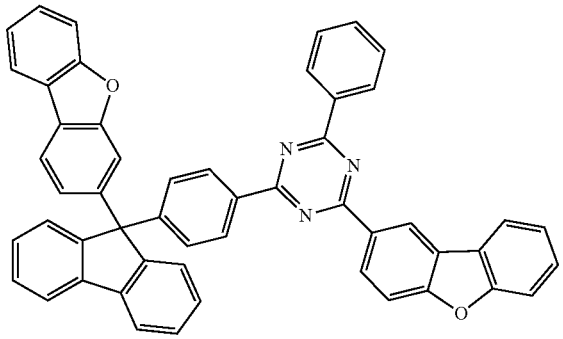

Inv 60

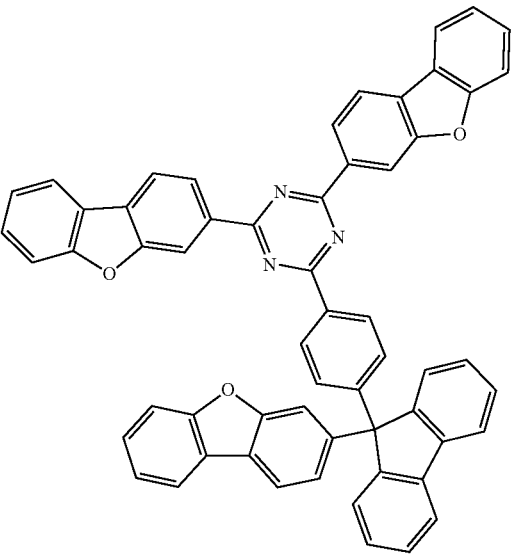

Inv 69

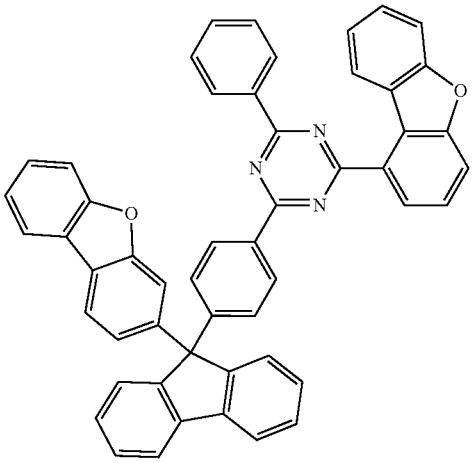

Inv 70
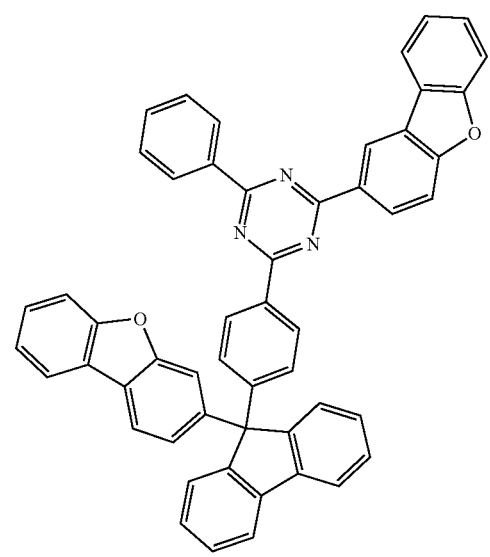
Inv 71
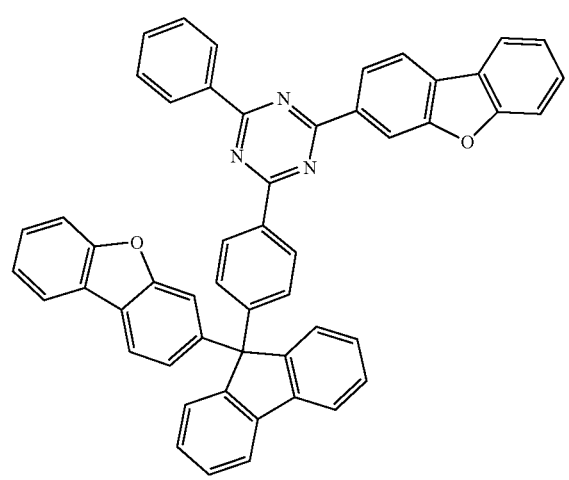
Inv 72
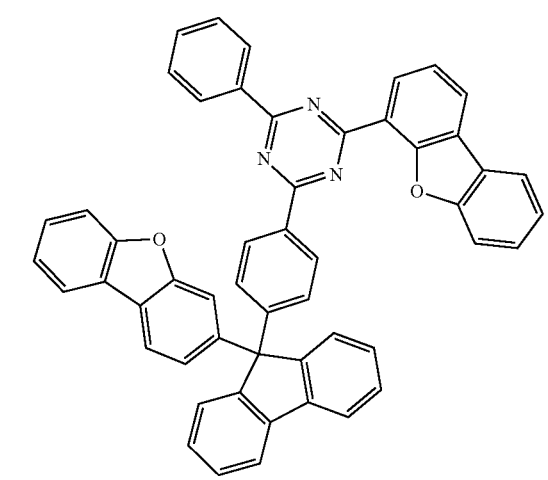
Inv 73
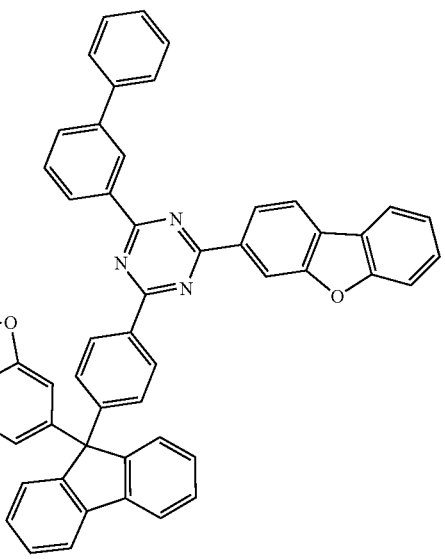
Inv 74
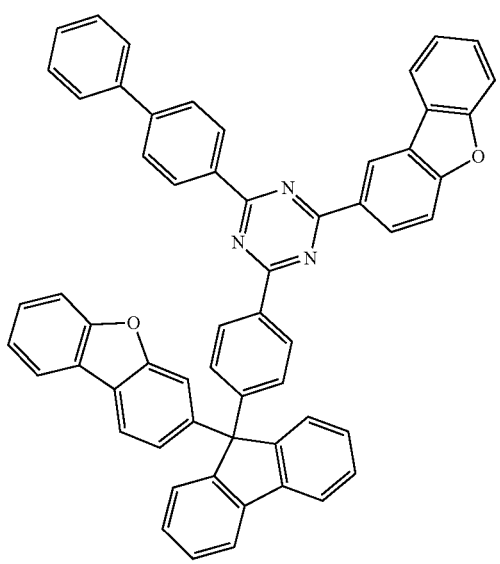

-continued
Inv 75
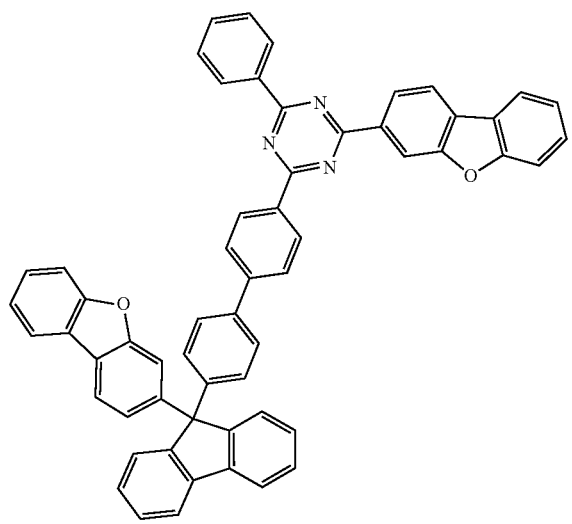
Inv 76
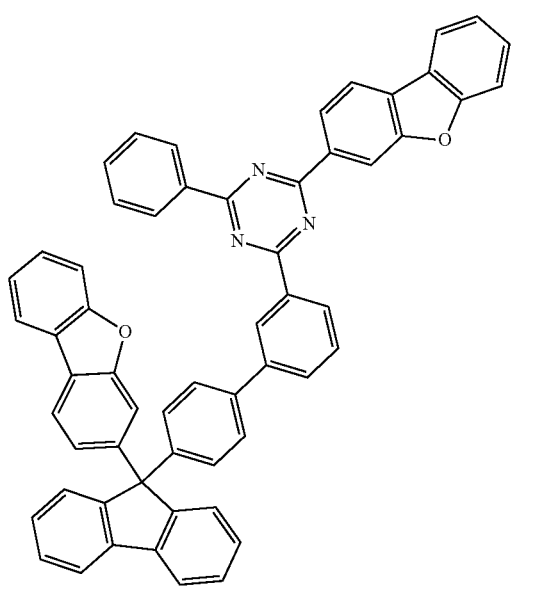
-continued
Inv 77
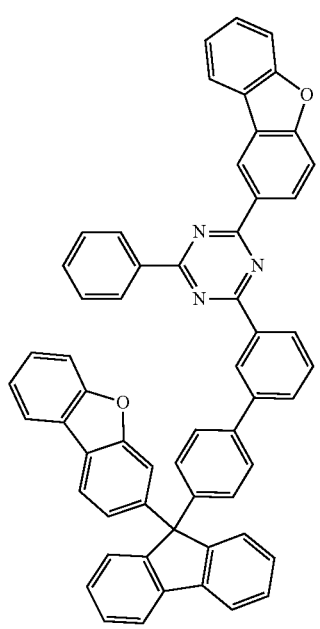
Inv 78

Inv 79
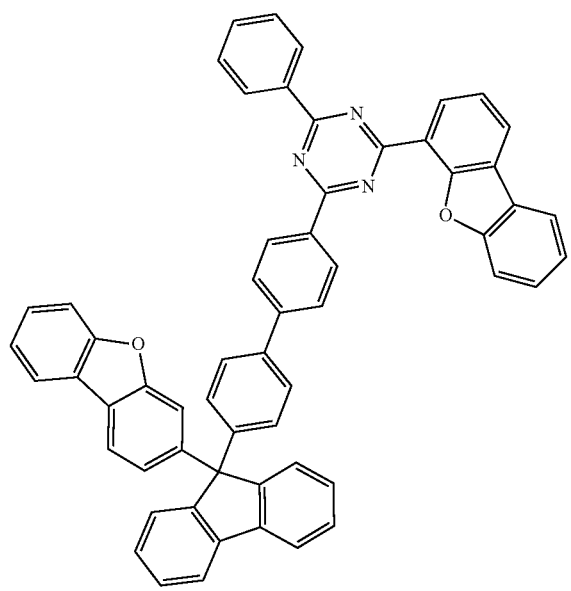
Inv 81
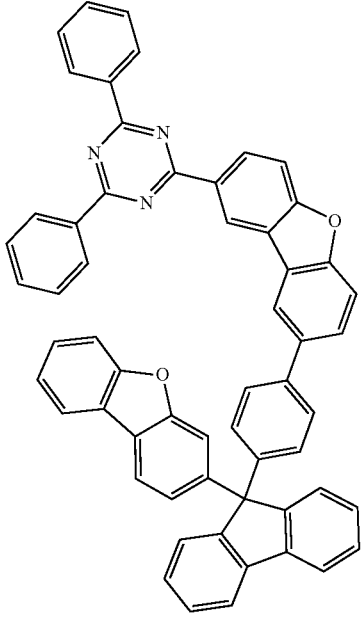
Inv 80
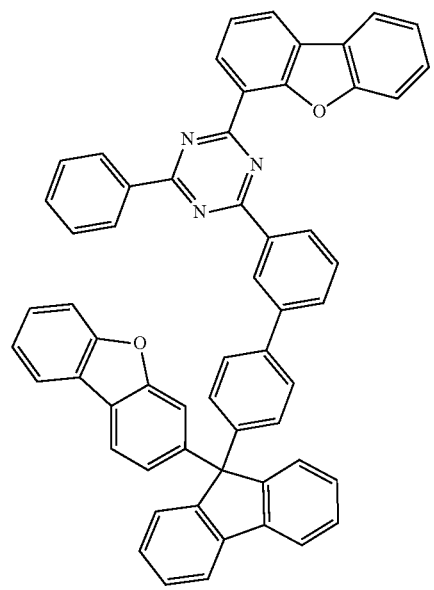
Inv 82
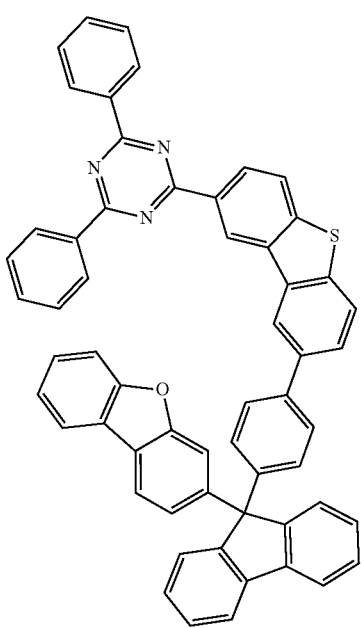

-continued
Inv 83
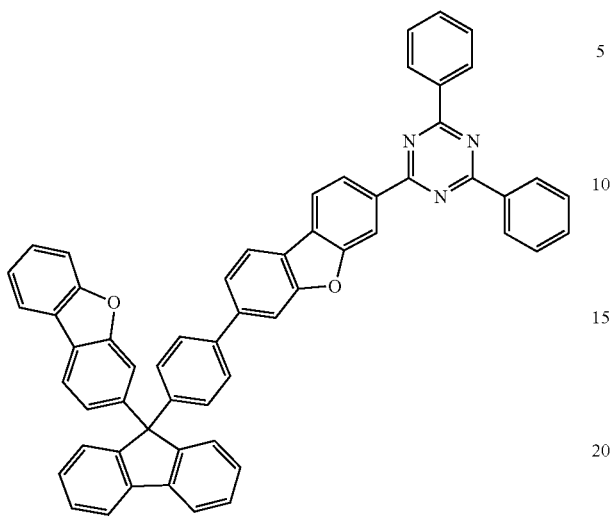
Inv 84
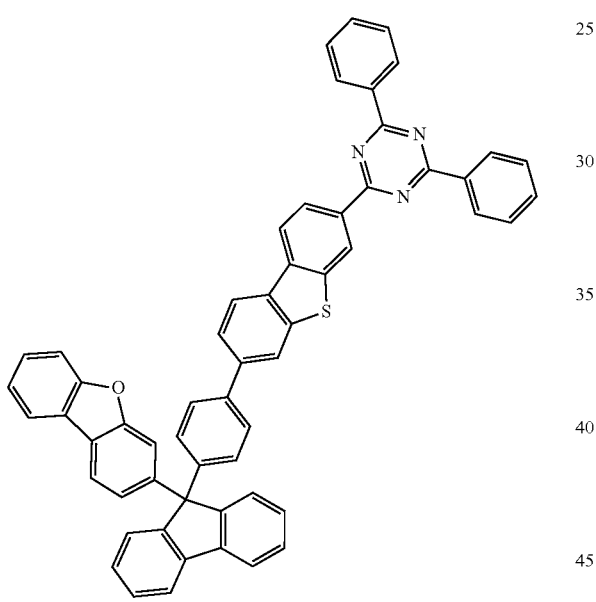
Inv 89
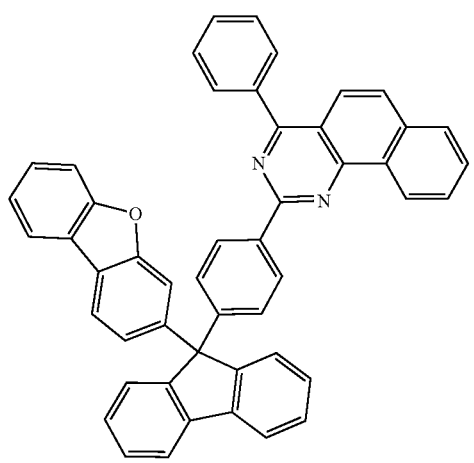
-continued
Inv 90
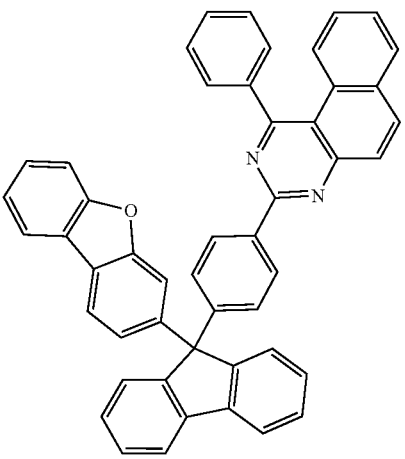
Inv 92
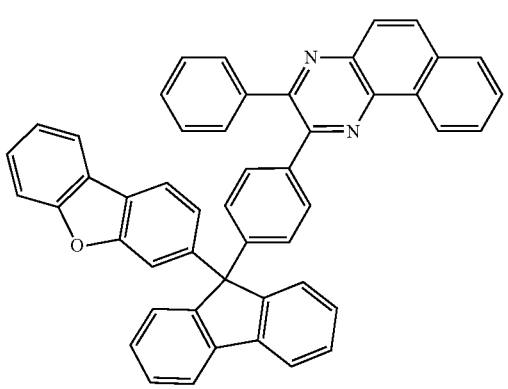
Inv 108
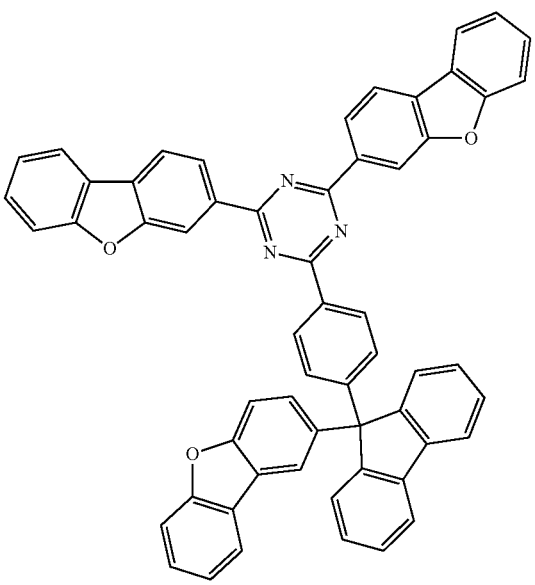

-continued
Inv 117
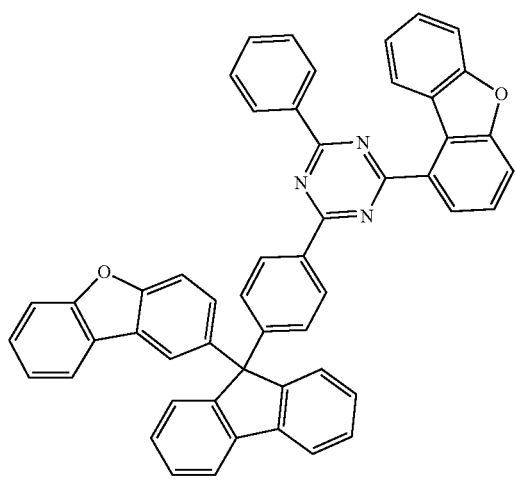
Inv 118
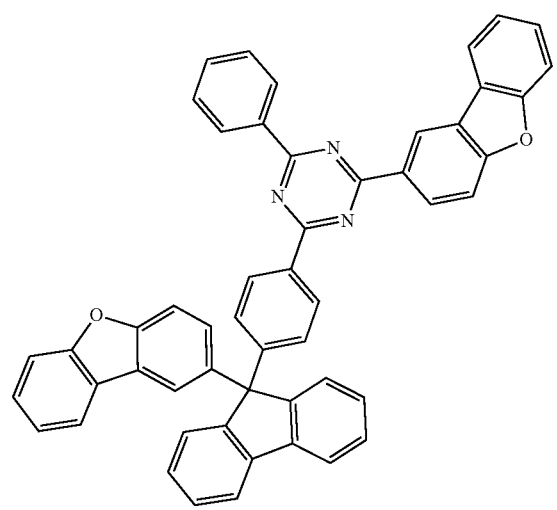
Inv 119
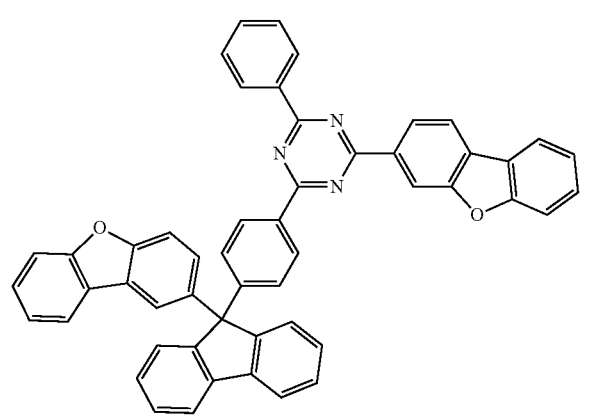
-continued
Inv 120
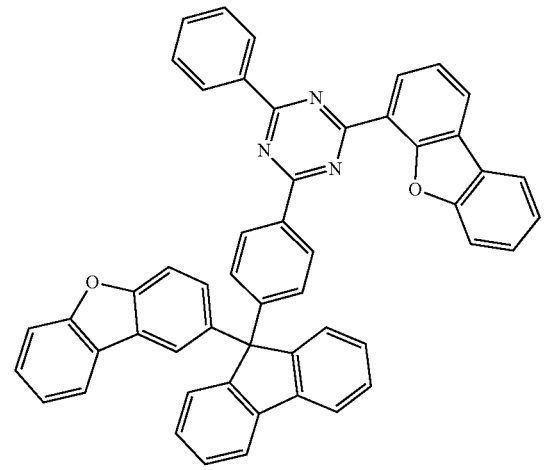
Inv 121
Inv 122
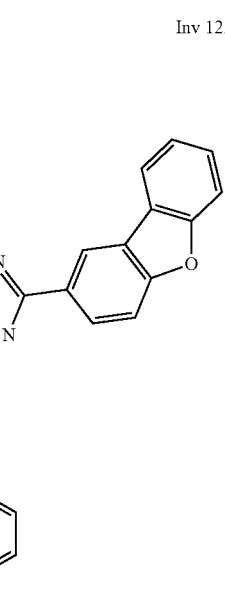

Inv 123
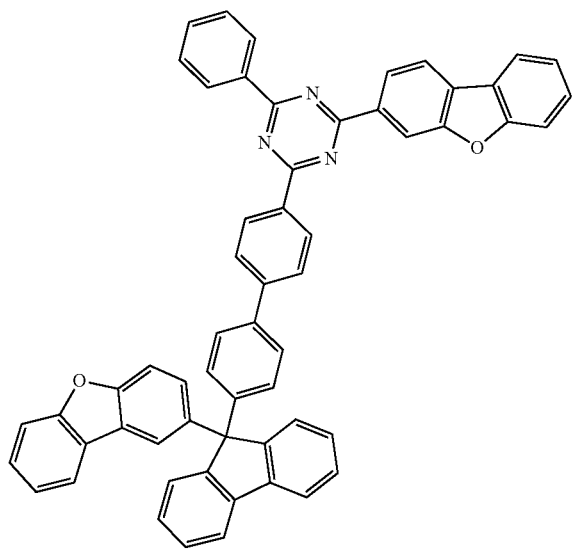
Inv 124
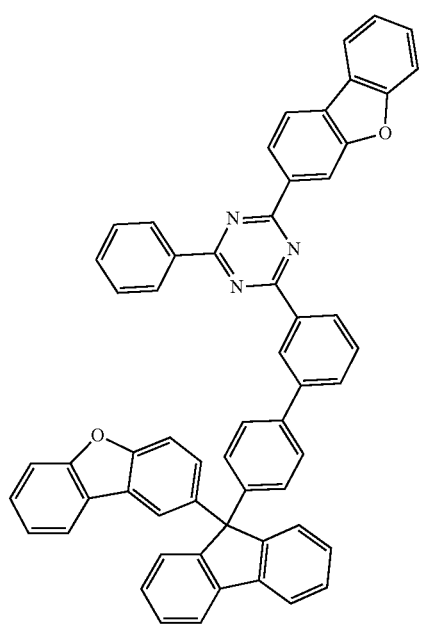
Inv 125
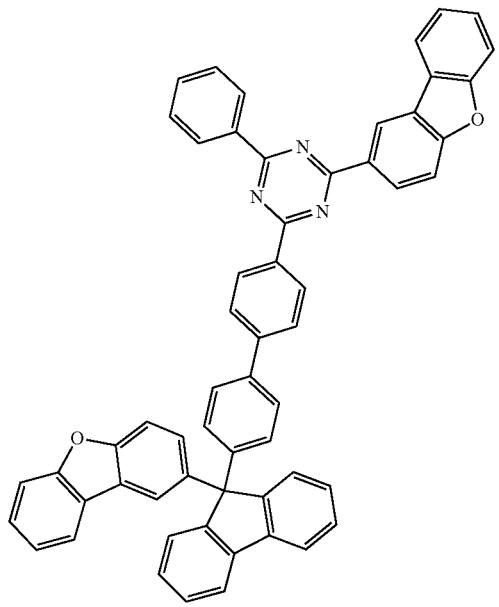
Inv 126
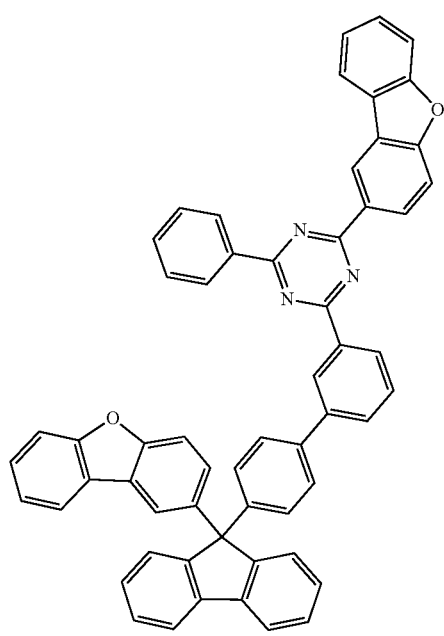

-continued
Inv 127
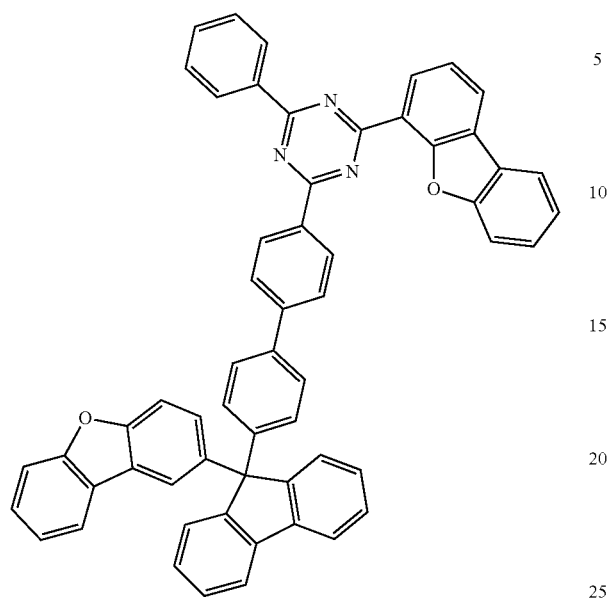
Inv 128
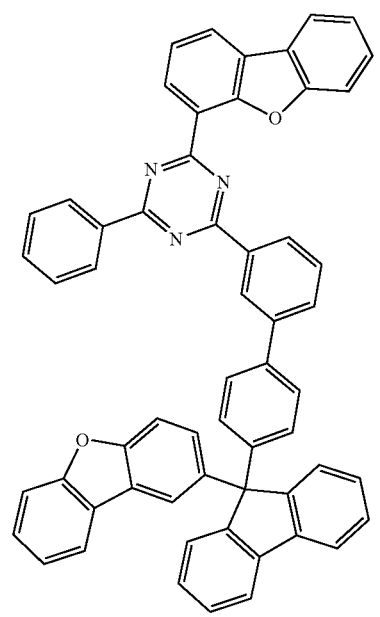
-continued
Inv 129
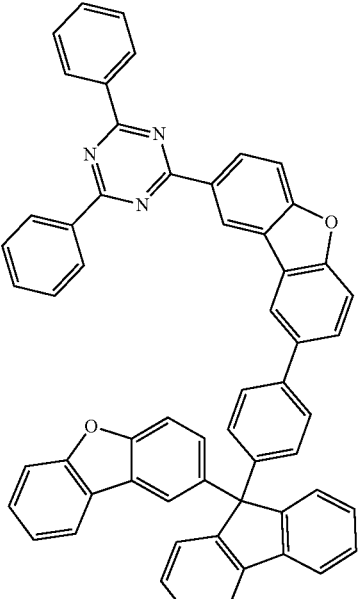
Inv 130

Inv 131
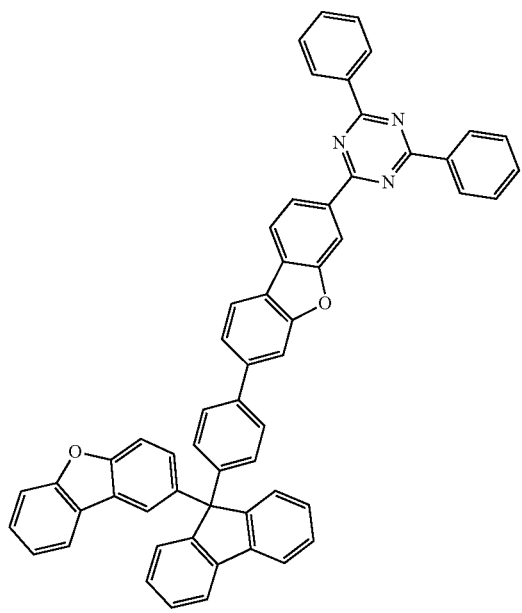
Inv 132
Inv 137
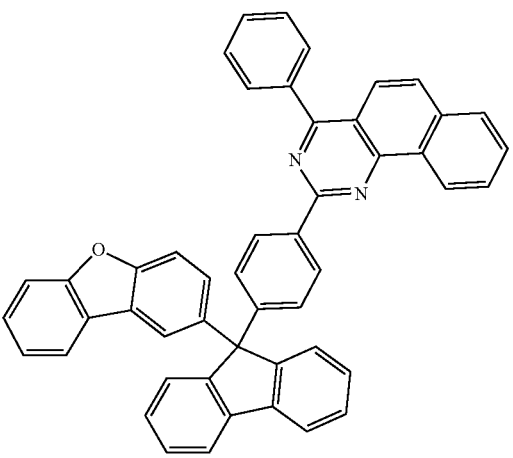
Inv 138
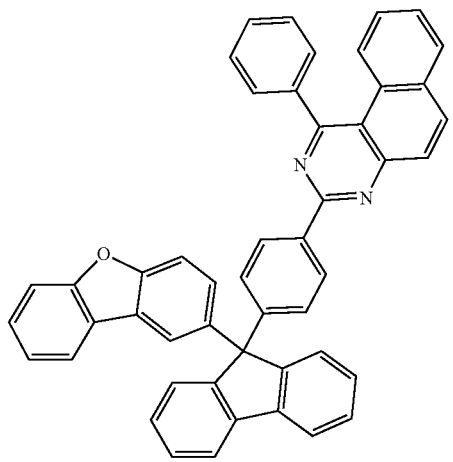
Inv 140
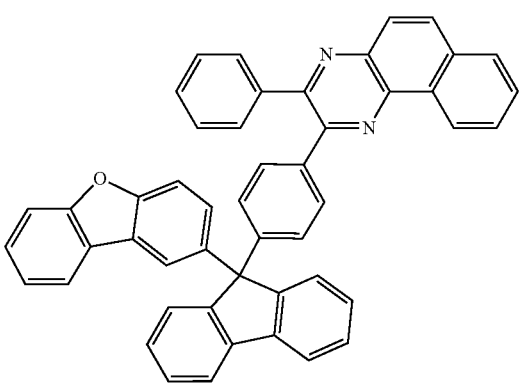

Inv 156
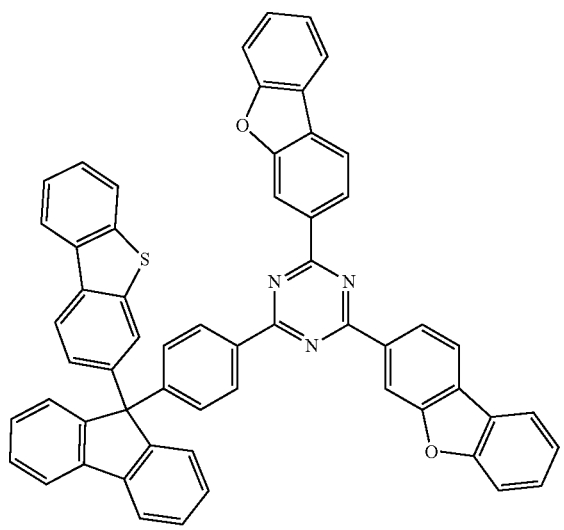
Inv 167
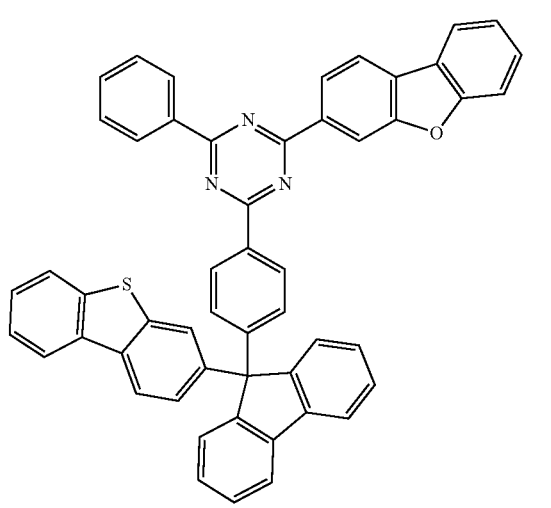
Inv 165
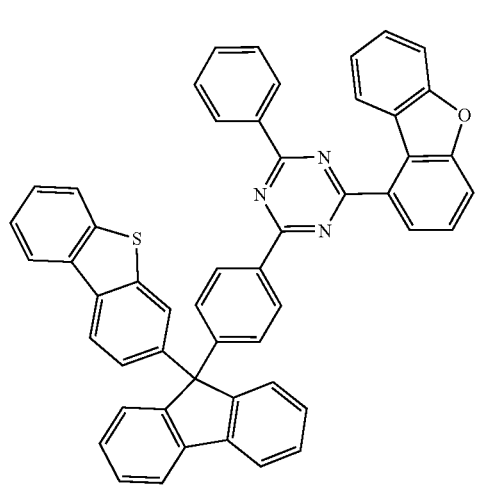
Inv 168
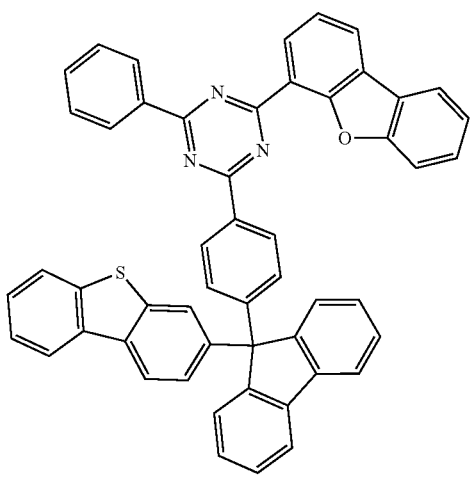
Inv 166
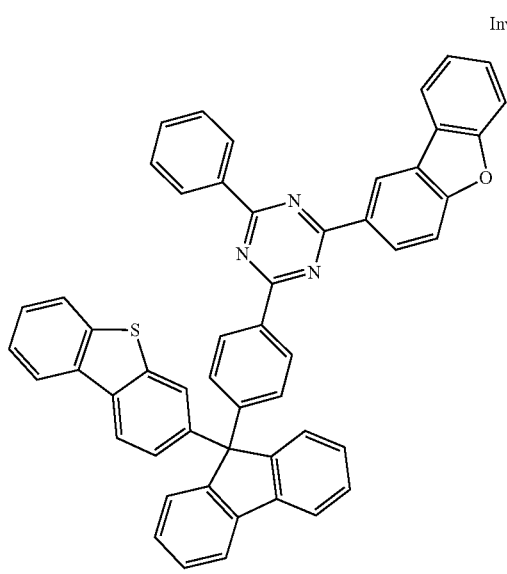
Inv 169
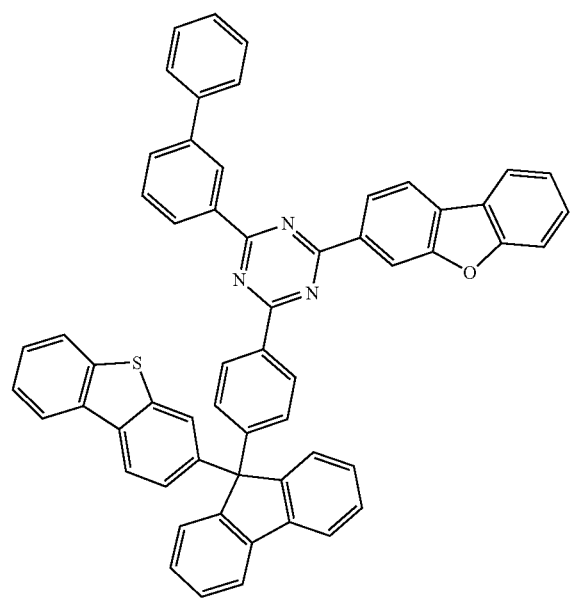

Inv 170
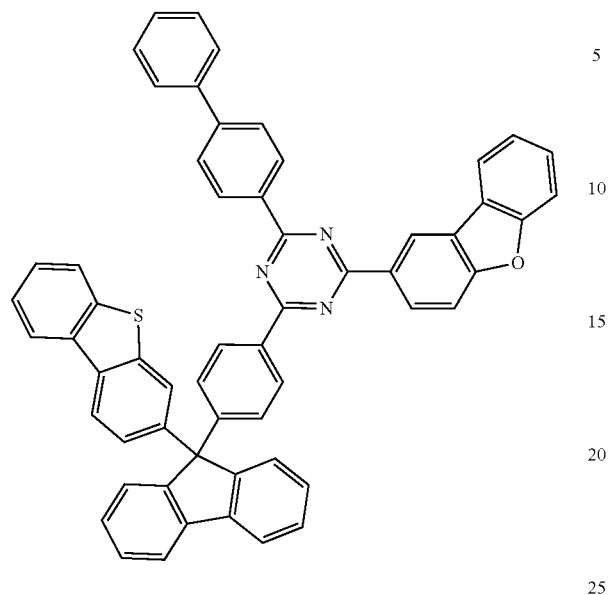
Inv 172
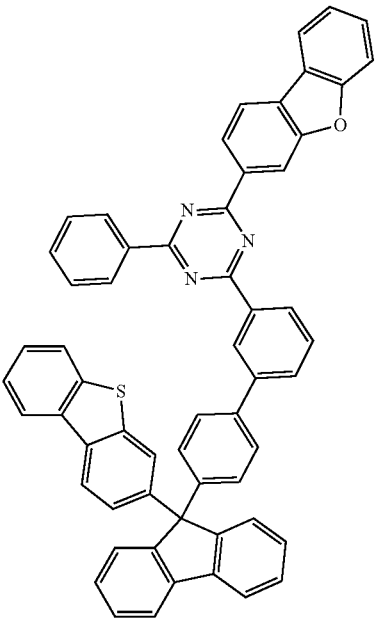
Inv 171
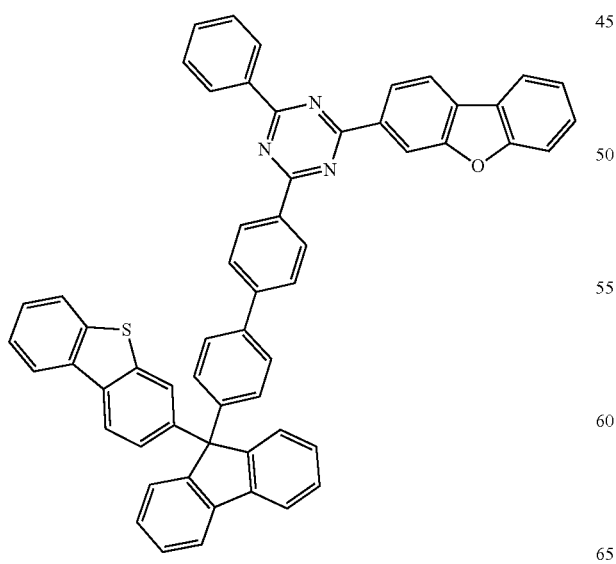
Inv 173
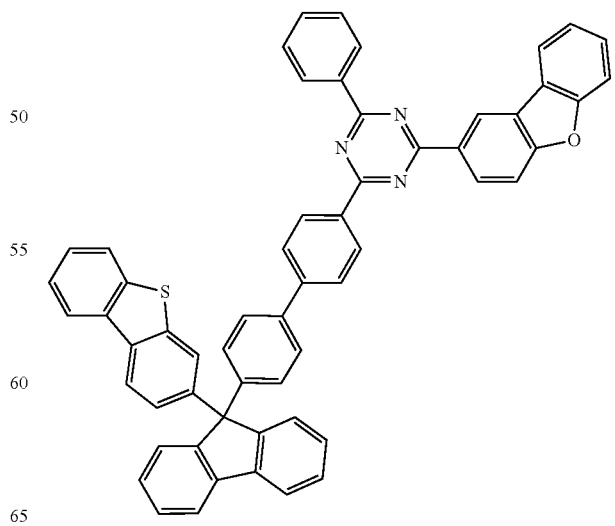

Inv 174
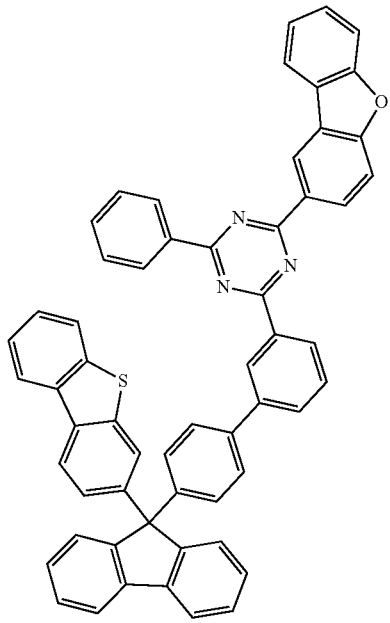
Inv 176
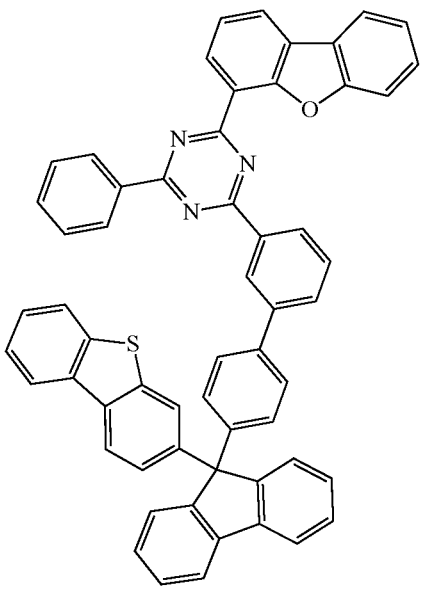
Inv 175
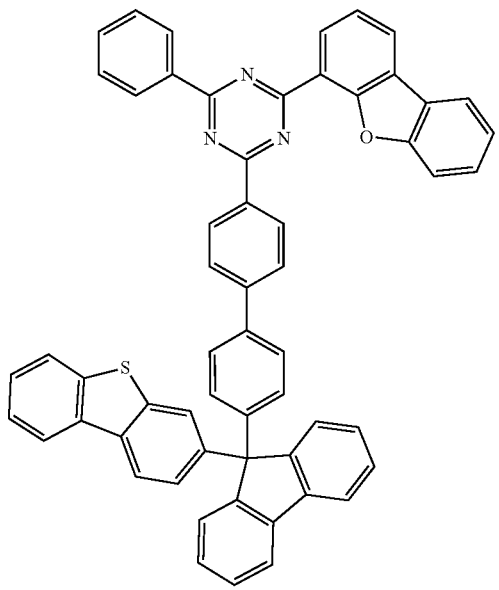
Inv 177
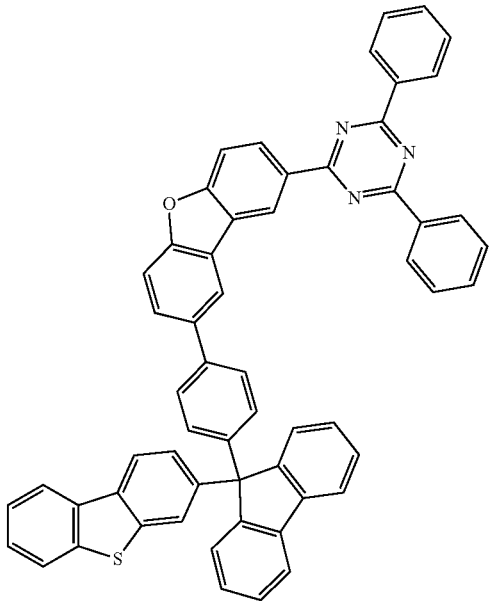

-continued
Inv 178
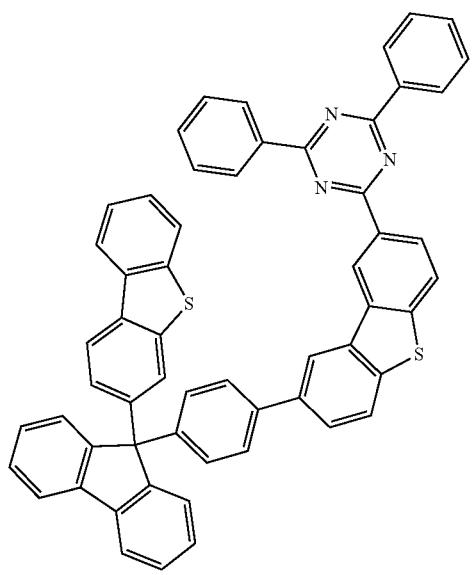
Inv 179
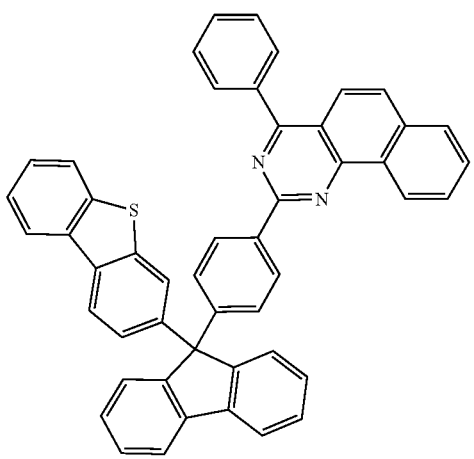
-continued
Inv 180
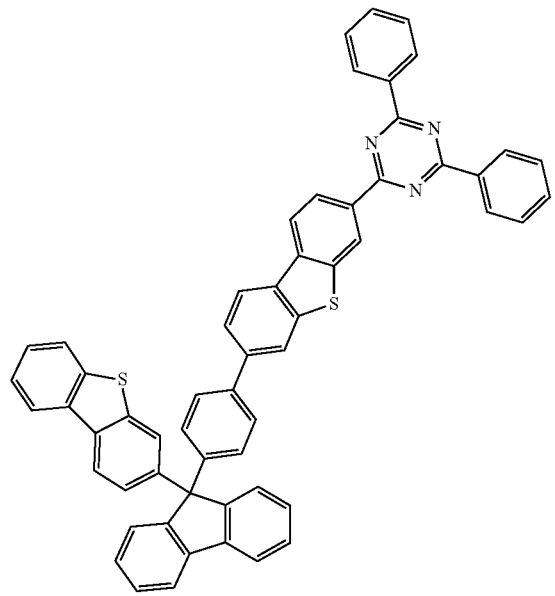
Inv 185
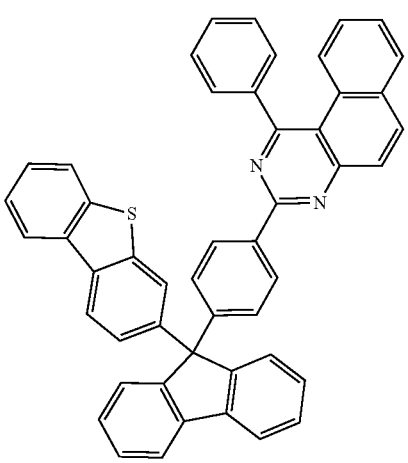
Inv 186

Inv 188
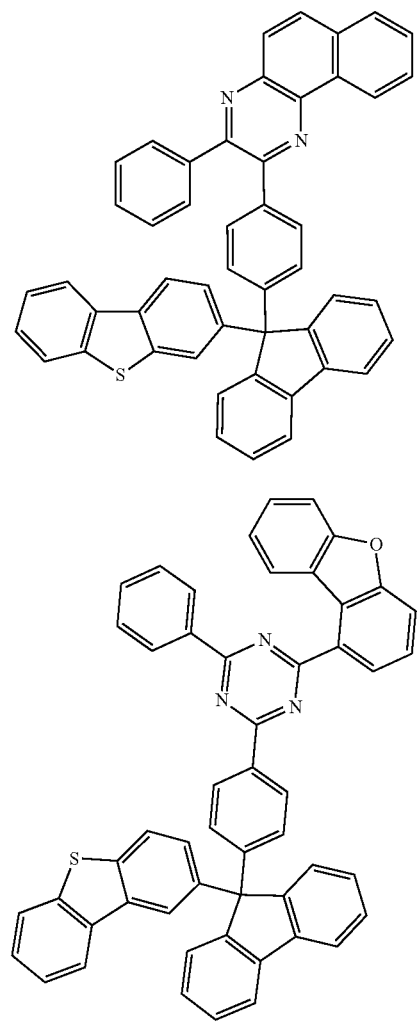
Inv 213
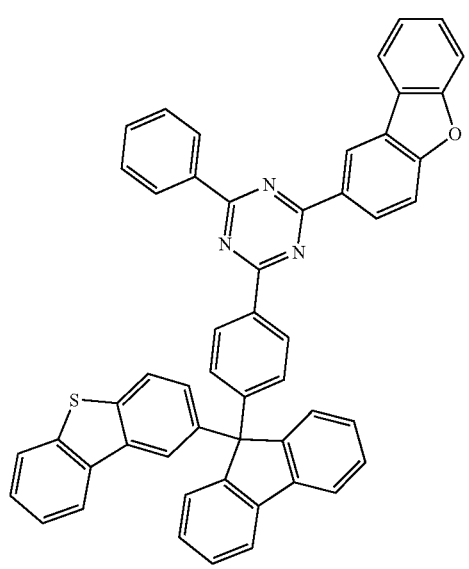
Inv 214
Inv 215
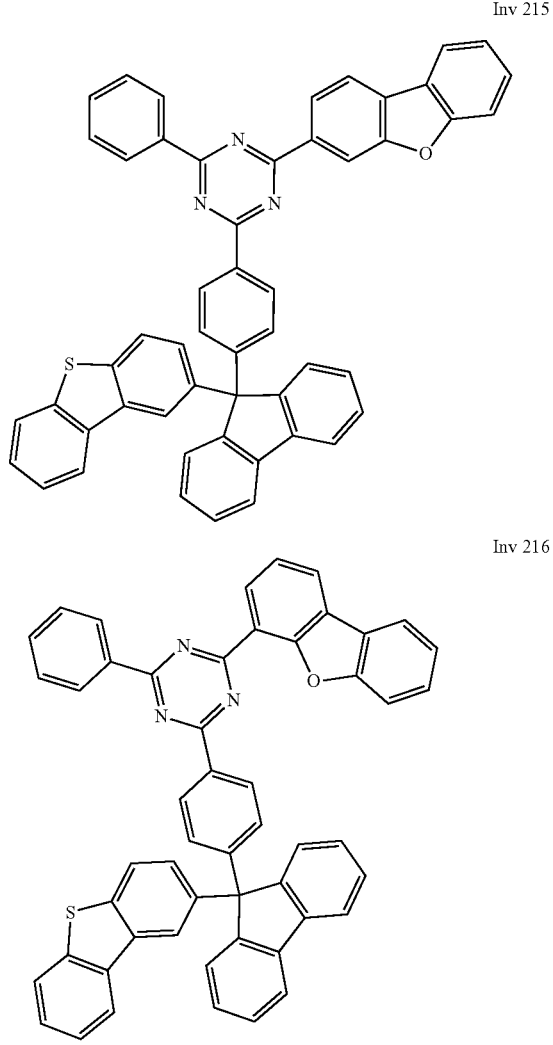
Inv 216
Inv 217
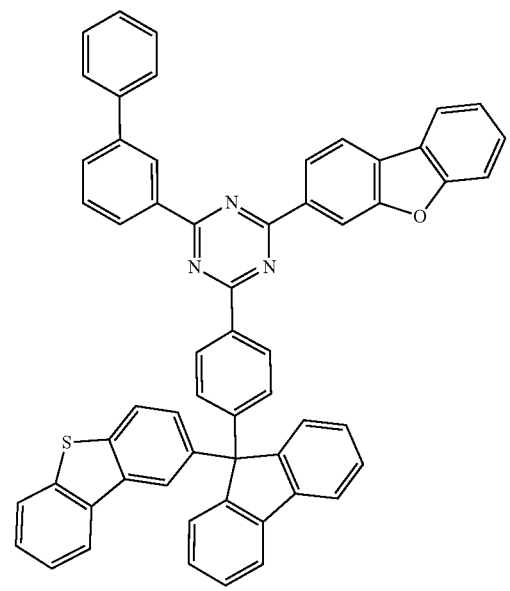

Inv 218
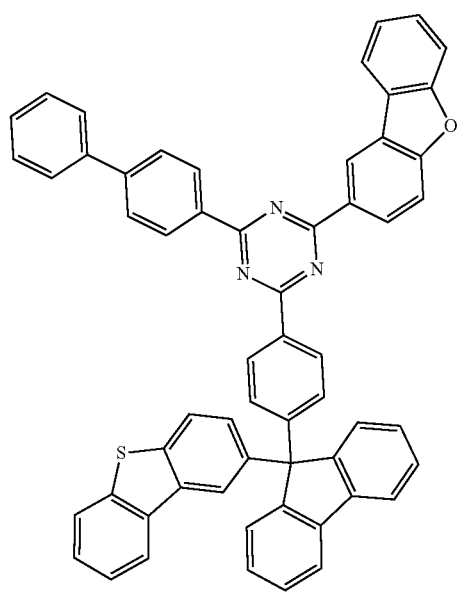
Inv 219
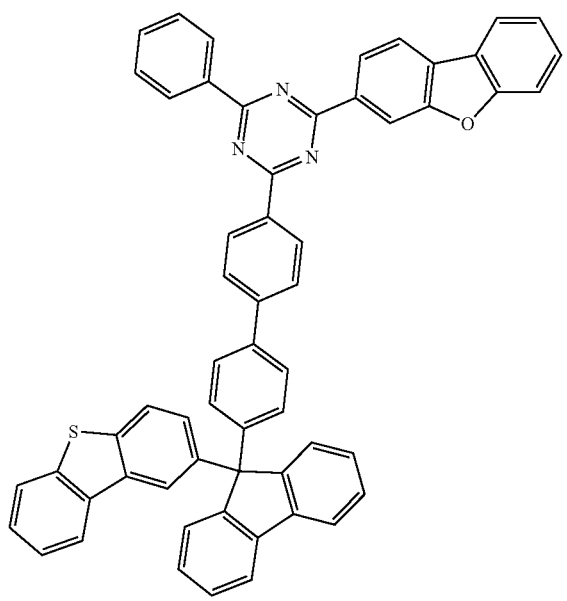
Inv 220
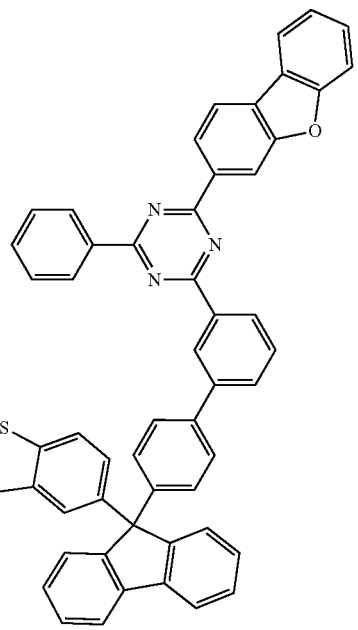
Inv 221
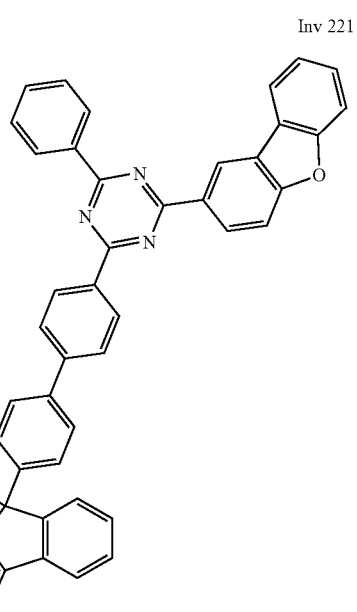

-continued
Inv 222
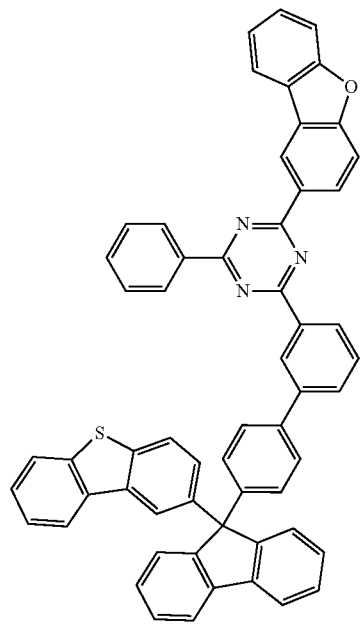
Inv 223
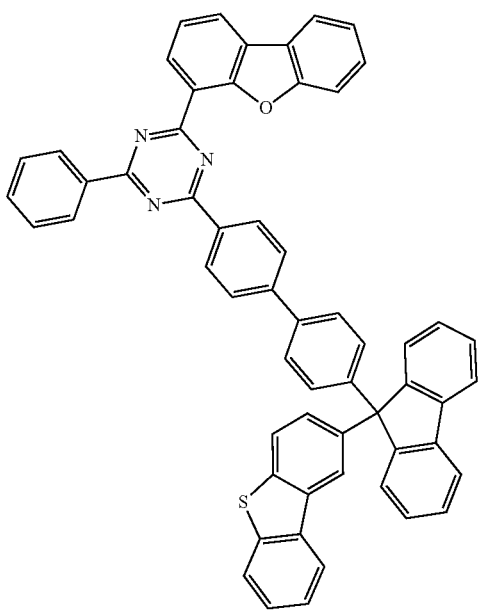
-continued
Inv 224
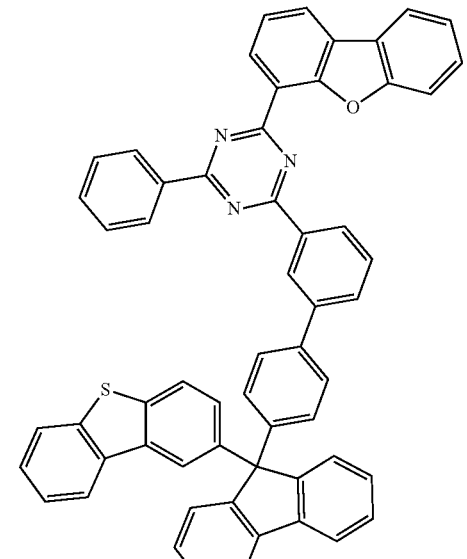
Inv 225
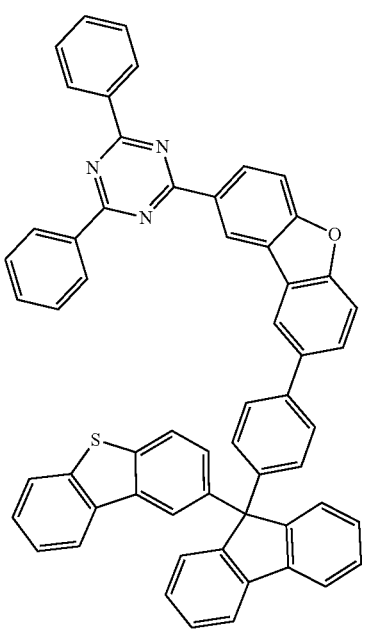

-continued
Inv 226
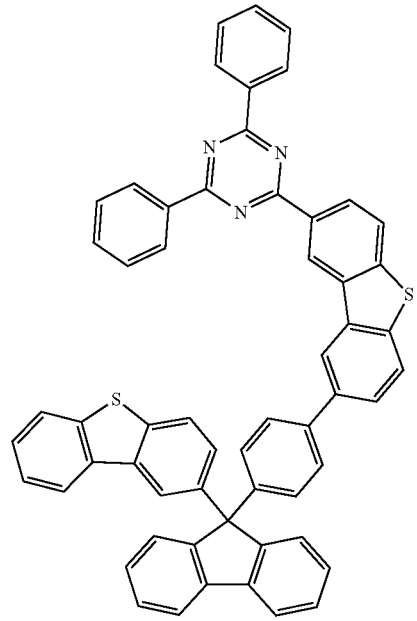
Inv 227
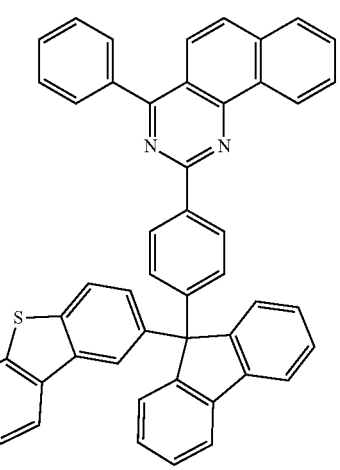
Inv 228
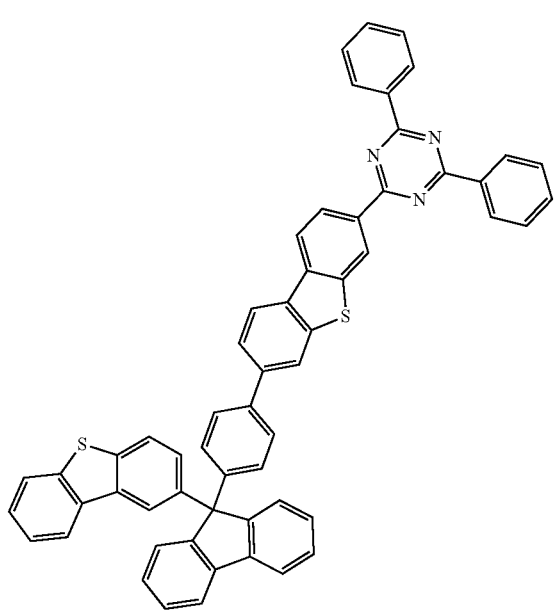
Inv 233
Inv 234
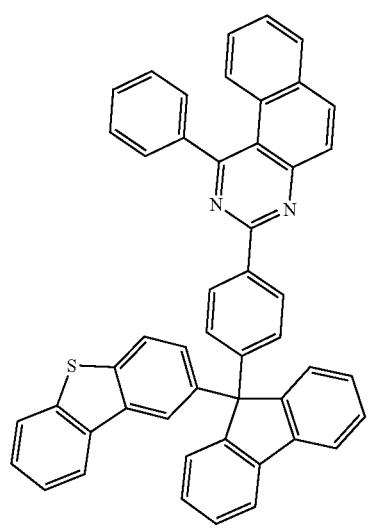

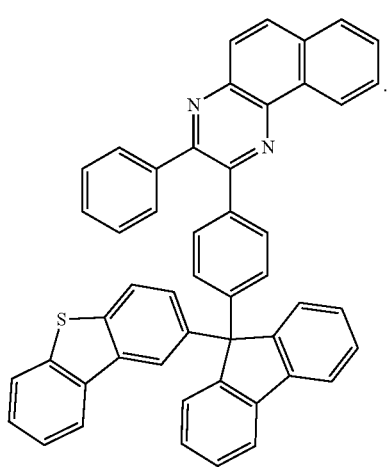
Inv 236
12. An organic electroluminescent device comprising:
an anode;
a cathode; and
one or more organic material layers provided between the anode and the cathode,
wherein at least one of the one or more organic material layers includes the compound of Chemical Formula 1 of claim 2.
* * * * *